(12) United States Patent
Aricò et al.

(10) Patent No.: US 9,267,163 B2
(45) Date of Patent: Feb. 23, 2016

(54) HYBRID EXPRESSION OF NEISSERIAL PROTEINS

(75) Inventors: Maria Aricò, Siena (IT); Maurizio Comanducci, Siena (IT); Cesira Galeotti, Monteriggioni (IT); Vega Masignani, Siena (IT); Marzia Monica Giuliani, Siena (IT); Mariagrazia Pizza, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 2155 days.

(21) Appl. No.: 11/067,260

(22) Filed: Feb. 25, 2005

(65) Prior Publication Data

US 2006/0051840 A1  Mar. 9, 2006

Related U.S. Application Data

(63) Continuation of application No. 10/220,480, filed as application No. PCT/IB01/00420 on Feb. 28, 2001, now abandoned.

(30) Foreign Application Priority Data

Feb. 28, 2000 (GB) .................................... 0004695.3
Nov. 13, 2000 (GB) .................................... 0027675.8

(51) Int. Cl.
| | | |
|---|---|---|
| A61K 39/00 | (2006.01) |
| C12P 21/02 | (2006.01) |
| C07K 14/22 | (2006.01) |
| C12Q 1/68 | (2006.01) |
| C12P 21/00 | (2006.01) |
| A61K 39/095 | (2006.01) |
| A61K 38/00 | (2006.01) |

(52) U.S. Cl.
CPC .............. *C12P 21/02* (2013.01); *A61K 39/095* (2013.01); *C07K 14/22* (2013.01); *C12P 21/00* (2013.01); *C12Q 1/689* (2013.01); *A61K 38/00* (2013.01); *A61K 2039/55505* (2013.01); *C07K 2319/00* (2013.01); *C12Q 2600/156* (2013.01)

(58) Field of Classification Search
CPC .............. C07K 14/22; C07K 16/1217; C07K 2319/00; C07K 14/005; C07K 14/245; A61K 39/095; A61K 39/00; A61K 2300/00; A61K 38/00; A61K 39/39; A61K 2039/55544; A61K 2039/53; A61K 48/00; A61K 2039/55555; A61K 39/085; A61K 39/09; A61K 39/092; A61K 2039/6037; A61K 39/116

See application file for complete search history.

(56) References Cited

U.S. PATENT DOCUMENTS

| | | | |
|---|---|---|---|
| 4,239,749 A | 12/1980 | Buchanan | |
| 5,270,176 A | 12/1993 | Dorschug et al. | |
| 5,288,641 A | 2/1994 | Roizman | |
| 5,422,120 A | 6/1995 | Kim | |
| 5,547,670 A | 8/1996 | Goldstein et al. | |
| 5,580,859 A | 12/1996 | Felgner et al. | |
| 5,591,624 A | 1/1997 | Barber et al. | |
| 5,763,188 A | 6/1998 | Ohno et al. | |
| 5,785,974 A | 7/1998 | Casal Alvarez et al. | |
| 6,013,267 A | 1/2000 | Blake et al. | |
| 6,028,049 A | 2/2000 | Jacobs et al. | |
| 6,100,380 A | 8/2000 | Green et al. | |
| 6,127,180 A | 10/2000 | Narva et al. | |
| 6,150,502 A | 11/2000 | Strachan | |
| 6,197,312 B1 | 3/2001 | Peak et al. | |
| 6,200,578 B1 | 3/2001 | St. Geme | |
| 6,248,329 B1 * | 6/2001 | Chandrashekar et al. | . 424/191.1 |
| 6,583,275 B1 | 6/2003 | Doucette-Stamm et al. | |
| 6,696,062 B1 | 2/2004 | Thonnard et al. | |
| 6,709,660 B1 * | 3/2004 | Scarlato et al. ............. | 424/250.1 |
| 6,914,131 B1 * | 7/2005 | Scarlato et al. ............. | 536/23.1 |
| 7,348,006 B2 | 3/2008 | Contorni et al. | |
| 7,368,261 B1 * | 5/2008 | Rappuoli ..................... | 435/69.1 |
| 7,504,111 B2 * | 3/2009 | Fontana et al. ............. | 424/249.1 |
| 7,576,176 B1 * | 8/2009 | Fraser et al. ................ | 530/350 |
| 7,604,810 B2 * | 10/2009 | Rappuoli ................... | 424/250.1 |
| 7,612,192 B2 * | 11/2009 | Fraser et al. ................ | 536/23.7 |
| 7,618,636 B1 * | 11/2009 | Masignani et al. ........ | 424/190.1 |
| 7,655,245 B2 * | 2/2010 | Scarlato et al. ............ | 424/250.1 |
| 7,700,119 B2 * | 4/2010 | Giuliani et al. ............ | 424/250.1 |
| 7,714,121 B2 * | 5/2010 | Scarlato et al. ............. | 536/23.7 |
| 7,749,518 B2 * | 7/2010 | Masignani et al. ........ | 424/256.1 |
| 7,785,608 B2 | 8/2010 | Zlotnick et al. | |
| 7,803,387 B2 * | 9/2010 | Arico et al. ................. | 424/250.1 |
| 7,862,827 B2 * | 1/2011 | Giuliani et al. ............. | 424/250.1 |
| 7,988,979 B2 * | 8/2011 | Fraser et al. ............... | 424/234.1 |
| 8,101,194 B2 | 1/2012 | Zlotnick et al. | |
| 8,114,960 B2 * | 2/2012 | Arico et al. .................... | 530/324 |
| 8,221,761 B1 * | 7/2012 | Grandi et al. .............. | 424/184.1 |
| 8,226,960 B2 | 7/2012 | Masignani et al. | |

(Continued)

FOREIGN PATENT DOCUMENTS

| | | |
|---|---|---|
| EP | 0273116 | 7/1988 |
| EP | 0345242 A2 | 12/1989 |

(Continued)

OTHER PUBLICATIONS

Tettelin et al, Expert Rev. Vaccines, 2006, 5/5:687-694.*
Bethell et al, Expert Rev. Vaccines, 2002, 1/1:75-84.*
Pizza et al, Science, Mar. 10, 2000, 287:1816-1820.*
Jolley et al, FEMS Microbiol. Rev., 2007, 31:89-96.*
Abad et al, Emerging Infectious Diseases, Apr. 2008, 14/4:688-689.*
Perrett et al, Expert Opin. Biol. Ther., 2005, 5/12:1611-1625.*
Telford, Cell Host & Microbe 3, Jun. 2008, pp. 408-416.*
Morley et al, Vaccine, 2002, 20:666-687.*

(Continued)

*Primary Examiner* — Nita M Minnifield
(74) *Attorney, Agent, or Firm* — Morrison & Foerster LLP

(57) ABSTRACT

Two or more Neisserial proteins (e.g. A and B) are expressed as a single hybrid protein which can be represented simply by the formula $NH_2$-A-B—COOH.

34 Claims, 5 Drawing Sheets

(56) References Cited

U.S. PATENT DOCUMENTS

| | | | |
|---|---|---|---|
| 8,273,360 B2* | 9/2012 | Pizza et al. | 424/250.1 |
| 8,293,251 B2* | 10/2012 | Scarlato et al. | 424/250.1 |
| 8,349,390 B2* | 1/2013 | Diaz et al. | 427/2.25 |
| 8,383,790 B2 | 2/2013 | Peak et al. | |
| 8,394,390 B2* | 3/2013 | Galeotti et al. | 424/250.1 |
| 8,398,988 B2 | 3/2013 | Contorni et al. | |
| 8,398,999 B2 | 3/2013 | Masignani et al. | |
| 8,466,167 B2* | 6/2013 | Wu et al. | 514/292 |
| 8,470,340 B2 | 6/2013 | Beernink et al. | |
| 8,524,251 B2* | 9/2013 | Fraser et al. | 424/250.1 |
| 8,563,007 B1* | 10/2013 | Zlotnick et al. | 424/250.1 |
| 8,574,597 B2* | 11/2013 | Zlotnick | 424/250.1 |
| 8,663,656 B2* | 3/2014 | Pizza | 424/249.1 |
| 8,703,914 B2* | 4/2014 | Arico et al. | 530/350 |
| 8,734,812 B1* | 5/2014 | Galeotti et al. | 424/250.1 |
| 8,834,888 B2 | 9/2014 | Contorni et al. | |
| 8,980,277 B2* | 3/2015 | Pizza | 424/197.11 |
| 8,980,286 B2* | 3/2015 | Comanducci et al. | 424/250.1 |
| 9,011,869 B2* | 4/2015 | Pizza | 424/192.1 |
| 9,056,075 B2* | 6/2015 | Pizza | 424/190.1 |
| 9,057,716 B2* | 6/2015 | Balocchi | A61K 39/095 |
| 9,067,987 B2* | 6/2015 | Galeotti et al. | 435/6 |
| 9,139,621 B2* | 9/2015 | Fraser | C07K 14/22 |
| 9,150,898 B2* | 10/2015 | Arico et al. | A61K 38/00 |
| 9,156,894 B2* | 10/2015 | Masignani et al. | C07K 14/22 |
| 2002/0160016 A1 | 10/2002 | Peak et al. | |
| 2004/0092711 A1* | 5/2004 | Arico et al. | 530/350 |
| 2004/0110670 A1* | 6/2004 | Arico et al. | 514/12 |
| 2004/0167068 A1 | 8/2004 | Zlotnick et al. | |
| 2005/0222385 A1* | 10/2005 | Pizza | 530/350 |
| 2005/0232936 A1 | 10/2005 | Arico et al. | |
| 2006/0051840 A1* | 3/2006 | Arico et al. | 435/69.1 |
| 2006/0171957 A1* | 8/2006 | Pizza | 424/190.1 |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0053926 A1 | 3/2007 | Masignani et al. | |
| 2007/0082014 A1* | 4/2007 | Costantino | 424/250.1 |
| 2007/0253984 A1 | 11/2007 | Khandke et al. | |
| 2008/0026002 A1 | 1/2008 | Danzig | |
| 2008/0131421 A1* | 6/2008 | Scarlato et al. | 424/130.1 |
| 2008/0241180 A1* | 10/2008 | Contorni | 424/190.1 |
| 2009/0232820 A1* | 9/2009 | Fraser et al. | 424/139.1 |
| 2009/0285845 A1* | 11/2009 | Masignani et al. | 424/190.1 |
| 2010/0015151 A1* | 1/2010 | Rappuoli et al. | 424/139.1 |
| 2010/0143418 A1* | 6/2010 | Contorni et al. | 424/250.1 |
| 2010/0233205 A1* | 9/2010 | Pizza et al. | 424/201.1 |
| 2010/0267931 A1* | 10/2010 | Arico et al. | 530/350 |
| 2010/0272725 A1* | 10/2010 | Scarlato et al. | 424/139.1 |
| 2011/0020390 A1 | 1/2011 | Pizza et al. | |
| 2012/0107339 A1 | 5/2012 | Granoff et al. | |
| 2012/0195919 A1* | 8/2012 | Pizza | 424/190.1 |
| 2012/0276129 A1* | 11/2012 | Galeotti et al. | 424/190.1 |
| 2013/0005667 A1* | 1/2013 | Arico et al. | 514/21.2 |
| 2013/0236489 A1* | 9/2013 | Serruto et al. | 424/190.1 |
| 2013/0253002 A1* | 9/2013 | Wu et al. | 514/293 |
| 2013/0274465 A1* | 10/2013 | Singh et al. | 540/542 |
| 2013/0328643 A1* | 12/2013 | Martin | 333/193 |
| 2014/0037668 A1* | 2/2014 | Giuliani et al. | 424/190.1 |
| 2014/0363462 A1 | 12/2014 | Arico et al. | |
| 2015/0079124 A1 | 3/2015 | Fraser et al. | |
| 2015/0086582 A1 | 3/2015 | Fraser et al. | |

FOREIGN PATENT DOCUMENTS

| | | | |
|---|---|---|---|
| EP | 0467714 | | 1/1992 |
| EP | 0474313 A | | 3/1992 |
| EP | 0176170 B1 | | 8/1992 |
| EP | 0334301 B1 | | 12/1998 |
| EP | 0415731 B1 | | 4/2003 |
| EP | 1645631 A2 | | 4/2006 |
| EP | 1790660 | * | 5/2007 |
| EP | 2042512 A2 | | 4/2009 |
| EP | 2351767 A2 | | 8/2011 |
| FR | 2 720 408 A1 | | 12/1995 |
| GB | 2200651 A | | 8/1988 |
| JP | 2003525050 A2 | * | 8/2003 |
| NL | 8901612 | | 7/1990 |
| WO | WO-90/06696 | | 6/1990 |
| WO | WO-9006696 | | 6/1990 |
| WO | WO-90/11092 A1 | | 10/1990 |
| WO | WO-92/05266 A2 | | 4/1992 |
| WO | WO 92/16643 A1 | | 10/1992 |
| WO | WO-93/06223 A1 | | 4/1993 |
| WO | WO-93/07282 A1 | | 4/1993 |
| WO | WO-93/07283 A1 | | 4/1993 |
| WO | WO-93/14778 A1 | | 8/1993 |
| WO | WO-9503413 | | 2/1995 |
| WO | WO-95/09232 A2 | | 4/1995 |
| WO | WO-95/13796 A1 | | 5/1995 |
| WO | WO-95/30763 A1 | | 11/1995 |
| WO | WO-96/05858 A1 | | 2/1996 |
| WO | WO-96/29412 A1 | | 9/1996 |
| WO | WO-9629412 | | 9/1996 |
| WO | WO-96/30519 A1 | | 10/1996 |
| WO | WO-96/31618 | | 10/1996 |
| WO | WO-97/11181 | | 3/1997 |
| WO | WO-9710844 | | 3/1997 |
| WO | WO 97/13860 A1 | | 4/1997 |
| WO | WO 97/28273 A1 | | 8/1997 |
| WO | WO-98/17805 | | 4/1998 |
| WO | WO-98/20734 A1 | | 5/1998 |
| WO | WO-98/28333 A2 | | 7/1998 |
| WO | WO-98/55604 A1 | | 12/1998 |
| WO | WO 99/24578 A2 | | 5/1999 |
| WO | WO-99/31132 | | 6/1999 |
| WO | WO 99/36544 A2 | | 7/1999 |
| WO | WO-99/55872 A1 | | 11/1999 |
| WO | WO-99/55873 | | 11/1999 |
| WO | WO 99/57280 A2 | | 11/1999 |
| WO | WO-99/58683 | | 11/1999 |
| WO | WO 00/22430 | * | 4/2000 |
| WO | WO 00/22430 A2 | | 4/2000 |
| WO | WO-00/42192 A1 | | 7/2000 |
| WO | WO-00/44890 A1 | | 8/2000 |
| WO | WO 00/50075 | * | 8/2000 |
| WO | WO-00/66741 A2 | | 11/2000 |
| WO | WO 00/71574 | * | 11/2000 |
| WO | WO-0066791 | | 11/2000 |
| WO | WO-0071725 | | 11/2000 |
| WO | WO-01/04316 A2 | | 1/2001 |
| WO | WO 01/31019 | * | 5/2001 |
| WO | WO-0152885 | | 7/2001 |
| WO | WO-01/55182 | | 8/2001 |
| WO | WO 01/64920 A2 | * | 9/2001 |
| WO | WO 01/64922 A2 | * | 9/2001 |
| WO | WO-0164920 | | 9/2001 |
| WO | WO-0164922 | | 9/2001 |
| WO | WO-03/009869 A1 | | 2/2003 |
| WO | WO 03/010194 | * | 2/2003 |
| WO | WO-03010194 | | 2/2003 |
| WO | WO 03/020756 A2 | * | 3/2003 |
| WO | WO-03020756 | | 3/2003 |
| WO | WO-03/063766 | | 8/2003 |
| WO | WO 2004/032958 A1 | * | 4/2004 |
| WO | WO 2004/201216 A1 | * | 4/2004 |
| WO | WO 2004/048404 | * | 6/2004 |
| WO | WO-2004/065603 A2 | | 8/2004 |
| WO | WO 2004/067030 A2 | * | 8/2004 |
| WO | WO-2004/094596 A2 | | 11/2004 |
| WO | WO 2004/112832 | * | 12/2004 |
| WO | WO 2005/032583 A2 | * | 4/2005 |
| WO | WO 2005/033148 A1 | * | 4/2005 |
| WO | WO 2005/102384 A2 | * | 11/2005 |
| WO | WO 2005/106009 | * | 11/2005 |
| WO | WO-2006/024954 A2 | | 3/2006 |
| WO | WO-2006/081259 | | 8/2006 |
| WO | WO-2007/060548 A2 | | 5/2007 |
| WO | WO-2007/127665 A2 | | 11/2007 |
| WO | WO 2008/001224 A2 | * | 1/2008 |
| WO | WO-2008/125985 A2 | | 10/2008 |
| WO | WO-2008/149238 A2 | | 12/2008 |
| WO | WO-2009/104097 A2 | | 8/2009 |

(56) References Cited

FOREIGN PATENT DOCUMENTS

| | | |
|---|---|---|
| WO | WO-2010/028859 A1 | 3/2010 |
| WO | WO-2010/046715 A1 | 4/2010 |
| WO | WO-00/43518 A1 | 7/2013 |

OTHER PUBLICATIONS

Jacobsson et al, Vaccine, 2009, 27:1579-1584.*
Feng et al, Infection and Immunity, 1996, 64/1:363-365.*
Boslego et al, In: Vaccines and Immunotherapy, Cryz, Ed., 1991, pp. 211-223.*
Ellis, In: Vaccines, Plotkin et al, Eds., 1988, pp. 568-574.*
Herbert et al, (Eds.) The Dictionary of Immunology, 1995, 3 pages.*
Guillen et al., "Expression in Escherichia Coli and Immunological Characterization of a Hybrid Class 1-P64K Protein from Neisseria Meningitidis," *Biotecnologia Aplicada* 13(4):271-275, 1996.
Leg Rain et al., "Production of Lipidated Meningococcal Transferrin Binding Protein 2 in Escherichia Coli," *Protein Expression and Purification* 6:570-578, 1995.
Renauld-Mongenie et al., "Identification of Human Transferrin-Binding Sites Within Meningococcal Transferrin-Binding Protein B," *J. Bacteriology* 197(20):6400-6407, 1997.
Ala'Aldeen et al. (1996). "The Meningococcal Transferrin-binding Proteins 1 and 2 are Both Surface Exposed and Generate Bactericidal Antibodies Capable of Killing Homologous and Heterologous Strains," Vaccine 14(1):49-53.
Bartsevich et al. (Mar. 7, 1997). "Molecular Identification of a Novel Protein That Regulates Biogenesis of Photosystem I, a Membrane Protein Complex," The Journal of Biological Chemistry 272(10):6382-6387.
Bowie, J. et al. (1990). "Deciphering the Message in Protein Sequences: Tolerance to Amino Acid Substitutions," Science 247: 1306-1310.
Bygraves et al. (1992). "Analysis of the Clonal Relationships Between Strains of Neisseria Meningitidis by Pulsed Field Gel Electrophoresis," Journal of General Microbiology 138:523-531.
Cann et al. (1989). "Detection of Antibodies to Common Antigens of Pathogenic and Commensal Neisseria Species," Journal of Medical Microbiology 30:23-30.
Caugant et al. (1987). "Genetic Structure of Neisseria Meningitidis Populations in Relation to Serogroup, Serotype, and Outer Membrane Protein Pattern," Journal of Bacteriology 169(6):2781-2792.
Christodoulides et al. (1994). "Immunization with a Multiple Antigen Peptide Containing Defined B- and T-Cell Epitopes: Production of Bacterial Antibodies Group B Neisseria Meningitidis," Microbiology 140:2951-2960.
Cooney et al. (1993). "Three Contiguous Lipoprotein Genes in Pasteurella haemolytica A1 which are Homologous to a Lipoprotein Gene in Haemophilus Influenza Type B," Infection and Immunity 61(11):4682-4688.
Cruse et al. Illustrated Dict. of Immunology, 2nd ed., CRC Press, 2003. pp. 46, 166, and 382.
Dempsey et al. (1991). "Physical Map of the Chromosome of Neisseria gonorrhoeae FA1090 with Locations of Genetic Markers, including Opa and Pil Genes," Journal of Bacteriology 173(17):5476-5486.
Devries et al. (Aug. 1996). "Invasion of Primary Nasopharyngeal Epithelial Cells by Neisseria meningitidis is Controlled by Phase Variation of Multiple Surface Antigens," Infection and Immunity 64(8):2998-3006.
Gervais et al. (1992). "Putative Lipoprotein Yaec Precursor," Database Swissport Acc No. p28635.
Greenspan et al. (1999). "Defining Epitopes: It's Not as Easy as It Seems," Nature Biotechnology 7:936-937.
Grifantini, R. et al. (2002). "Previously Unrecognized Vaccine Candidates against Group B Meningococcus Identified by DNA Microarrays," Nature Biotechnology 20(9): 914-921.
Herbert, W. et al. (1985). The Dictionary of Immunology. Academic Press: London $3^{rd}$ edition, pp. 58-59.

Holmes, E. (2001). "PSMA Specific Antibodies and their Diagnostic and Therapeutic Use," Expert Opinion on Investigational Drugs 10(3): 511-519.
Maiden et al. (1998). "Multilocus Sequence Typing: a Portable Approach to the Identification of Clones within Populations of Pathogenic Microorganisms," Proceedings of the National Academy of Sciences USA 95:3140-3145.
McGuinness et al. (1993). "Class 1 outer membrane protein of Neisseria meningitidis: epitope analysis of the antigenic diversity between strains, implications for subtype definition and molecular epidemiology," Mol Microbiol. 7:505-514.
Moudallal et al. (1982). "Monoclonal anti bodies as probes of the antigenic structure of tobacco mosaic virus," EMBO Journal 1:1005-1010.
Ni et al. (1992). "Phylogenetic and Epidemiological Analysis of Neisseria meningitidis Using DNA Probes," Epidemiology and Infection 109:227-239.
Perkins et al. (1998). "Immunogenicity of two efficacious outer membrane protein-based serogroup B meningococcal vaccines among young adults in Iceland," The Journal of Infectious Disease 177:683-691.
Pettersson et al. (1999). "Sequence Variability of the Meningococcal Lactoferrin-binding Protein LbpB," Gene 231:105-110.
Pizza et al. (Mar. 10, 2000). "Identification of Vaccine Candidates Against Serogroup B Meningococcus by Whole-Genome Sequencing," Science 287(5459):1816-1820.
Poolman et al. (1985). "Colony Variants of Neisseria Meningitidis Strain 2996 (B:2b:P1.2): Influence of Class-5 Out Membrane Proteins and Lipolysaccharides," J. Med. Microbiol. 19:203-209.
Poolman et al. (1988). "Outer membrane protein serosubtyping of Neisseria meningitidis," European Journal of Clinical Microbiology and Infectious Diseases 7(2):291-292.
Poolman (1995). "Development of a Meningococcal Vaccine," Infectious Agents and Disease 4:13-28.
Roitt, I. et al. (1993). Immunology. Mosby: St. Louis, $4^{th}$ edition, pp. 7,7-7,8.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Seiler et al. (1996). "Allelic polymorphism and site-specific recombination in the opc locus of Neisseria meningitidis," Molecular Microbiology 19(4):841-856.
Tettelin et al. (Mar. 10, 2000). "Complete Genome Sequence of Neisseria meningitidis Serogroup B Strain MC58," Science 287(5459):1809-1815.
Thompson et al. (1994). "Clustal W: Improving the Sensitivity of Progressive Multiple Sequence Alignment through Sequence Weighting, Position-specific Gap Penalties and Weight Matrix Choice," Nucleic Acids Research 22(22):4673-4680.
Thompson et al. (1998). "Multiple Sequence Alignment with Clustal X," Trends in Biochemical Sciences 23:403-405.
Van Der Lay et al. (1992). "Construction of a Multivalent Meningococcal Vaccine Strain Based on the Class I Outer Membrane Protein," Infection and Immunity 60(8): 3516-3161.
Van Der Lay et al. (1995). "Construction of Neisseria Meningitidis Strains Carrying Multiple Chromosomal Copies of the PorA Gene for Use in Production of a Multivalent Outer Membrane Vesicle Vaccine," Vaccine 13(4): 401-107.
Virji et al. (1992). "Variations in the Expression of Pili: the Effect on Adherence of Neisseria meningitidis to Human Epithelial and Endothelial Cells," Molecular Microbiology 6:1271-1279.
Wolff et al. (1992). "Phylogeny and Nucleotide Sequence of a 23S rRNA Gene from Neisseria gonorrhea and Neisseria meningitidis," Nucleic Acids Research 20(17):4657.
Parkhill et al. (Mar. 2000) "Complete DNA sequence of a serogroup A strain of Neisseria meningitides Z2491" 404: 502-505.
1997-11-17-NM_shotgun.dbs and 1997-12-15-NM.dbs, located at <ftp://ftp.sanger.ac.uk/pub/pathogens/nm/old data/>.
Accession No. A61824 from PCT Patent Publication No. WO 97/11181. Created Mar. 9, 1998. (2 pages).

(56) References Cited

OTHER PUBLICATIONS

Ala'Aldeen et al. (1994). "Vaccine potential of meningococcal FrpB: studies on surface exposure and functional attributes of common epitopes," Vaccine, 12(6):535-541.
Alignment: SEQ ID No. 1 of WO 99/58683 (D4) against SEQ ID No. 3 of the Patent, executed on Jul. 19, 2010.
Alignment: SEQ ID No. 2 of WO 99/31132 (D2) against SEQ ID No. 2 of the Patent, executed on Jul. 16, 2010.
Alignment: SEQ ID No. 2 of WO 99/58683 (D4) against SEQ ID No. 2 of the Patent, executed on Jul. 15, 2010.
Alignment: SEQ ID No. 2 of WO 99/58683 (D4) against SEQ ID No. 4 of the Patent, executed on Jul. 14, 2010.
Alignment: SEQ ID No. 4 of the Patent against SEQ ID No. 2 of the Patent, executed on Jul. 15, 2010.
Alignment: SEQ ID No. 4 of the Patent against SEQ ID No. 6 of the Patent, executed on Jul. 16, 2010.
Alignment: U41852 nt sequence against SEQ ID No. 1 of the Patent, executed on Jul. 16, 2010.
Alignment: U41852 nt sequence against SEQ ID No. 3 of the Patent, executed on Jul. 16, 2010.
Alignment: U41852 nt sequence against SEQ ID No. 5 of the Patent, executed on Jul. 16, 2010.
Altschul et al. (1997). "Gapped BLAST and PSI-BLAST: a New Generation of Protein Database Search Programs," *Nucleic Acids Research* 25:3389-3402.
Anonymous third party observations: Observations under Article 115 EPC.
Appendix I to Statement of Grounds of Appeal filed by df-mp on Sep. 28, 2012, in relation to EP1645631, 1 pages.
Appendix II to Statement of Grounds of Appeal filed by df-mp on Sep. 28, 2012, in relation to EP1645631, 2 pages.
Beernick (Jul. 2010) "Impaired immungenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
Berkner. (1988). "Development of Adenovirus Vectors for the Expression of Heterologous Genes," *Biotechniques* 6: 616-629.
Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116 and 124.
Berzofsky, J. A. (1985). "Intrinsic and Extrinsic Factors in Protein Antigenic Structure," *Science* 229(4717):932-940.
Bouvier et al. (1991). "A gene for a new lipoprotein in the dapA-purC interval of the Escherichia coli chromosome," J Bacteriol 173(17):5523-5531.
Bowe et al. (Jul. 2004) "Mucosal vaccination against serogroup B meningococci: induction of bacterial antibodies and cellular immunity following intranasal immunization with NadA of *Neisseria meningitides* and mutants of *Escherichia coli* heat-labile enterotoxin," Infection and Immunity, 72: 4052-4060.
Cannon (1989). "Conserved Lipoproteins of Pathogenic Neisseria Species Bearing the H.8 Epitope: Lipid-Modified Azurin and H.8 Outer Membrane Protein," Clinical Microbiology Reviews j2(Suppl.):S1-S4.
Cantini et al. (Mar. 2006). "Solution Structure of the Immunodominant Domain of Protective Antigen GNA 1870 of Neisseria meningitidis," *Journal of Biological Chemistry* 281(11): 7220-7227.

Capecchi et al. (2005) "*Neisseria meningitides* NadA is a new invasion which promotes bacterial adhesion to and penetration into human epithelial cells," Molecular Microbiology, 55: 687-698.
Carson, S. D. B. et al. (May 1999). "Ferric Enterobactin Binding and Utilization by Neisseria gonorrhoeae," *Journal of Bacteriology* 18:2895-2901.
Centers for Disease Control and Prevention (Feb. 14, 1997), "Control and Prevention of Meningococcal Disease: Recommendations of the Advisory Committee on Immunization Practices (ACIP)," MMWR 46(RR-5): 1-51.
Centers for Disease Control and Prevention (Feb. 14, 1997), "Control and Prevention of Serogroup C Menengoccal Disease: Evaluation and Management of Suspected Outbreaks: Recommendations for the Advisory Committee on Immunization Practices (ACIP)," MMWR 46(RR-5): 13-21.
Chen, et al. (1994). "Determination of the optimal aligned spacing between the Shine-Dalgarno sequence and the translation initiation codon of *Escherichia coli* mRNAs," Nucleic Acids Res. 22(23):4953-4957.
Comanducci et al. (Jul. 2004) "NadA diversity and carriage in *Neisseria meningitides*," Infection and Immunity, 72: 4217-4223.
Comanducci, M. (2002). "NadA, a Novel Vaccine Candidate of Neisseria Meningitides," Journal of Experimental Medicine 195(11): 1445-1454.
Connelly et al. (1995). "In vivo Gene Delivery and Expression of Physiological Levels of Functional Human Factor VIII in Mice," *Human Gene Therapy* 6:185-193.
Cordis, "Preparation of meningococcal antigens," posted online on Feb. 2, 2005, 2 pages.
Database accession No. NMB1994 (cf. XP2231040) (Tettelin et al.), uploaded Oct. 1, 2000.
Declaration by Dr. Ellen Murphy, Ph.D., dated Sep. 14, 2011, submitted in opposition proceedings for EP1645631, 4 pages.
Declaration by Dr. Julian Parkhill dated Jun. 12, 2008, submitted in opposition proceedings for EP1645631, 2 pages.
Declaration by E. Richard Moxon dated Feb. 16, 2013, submitted in opposition proceedings for EP1645631, 5 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Delgado et al. (2007). "Lipoprotein NMB0928 from Neisseria meningitidis serogroup B as a novel vaccine candidate," Vaccine 25:8420-8431.
Dinthilhac and Claverys (1997). "The adc locus, which affects competence for genetic transformation in Streptococcus pneumoniae, encodes an ABC transporter with a putative lipoprotein homologous to a family of streptococcal adhesins," Res Bicrobiol 148:119-131.
Donnelly et al. (1997). "DNA Vaccines," *Annual Review of Immunology* 15:617-648.
EBI Accession No. Q9K0G2. Last updated Oct. 1, 2000. (3 pages).
Esposti et al. (1990). "Critical Evaluation of the Hydropathy of Membrane Proteins," *European Journal of Biochemistry* 190:207-219.
European Search Opinion and Partial European Search Report mailed Feb. 27, 2007, for EP Application 06076711.8 filed May 19, 2000, 16 pages.
Examination Report dated Jun. 23, 2005 for for EP application No. 98 946 675.0. 3 pages.
Examination Report dated Nov. 20, 2008 for for EP application No. 98 946 675.0. 3 pages.
Facts and Submissions dated May 21, 2012, in relation to EP1645631, 30 pages.
Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.

(56) References Cited

OTHER PUBLICATIONS

Feavers et al. (2009). "Meningococcal protein antigens and vaccines," Vaccine 275:B42-B50.
Fleischmann et al. (1995). "Whole-Genome Random Sequencing and Assembly of Haemophilus influenzae Rd," Science 269:496-501.
Fletcher et al. (2004). "Vaccine Potential of the Neisseria meningitidis 2086 Lipoprotein," *Infection and Immunity* 72(4): 2088-2100.
Fontana et al. (2002). A genomic approach Abstract from the 13*th* International Pathogenic Neisseria Conference, Oslo, Norway, Sep. 1-6, 2002. p. 248.
Forest et al. (1997). "Type-4 pilus-structure: ourside to inside and top to bottom—a minireview," Gene 192:165-169.
Fraser et al. (1997). "Genomic sequence of a lyme disease spirochaete, Borrelia burgdorferi," Nature 390:580-586.
Fraser et al. (1998). "Complete genome sequence of Treponema pallidum, the syphilis spirochete," Science 281:375-388.
Gao et al. (1989). "Identification and Characterization of T Helper Epitopes in the Nucleoprotein of Influenza A Virus," *Journal of Immunology* 143:3007-3014.
GenBank Accession No. A61829, last updated Mar. 9, 1998, located at <http://www.ncbi.nlm.nih.gov/entrez/viewer.fcgi?db=nuccore&id=3715998>, last visited on Nov. 20, 2008, 2 pages. (See sequence alignments for SEQ ID Nos. 465, 463.).
GenBank Accession No. AJ001740, last updated May 21, 1998, located at <http://www.ncbi.nlm.nih.gov/entrez/viewer.fcgi?db=nuccore&id=3152399>, last visited on Nov. 20, 2008, 2 pages.(See sequence alignments for SEQ ID Nos. 653, 649, 651).
GenBank Accession No. HIU20229, last updated Feb. 9, 1995, located at <http://www.ncbi.nlm.nih.gov/entrez/viewer.fcgi?db=nuccore&id=644850>, last visited on Nov. 20, 2008, 5 pages. (See sequence alignments for SEQ ID Nos. 131,127, and 125).
GenBank Accession No. U41852, last updated Mar. 11, 2005, located at <http://www.ncbi.nlm.nih.gov/nuccore/U41852> visited on Nov. 6, 2012. (3 pages).
GenBank Accession No. U56744, last updated Oct. 21, 1996, located at <http://www.ncbi.nlm.nih.gov/nuccore/U56744> visited on Nov. 6, 2012. (1 page).
GenPept accession No. AAF42204, "hypothetical protein NMB1870 [Neisseria meningitidis MC58]," retrieved on Sep. 26, 2012, 2 pages.
Giuliani et al. (2006). "A universal vaccine for serogroup B meningococcus," PNAS 103(29):10834-10839.
Giuliani et al. (2010). "Measuring antigen-specific bactericidal responses to a multicomponent vaccine against serogroup B meningococcus," Vaccine 28:5023-5030.
Giuliani et al. (Feb. 2005). "The Region Comprising Amino Acids 100 to 255 of Neisseria meningitidis Lipoprotein GNA 1870 Elicits Bactericidal Antibodies," *Infection and Immunity* 73(2): 1151-1160.
Gold and Stormo (1987). "Translation Initiation", in Escherichia con and Salmonella typhimurium, Cellular and Molecular Biology, Ed. Neidhardt, pp. 1302-1307.
Gomez et al. (1996). "Antigenicity, cross-reactivity and surface exposure of the Neisseria meningitidis 37 kDa protein (Fbp)," Vaccine 14(14): 1340-1346.
Grandi (2005). "Reverse vaccinology: a critical analysis," in Encyclopedia of Genetics, Genomics, Proteomics and Bioinformatics, pp. 1322-1326.
Granoff, DM. (2009). Relative importance of complement-mediated bactericidal and opsonic activity for protection against meningococcal disease. Vaccine 27(Supplement 2): B117-B125.
Hayashi and Wu, "Identification and characterization of lipid-modified proteins in bacteria," Chapter 10 in Lipid Modifications of Proteins: A Practical Approach, Hooper and Turner (eds.), published in 1992, 27 pages.
Hou et al. (2005) "Protective antibody responses elicited by a meningococcal outer membrane vesicle vaccine with overexpressed genome-derived neisserial antigen 1870," J Infect Dis 192(4):580-90.
Hung et al. (2011). "The Neisseria meningitidis macrophage infectivity potentiator protein induces cross-strain serum bactericidal sctivity and is a potential serogroup B vaccine candidate," Infect Immun 79(9):3784-3791.
JCVI-CMR website showing Z2491 Sanger sequence (http://cmr.jcvi.org/tigr-scripts/CMR/shared/Genomes.cgi and links). (2010).
Jiang et al., (2010) "Broad vaccine coverage predicted for a bivalent recombinant factor H binding protein based vaccine to prevent serogroup B meningococcal disease" Vaccine 28:6086-6093.
Johnson et al. (1999). "Analysis of the human Ig isotype response to lactoferrin binding protein A from Neisseria meningitidis," FEMS Immun. Med. Microbial. 25(4): 349-354.
Jolly. (1994). "Viral Vector Systems for Gene Therapy," *Cancer Gene Therapy* 1:51-64.
Juncker et al. (2003). "Prediction of lipoprotein signal peptides in gram-negative bacteria," Protein Sci 12:1652-1662.
Kimura et al. (1994). "Retroviral Delivery of DNA into the Livers of Transgenic Mice Bearing Premalignant and Malignant Hepatocellular Carcinomas," *Human Gene Therapy* 5:845-852.
Koeberling et al. (2007). "Improved immunogenicity of a H44/76 group B outer membrane vesicle vaccine with over-expressed genome-derived Neisserial antigen 1870," Vaccine 25(10):1912-1920.
Kohler et al. (1975). "Continuous Cultures of Fused Cells Secreting Antibody of Predefined Specificity," *Nature* 256:495-496.
Lederman et al. (1991). "A single amino acid substitution in a common African allele of the CD4 molecule ablates binding of the monoclonal antibody, OKT4," Molecular Immunology 28(11):1171-1181.
Li et al. (1980). "beta-Endorphin omission analogs: dissociation of immunoreactivity from other biological activities," Proc Natl Acad Sci. USA 77:3211-3214.
Liebl et al. (1997). "Properties and gene structure of the Thermotoga maritima alpha-amylase AmyA, a putative lipoprotein of a hyperthermophilic bacterium," J Bacteriol 179(3):941-948.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Martin et al. (2003). "Experimentally revised repertoire of putative contingency loci in *Neisseria meningitidis* strain MC58: evidence for a novel mechanism of phase variation," Molecular Microbiology 50(1):245-257.
Masignani V. (Mar. 17. 2003). "Vaccination against Neisseria meningitidis using three variants of the lipoprotein GNA1870," J. Exp. Med. 197(6):789-799.
Mikayama et al. (1993). "Molecular cloning and functional expression of a cDNA encoding glycosylation-inhibiting factor," *Proc. Natl. Acad. Sci. USA* 90(21): 10056-10060.
Milagres et al. (1998). "Specificity of bactericidal antibody response to serogroup B meningococcal strains in Brazilian children after immunization with an outer membrane vaccine," Infection and Immun. 66(10): 4755-4781.
Morris et al. (1994). "Nucleotide Sequence Analysis and Potential Environmental Distribution of a Ferric Pseudobactin Receptor Gene of Pseudomonas sp. Strain M114," *Molecular and General Genetics* 242:9-16.
Moxon (1997). "Applications of molecular microbiology to vaccinology," Lancet 350(9086):1240-1244.
Munkley, et al. (1991). "Blocking of bactericidal killing of Neisseria meningitidis by antibodies directed against slacc 4 outer membrane proteins," Microbial Pathogenesis 11: 447-452.
Murphy et al., (2009) "Sequence diversity of the factor H binding protein vaccine candidate in epidemiologically relevant strains of serogroup B Neisseria meningitidis" J Infect Dis 200:379-389.
Nassif (2000). "A Furtive Pathogen Revealed," Science 287:1767-1768.

(56) References Cited

OTHER PUBLICATIONS

Nassif et al. (1997). "Type-4 pili and meningococcal adhesiveness," Gene 192:149-153.
Notice of Opposition against European Patent EP 1645631, granted on Oct. 24, 2007. Opposition filed on Jul. 23, 2008. 20 pages.
Novartis (Jan. 22, 2013) "Novartis receives EU approval for Bexsero®, first vaccine to prevent the leading cause of life-threatening meningitis across Europe," Media Release, 3 pages.
Novartis (Oct. 9, 2008) "New Phase II data show Novartis investigational Meningitis B vaccine may also protect infants six months and older," Media Release, 4 pages.
Opposition to European Patent No. 1194560 B1, granted on Jul. 4, 2007 in the name of Novartis Vaccines and Diagnostics S.r.l.. Opposition filed by GlaxoSmithKline Biologicals S.A. on Apr. 4, 2008.
Pajon et al. (2010). "Frequency of factor H-binding protein modular groups and susceptibility to cross-reactive bactericidal activity in invasive meningococcal isolates" Vaccine 28:2122-2129.
Parkhill, "Campylobacter jejuni genome sequence at the Sanger Centre," Post on BIOSCI/Bionet of May 8, 1998.
Paruchuri et al. (Jan. 1990). "Identification and Characterization of a Neisseria gonorrhoea Gene Encoding a Glycolipid-binding Adhesion," *Proceedings of the National Academy of Sciences USA* 87:333-337.
Patentees' Response to Opposition against European Patent EP 1645631, granted on Oct. 24, 2007. 13 pages.
Pettersson, et al. (2006). "Vaccine potential of the Neisseria meningitidis lactoferrin-binding proteins LbpA and LbpB," Vaccine 24(17):3545-3557.
Pizza et al. (2008) "Factor H-binding protein, a unique meningococcal vaccine antigen" Vaccine 26S:I46-8.
Pohlner et al. (1987). "Gene structure and extracellular secretion of Neisseria gonorrhoeae IgA protease," Nature 325(6103):458-462.
Poulsen et al. (1989). "Cloning and Sequencing of the Immunoglobulin A1 Protease Gene (iga) of Haemophilus influenzae Serotype b," Infection and Immunity 57:3097-3105.
Progress through the Sanger Institute FTP server (May 12, 2009), 15 pages.
Prosite, "ScanProsite Results Viewer: USERSEQ1 (280aa)," retrieved on Jun. 21, 2012, 1 page.
PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT prediction result for SEQ ID No. 2 (Mar. 30, 2010), 1 page.
Pugsley (1993). "The complete general secretory pathway in gram-negative bacteria," Microbiological Rev 5(1):50-108.
Quakyi et al. (1992). "Development of a Malaria T-cell Vaccine for Blood Stage Immunity," *Scandinavian Journal of Immunology* Suppl. 11:9-16.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Response to Communication, filed in EP Application No. 07075161. 5. Oct. 28, 2009.
Rinaudo et al. (2009). "Vaccinology in the genome era", The Journal of Clinical Investigation, 119(9):2515-2525.
Roberts et al. (1996). "Prediction of HIV Peptide Epitopes by a Novel Algorithm," *AIDS Research and Human Retroviruses* 12:593-610.
Robinson et al. (1997). "DNA Vaccines," *Seminars in Immunology* 9:271-283.
Rosenfeld et al. (1991). "Adenovirus-mediated Transfer of a Recombinant α-Antitrypsin Gene to the Lung Epithelium In vivo," Science 252:431-434.
Rudel et al. (1995). "Neisseria PilC protein identified as type-4 pilus tip-located adhesin," Nature 373:357-359.
Sanger Centre's "Projects" website as of Dec. 10, 1997 as retrievable via http://web.archive.org.

Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.
Schryvers et al. (1999). "Iron Acquisition Systems in the Pathogenic Neisseria," *Molecular Microbiology* 32(6)1117-1123.
Seib et al. (2010). "Influence of serogroup B meningococcal vaccine antigens on growth and survival of the mengococcus in vitro and in ex vivo and in vivo models of infection," Vaccine 28(12):2416-2427.
Sepulvada et al. (1975). "Primary Structure of Porcine Pepsin," *Journal of Biological Chemistry*, 250(13):5082-5088.
Sequence for "Putative Lipoprotein [*Neisseria meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Serruto et al. (2010). "Neisseria meningitidis GNA2132, a heparin-binding protein that induces protective immunity in humans," PNAS 107(8):3770-3775.
Shevchik et al. (1996). "Characterization of pectin methylesterase B, an outer membrane lipoprotein of Erwinia chrysanthemi 3937," Mole Microbiol 19(3):455-466.
St. Geme III et al. (1994). "A *Haemophilus influenzae* IgA Protease-like Protein Promotes Intimate Interaction with Human Epithelial Cells," *Molecular Microbiology* 14(2):217-233.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Sutcliffe et al. (1983). "Antibodies That React with Predetermined Sites on Proteins," Science 219(4585):660-666.
Szoka et al. (1978). "Procedure for Preparation of Liposomes with Large Internal Aqueous Space and High Capture by Reverse-phase Evaporation," *Proceedings of the National Academy of Sciences USA* 75:4194-4198.
Telford et al. (2003). "Genomic and Proteomics in Vaccine Design", in *New Bacterial Vaccines*. edited by Ellis et al. Kleweur Academic/Plenum Publishers, USA. pp. 1-11.
Tettelin et al. (2000). "Hypothetical protein (Neisseria meningitidis serogroup B)," Database GENSEQ (Online), Accession No. Q9K0Y5.
Tettelin et al. (2000). "TonB-dependent receptor (Neisseria meningitidis serogroup B)," Database GENSEQ (Online), Accession No. Q9JXU3.
The printed output from the NCBI open reading frame finder (Oct. 20, 2008), 12 pages.
TIGR website as of 1998, 8 pages.
Tinsley, C. R. et al. (Oct. 1996). "Analysis of the Genetic Differences Between Neisseria meningitidis and Neisseria gonorrhoeae: Two Closely Related Bacteria Expressing Two Different Pathogenicities," *Proceedings of the National Academy of Sciences of USA* 93:11109-11114.
Tramont, (1976) "Specificity of inhibition of epithelial cell adhesion of Neisseria gonorrhoeae." Infection and Immunity 14:593-595.
Turner et al. (2006). "Characterization of MspA, an Immunogenic Autotransporter Protein That Mediates Adhesion of Epithelial and Endothelial Cells in *Neisseria meningitidis*," Infection and Immunity 74(5):2957-2964.

(56) References Cited

OTHER PUBLICATIONS

UniProtKB/TrEMBL Accession No. Q9X7H1, last updated Feb. 10, 2009, located at <http://www.uniprot.org/uniprot/Q9X7H1.txt> visited on May 12, 2009. (2 pages).
United States Office Action mailed on Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "Neisseria Spp, Polypeptide, Gene Sequence and Uses Thereof," filed Sep. 1, 1998.
von Heijne (1989). "The structure of signal peptides from bacterial lipoproteins," Protein Engineering 2(7):531-534.
Wedege, E. et al. (Feb. 1986). "Human Antibody Response to a Group B Serotype 2a Meningococcal Vaccine Determined Immunoblotting," *Infection and Immunity* 51(2):571-578.
Welsch et al. (2003). "Antibody to genome-derived neisserial antigen 2132, a Neisseria meningitidis candidate vaccine, confers protection against bacteremia in the absence of complement-mediated bactericidal activity" Journal of Infectious Diseases 188 (11):1730-1740.
Welsch et al. (2004). "Protective Activity of Monclonal Antibodies to Genome-Derived Neisserial Antigen 1870, a Neisseria meningitidis Candidate Vaccine," *The Journal of Immunology* 172: 5606-5615.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
Wu et al. (1996). "A protein class database organized with ProSite protein groups and PIR superfamilies," J Comp Biol 3(4):547-561.
Yumoto et al. (1996). "Cloning, sequencing and expression of an Eikenella corrodens gene encoding a component protein of the lectin-like adhesin complex," Gene 183(1-2): 115-121.
Zhu et al. (2005) "Evaluation of recombinant lipidated P2086 protein as a vaccine candidate for group B Neisseria meningitidis in a murine nasal challenge model," Infect Immun 73(10):6838-45.
Adams (1996). "Should Non-Peer-Reviewed Raw DNA Sequence Data Release Be Forced on the Scientific Community?," Science, 274: 534-536.
Aderson et al. (2010). "Effectiveness of a bivalent factor H binding protein vaccine across Neisseria meningitidis serogroups," 17th International Pathogenic Neisseria Conference 2010, p. 196.
Ala'Aldeen et al. (2010) "Human antibody response to the meningococcal factor H binding protein (LP2086) during invasive disease, colonization and carriage," Vaccine 28:7667-75.
Alignment of SEQ ID No: 19 of EP2327719 against SEQ ID Nos: 92, 94, 96, 98, 100, 102, 104, 106, and 108 of WO/2003/063766, filed in opposition against EP2327719, submitted May 20, 2015, 9 pages.
Alignment of SEQ ID No: 42 of EP2258716 against SEQ ID No: 41 of EP2258716, filed in opposition against EP2258716, submitted Apr. 16, 2015, 1 page.
Alignment of SEQ ID No: 42 of EP2258716 against SEQ ID Nos: 50, 52, 54, 56, 58, 60, 62, 64, 66, 68, 70, and 72 of WO/2003/063766, filed in opposition against EP2258716, submitted Apr. 16, 2015, 12 pages.
Ambrose et al. (2006). "Characterization of LP2086 expression in Neisseria meningitidis," 15th International Pathogenic Neisseria Conference 2006, p. 103.
Amended Defence and Counterclaim, Jul. 24, 2015, Claim No. HP-2015-000022, *Glaxosmithkline UK Ltd v. Wyeth Holdings LLC*, 4 pages.

Anderson et al. (2008). "Functional cross-reactive antibodies are elicited by a group B Neisseria meningitidis bivalent recombinant lipidated LP2086 vaccine in cynomolgusmacaques," 16th International Pathogenic Neisseria Conference (IPNC) P100, pp. 170-171.
Anderson et al. (2009). "Development of a factor H binding protein vaccine for broad protection against invasive Neisseria meningitidis serogroup B (MnB) disease," 10th European Meningococcal Disease Society Congress 2009, p. 39.
Anderson et al. (2009). "Epidemiology of the serogroup B Neisseria meningitidis (MnB) factor H binding protein and implications for vaccine development," European Society for Paediatric Infectious Disease Symposium 2009, p. 505.
Anderson et al. (2012). "Potential impact of the bivalent rLP2086 vaccine on Neisseria meningitidis invasive disease and carriage isolates in two adolescent populations," European Society for Paediatric Infectious Disease Symposium 2012, p. 807.
Anderson et al. (2013) "Potential impact of the bivalent rLP2086 vaccine on Neisseria meningitidis carriage and invasive serogroup B disease," Hum Vacc Immunotherap 9:471-9.
Annex 1 to the Amended Defence and Counterclaim, Jun. 24, 2015, Claim No. HP-2015-000022, *Glaxosmithkline UK Ltd v. Wyeth Holdings LLC*, 40 pages.
Beernink et al. (2011). "A meningococcal factor H binding protein mutant that eliminates factor H binding enhances protective antibody responses to vaccination," J Immunol, 186(6):3606-14.
BenMohamed et al. (2002). "Lipopeptide vaccines-yesterday, today, and tomorrow," Lancet 2(7):425-431.
Bentley et al. (2004). Identification of two immunologically distinct domains on the LP2086 outer membrane lipoprotein of Neisseria meningitidis, 14th International Pathogenic Neisseria Conference 2004, p. 144.
Biswas et al. (1995). "Characterization of IbpA, the structural gene for a lactoferrin receptor in Neisseria gonorrhoeae," Infection and Immunity, 63(8): 2958-2967.
Blattner et al. (1997). "The complete genome sequence of Escherichia coli K-12," Science 277 (5331): 1453-1474.
Brendish and Read. (2015). "Neisseria meningitidis serogroup B bivalent factor H binding protein vaccine," Expert Rev. Vaccines, 14(4):493-503.
CECMED (Dec. 2, 2011), "Resumen de las Caracteristicas del Producto: VA-MENGOC-BC," Ministerio de Salud Publica de Cuba, 4 pages. (3 page English translation included).
Claimants Amended Grounds of Invalidity under CPR 17.1 (2)(a) on Jul. 16, 2015, in respect of European Patent (UK) No. 2,343,308. In the High Court of Justice Chancery Division Patents Court, between GlaxoSmithKline UK Limited and Wyeth Holdings LLC. 9 pages.
Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1> 3 pages.
Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1> 4 pages.
Cohn et al. (2010). "Potential Impact of Serogroup B Vaccines: Prevalence of candidate vaccine antigens among invasive Neisseria meningitidis isolates in the United States," 17th International Pathogenic Neisseria Conference 2010, p. 77.
Cole et al. (1998). "Deciphering the biology of Mycobacterium tuberculosis from the complete genome sequence," Nature 394:651-653.
Database UniProt (Oct. 1, 2000), "SubName: Full=Uncharacterized protein" retrieved from EBI, accession no. Q9JXV4 Database accession no. Q9JXV4. 2 pages.
de Moraes JC, et al. (1992). Protective efficacy of a serogroup B meningococcal vaccine in Sao Paulo, Brazil. Lancet 340: 1074-1078.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).

(56) References Cited

OTHER PUBLICATIONS

Decision revoking the European Patent, filed in opposition against EP1976990, dated Nov. 11, 2013, 15 pages.
Decision to refuse a patent application, filed in the Opposition against EP1645631, dated Apr. 28, 2009, 7 pages.
Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Dlawer et al. (2010). "Human antibody responses to the meningococcal factor H binding protein LP2086 during invasive disease," 17th International Pathogenic Neisseria Conference 2010, p. 130.
Donnelly et al. (2010). "Qualitative and quantitative assessment of meningococcal antigens to evaluate the potential strain coverage of protein-based vaccines," Proc Natl Acad Sci U S A, 107(45):19490-5.
Elzanowski et al. (2013). "The Genetic Codes, a compilation," Retrieved from http://www.bioinformatics.org/JaMBW/2/3/TranslationTables.html. 16 pages.
Experimental data: expression of NspA, fHBP and GNA2132 in N. meningitidis, filed in opposition against EP1534326, dated Aug. 4, 2010. 2 pages.
Experimental Report, Submitted on Mar. 23, 2015, filed in relation to EP2411048, 2 pages.
Galeano et al. (1995). "Efectividad de una vacuna antimeningocócica en una cohorte de itagui, Colombia, 1995," Epidemiologico de Antioquia 20(2), 8 pages. (9 page English translation included).
Gene Browser, Nature Technology Corporation, filed in the Opposition against EP1645631, dated Jun. 26, 2013, 6 pages.
Gil et al. (2009). "Proteomic study via a non-gel based approach of meningococcal outer membrane vesicle vaccine obtained from strain CU385," Human Vaccines 5(5):347-356.
Gorringe et al. (2009). "16th International Pathogenic Neisseria Conference: recent progress towards effective meningococcal disease vaccines," Human Vaccines 5(2):53-56.
Harris et al. (2008). "Development and qualification of serum bactericidal assays for Neisseria meningitidis serogroup B," 16th International Pathogenic Neisseria Conference 2008, pp. 268-269.
Harris et al. (2010). "Robustness of the Serum Bactericidal Activity (SBA) Assay for Neisseria meningitidis serogroup B," 17th International Pathogenic Neisseria Conference 2010, p. 169.
Harris et al. (2011) "Preclinical evidence for the potential of a bivalent fHBP vaccine to prevent Neisseria meningitidis serogroup C disease," Human Vaccines 7:1 (suppl) 1-7.
Hem et al. (1995). "Structure and properties of aluminum-containing adjuvants," Vaccine Design. Subunit and Adjuvant Approach, pp. 249-276.
Hodge et al. (2006). "Development of a luminex-based meningococcal rLP2086-specific human IgG assay," 15th International Pathogenic Neisseria Conference 2006, p. 113.
Hoiseth et al. (2008). "LP2086 and MLST distribution in epidemiologically relevant strains of serogroup B Neisseria meningitidis," 16th International Pathogenic Neisseria Conference 2008, p. 205.
Hoist et al. (2014). "Variability of genes encoding surface proteins used as vaccine antigens in meningococcal endemic and epidemic strain panels from Norway," Vaccine 32:2722-2731.
Interlocutory decision in opposition proceedings, filed in the Opposition against EP1645631, dated May 21, 2012, 82 pages.
Jansen et al. (2008). "Bivalent recombinant LP2086 vaccine to provide broad protection against Neisseria meningitidis B disease: immunological correlates of protection and how to assess coverage against invasive MnB strains," 16th International Pathogenic Neisseria Conference 2008, pp. 80-81.
Jansen et al. (2009). "Development of a bivalent factor H binding protein vaccine to broadly protect against invasive Neisseria meningitides serogroup B (MnB) disease," European Society for Paediatric Infectious Disease Symposium 2009, p. 311.
Jansen et al. (2010). "Estimating effectiveness for Neisseria meningitidis serogroup B (MnB) vaccine candidates composed of non-serogroup specific antigens," 17th International Pathogenic Neisseria Conference 2010, p. 37.
Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.
Jiang et al. (2003). "Using rate of acid neutralization to characterize aluminum phosphate adjuvant," Pharma Dev Tech 8(4):349-356.
Jiang et al. (2006). "Serum IgG response induced by a bivalent recombinant LP2086 provides broad protection against serogroup B Neisseria meningitidis," 15th International Pathogenic Neisseria Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic Neisseria Conference 2008, pp. 57-58.
Jones et al. (2009). "Generation of human serum complement lots that perform consistently for use in Neisseria meningitidis serogroup B (MnB) vaccine clinical trials," European Society for Paediatric Infectious Disease Symposium 2009, p. 566.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Kovacs-Simon et al. (2011). "Lipoproteins of Bacterial Pathogens," Infect Immun 79(2):548-561.
Lewis et al. (2010). "The meningococcal vaccine candidate neisserial surface protein A (NspA) binds to factor H and enhances meningococcal resistance to complement," PLoS Pathogens 6(7):e1001027. 20 pages.
Liechti et al. (2012). "Outer membrane biogenesis in Escherichia coli, Neisseria meningitidis, and Helicobacter pylori: paradigm deviations in H. pylori," Front Cell and Infect Microbiol 2:article 29. 18 pages.
Lindblad, (2004). "Aluminium compounds for use in vaccines," Immunol Cell Biol.,82(5):497-505.
Litt et al. (2004). "Putative vaccine antigens from Neisseria meningitidis recognized by serum antibodies of young children convalescing after meningococcal disease," J Infect Dis 190(8):1488-97.
Madico et al. (2006). "The meningococcal vaccine candidate GNA1870 binds the complement regulatory protein factor H and enhances serum resistance," J Immunol 177(1):501-510.
Magagnoli et al. (2009). "Structural organization of NadADelta(351-405), a recombinant MenB vaccine component, by its physicochemical characterization at drug substance level," Vaccine, 27(15):2156-70.
Marshall et al. (2008). "A randomized, placebo-controlled, double-blind, phase 1 trial of ascending doses of meningococcal group B rLP2086 vaccine in healthy adults," 16th International Pathogenic Neisseria Conference 2008, pp. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Martin et al. (1998). "New Zealand epidemic of meningococcal disease identified by a strain with phenotype B:4:P1.4," JID 177:497-500.
Mascioni et al. (2008). "Determination of the domain and solution structure of rLP2086, a meningococcal vaccine candidate and human factor H binding protein," 16th International Pathogenic Neisseria Conference 2008, pp. 77-78.
Mascioni et al. (2009) "Structural basis for the immunogenic properties of the meningococcal vaccine candidate LP2086," J Biol Chem 284:8738-46.

(56) References Cited

OTHER PUBLICATIONS

Mascioni et al. (2010) "NMR dynamics and antibody recognition of the meningococcal lipidated outer membrane protein LP2086 in micellar solution," Biochim Biophys Acta 1798:87-93.
McNeil et al. (2009) "Detection of LP2086 on the cell surface of Neisseria meningitidis and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic Neisseria Conference 2010, p. 94.
McNeil et al. (2013) "Role of factor H binding protein in Neisseria meningitidis virulence and its potential as a vaccine candidate to broadly protect against meningococcal disease," Microbiol Mol Biol Rev 77:234.
Meyer et al. (1984). "Pilus genes of Neisseria gonorrheae: Chromosomal organization and DNA sequence," Proc. Natl. Acad. Sci. USA 81: 6110-6114.
Minutes of the oral proceedings, filed in the Opposition against EP1645631, dated Feb. 11, 2014, 4 pages.
Murphy et al. (2008). "Sequence diversity of vaccine candidate LP2086 in Neisseria meningitidis serogroup B strains causing invasive disease," 16th International Pathogenic Neisseria Conference 2008, p. 61.
Murphy et al. (2010). "Prevalence of Factor H Binding Protein (fHBP) Variants in N. meningitidis Carriage Isolates," 17th International Pathogenic Neisseria Conference 2010, p. 96.
Notice of Opposition against EP 1562983, filed on Jul. 1, 2014, 23 pages.
Notice of Opposition filed May 24, 2012, filed in opposition against EP1976990, 19 pages.
Notice of opposition, filed in opposition against EP2258716, dated Apr. 16, 2015, 12 pages.
Notice of opposition, filed in opposition against EP2327719, dated May 20, 2015, 14 pages.
Novartis (Jun. 9, 2011). "Novartis candidate vaccine Bexsero® shows significant potential in providing broad coverage against meningococcal serogroup B infections." Media Release, 6 pages.
Novartis internal data, filed in relation to EP1902726, submitted on Apr. 13, 2015, 1 page.
Ochoa, Rolando (2008). "Main projects on research, development and manufacturing of human vaccines," excerpt from presentation at BioQatar Symposium 2008, 4 slides.
Opponent's Further Submission in Preparation of the Oral Proceedings, filed in the Opposition against EP1645631, dated Nov. 3, 2011, 6 pages.
Opponent's Response to the Patentee's Submission dated Feb. 18, 2013, filed in the Opposition against EP1645631, dated Jul. 24 2014, 34 pages.
Opponents Final Written Submission in Preparation of Oral Proceedings, filed in the Opposition against EP1645631, dated Sep. 14, 2011, 28 pages.
ORF Finder (2013). "Bacterial Code," Retrieved from http://www.ncbi.nlm.nih.gov/gorf/gorf.html, 3 pages.
Pajon et al. (2012). "Design of meningococcal factor H binding protein mutant vaccines that do not bind human complement factor H," Infect Immun 80:2667-2677.
Patentee's response to notice of opposition, filed in opposition against EP1562983, dated Feb. 16, 2015, 9 pages.
Patentee's Submissions under Rule 116 EPC, filed in the Opposition against EP1645631, dated Sep. 13, 2011, 13 pages.
Perez et al. (2010). "Community acquired bacterial meningitis in Cuba: a follow up of a decade," BMC Infectious Diseases 10:130, 9 pages.
Pillai et al. (2005) "Outer membrane protein (OMP) based vaccine for Neisseria meningitidis serogroup B," Vaccine 23(17-18):2206-2209.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Richmond et al. (2008). "A randomized, observer-blinded, active control, phase 1 trial of meningococcal serogroup B rLP2086 vaccine in healthy children and adolescents aged 8 to 14 years," 16th International Pathogenic Neisseria Conference 2008, p. 270-271.
Richmond et al. (2010). "Safety & immunogenicity of serogroup B Neisseria meningitidis (MnB) rLP2086 vaccine in adults and adolescent subjects: overview of 3 clinical trials," 17th International Pathogenic Neisseria Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent Neisseria meningitidis recombinant lipidated factor H binding protein vaccine in young adults: Results of a randomized, controlled, dose-escalation phase 1 trial," Vaccine 30(43):6163-74.
Richmond et al. (2012) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Rodriguez et al. (1999). "The epidemiological impact of antimeningococcal B vaccination in Cuba," Mem Inst Oswaldo Cruz 94(4):433-440.
Sandbu et al. (2007). "Immunogenicity and safety of a combination of two serogroup B meningococcal outer membrane vesicle vaccines," Clin Vaccine Immunol, 14(9):1062-9.
Seeber et al. (1991). "Predicting the adsorption of proteins by aluminum-containing adjuvants," Vaccine 9(3):201-203.
Seib et al. (2011). "Characterization of Diverse Subvariants of the Meningococcal Factor H (fH) Binding Protein for their Ability to Bind fH, to Mediate Serum Resistance, and to Induce Bactericidal Antibodies," Infect Immun, 79(2):970-81.
Sheldon et al. (2011). "Phase 1, Randomized, Open-Label, Study to Assess the Safety and Immunogenicity of Serogroup B Neisseria Meningitidis (Mnb) rLP2086 Vaccine in Healthy Adults," 14th Annual Conference on Vaccine Research, 2011, pp. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Sierra GV, et al. (1991). Vaccine against group B Neisseria meningitidis: protection trial and mass vaccination results in Cuba. NIPH Ann 14: 195-207.
Sprengart et al. (1997). "Functional importance of RNA interactions in selection of translation initiation codons," Molecular Microbiology, 24(1): 19-28.
Statement of Grounds of Appeal, dated Mar. 23, 2015, filed in relation to EP2411048, 8 pages.
Statement of grounds of appeal, filed in relation to EP1902726, dated Apr. 13, 2015, 9 pages.
Submission in opposition proceedings by Carpmaels and Ransford filed in EP1737486 on Jun. 12, 2015, 2 pages.
Submission in opposition proceedings by Pfizer Inc. filed against EP1737486 on Jun. 12, 2015, 7 pages.
Submission of the Patentee of Jul. 6, 2012, filed Jun. 24, 2014, in the Opposition against EP1645631, 4 pages.
Summons to oral proceedings pursuant to Rule 115(1) EPC, filed in the Opposition against EP1645631, dated Nov. 11, 2013, 12 pages.
Supplementary Submission to the Grounds of Appeal, filed in the Opposition against EP1645631, dated Sep. 28, 2012, 2 pages.
Swaminathan (1996). "Molecular cloning of the three base restriction endonuclease R.CviJI from eukaryotic Chlorella virus IL-3A," Nucleic Acids Research, 24(13): 2463-2469.
Tan et al. (2010). "Advances in the development of vaccines against Neisseria meningitidis," NEJM 362(16):1511-1520.
Tavano et al. (2011). "Mapping of the Neisseria meningitidis NadA cell-binding site: Relevance of predicted α-helices in the NH2-terminal and dimeric coiled-coil regions," J Bacteriol 193(1):107-115.
TIGR Microbial Database, filed in the Opposition against EP1645631, dated Jun. 20, 2012, 14 pages.

(56) References Cited

OTHER PUBLICATIONS

UniProt accession No. C0JF81, Murphy et al., Last modified on May 5, 2009. 4 pages.
U.S. Appl. No. 60/328,101, "Novel immunogenic compositions for the prevention and treatment of meningococcal disease," filed Oct. 11, 2001. 253 pages.
U.S. Appl. No. 60/406,934, "Novel immunogenic compositions for the prevention and treatment of meningococcal disease," filed Aug. 30, 2002. 190 pages.
U.S. Appl. No. 60/647,911, "GNA 1870-based vesicle vaccines for broad spectrum protection against diseases caused by Neisseria meningitidis," filed Jan. 27, 2005. 99 pages.
Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.
Voulhoux and Tommassen (2002). "Transport of lipoproteins to the cell surface in Neisseria meningitidis," 13th International Pathogenic Neisseria Conference 2002, p. 31.
Wang et al. (2010). "Prevalence and genetic diversity of candidate vaccine antigens among invasive Neisseria meningitidis isolates in the United States," 17th International Pathogenic Neisseria Conference 2010, p. 122.
Welsch et al. (2002). "Genome-derived antigen (GNA) 2132 elicits protective serum antibodies to groups B and C Neisseria meningitidis strains," 13th International Pathogenic Neisseria Conference 2002, p. 25.
Written Submission to Oral Proceedings, filed in opposition against EP1976990, dated Jul. 24, 2013, 11 pages.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B Neisseria meningitidis in a murine nasal challenge model," 14th International Pathogenic Neisseria Conference 2004, p. 199.
Zhu et al. (2006) "Intranasal immunization of mice with recombinant lipidated P2086 protein reduces nasal colonization of group B Neisseria meningitidis," Vaccine 24:5420-5.
Zhu et al. (2006). "Effective immunization strategy against group B Neisseria meningitidis using purified recombinant lipidated P2086 protein," 15th International Pathogenic Neisseria Conference 2006, p. 47.
Zlotnick et al. (2009). "Epidemiology of the serogroup B Neisseria meningitidis (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of N. meningitidis," 17th International Pathogenic Neisseria Conference 2010, p. 38.
Zollinger et al. (2010). "Design and evaluation in mice of a broadly protective meningococcal group B native outer membrane vesicle vaccine," Vaccine, 28(31):5057-5067.

\* cited by examiner

FIGURE 1 — ΔG287—919
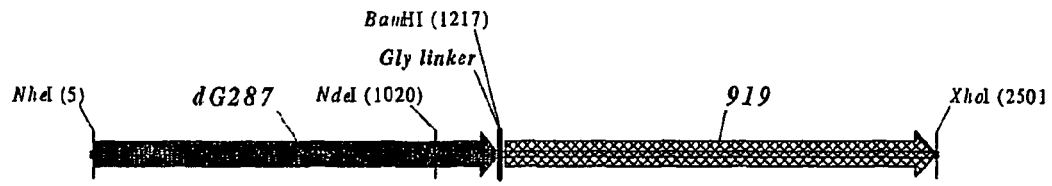
FIGURE 2 — ΔG287—953
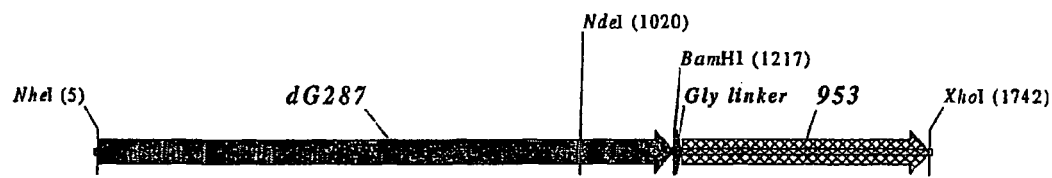
FIGURE 3 — ΔG287—961
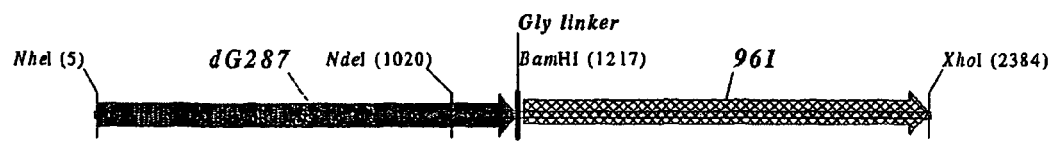
FIGURE 4 — ΔG287NZ—919
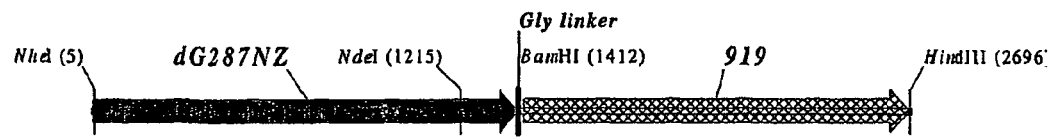
FIGURE 5 — ΔG287NZ—953
FIGURE 6 — ΔG287NZ—961

FIGURE 7 — ΔG983-ORF46.1
FIGURE 8 — ΔG983-741
FIGURE 9 — ΔG983-961
FIGURE 10 — ΔG983-961c
FIGURE 11 — ΔG741-961
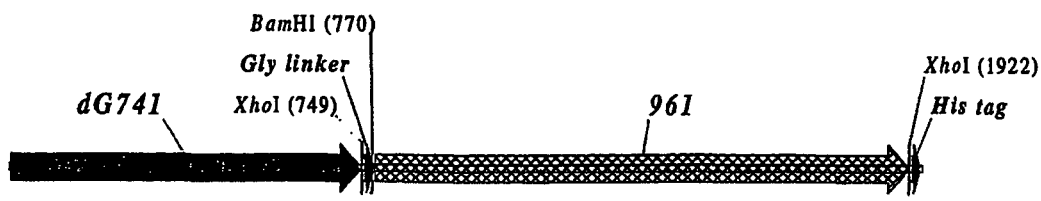

FIGURE 12 — ΔG741-961c
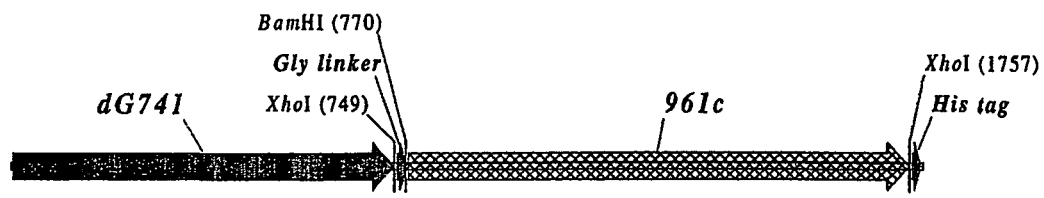
FIGURE 13 — ΔG741-983
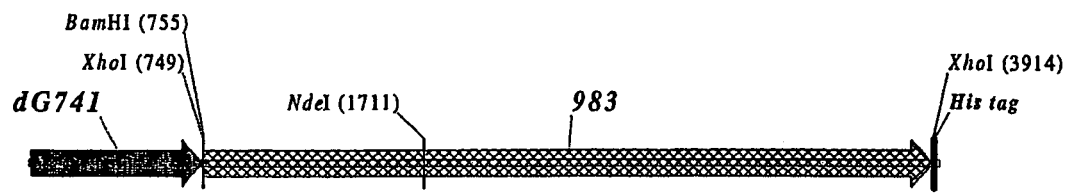
FIGURE 14 — ΔG741-ORF46.1
FIGURE 15 — ORF46.1-741
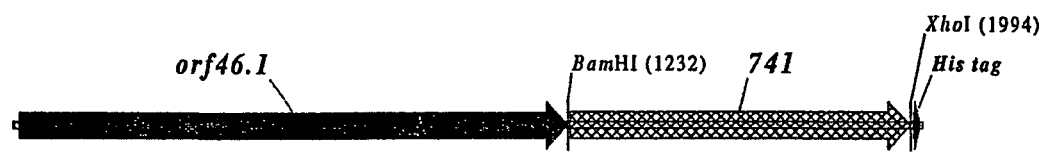
FIGURE 16 — ORF46.1-961
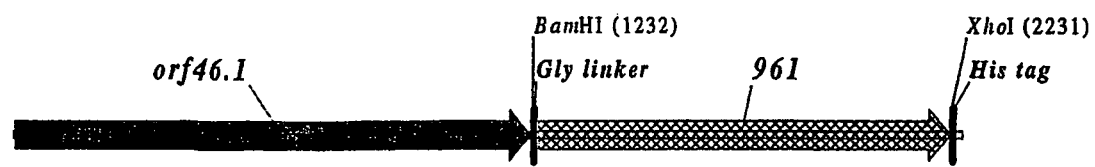

FIGURE 17 — ORF46.1—961c
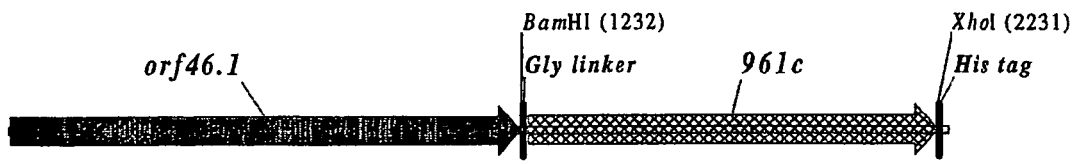
FIGURE 18 — 961-ORF46.1
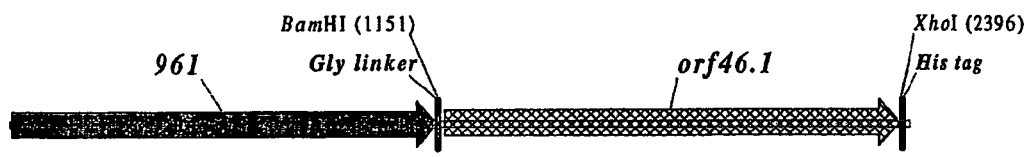
FIGURE 19 — 961-741
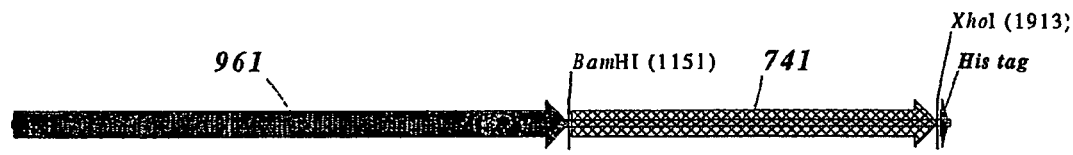
FIGURE 20 — 961-983
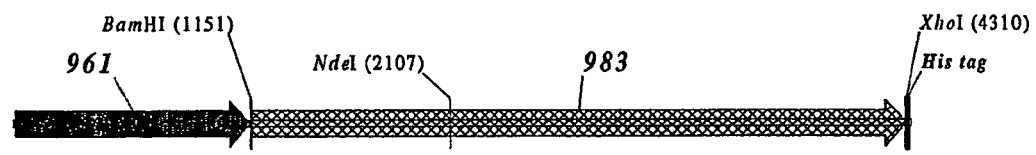
FIGURE 21 — 961c-ORF46.1
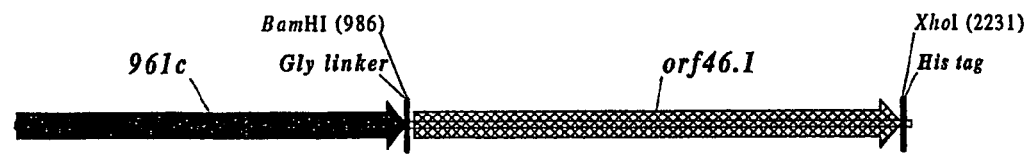
FIGURE 22 — 961c-741
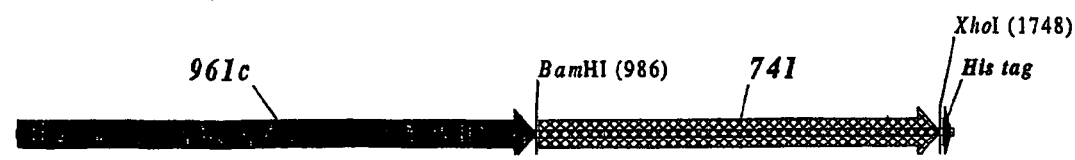

FIGURE 23 — 961c-983
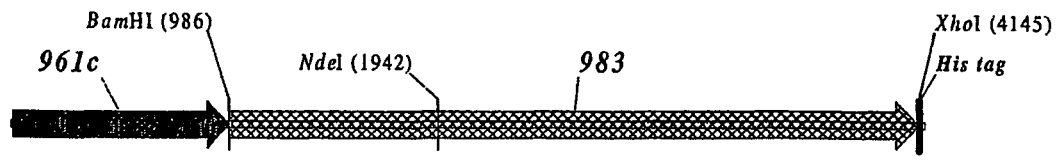
FIGURE 24 — 961cL-ORF46.1
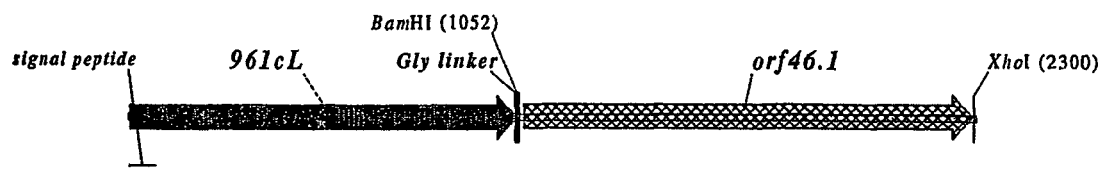
FIGURE 25 — 961cL-741
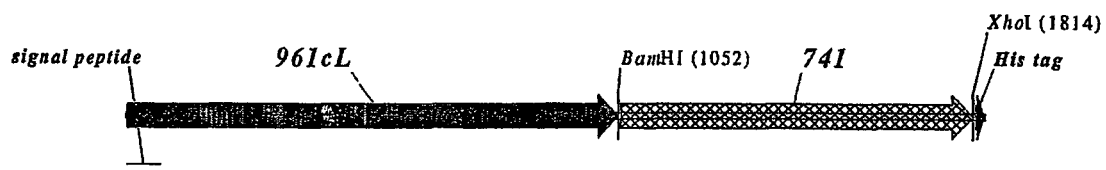
FIGURE 26 — 961cL-983
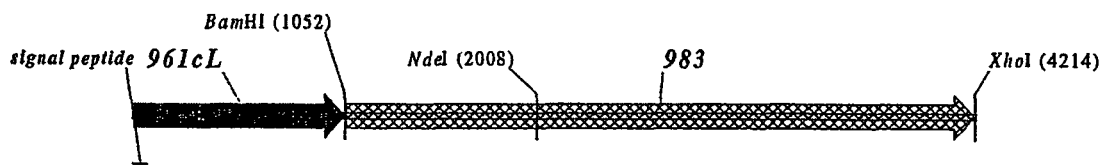

HYBRID EXPRESSION OF NEISSERIAL PROTEINS

This application is a Continuation application of prior application Ser. No. 10/220,480, filed Aug. 28, 2002, which was the National Stage of International Application No. PCT/IB01/00420, filed Feb. 28, 2001, which claims the benefit of GB 0004695.3, filed Feb. 28, 2000 and GB 0027675.8, filed Nov. 13, 2000, from which applications priority is claimed pursuant to the provision of 35 U.S.C. §§119/120 and which applications are incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 23002099501SUBSEQLIST.txt, date recorded: Mar. 29, 2010, size: 5,840 KB).

All documents cited herein are incorporated by reference in their entirety.

TECHNICAL FIELD

This invention is in the field of protein expression. In particular, it relates to the heterologous expression of proteins from *Neisseria* (e.g. *N. gonorrhoeae* or, preferably, *N. meningitidis*).

BACKGROUND ART

International patent applications WO99/24578, WO99/36544, WO99/57280 and WO00/22430 disclose proteins from *Neisseria meningitidis* and *Neisseria gonorrhoeae*. These proteins are typically described as being expressed in *E. coli* (i.e. heterologous expression) as either N-terminal GST-fusions or C-terminal His-tag fusions, although other expression systems, including expression in native *Neisseria*, are also disclosed.

It is an object of the present invention to provide alternative and improved approaches for the heterologous expression of these proteins. These approaches will typically affect the level of expression, the ease of purification, the cellular localisation of expression, and/or the immunological properties of the expressed protein.

DISCLOSURE OF THE INVENTION

In accordance with the invention, two or more (e.g. 3, 4, 5, 6 or more) proteins of the invention are expressed as a single hybrid protein. It is preferred that no non-Neisserial fusion partner (e.g. GST or poly-His) is used.

This offers two advantages. Firstly, a protein that may be unstable or poorly expressed on its own can be assisted by adding a suitable hybrid partner that overcomes the problem. Secondly, commercial manufacture is simplified—only one expression and purification need be employed in order to produce two separately-useful proteins.

Thus the invention provides a method for the simultaneous heterologous expression of two or more proteins of the invention, in which said two or more proteins of the invention are fused (i.e. they are translated as a single polypeptide chain).

The method will typically involve the steps of: obtaining a first nucleic acid encoding a first protein of the invention; obtaining a second nucleic acid encoding a second protein of the invention; ligating the first and second nucleic acids. The resulting nucleic acid may be inserted into an expression vector, or may already be part of an expression vector.

Where just two proteins are joined, the hybrid protein can be represented simply by the formula $NH_2$-A-B—COOH. A and B can each be selected from any Neisserial proteins, and in particular those represented by SEQ#s 122-4447. The method is well suited to the expression of proteins orf1, orf4, orf25, orf40, Orf46/46.1, orf83, 233, 287, 292L, 564, 687, 741, 907, 919, 953, 961 and 983.

The 42 hybrids indicated by 'X' in the following table of form $NH_2$-A-B—COOH are preferred:

| A | B | | | | | | |
|---|---|---|---|---|---|---|---|
| | ORF46.1 | 287 | 741 | 919 | 953 | 961 | 983 |
| ORF46.1 | | X | X | X | X | X | X |
| 287 | X | | X | X | X | X | X |
| 741 | X | X | | X | X | X | X |
| 919 | X | X | X | | X | X | X |
| 953 | X | X | X | X | | X | X |
| 961 | X | X | X | X | X | | X |
| 983 | X | X | X | X | X | X | |

Preferred proteins to be expressed as hybrids are thus ORF46.1, 287, 741, 919, 953, 961 and 983. These may be used in their essentially full-length form, or poly-glycine deletions (ΔG) forms may be used (e.g. ΔG-287, ΔGTbp2, ΔG741, ΔG983 etc.), or truncated forms may be used (e.g. Δ1-287, Δ2-287 etc.), or domain-deleted versions may be used (e.g. 287B, 287C, 287BC, $ORF46_{1-433}$, $ORF46_{433-608}$, ORF46, 961c etc.) and so on.

Particularly preferred are: (a) a hybrid protein comprising 919 and 287; (b) a hybrid protein comprising 953 and 287; (c) a hybrid protein comprising 287 and ORF46.1; (d) a hybrid protein comprising ORF1 and ORF46.1; (e) a hybrid protein comprising 919 and ORF46.1; (f) a hybrid protein comprising ORF46.1 and 919; (g) a hybrid protein comprising ORF46.1, 287 and 919; (h) a hybrid protein comprising 919 and 519; and (i) a hybrid protein comprising ORF97 and 225.

Further embodiments are shown in the drawings and include ΔG287-919, ΔG287-953, ΔG287-961, ΔG983-ORF46.1, ΔG983-741, ΔG983-961, ΔG983-961C, ΔG741-961, ΔG741-961C, ΔG741-983, ΔG741-ORF46.1, ORF46.1-741, ORF46.1-961, ORF46.1-961C, 961-ORF46.1, 961-741, 961-983, 961C-ORF46.1, 961C-741, 961C-983, 961CL-ORF46.1, 961CL-741, and 961CL-983.

Where 287 is used, it is preferably at the C-terminal end of a hybrid; if it is to be used at the N-terminus, if is preferred to use a ΔG form of 287 is used (e.g. as the N-terminus of a hybrid with ORF46.1, 919, 953 or 961).

Where 287 is used, this is preferably from strain 2996 or from strain 394/98.

Where 961 is used, this is preferably at the N-terminus. Domain forms of 961 may be used.

Alignments of polymorphic forms of ORF46, 287, 919 and 953 are disclosed in WO00/66741. Any of these polymorphs can be used according to the present invention.

Preferably, the constituent proteins (A and B) in a hybrid protein according to the invention will be from the same strain.

The fused proteins in the hybrid may be joined directly, or may be joined via a linker peptide e.g. via a poly-glycine linker (i.e. $G_n$ where n=3, 4, 5, 6, 7, 8, 9, 10 or more) or via a short peptide sequence which facilitates cloning. It is evidently preferred not to join a ΔG protein to the C-terminus of a poly-glycine linker.

The fused proteins may lack native leader peptides or may include the leader peptide sequence of the N-terminal fusion partner.

Host

It is preferred to utilise a heterologous host. The heterologous host may be prokaryotic or eukaryotic. It is preferably *E. coli*, but other suitable hosts include *Bacillus subtilis*, *Vibrio cholerae*, *Salmonella typhi*, *Salmonenna typhimurium*, *Neisseria meningitidis*, *Neisseria gonorrhoeae*, *Neisseria lactamica*, *Neisseria cinerea*, *Mycobateria* (e.g. *M. tuberculosis*), yeast etc.

Vectors, Hosts etc.

As well as the methods described above, the invention provides (a) nucleic acid and vectors useful in these methods (b) host cells containing said vectors (c) proteins expressed or expressable by the methods (d) compositions comprising these proteins, which may be suitable as vaccines, for instance, or as diagnostic reagents, or as immunogenic compositions (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against Neisserial bacteria, and/or (3) a reagent which can raise antibodies against Neisserial bacteria and (g) a method of treating a patient, comprising administering to the patient a therapeutically effective amount of these compositions.

Sequences

The invention also provides a protein or a nucleic acid having any of the sequences set out in the following examples. It also provides proteins and nucleic acid having sequence identity to these. As described above, the degree of 'sequence identity' is preferably greater than 50% (eg. 60%, 70%, 80%, 90%, 95%, 99% or more).

Nomenclature Herein

The 2166 protein sequences disclosed in WO99/24578, WO99/36544 and WO99/57280 are referred to herein by the following SEQ# numbers:

| Application | Protein sequences | SEQ# herein |
|---|---|---|
| WO99/24578 | Even SEQ IDs 2-892 | SEQ#s 122-567 |
| WO99/36544 | Even SEQ IDs 2-90 | SEQ#s 568-612 |
| WO99/57280 | Even SEQ IDs 2-3020 | SEQ#s 613-2122 |
|  | Even SEQ IDs 3040-3114 | SEQ#s 2123-2160 |
|  | SEQ IDs 3115-3241 | SEQ#s 2161-2287 |

In addition to this SEQ# numbering, the naming conventions used in WO99/24578, WO99/36544 and WO99/57280 are also used (e.g. 'ORF4', 'ORF40', 'ORF40-1' etc. as used in WO99/24578 and WO99/36544; 'm919', 'g919' and 'a919' etc. as used in WO99/57280).

The 2160 proteins NMB0001 to NMB2160 from Tettelin et al. [*Science* (2000) 287:1809-1815] are referred to herein as SEQ#s 2288-4447 [see also WO00/66791].

The term 'protein of the invention' as used herein refers to a protein comprising:

(a) one of sequences SEQ#s 122-4447; or
(b) a sequence having sequence identity to one of SEQ#s 122-4447; or
(c) a fragment of one of SEQ#s 122-4447.

The degree of 'sequence identity' referred to in (b) is preferably greater than 50% (eg. 60%, 70%, 80%, 90%, 95%, 99% or more). This includes mutants and allelic variants [e.g. see WO00/66741]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The 'fragment' referred to in (c) should comprise at least n consecutive amino acids from one of SEQ#s 122-4447 and, depending on the particular sequence, n is 7 or more (eg. 8, 10, 12, 14, 16, 18, 20, 25, 30, 35, 40, 50, 60, 70, 80, 90, 100 or more). Preferably the fragment comprises an epitope from one of SEQ#s 122-4447. Preferred fragments are those disclosed in WO00/71574 and WO01/04316.

Preferred proteins of the invention are found in *N. meningitidis* serogroup B.

Preferred proteins for use according to the invention are those of serogroup B *N. meningitidis* strain 2996 or strain 394/98 (a New Zealand strain). Unless otherwise stated, proteins mentioned herein are from *N. meningitidis* strain 2996. It will be appreciated, however, that the invention is not in general limited by strain. References to a particular protein (e.g. '287', '919' etc.) may be taken to include that protein from any strain.

It will be appreciated that references to "nucleic acid" includes DNA and RNA, and also their analogues, such as those containing modified backbones, and also peptide nucleic acids (PNA) etc.

BRIEF DESCRIPTION OF DRAWINGS

FIGS. 1 to 26 show hybrid proteins according to the invention.

FIG. 1: Gene construct used to express the ΔG287-919 hybrid protein

FIG. 2: Gene construct used to express the ΔG287-953 hybrid protein

FIG. 3: Gene construct used to express the ΔG287-961 hybrid protein

FIG. 4: Gene construct used to express the ΔG287NZ-919 hybrid protein

FIG. 5: Gene construct used to express the ΔG287NZ-953 hybrid protein

FIG. 6: Gene construct used to express the ΔG287NZ-961 hybrid protein

FIG. 7: Gene construct used to express the ΔG983-ORF46.1 hybrid protein

FIG. 8: Gene construct used to express the ΔG983-741 hybrid protein

FIG. 9: Gene construct used to express the ΔG983-961 hybrid protein

FIG. 10: Gene construct used to express the ΔG983-961c hybrid protein

FIG. 11: Gene construct used to express the ΔG741-961 hybrid protein

FIG. 12: Gene construct used to express the ΔG741-961c hybrid protein

FIG. 13: Gene construct used to express the ΔG741-983 hybrid protein

FIG. 14: Gene construct used to express the ΔG741-ORF46.1 hybrid protein

FIG. 15: Gene construct used to express the ORF46.1-741 hybrid protein

FIG. 16: Gene construct used to express the ORF46.1-961 hybrid protein

FIG. 17: Gene construct used to express the ORF46.1-961c hybrid protein

FIG. 18: Gene construct used to express the 961-ORF46.1 hybrid protein

FIG. 19: Gene construct used to express the 961-741 hybrid protein

FIG. 20: Gene construct used to express the 961-983 hybrid protein

FIG. 21: Gene construct used to express the 961c-ORF46.1 hybrid protein

FIG. 22: Gene construct used to express the 961c-741 hybrid protein

FIG. 23: Gene construct used to express the 961c-983 hybrid protein

FIG. 24: Gene construct used to express the 961cL-ORF46.1 hybrid protein

FIG. 25: Gene construct used to express the 961cL-741 hybrid protein

FIG. 26: Gene construct used to express the 961cL-983 hybrid protein

MODES FOR CARRYING OUT THE INVENTION

Example 1

Hybrids of ORF46

The complete ORF46 protein from *N. meningitidis* (serogroup B, strain 2996) has the following sequence (SEQ ID NO: 1):

```
  1 LGISRKISLI LSILAVCLPM HAHASDLAND SFIRQVLDRQ HFEPDGKYHL
 51 FGSRGELAER SGHIGLGKIQ SHQLGNLKIQ QAAIKGNIGY IVRFSDHGHE
101 VHSPFDNHAS HSDSDEAGSP VDGFSLYRIH WDGYEHHPAD GYDGPQGGGY
151 PAPKGARDIY SYDIKGVAQN IRLNLTDNRS TGQRLADRFH NAGSMLTQGV
201 GDGFKRATRY SPELDRSGNA AEAFNGTADI VKNIIGAAGE IVGAGDAVQG
251 ISEGSNIAVM HGLGLLSTEN KMARINDLAD MAQLKDYAAA AIRDWAVQNP
301 NAAQGIEAVS NIFMAAIPIK GIGAVRGKYG LGGITAHPIK RSQMGAIALP
351 KGKSAVSDNF ADAAYAKYPS PYHSRNIRSN LBQRYGKENI TSSTVPPSNG
401 KNVKLADQRH PKTGVPFDGK GFPNFEKHVK YDTKLDIQEL SGGGIPKAKP
451 VSDAKPRWEV DRKLNKLTTR EQVEKNVQEI RNGNKNSNFS QHAQLEREIN
501 KLKSADEINF ADGMGKFTDS MNDKAFSRLV KSVKENGFTN PVVEYVEING
551 KAYIVRGNNR VFAARYLGRI HELKFKKVDF PVPNTSWKNP TDVLNESGNV
601 KRPRYRSK*
```

The leader peptide is underlined.

The sequences of ORF46 from other strains can be found in WO00/66741.

ORF46 has been fused at its C-terminus and N-terminus with 287, 919, and ORF1. The hybrid proteins were generally insoluble, but gave some good ELISA and bactericidal results (against the homologous 2996 strain):

| Protein | ELISA | Bactericidal Ab |
|---|---|---|
| Orf1-Orf46.1-His | 850 | 256 |
| 919-Orf46.1-His | 12900 | 512 |
| 919-287-Orf46-His | n.d. | n.d. |
| Orf46.1-287His | 150 | 8192 |
| Orf46.1-919His | 2800 | 2048 |
| Orf46.1-287-919His | 3200 | 16384 |

For comparison, 'triple' hybrids of ORF46.1, 287 (either as a GST fusion, or in ΔG287 form) and 919 were constructed and tested against various strains (including the homologous 2996 strain) versus a simple mixture of the three antigens. FCA was used as adjuvant:

| | 2996 | BZ232 | MC58 | NGH38 | F6124 | BZ133 |
|---|---|---|---|---|---|---|
| Mixture | 8192 | 256 | 512 | 1024 | >2048 | >2048 |
| ORF46.1-287-919his | 16384 | 256 | 4096 | 8192 | 8192 | 8192 |
| ΔG287-919-ORF46.1his | 8192 | 64 | 4096 | 8192 | 8192 | 16384 |
| ΔG287-ORF46.1-919his | 4096 | 128 | 256 | 8192 | 512 | 1024 |

Again, the hybrids show equivalent or superior immunological activity.

Hybrids of two proteins (strain 2996) were compared to the individual proteins against various heterologous strains:

| | 1000 | MC58 | F6124 (MenA) |
|---|---|---|---|
| ORF46.1-His | <4 | 4096 | <4 |
| ORF1-His | 8 | 256 | 128 |
| ORF1-ORF46.1-His | 1024 | 512 | 1024 |

Again, the hybrid shows equivalent or superior immunological activity.

Example 2

Hybrids of ΔG287

The deletion of the $(Gly)_6$ sequence in 287 was found to have a dramatic effect on protein expression. The protein lacking the N-terminal amino acids up to GGGGGG is called 'ΔG287'. In strain MC58, its basic sequence (leader peptide underlined) is (SEQ ID NO: 2):

```
  SPDVKS ADTLSKPAAP VVSEKETEAK EDAPQAGSQG QGAPSAQGSQ DMAAVSEENT
GNGGAVTADN PKNEDEVAQN DMPQNAAGTD SSTPNHTPDP NMLAGNMENQ ATDAGESSQP
ANQPDMANAA DGMQGDDPSA GGQNAGNTAA QGANQAGNNQ AAGSSDPIPA SNPAPANGGS
NFGRVDLANG VLIDGPSQNI TLTHCKGDSC SGNNFLDEEV QLKSEFEKLS DADKISNYKK
DGKNDKFVGL VADSVQMKGI NQYIIFYKPK PTSFARFRRS ARSRRSLPAE MPLIPVNQAD
TLIVDGEAVS LTGHSGNIFA PEGNYRYLTY GAEKLPGGSY ALRVQGEPAK GEMLAGAAVY
NGEVLHPHTE NGRPYPTRGR FAAKVDFGSK SVDGIIDSGD DLHMGTQKFK AAIDGNGFKG
TWTENGSGDV SGKFYGPAGE EVAGKYSYRP TDAEKGGFGV FAGKKEQD*
```

ΔG287, with or without His-tag ('ΔG287-His' and 'ΔG287K', respectively), are expressed at very good levels in comparison with the '287-His' or '287$^{untagged}$', On the basis of gene variability data, variants of ΔG287-His were expressed in *E. coli* from a number of MenB strains, in particular from strains 2996, MC58, 1000, and BZ232. The results were also good—each of these gave high ELISA titres and also serum bactericidal titres of >8192. ΔG287K, expressed from pET-24b, gave excellent titres in ELISA and the serum bactericidal assay.

Deletion of poly-Gly sequences is also applicable to Tbp2 (NMB0460), 741 (NMB 1870) and 983 (NMB1969). When cloned in pET vector and expressed in *E. coli* without the sequence coding for their leader peptides and without poly-Gly (i.e. as "ΔG forms"), the same effect was seen—expression was good in the clones carrying the deletion of the poly-glycine stretch, and poor or absent if the glycines were present in the expressed protein.

ΔG287 was fused directly in-frame upstream of 919, 953, 961 (sequences shown below) and ORF46.1:

ΔG287-919

(SEQ ID NO: 3)

ATGGCTAGCCCCGATGTTAAATCGGCG-
GACACGCTGTCAAAACCGGCCGCTCCTGTTGTTGC

TGAAAAAGAGACAGAGGTAAAAGAAGAT-
GCGCCACAGGCAGGTTCTCAAGGACAGGGCGCGC

CATCCACACAAGGCAGCCAAGATATG-
GCGGCAGTTTCGGCAGAAAATACAGGCAATGGCGGT

GCGGCAACAACGGACAAACCCAAAAAT-
GAAGACGAGGGACCGCAAAATGATATGCCGCAAAA

TTCCGCCGAATCCGCAAATCAAACAGG-
GAACAACCAACCCGCCGATTCTTCAGATTCCGCCC

CCGCGTCAAACCCTGCACCTGCGAATG-
GCGGTAGCAATTTTGGAAGGGTTGATTTGGCTAAT

GGCGTTTTGATTGATGGGCCGTCG-
CAAAATATAACGTTGACCCACTGTAAAGGCGATTCTTG

TAATGGTGATAATTTATTGGATGAA-
GAAGCACCGTCAAAATCAGAATTTGAAAATTTAAATG

AGTCTGAACGAATTGAGAAATATAA-
GAAAGATGGGAAAAGCGATAAATTTACTAATTTGGTT

GCGACAGCAGTTCAAGCTAATGGAAC-
TAACAAATATGTCATCATTTATAAAGACAAGTCCGC

TTCATCTTCATCTGCGCGATTCAGGCGT-
TCTGCACGGTCGAGGAGGTCGCTTCCTGCCGAGA

TGCCGCTAATCCCCGTCAATCAGGCG-
GATACGCTGATTGTCGATGGGGAAGCGGTCAGCCTG

ACGGGGCATTCCGGCAATATCTTCGCGC-
CCGAAGGGAATTACCGGTATCTGACTTACGGGGC

GGAAAAATTGCCCGGCGGATCGTATGC-
CCTCCGTGTGCAAGGCGAACCGGCAAAAGGCGAAA

TGCTTGCTGGCACGGCCGTGTACAACG-
GCGAAGTGCTGCATTTTCATACGGAAAACGGCCGT

CCGTACCCGACTAGAGGCAGGTTTGCCG-
CAAAAGTCGATTTCGGCAGCAAATCTGTGGACGG

CATTATCGACAGCGGCGATGATTTG-
CATATGGGTACGCAAAAATTCAAAGCCGCCATCGATG

-continued

```
GAAACGGCTTTAAGGGGACTTGGACG-
GAAAATGGCGGCGGGGATGTTTCCGGAAGGTTTTAC

GGCCCGGCCGGCGCGGAAGTGGCGG-
GAAAATACAGCTATCGCCCGACAGATGCGGAAAAGGG

CGGATTCGGCGTGTTTGCCGGCAAAAAA-
GAGCAGGATGGATCCGGAGGAGGAGGATGCCAAA

GCAAGAGCATCCAAACCTTTCCGCAAC-
CCGACACATCCGTCATCAACGGCCCGGACCGGCCG

GCCGGTCGGCATCCCCGACCCCGCCG-
GAACGACGGTCGGCGGCGGCGGGGCCGTCTATACCG

TTGTACCGCACCTGTCCCTGC-
CCCACTGGGCGGCGCAGGATTTCGCCAAAAGCCTGCAATCC

TTCCGCCTCGGCTGCGC-
CAATTTGAAAAACCGCCAAGGCTGGCAGGATGTGTGCGCCCAAGC

CTTTCAAACCCCCGTCCATTCCTTTCAG-
GCAAAACAGTTTTTTGAACGCTATTTCACGCCGT

GGCAGGTTGCAGGCAACGGAAGCCTTGC-
CGGTACGGTTACCGGCTATTACGAGCCGGTGCTG

AAGGGCGACGACAGGCGGACGGCA-
CAAGCCVGTTCCCGATTTACGGTATTCCCGACGATTTT

ATCTCCGTCCCCCTGCCTGCCG-
GTTTGCGGAGCGGAAAAGCCCTTGTCCGCATCAGGCAGAC

GGGAAAAAACAGCGGCACAATCGA-
CAATACCGGCGGCACACATACCGCCGACCTCTCCCGAT

TCCCCATCACCGCGCGCACAACGGCAAT-
CAAAGGCAGGTTTGAAGGAAGCCGCTTCCTCCCC

TACCACACGCGCAACCAAATCAACGGCG-
GCGCGCTTGACGGCAAAGCCCCGATACTCGGTTA

CGCCGAAGACCCCGTCGAACTTTTTTT-
TATGCACATCCAAGGCTCGGGCCGTCTGAAACCCC

GTCCGGCAAATACATCGGCTATGCCGA-
CAAAAACGAACATCCCTACGTTTCCATCGGACGCT

ATATGGCGGACAAAGGCTACCT-
CAAGCTCGGGCAGACCTCGATGCAGGGCATCAAAGCCTAT

ATGCGGCAAAATCCGCAACGCCTCGC-
CGAAGTTTTGGGTCAAAACCCCAGCTATATCTTTTT

CCGCGAGCTTGCCGGAAGCAGCAAT-
GACGGTCCCGTCGGCGCACTGGGCACGCCGTTGATGG

GGGAATATGCCGGCGCAGTCGACCG-
GCACTACATTACCTTGGGCGCGCCCTTATTTGTCGCC

ACCGCCCATCCGGTTACCCGCAAAGC-
CCTCAACCGCCTGATTATGGCGCAGGATACCGGCAG

CGCGATTAAAGGCGCGGTGCGCGTGGAT-
TATTTTTGGGGATACGGCGACGAAGCCGGCGAAC

TTGCCGGCAAACAGAAAACCACGGGT-
TACGTCTGGCAGCTCCTACCCAACGGTATGAAGCCC

GAATACCGCCCGTAACTCGAG
```

(SEQ ID NO: 4)
```
  1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KPTNLVATAV QANGTNKYVI

201 IYKDKSASSS SASFRRSARS RRSLPAEMPL IPVNQADTLI VDGEAVSLTG

251 HSGNIFAPEG NYRYLTYGAE KLPGGSYALR VQGEPAKGEM LAGTAVYNGE
```

```
301 VLHFHTENGR PYPTRGRFAA KVDFGSKSVD GIIDSGDDLH MGTQKFKAAI

351 DGNGFKGTWT ENGGGDVSGR FYGPAGEEVA GRYSYRPTDA EKGGFGVFAG

401 KKEQDGSGGG GCQSKSIQTF PQPDTSVING PDRPVGIPDP AGTTVGGGGA

451 VYTVVPHLSL PHWAAQDFAK SLQSFRLGCA NLKNRQGWQD VCAQAFQTPV

501 HSFQAKQFFE RYFTPWQVAG NGSLAGTVTG YYEPVLKGDD RRTAQARFPI

551 YGIPDDFISV PLPAGLRSGK ALVRIRQTGK NSGTIDNTGG THTADLSRFP

601 ITARTTAIKG RFEGSRFLPY HTRNQINGGA LDGKAPILGY AEDPVELFFM

651 HIQGSGRLKT PSGKYIRIGY ADKNEHPYVS IGRYMADKGY LKLGQTSMQG

701 IKAYMRQNPQ RLAEVLGQNP SYIFFRELAG SSNDGPVGAL GTPLMGEYAG

751 AVDRHYITLG APLFVATAHP VTRKALNRLI MAQDTGSAIK GAVRVDYFWG

801 YGDEAGELAG KQKTTGYVWQ LLPNGMKPEY RP*
```

ΔG287-953

(SEQ ID NO: 5)

```
ATGGCTAGCCCCGATGTTAAATCGGCG-
GACACGCTGTCAAAACCGGCCGCTCCTGTTGTTGC

TGAAAAAGAGACAGAGGTAAAAGAAGAT-
GCGCCACAGGCAGGACAGGGCGCGCCATCCACAC

AAGGCAGCCAAGATATGGCG-
GCAGTTTCGGCAGAAAATACAGGCAATGGCGGTGCGGCAACA

ACGGACAAACCCAAAAATGAAGACGAGG-
GACCGCAAAATGATATGCCGCAAAATTCCGCCGA

ATCCGCAAATCAAACAGGGAACAAC-
CAACCCGCCGATTCTTCAGATTCCGCCCCCGCGTCAA

ACCTGCACCTGCGAATGGCGGTAG-
CAATTTTGGAAGGGTTGATTTGGCTAATGGCGTTTTGA

TTGATGGGCCGTCGCAAAATATAACGT-
TGACCCACTGTAAAGGCGATTCTTGTAATGGTGAT

AATTTATTGGATGAAGAAGCACCGT-
CAAAATCAGAATTTGAAAATTTAAATGAGTCTGAACG

AATTGAGAAATATAAGAAAGATGG-
GAAAAGCGATAAATTTACTAATTTGGTTGCGACAGCAG

TTCAAGCTAATGGAACTAACAAATATGT-
CATCATTTATAAAGACAAGTCCGCTTCATCTTCA

TCTGCGCGATTCAGGCGTTCTGCACG-
GTCGAGGAGGTCGCTTCCTGCCGAGATGCCGCTAAT

CCCCGTCAATCAGGCGGATACGCTGAT-
TGTCGATGGGGAAGCGGTCAGCCTGACGGGGCATT

CCGGCAATATCTTCGCGCCCGAAGG-
GAATTACCGGTATCTGACTTACGGGGCGGAAAAATTG

CCCGGCGGATCGTATGCCCTCCGTGTG-
CAAGGCGAACCGGCAAAAGGCGAAATGCTTGCTGG

CACGGCCGTGTACAACGGCGAAGTGCTG-
CATTTTCATACGGAAAACGGCCGTCCGTACCCGA

CTAGAGGCAGGTTTGCCGCAAAAGTC-
GATTTCGGCAGCAAATCTGTGGACGGCATTATCGACA

GCGGCGATGATTTGCATATGGGTACG-
CAAAAATTCAAAGCCGCCATCGATGGAAACGGTTTA

AGGGGACTTGGACGGAAAATGGCG-
GCGGGGATGTTCCGGAAGGTTTTACGCCCGGCCGGCG

AGGAAGTGGCGGGAAAATACAGC-
TATCGCCCGACAGATGCGGAAAAGGGCGGATTGGCGTGT

TTGCCGGCAAAAAAGAGCAGGATGGATC-
CGGAGGAGGAGGAGCCACCTACAAAGTGGACGAA
```

TATCACGCCAACGCCCGTTTCGCCATC-
GACCATTTCAACACCAGCACCAACGTCGGCGGTTT

TTACGGTCTGACCGGTTCCGTCGAGTTC-
GACCAAGCAAAACGCGACGGTAAAATCGACATCA

CCATCCCCGTTGCCAACCTGCAAAGCG-
GTTCGCAACACTTTACCGACCACCTGAAATCAGCC

GACATCTTCGATGCCGCCCAATATCCG-
GACATCCGCTTTGTTTCCACCAAATTCAACTTCAA

CGGCAAAAAACTGGTTTCCGTTGACG-
GCAACCTGACCATGCACGGCAAAACCGCCCCCGTCA

AACTCAAAGCCGAAAAATTCAACTGC-
TACCAAAGCCCGATGGCGAAAACCGAAGTTTGCGGC

GGCGACTTCAGCACCACCATCGACCG-
CACCAAATGGGGCGTGGACTACCTCGTTAACGTTGG

TATGACCAAAAGCGTCCGCATGACATCCAAATCGAGGCAGCCAAACAATAACTCGAG

```
                                                 (SEQ ID NO: 6)
  1MASPDVKSAD TLSKPAAPVV AEKETEVKED APQAGSQGQG APSTQGSQDM

51AAVSAENTGN GGAATTDKPK NEDEGPQNDM PQNSAESANQ TGNNQPADSS

101DSAPASNPAP ANGGSNFGRV DLANGVLIDG PSQNITLTHC KGDSCNGDNL

151LDEEAPSKSE FENLNESERI EKYKKDGKSD KFTNLVATAV QANGTNKYVI

201IYKDKSASSS SARFRRSARS RRSLPAEMPL IPVNQADTLI VDGEAVSLTG

251HSGNIFAPEG NYRYLTYGAE KLPGGSYALR VQGEPAKGEM LAGTAVYNGE

301VLHFHTENGR PYPTRGRFAA KVDFGSKSVD GIIDSGDDLH MGTQKFKAAI

351DGNGFKGTWT ENGGGDVSGR FYGPAGEEVA GKYSYRPTDA EKGGFGVFAG

401KKEQDGSGGG GATYKVDEYH ANARFAIDHF NTSTNVGGFY GLTGSVEFDQ

451AKRDGKIDIT IPVANLQSGS QHFTDHLKSA DIFDAAQYPD IRFVSTKFNF

501NGKKLVSVDG NLTMHGKTAP VKLKAEKFNC YQSPMAKTEV CGGDFSTTID

551RTKWGVDYLV NVGMTKSVRI DIQIEAAKQ*
```

ΔG287-961
                                                 (SEQ ID NO: 7)
ATGGCTAGCCCCGATGTTAAATCGGCG-
GACACGCTGTCAAAACCGGCCGCTCCTGTTGTTGC

TGAAAAAGAGACAGAGGTAAAAGAAGAT-
GCGCCACAGGCAGGTTCTCAAGGACAGGGCGCGC

CATCCACACAAGGCAGCCAAGATGGCG-
GCAGTTTCGGCAGAAAATACAGGCAATGGCGGTGC

GGCAACAACGGACAAACCCAAAAATGAA-
GACGAGGGACCGCAAAATGATATGCCGCAAAATT

CCGAATCCGCAAATCAAACAGGGAA-
CAACCAACCCGCCGATTCTTCAGATTCCGCCCCCGCG

TCAAACCCTGCACCTGCGAATGGCGG-
TAGCAATTTTGGAAGGGTTGATTTGGCTAATGGCGT

TTTGATTGATGGGCCGTCG-
CAAAATATAACGTTGACCCACTGTAAAGGCGATTCTTGTAATG

GTGATAATTTATTGGATGAAGAAGCAC-
CGTCAAAATCAGAATTTGAAAATTTAAATGAGTCT

GAACGAATTGAGAAATATAAGAAA-
GATGGGAAAAGCGATAAATTTACTAATTTGGTTGCGAC

AGCAGTTCAAGCTAATGGAACTAA-
CAAATATGTCATCATTTATAAAGACAAGTCCGCTTCAT

CTTCATCTGCGCGATTCAGGCGTTCTG-
CACGGTCGAGGAGGTCGCTTCCTGCCGAGATGCCG

-continued

```
CTAATCCCCGTCAATCAGGCG-
GATACGCTGATTGTCGATGGGGAAGCGGTCAGCCTGACGGG

GCATTCCGGCAATATCTTCGCGC-
CCGAAGGGAATTACCGGTATCTGACTTACGGGGCGGAAA

AATTGCCCGGCGGATCGTATGCCCTC-
CGTGTGCAAGGCGAACCGGCAAAAGGCGAAATGCTT

GCTGGCACGGCCGTGTACAACGGC-
GAAGTGCTGCATTTCATACGGAAAACGGCCGTCCGTAC

CCGACTAGAGGCAGGTTTGCCG-
CAAAAGTCGATTTCGGCAGCAAATCTGTGGACGGCATTAT

CGACAGCGGCGATGATTTGCATATGGG-
TACGCAAAAATTCAAAGCCGCCATCGATGGAAACG

GCTTTAAGGGGACTTGGACGGAAAATG-
GCGGCGGGGATGTTTCCGGAAGGTTTTACGGCCCG

GCCGGCGAGGAAGTGGCGGGAAAATA-
CAGCTATCGCCCGACAGATGCGGAAAAGGGCGGATT

CGGCGTGTTTGCCGGCAAAAAGAGCAG-
GATGGATCCGGAGGAGGAGGAGCCACAAACGACG

ACGATGTTAAAAAAGCTGCCACTGTGGC-
CATTGCTGCTGCCTACAACAATGGCCAAGAAATC

AACGGTTTCAAAGCTGGAGAGACCATC-
TACGACATTGATGAAGACGGCACAATTACCAAAAA

AGACGCAACTGCAGCCGATGTTGAAGC-
CGACGACTTTAAAGGTCTGGGTCTGAAAAAGTCG

TGACTAACCTGACCAAAACCGTCAAT-
GAAAACAAACAAAACGTCGATGCCAAAGTAAAAGCT

GCAGAATCTGAAATAGAAAGTTAACAAC-
CAAGTTAGCAGACACTGATGCCGCTTTAGCAGAT

ACTGATCCGCTCTGGATGCAACCAC-
CAACGCCTTGAATAAATTGGGAGAAAATATAACGACA

TTTGCTGAAGAGACTAAGACAAATATCG-
TAAAAATTGATGAAAAATTAGAAGCCGTGGCTGA

TACCGTCGACAAGCATGCCGAAGCAT-
TCAACGATATCGCCGATTCATTGGATGAAACCAACA

CTAAGGCAGACGAAGCCGTCAAACGC-
CAATGAAGCCAAACAGACGGCCGAAGAACCAACAAA

ACGTCGATGCCAAAGTAAAAGCTGCA-
GAAACTGCAGCAGGCAAAGCCGAAGCTGCCGCTGGC

ACAGCTAATACTGCAGCCGACAAGGC-
CGAAGCTGTCGCTGCAAAAGTTACCGACATCAAAGC

TGATATCGCTACGAACAAAGATAATAT-
TGCTAAAAAAGCAAACAGTGCCGACGTGTACACCA

GAGAAGAGTCTGACAGCAAATTTGTCA-
GAATTGATGGTCTGAACGCTACTACCGAAAAATTG

GACACAGCTTGGCTTCTGCTGAAAAATC-
CATTGCCGATCACGATACTCGCCTGAACGGTTTG

GATAAAACAGTGTCAGACCTGCGCAAA-
GAAACCCGCCAAGGCCTTGCAGAACAAGCCGCGCT

CTCCGGTCTGTTCCAACCTTA-
CAACGTGGGTCGGTTCAATGTAACGGCTGCAGTCGGCGGCT

ACAAATCCGAATCGGCAGTCGCCATCGG-
TACCGGCTTCCGCTTTACCGAAACTTTGCCGCCA

AAGCAGGCGTGGCAGTCGGCACTTCGTC-
CGGTTCTTCCGCAGCCTACCATGTCGGCGTCAAT

TACGAGTGGTAACTCGAG
```

```
                                                       (SEQ ID NO: 8)
  1 MASPDVKSAD TLSKPAAPVV AEKETEVKED APQAGSQGQG APSTQGSQDM

51 AAVSAENTGN GGAATTDKPK NEDEGPQNDM PQNSAESANQ TGNNQPADSS

101 DSAPASNPAP ANGGSNFGRV DLANGVLIDG PSQNITLTHC KGDSCNGDNL

151 LDEEAPSKSE FENLNESERI EKYKKDGKSD KFTNLVATAV QANGTNKYVI

201 IYKDKSASSS SARFRRSARS RRSLPAEMPL IPVNQADTLI VDGEAVSLTG

251 HSGNIFAPEG NYRYLTYGAE KLPGGSYALR VQGEPAKGEM LAGTAVYNGE

301 VLHFHTENGR PYPTRGRFAA KVDFGSKSVD GIIDSGDDLH MGTQKFKAAI

351 DGNGFKGTWT ENGGGDVSGR FYGPAGEEVA GKYSYRPTDA EKGGFGVFAG

401 KKEQDGSGGG GATNDDDVKK AATVAIAAAY NNGQEINGFK AGETIYDIDE

451 DGTITKKDAT AADVEADDFK GLGLKKVVTN LTKTVNENKQ NVDAKVKAAE

501 SEIEKLTTKL ADTDAALADT DAALDATTNA LNKLGENITT FAEETKTNIV

551 KIDEKLEAVA DTVDKHAEAF NDIADSLDET NTKADEAVKT ANEAKQTAEE

601 TKQNVDAKVK AAETAAGKAE AAAGTANTAA DKAEAVAAKV TDIKADIATN

651 KDNIAKKANS ADVYTREESD SKFVRIDGLN ATTEKLDTRL ASAEKSIADH

701 DTRLNGLDKT VSDLRKETRQ GLAEQAALSG LFQPYNVGRF NVTAAVGGYK

751 SESAVAIGTG FRFTENFAAK AGVAVGTSSG SSAAYHVGVN YEW*
```

|                | ELISA  | Bactericidal |
|----------------|--------|--------------|
| ΔG287-953-His  | 3834   | 65536        |
| ΔG287-961-His  | 108627 | 65536        |

The bactericidal efficacy (homologous strain) of antibodies raised against the hybrid proteins was compared with antibodies raised against simple mixtures of the component antigens (using 287-GST) for 919 and ORF46.1:

|         | Mixture with 287 | Hybrid with ΔG287 |
|---------|------------------|-------------------|
| 919     | 32000            | 128000            |
| ORF46.1 | 128              | 16000             |

Data for bactericidal activity against heterologous MenB strains and against serotypes A and C were also obtained:

|              | 919     |        | ORF46.1 |        |
|--------------|---------|--------|---------|--------|
| Strain       | Mixture | Hybrid | Mixture | Hybrid |
| NGH38        | 1024    | 32000  | —       | 16384  |
| MC58         | 512     | 8192   | —       | 512    |
| BZ232        | 512     | 512    | —       | —      |
| MenA (F6124) | 512     | 32000  | —       | 8192   |
| MenC (C11)   | >2048   | >2048  | —       | —      |
| MenC (BZ133) | >4096   | 64000  | —       | 8192   |

The hybrid proteins with ΔG287 at the N-terminus are therefore immunologically superior to simple mixtures, with ΔG287-ORF46.1 being particularly effective, even against heterologous strains. ΔG287-ORF46.1K may be expressed in pET-24b.

The same hybrid proteins were made using New Zealand strain 394/98 rather than 2996:

```
ΔG287NZ-919
                                                       (SEQ ID NO: 9)
ATGGCTAGCCCCGATGTCAAGTCGGCGGACACGCTGTCAAAACCTGCCGC

CCCTGTTGTTTCTGAAAAAGACAGAGGCAAAGGAAGATGCGCCACAGGCA

GGTTCTCAAGGACAGGGCGCGCCATCCGCACAAGGCGGTCAAGATATGGC

GGCGGTTTCGGAAGAAAATACAGGCAATGGCGGTGCGGCAGCAACGGACA

AACCCAAAAATGAAGACGAGGGGCGCAAAATGATATGCCGCAAAATGCC

GCCGATACAGATAGTTTGACACCGAATCACACCCCGGCTTCGAATATGCC

GGCCGGAAATATGGAAAACCAAGCACCGGATGCCGGGAATCGGAGCAGCC

GGCAAACCAACCGGATATGGCAAATACGGCGGACGGAATGCAGGGTGACG

ATCCGTCGGCAGGCGGGGAAAATGCCGGCAATACGGCTGCCCAAGGTACA

AATCAAGCCGAAAACAATCAAACCGCCGGTTCTCAAAATCCTGCCTCTTC
```

-continued

```
AACCAATCCTAGCGCCACGAATAGCGGTGGTGATTTTGGAAGGACGAACG
TGGGCAATTCTGTTGTGATTGACGGGCCGTCGCAAAATATAACGTTGACC
CACTGTAAAGGCGATTCTTGTAGTGGCAATAATTTCTTGGATGAAGAAGT
ACAGCTAAAATCAGAATTTGAAAAATTAAGTGATGCAGACAAAATAAGTA
ATTACAAGAAAGATGGGAAGAATGACGGGAAGAATGATAAATTTGTCGGT
TTGGTTGCCGATAGTGTGCAGATGAAGGGAATCAATCAATATATTATCTT
TTATAAACCTAAACCCACTTCATTTGCGCGATTTAGGCGTTCTGCACGGT
CGAGGCGGTCGCTTCCGGCCGAGATGCCGCTGATTCCCGTCAATCAGGCG
GATACGCTGATTGTCGATGGGAAGCGGTCAGCCTGACGGGCATTCCGGCA
ATATCTTCGCGCCCGAAGGGAATTACCGGTATCTGACTTACGGGGCGGAA
AAATTGCCCGGCGGATCGTATGCCCTCCGTGTTCAAGGCGAACCTTCAAA
AGGCGAAATGCTCGCGGGCACGGCAGTGTACAACGGCGAAGTGCTGCATT
TTCATACGGAAAACGGCCGTCCGTCCCCGTCCAGAGGCAGGTTTGCCGCA
AAAGTCGATTTCGGCAGCAAATCTGTGGACGGCATTATCGACAGCGGCGA
TGGTTTGCATATGGGTACGCAAAAATTCAAAGCCGCCATCGATGAAACG
GCTTTAAGGGGACTTGGACGGAAAATGGCGGCGGGGATGTTTCCGGAAAG
TTTACGGCCCGGCCGGCGAGGAAGTGGCGGGAAAATACAGCTATCGCCCA
ACAGATGCGGAAAAGGGCGGATTCGGCGTGTTTGCCGGCAAAAAAGAGCA
GGATGGATCCGGAGGAGGAGGATGCCAAAGCAAGAGCATCCAAACCTTTC
CGCAACCCGACACATCCGTCATCAACGGCCCGGACCGGCCGGTCGGCATC
CCCGCCGGAACGACGGTCGGCGGCGGCGGGGCCGTCATATACCGTTGTAC
CGCACCTGTCCCTGCCCCACTGGGCGGCGCAGGATTTCGCCAAAAGCCTG
CAATCCTTCCGCCTCGGCTGCGCCAATTTGAAAAACCGCCAAGGCTGGCT
GGCAGGATGTGTGCGCCCAAGCCTTTCAAACCCCCGTCCATTCCCTTTCA
GGCAAAACAGTTTTTTGAACGCTATTTCACGCCGTGGCAGGTTGCAGGCA
ACGGAAGCCTTGCCGGTACGGTTACCGGCTATTACGAGCCGGTGCTGAAG
GGCGACGACAGGCGGACGGCACAAGCCCGCTTCCCGATTTACGTATTCCC
GACGATTTTATCTCCGTCCCCCTGCCTGCCGGTTTGCGGAGCGGAAAAGC
CCTTGTCCGCATCAGGCAGACGGGAAAAAACAGCGGCACAATCGACAATA
CCGGCGGCACACATACCGCCGACCTCTCCCGATTCCCCATCACCGCGCGC
ACAACGGCAATCAAAGGCAGGTTTGAAGGAAGCCGCTTCCTCCCCTACCA
CACGCGCAACCAAATCAACGGCGGCGCGCTTGACGGCAAAGCCCCGATAC
TCGGTTACGCCGAAGACCCCGTCGAACTTTTTTTATGCACATCCAAGGC
TCGGGCCGTCTGAAAACCCCGTCCGGCAAATACATCCGCATCGGCTATGC
CGACAAAAACGAACATCCCTACGTTTCCATCGGACGCTATATGGCGGACA
AGGCTACCTCAAGCTCGGGCAGACCTCGATGCAGGGCATCAAAGCCTATA
TGCGGCAAAATCCGCAACGCCTCGCCGAAGTTTTGGGTCAAAACCCCAGC
TATATCTTTTTCCGCGAGCTTGCCGGAAGCAGCAATGACGGTCCCGTCGG
CGCACTGGGCACGCCGTTGATGGGGGAATATGCCGGCGCAGTCGACCGGC
AGTCGACCGGCACTACATTACCTTGGGCGCGCCCTTATTTGTCGCCACCG
CCCATCCGGTTACCCGCAAAGCCCTCAACCGCCTGATTATGGCGCAGGAT
```

```
ACCGGCAGCGCGATTAAAGGCGCGGTGCGCGTGGATTATTTTTGGGGATA

CGGCGACGAAGCCGGCGAACTTGCCGGCAAACAGAAAACCACGGGTTACG

TCTGGCAGCTCCTACCCAACGGTATGAAGCCCGAATACCGCCCGTAAAAG

CTT
```

(SEQ ID NO: 10)

```
  1 MASPDVKSAD TLSKPAAPVV SEKETEAKED APQAGSQGQG APSAQGQQDM

51 AAVSEENTGN GGAAATDKPK NEDEGAQNDM PQNAADTDSL TPNHTPASNM

101 PAGNMENQAP DAGESEQPAN QPDMANTADG MQGDDPSAGG ENAGNTAAQG

151 TNQAENNQTA GSQNPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQMK GINQYIIFYK PKPTSFARFR RSARSRRSLP AEMPLIPVNQ

301 ADTLIVDGEA VSLTGHSGNI PAPEGNYRYL TYGAEKLPGG SYALRVQGEP

351 SKGEMLAGTA VYNGEVLHFH TENGRPSPSR GRFAAKVDFG SKSVDGIIDS

401 GDGLHMGTQK FKAAIDGNGF KGTWTENGGG DVSGKFYGPA GEEVAGKYSY

451 RPTDAEKGGF GVFAGKKEQD GSGGGGCQSK SIQTFPQPDT SVINGPDRPV

501 GIPDPAGTTV GGGGAVYTVV PHLSLPHWAA QDFAKSLQSF RLGCANLKNR

551 QGWQDVCAQA FQTPVHSFQA KQFFERYFTP WQVAGNGSLA GTVTGYYEPV

601 LKGDDRRTAQ ARFPIYGIPD DFISVPLPAG LRSGKALVRI RQTGKNSGTI

651 DNTGGTHTAD LSRFPITART TAIKGEFEGS RFLPYHTRNQ INGGALDGKA

701 PILGYAEDPV ELFFMHIQGS GRLKTPSGKY IRIGYADKNE HPYVSIGRYM

751 ADKGYLKLGQ TSMQGIKAYM RQNPQRLAEV LGQNPSYIFF RELAGSSNDG

801 PVGALGTPLM GEYAGAVDRH YITLGAPLFV ATAHPVTRKA LNRLIMAQDT

851 GSAIKGAVRV DYFWGYGDEA GELAGKQKTT GYVWQLLPNG MKPEYRP*
```

ΔG287NZ-953

(SEQ ID NO: 11)

```
ATGGCTAGCCCCGATGTCAAGTCGGCGGACACGCTGTCAAAACCTGCCGC

CCCTGTTGTTTGAAAAAGAGACAGAGGCAAAGGAAGATGCGCCACAGGCA

GGTTCTCAAGGACAGGGCGCGCCATCCGCACAAGGCGGTCAAGATATGGC

GGCGGTTTCGGAAGAAAATACAGGCAATGGCGGTGCGGCAGCAACGGACA

AACCCAAAAATGAGACGAGGGGGCAAAATGATATGCCGCAAAATGCCGC

CGATACAGATAGTTTGACACCGAATCACACCCCGGCTTCGAATATGCCGG

CCGGAAATATGGAAAACCAAGCACCGGATGCCGGGGAATCGGAGCAGCCG

GCAAACCAACCGGATATGGCAAATACGGCGGACGGAATGCAGGGTGACGA

TCCGTCGGCAGGCGGGGAAAATGCCGGCAATACGGCTGCCCAAGGTACAA

ATCAAGCCGAAAACAATCAAACCGCCGGTTCTCAAAATCCTGCCTCTTCA

ACCAATCCTAGCGCCACGAATAGCGGTGGTGATTTTGGAAGGACGAACGT

GGGCAATTCTGTTGTGATTGACGGGCCGTCGCAAAATATAACGTTGACCC

ACTGTAAAGGCGATTCTTGTAGTGGCAATAATTTCTTGGATGAAGAAGTA

CAGCTAAAATCAGAATTTGAAAAATTAAGTGATGCAGACAAAATAAGTAA

TTACAAGAAAGATGGGAAGAATGACGGGAAGAATGATAAATTTGTCGGTT

TGGTTGCCGATAGTGTGCAGATGAAGGGAATCAATCAATATATTATCTTT

TATAAACCTAAACCCACTTCATTTGCGCGATTTAGGCGTTCTGCACGGTC
```

-continued

```
GAGGCGGTCGCTTCCGGCCGAGATGCCGCTGATTCCCGTCAATCAGGCGG
ATACGCTGATTGTCGATGGGGAAGCGGTCAGCCTGACGGGGCATTCCGGC
AATATCTTCGCGCCCGAAGGGAATTACCGGTATCTGACTTACGGGGCGGA
AAAATTGCCCGGCGGATCGTATGCCCTCCGTGTTCAAGGCGAACCTTCAA
AAGGCGAAATGCTCGCGGGCACGGCAGTGTACAACGGCGAAGTGCTGCAT
TTTCATACGGAAAACGGCCGTCCGTCCCCGTCCAGAGGCAGGTTTGCCGC
AAAAGTCGATTTCGGCAGCAAATCTGTGGACGGCATTATCGACAGCGGCG
ATGGTTTGCATATGGGTACGCAAAAATTCAAAGCCGCCATCGATGGAAAC
GGCTTTAAGGGGACTTGGACGGAAAATGGCGGCGGGGATGTTTCCGGAAA
GTTTTACGGCCCGGCCGGCGAGGAAGTGGCGGGAAAATACAGCTATCGCC
CAACAGATGCGGAAAAGGGCGGATTCGGCGTGTTTGCCGGCAAAAAAGAG
CAGGATGGATCCGGAGGAGGAGGAGCCACCTACAAAGTGGACGAATATCA
CGCCAACGCCCGTTTCGCCATCGACCATTTCAACACCAGCACCAACGTCG
GCGGTTTTTACGGTCTGACCGGTTCCGTCGAGTTCGACCAAGCAAAACGC
GACGGTAAAATCGACATCACCATCCCCGTTGCCAACCTGCAAAGCGGTTC
GCAACACTTTACCGACCACCTGAAATCAGCCGACATCTTCGATGCCGCCC
AATATCCGGACATCCGCTTTGTTTCCACCAAATTCAACTTCAACGGCAAA
AAACTGGTTTCCGTTGACGGCAACCTGACCATGCACGGCAAAACCGCCCC
CGTCAAACTCAAAGCCGAAAAATTCAACTGCTACCAAAGCCCGATGGCGA
AAACCGAAGTTTGCGGCGGCGACTTCAGCACCACCATCGACCGCACCAAA
TGGGGCGTGGACTACCTCGTTAACGTTGGTATGACCAAAAGCGTCCGCAT
CGACATCCAAATCGAGGCAGCCAAACAATAAAAGCTT
```

(SEQ ID NO: 12)
```
  1 MASPDVKSAD TLSKPAAPVV SEKETEAKED APQASQGQG  APSAQGGQDM
 51 AAVSEENTGN GGAAATDKPK NEDEGAQNDM PQNAADTDSL TPNHTPASNM
101 PAGNMENQAP DAGESEQPAN QPDMANTADG MQGDDPSAGG ENAGNTAAQG
151 TNQAENNQTA GSQNPASSTN PSATNSGGDF GRTNVGNSVV IDGPSQNITL
201 THCKGDSCSG NNFLDEEVQL KSEFEKLSDA DKISNYKKDG KNDGKNDKFV
251 GLVADSVQMK GINQYIIFYK PKPTSFARFR RSARSRRSLP AEMPLIPVNQ
301 ADTLIVDGEA VSLTGHSGNI FAPEGNYRYL TYGAEKLPGG SYALRVQGEP
351 SKGEMLAGTA VYNGEVLHFH TENGRPSPSR GRFAAKVDFG SKSVDGIIDS
401 GDGLHMGTQK FKAAIDGNGF KGTWTENGGG DVSGKFYGPA GEEVAGKYSY
451 RPTDAEKGGF GVFAGKKEQD GSGGGGATYK VDEYHANARF AIDHFNTSTN
501 VGGFYGLTGS VEFDQAKRDG KIDITIPVAN LQSGSQHFTD HLKSADIFDA
551 AQYPDIRFVS TKFNFNGKKL VSVDGNLTMH GKTAPVKLKA EKFNCYQSPM
601 AKTEVCGGDF STTIDRTKWG VDYLVNVGMT KSVRIDIQIE AAKQ*
```

ΔG287NZ-961

(SEQ ID NO: 13)
```
ATGGCTAGCCCCGATGTCAAGTCGGCGGACACGCTGTCAAAACCTGCCGC
CCCTGTTGTTTCTGAAAAAGAGACAGAGGCAAAGGAAGATGCGCCACAGG
CAGGTTCTCAAGGACAGGGCGCGCCATCCGCACAAGGCGGTCAAGATATG
GCCGGCGGTTTCGGAAGAAAATACAGGCAATGGCGGTGCGGCAGCAACGG
```

-continued

```
ACAAACCCAAAAATGAAGACGAGGGGGCGCAAAATGATATGCCGCAAAAT

GCCGCCGATACAGATAGTTTGACACCGAATCACACCCCGGCTTCGAATAT

GCCGGCCGGAAATATGGAAAACCAAGCACCGGATGCCGGGGAATCGGAGC

AGCCGGCAAACCAACCGGATATGGCAAATACGGCGGACGGAATGCAGGGT

GACGATCCGTCGGCAGGCGGGGAAAATGCCGGCAATACGGCTGCCCAAGG

TACAAATCAAGCCGAAAACAATCAAACCGCCGGTTCTCAAAATCCTGCCT

CTTCAACCAATCCTAGCGCCACGAATAGCGGTGGTGATTTTGGAAGGACG

AACGTGGGCAATTCTGTTGTGATTGACGGGCCGTCGCAAAATATAACGTT

GACCCACTGTAAAGGCGATTCTTGTAGTGGCAATAATTTCTTGGATGAAG

AAGTACAGCTAAAATCAGAATTTGAAAAATTAAGTGATGCAGACAAAATA

AGTAATTACAAGAAAGATGGGAAGAATGACGGGAAGAATGATAAATTTGT

CGGTTTGGTTGCCGATAGTGTGCAGATGAAGGGAATCAATCAATATATTA

TCTTTTATAAACCTAAACCCACTTCATTTGCGCGATTTAGGCGTTCTGCA

CGGTCGAGGCGGTCGCTTCCGGCCGAGATGCCGCTGATTCCCGTCAATCA

GGCGGATACGCTGATTGTCGATGGGGAAGCGGTCAGCCTGACGGGGCATT

CCGGCAATATCTTCGCGCCCGAAGGGAATTACCGGTATCTGACTTACGGG

GCGGAAAAATTGCCCGGCGGATCGTATGCCCTCCGTGTTCAAGGCGAACC

TTCAAAAGGCGAAATGCTCGCGGGCACGGCAGTGTACAACGGCGAAGTGC

TGCATTTTCATACGGAAAACGGCCGTCCGTCCCCGTCCAGAGGCAAGGTT

TGCCGCAAAAGTCGATTTCGGCAGCAAATCTGTGGACGGCATTATCGACA

GCGGCGATGGTTTGCATATGGGTACGCAAAAATTCAAAGCCGCCATCGAT

GGAAACGGCTTTAAGGGGACTTGGACGGAAAATGGCGGCGGGGATGTTTC

CGGAAAGTTTTACGGCCCGGCCGGCGAGGAAGTGGCGGGAAAATACAGCT

ATCGCCCAACAGATGCGGAAAAGGGCGGATTCGGCGTGTTTGCCGGCAAA

AAAGAGCAGGATGGATCCGGAGGAGGAGGAGCCACAAACGACGACGATGT

TAAAAAAGCTGCCACTGTGGCCATTGCTGCTGCCTACAACAATGGCCAAG

AAATCAACGGTTTCAAAGCTGGAGAGACCATCTACGACATTGATGAAGAC

GGCACAATTACCAAAAAAGACGCAACTGCAGCCGATGTTGAAGCCGACGA

CTTTAAAGGTCTGGGTCTGAAAAAAGTCGTGACTAACCTGACCAAAACCG

TCAATGAAAACAAACAAAACGTCGATGCCAAAGTAAAAGCTGCAGAATCT

GAAATAGAAAAGTTAACAACCAAGTTAGCAGACACTGATGCCGCTTTAGC

AGATACTGATGCCGCTCTGGATGCAACCACCAACGCCTTGAATAAATTGG

GAGAAAATATAACGACATTTGCTGAAGAGACTAAGACAAATATCGTAAAA

ATTGATGAAAATTAGAAGCCGTGGCTGATACCGTCGACAAGCATGCCGA

AGCATTCAACGATATCGCCGATTCATTGGATGAAACCAACACTAAGGCAG

ACGAAGCCGTCAAAACCGCCAATGAAGCCAAACAGACGGCCGAAGAAACC

AAACAAAACGTCGATGCCAAAGTAAAAGCTGCAGAAACTGCAGCAGGCAA

AGCCGAAGCTGCCGCTGGCACAGCTAATACTGCAGCCGACAAGGCCGAAG

CTGTCGCTGCAAAAGTTACCGACATCAAAGCTGATATCGCTACGAACAAA

GATAATATTGCTAAAAAAGCAAACAGTGCCGACGTGTACACCAGAGAAGA
```

-continued
```
GTCTGACAGCAAATTTGTCAGAATTGATGGTCTGAACGCTACTACCGAAA

AATTGGACACACGCTTGGCTTCTGCTGAAAAATCCATTGCCGATCACGAT

ACTCGCCTGAACGGTTTGGATAAAACAGTGTCAGACCTGCGCAAAGAAAC

CCGCCAAGGCCTTGCAGAACAAGCCGCGCTCTCCGGTCTGTTCCAACCTT

ACAACGTGGGTCGGTTCAATGTAACGGCTGCAGTCGGCGGCTACAAATCC

GAATCGGCAGTCGCCATCGGTACCGGCTTCCGCTTACCGAAAACTTTGCC

GCCAAAGCAGGCGTGGCAGTCGGCACTTCGTCCGGTTCTTCCGCAGCCTA

CCATGTCGGCGTCAATTACGAGTGGTAAAAGCTT
```

```
                                                  (SEQ ID NO: 14)
  1 MASPDVKSAD TLSKPAAPVV SEKETEAKED APQAGSQGQG APSAQGGQDM

51 AAVSEENTGN GGAAATDKPK NEDEGAQNDM PQNAADTDSL TPNHTPASNM

101 PAGNMENQAP DAGESEQPAN QPDMANTADG MQGDDPSAGG ENAGNTAAQG

151 TNQAENNQTA GSQNPASSTN PSATNSGGDF GRTNVGNSVV IDGPSQNITL

201 THCKGDSCSG NNFLDEEVQL KSEFEKLSDA DKISNYKKDG KNDGKNDKFV

251 GLVADSVQMK GINQYIIFYK PKPTSFARFR RSARSRRSLP AEMPLIPVNQ

301 ADTLIVDGEA VSLTGHSGNI FAPEGNYRYL TYGAEKLPGG SYALRVQGEP

351 SKGEMLAGTA VYNGEVLHFH TENGRPSPSR GRFAAKVDFG SKSVDGIIDS

401 GDGLHMGTQK FKAAIDGNGF KGTWTENGGG DVSGKFYGPA GEEVAGKYSY

451 RPTDAEKGGF GVFAGKKEQD GSGGGGATND DDVKKAATVA IAAAYNNGQE

501 INGFKAGETI YDIDEDGTIT KKDATAADVE ADDFKGLGLK KVVTNLTKTV

551 NENKQNVDAK VKAAESEIEK LTTKLADTDA ALADTDAALD ATTNALNKLG

601 ENITTFAEET KTNIVKIDEK LEAVADTVDK HAEAFNDIAD SLDETNTKAD

651 EAVKTANEAK QTAEETKQNV DAKVKAAETA AGKAEAAAGT ANTAADKAEA

701 VAAKVTDIKA DIATNKDNIA KKANSADVYT REESDSKFVR IDGLNATTEK

751 LDTRLASAEK SIADHDTRLN GLDKTVSDLR KETRQGLAEQ AALSGLFQPY

801 NVGRFNVTAA VGGYKSESAV AIGTGFRFTE NFAAKAGVAV GTSSGSSAAY

851 HVGVNYEW*
```

Example 3

Hybrids of ΔG983

Protein 983 has the following sequence:

```
983 (SEQ ID NO: 15)                           → ΔG983
  1 MRTTPTFPTK TFKPTAMALA VATTLSACLG GGGGGTSAPD FNAGGTGIGS

51 NSRATTAKSA AVSYAGIKNE MCKDRSMLCA GRDDVAVTDR DAKINAPPPN

101 LHTGDFPNPN DAYKNLINLK PAIEAGYTGR GVEVGIVDTG ESVGSISFPE

151 LYGRKEHGYN ENYKNYTAYM RKEAPEDGGG KDIEASFDDE AVIETEAKPT

201 DIRHVKEIGH IDLVSHIIGG RSVDGRPAGG IAPDATLHIM NTNDETKNEM

251 MVAAIRNAWV KLGERGVRIV NNSFGTTSRA GTADLFQIAN SEEQYRQALL

301 DYSGGDKTDE GIRLMQQSDY GNLSYHIRNK NMLFIPSTGN DAQAQPNTYA

351 LLPFYEKDAQ KGIITVAGVD RSGEKFKREM YGEPGTEPLE YGSNHCGITA

401 MWCLSAPYEA SVRFTRTNPI QIAGTSFSAP IVTGTAALLL QKYPWMSNDN
```

```
451 LRTTLLLTTAQ DIGAVGVDSK FGWGLLDAGK AMNGPASFPF GDFTADTKGT

501 SDIAYSFRND ISGTGGLIKK GGSQLQLHGN NTYTGKTIIE GGSLVLYGNN

551 KSDMRVETKG ALIYNGAASG GSLNSDGIVY LADTDQSGAN ETVHIKGSLQ

601 LDGKGTLYTR LGKLLKVDGT AIIGGKLYMS ARGKGAGYLN STGRRVPFLS

651 AAKIGQDYSF FTNIETDGGL LASLDSVEKT AGSEGDTLSY YVRRGNAART

701 ASAAAHSAPA GLKHAVEQGG SNLENLMVEL DASESSATPE TVETAAADRT

751 DMPGIRPYGA TFRAAAAVQH ANAADGVRIF NSLAATVYAD STAAHADMQG

801 RRLKAVSDGL DHNGTGLRVI AQTQQDGGTW EQGGVEGKMR GSTQTVGIAA

851 KTGENTTAAA TLGMGRSTWS ENSANAKTDS ISLFAGIRHD AGDIGYLKGL

901 FSYGRYKNSI SRSTGADEHA EGSVNGTLMQ LGALGGVNVP FAATGDLTVE

951 GGLRYDLLKQ DAFAEKGSAL GWSGNSLTEG TLVGLAGLKL SQPLSDKAVL

1001 FATAGVERDL NGRDYTVTGG FTGATAATGK TGARNMPHTR LVAGLGADVE

1051 FGNGWNGLAR YSYAGSKQYG NHSGRVGVGY RF*
```

ΔG983 thus has the following basic sequence (SEQ ID NO: 16):

```
                                       TSAPD FNAGGTGIGS
NSRATTAKSA AVSYAGIKNE MCKDRSMLCA GRDDVAVTDR DAKINAPPPN
LHTGDFPNPN DAYKNLINLK PAIEAGYTGR GVEVGIVDTG ESVGSISFPE
LYGRKEHGYN ENYKNYTAYM RKEAPEDGGG KDIEASFDDE AVIETEAKPT
DIRHVKEIGH IDLVSHIIGG RSVDGRPAGG IAPDATLHIM NTNDETKNEM
MVAAIRNAWV KLGERGVRIV NNSFGTTSRA GTADLFQIAN SEEQYRQALL
DYSGGDKTDE GIRLMQQSDY GNLSYHIRNK NMLFIPSTGN DAQAQPNTYA
LLPFYEKDAQ KGIITVAGVD RSGEKFKREM YGEPGTEPLE YGSNHCGITA
MWCLSAPYEA SVRFTRTNPI QIAGTSFSAP IVTGTAALLL QKYPWMSNDN
LRTTLLLTTAQ DIGAVGVDSK FGWGLLDAGK AMNGPASFPF GDFTADTKGT
SDIAYSFRND ISGTGGLIKK GGSQLQLHGN NTYTGKTIIE GGSLVLYGNN
KSDMRVETKG ALIYNGAASG GSLNSDGIVY LADTDQSGAN ETVHIKGSLQ
LDGKGTLYTR LGKLLKVDGT AIIGGKLYMS ARGKGAGYLN STGRRVPFLS
AAKIGQDYSF FTNIETDGGL LASLDSVEKT AGSEGDTLSY YVRRGNAART
ASAAAHSAPA GLKHAVEQGG SNLENLMVEL DASESSATPE TVETAAADRT
DMPGIRPYGA TFRAAAAVQH ANAADGVRIF NSLAATVYAD STAAHADMQG
RRLKAVSDGL DHNGTGLRVI AQTQQDGGTW EQGGVEGKMR GSTQTVGIAA
KTGENTTAAA TLGMGRSTWS ENSANAKTDS ISLFAGIRHD AGDIGYLKGL
FSYGRYKNSI SRSTGADEHA EGSVNGTLMQ LGALGGVNVP FAATGDLTVE
GGLRYDLLKQ DAFAEKGSAL GWSGNSLTEG TLVGLAGLKL SQPLSDKAVL
FATAGVERDL NGRDYTVTGG FTGATAATGK TGARNMPHTR LVAGLGADVE
FGNGWNGLAR YSYAGSKQYG NHSGRVGVGY RF*
```

ΔG983 was expressed as a hybrid, with ORF46.1, 741, 961 or 961c at its C-terminus:

ΔG983-ORF46.1
(SEQ ID NO: 17)
ATGACTTCTGCGCCCGACTTCAATGCAGGCGGTACCGGTATCGGCAGCAA

CAGAGAGCAACAACAGCGAAATCAGCAGCAGTATCTTACGCCGGTATCAA

-continued

```
GAACGAAATGTGCAAAGACAGAAGCATGCTCTGTGCCGGTCGGGATGACG
TTGCGGTTACAGACAGGGATGCCAAAATCAATGCCCCCCCCCCGAATCTG
CATACCGGAGACTTTCCAAACCCAAATGACGCATACAAGAATTTGATCAA
CCTAAACCTGCAATTGAAGCAGGCTATACAGGACGCGGGGTAGAGGTAGG
TATCGTCGACACAGGCGAATCCGTCGGCAGCATATCCTTTCCCGAACTGT
ATGGCAGAAAAGAACACGGCTATAACGAAAATTACAAAAACTATACGGCG
TATATGCGGAAGGAAGCGCCTGAAGACGGAGGCGGTAAAGACATTGAAGC
TTCTTTCGACGATGAGGCCGTTATAGAGACTGAAGCAAAGCCGACGGATA
TCCGCCACGTAAAAGAAATCGAACACATCGATTTGGTCTCCCATATTATT
GGCGGGCGTTCCGTGGACGGCAGACCTGCAGGCGGTATTGCGCCCGATGC
GACGCTACACATAATGAATACGAATGATGAAACCAAGAACGAAATGATGG
TTGCAGCCATCCGCAATGCATGGGTCAAGCTGGGCGAACGTGGCGTGCGC
ATCGTCAATAACAGTTTTGGAACAACATCGAGGGCAGGCACTGCCGACCT
TTTCCAAATAGCCAATTCGGAGGAGCAGTACCGCCAAGCGTTGCTCGACT
ATTCCGGCGGTGATAAAACAGACGAGGGTATCCGCCTGATGCAACAGAGC
GATTACGGCAACCTGTCCTACCACATCCGTAATAAAAACATGCTTTTCAT
CTTTTCGACAGGCAATGACGCACAAGCTAGCCCAACACATATGCCCTATT
GCCATTTTATGAAAAAGACGCTCAAAAAGGCATTATCACAGTCGCAGGCG
TAGACCGCAGTGGAGAAAAGTTCAAACGGGAAATGTATGGAGAACCGGGT
ACAGAACCGCTTGAGTATGGCTCCAACCATTGCGGAATTACTGCCATGTG
GTGCCTGTCGGCACCCTATGAAGCAAGCGTCCGTTTCACCCGTACAAACC
CGATTCAAATTGCCGGAACATCCTTTTCCGCACCCATCGTAACCGGCACG
GGGCGGCTCTGCTGCAGAAATACCCGTGGATGAGCAACGACAACCTGCGT
ACCACGTTGCTGACGACGGCTCAGGACATCGGTGCAGTCGGCGTGGACAG
CAAGTTCGGCTGGGGACTGCTGGATGCGGGTAAGGCCATGAACGGACCCG
CGTCCTTTCCGTTCGGCGACTTTACCGCCGATACGAAAGGTACATCCGAT
ATTGCCTACTCCTTCCGTAACGACATTTCAGGCACGGGCGGCCTGATCAA
AAAAGGCGGCAGCCAACTGCAACTGCACGGCAACAACACCTATACGGGCA
AAACCATTATCGAAGGCGGTTCGCTGGTGTTGTACGGCAACAACAAATCG
GATATGCGCGTCGAAACCAAAGGTGCGCTGATTTATAACGGGCGGCATC
CGGCGGCAGCCTGAACAGCGACGGCATTGTCTATCTGGCAGATACCGACC
AATCCGGCGCAAACGAAACCGTACACATCAAAGGCAGTCTGCAGCTGGAC
GGCAAAGGTACGCTGTACACACGTTTGGGCAAACTGCTGAAAGTGGACGG
TACGGCGATTATCGGCGGCAAGCTGTACATGTCGGCACGCGGCAAGGGGG
CAGGCTATCTCAACAGTACCGGACGACGTGTTCCCTTCCTGAGTGCCGCC
AAAATCGGGCAGGATTATTCTTTCTTCACAAACATCGAAACCGACGGCGG
CCTGCTGGCTTCCCTCGACAGCGTCGAAAAAACAGCGGGCAGTGAAGGCG
ACACGCTGTCCTATTATGTCCGTCGCGGCAATGCGGCACGGACTGCTTCG
GCAGCGGCACATTCCGCGCCCGCCGGTCTGAAACACGCCGTAGAACAGGG
CGGCAGCAATCTGGAAAACCTGATGGTCGAACTGGATGCCTCCGAATCAT
CCGCAACACCCGAGACGGTTGAAACTGCGGCAGCCGACCGCACAGATATG
```

-continued

```
CCGGGCATCCGCCCCTACGGCGCAACTTTCCGCGCAGCGGCAGCCGTACA

GCATGCGAATGCCGCCGACGGTGTACGCATCTTCAACAGTCTCGCCGCTA

CCGTCTATGCCGACAGTACCGCCGCCCATGCCGATATGCAGGGACGCCGC

CTGAAAGCCGTATCGGACGGGTTGGACCACAACGGCACGGGTCTGCGCGT

CATCGCGCAAACCCAACAGGACGGTGGAACGTGGGAACAGGGCGGTGTTG

AAGGCAAATGCGCGGCAGTACCCAAACCGTCGGCATTGCCGCGAAAACC

GGCGAAAATACGACAGCAGCCGCCACACTGGGCATGGGACGCAGCACATG

GAGCGAAAACAGTGCAAATGCAAAAACCGACAGCATTAGTCTGTTTGCAG

GCATACGGCACGATGCGGGCGATATCGGCTATCTCAAAGGCCTGTTCTCC

TACGGACGCTACAAAAACAGCATCAGCCGCAGCACCGGTGCGGACGAACA

TGCGGAAGGCAGCGTCAACGGCACGCTGATGCAGCTGGGCGCACTGGGCG

GTGTCAACGTTCCGTTTGCCGCAACGGGAGATTTGACGGTCGAAGGCGGT

CTGCGCTACGACCTGCTCAAACAGGATGCATTCGCCGAAAAAGGCAGTGC

TTTGGGCTGGAGCGGCAACAGCCTCACTGAAGGCACGCTGGTCGGACTCG

CGGGTCTGAAGCTGTCGCAACCCTTGAGCGATAAAGCCGTCCTGTTTGCA

ACGGCGGGCGTGGAACGCGACCTGAACGGACGCGACTACACGGTAACGGG

CGGCTTTACCGGCGCGACTGCAGCAACCGGCAAGACGGGGGCACGCAATA

TGCCGCACACCCGTCTGGTTGCCGGCCTGGGCGCGGATGTCGAATTCGGC

AACGGCTGGAACGGCTTGGCACGTTACAGCTACGCCGGTTCCAAACAGTA

CGGCAACCACAGCGGACGAGTCGGCGTAGGCTACCGGTTCCTCGACGGTG

GTGGCGGAGGCACTGGATCCTCAGATTTGGCAAACGATTCTTTTATCCGG

CAGGTTCTCGACCGTCAGCATTTCGAACCCGACGGGAAATACCACCTATT

CGGCAGCAGGGGGGAACTTGCCGAGCGCAGCGGCCATATCGGATTGGGAA

AAATACAAAGCCATCAGTTGGGCAACCTGATGATTCAACAGGCGGCCATT

AAAGGAAATATCGGCTACATTGTCCGCTTTTCCGATCACGGGCACGAAGT

CCATTCCCCCTTCGACAACCATGCCTCACATTCCGATTCTGATGAAGCCG

GTAGTCCCGTTGACGGATTTAGCCTTTACCGCATCCATTGGGACGGATAC

GAACACCATCCCGCCGACGGCTATGACGGGCCACAGGGCGGCGGCTATCC

CGCTCCCAAAGGCGCGAGGGATATATACAGCTACGACATAAAAGGCGTTG

CCCAAAATATCCGCCTCAACCTGACCGACAACCGCAGCACCCGACAACGG

CTTGCCGACCGTTTCCACAATGCCGGTAGTATGCTGACGCAAGGAGTAGG

CGACGGATTCAAACGCGCCACCCGATACAGCCCCGAGCTGGACAGATCGG

GCAATGCCGCCGAAGCCTTCAACGGCACTGCAGATATCGTTAAAAACATC

ATCGGCGCGGCAGGAGAAATTGTCGGCGCAGGCGATGCCGTGCAGGGCAT

AAGCGAAGGCTCAAACATTGCTGTCATGCACGGCTTGGGTCTGCTTTCCA

CCGAAAACAAGATGGCGCGCATCAACGATTTGGCAGATATGGCGCAACTC

AAAGACTATGCCGCAGCAGCCATCCGCGATTGGGCAGTCCAAAACCCCAA

TGCCGCACAAGGCATAGAAGCCGTCAGCAATATCTTTATGGCAGCCATCC

CCATCAAAGGGATTGGAGCTGTTCGGGGAAAATACGGCTTGGGCGGCATC

ACGGCACATCCTATCAAGCGGTCGCAGATGGGCGCGATCGCATTGCCGAA
```

-continued
```
AGGGAAATCCGCCGTCAGCGACAATTTTGCCGATGCGGCATACGCCAAAT

ACCCGTCCCCTTACCATTCCCGAAATATCCGTTCAAACTTGGAGCAGCGT

TACGGCAAAGAAAACATCACCTCCTCAACCGTGCCGCCGTCAAACGGCAA

AAATGTCAAACTGGCAGACCAACGCCACCCGAAGACAGGCGTACCGTTTG

ACGGTAAAGGGTTTCCGAATTTTGAGAAGCACGTGAAATATGATACGCTC

GAGCACCACCACCACCACCACTGA
```

```
                                              (SEQ ID NO: 18)
   1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVRIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVRR GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNQ TGLRVIAQTQ QDGGTWEQGG

801 VEGKMRGSTQ TVGIAAKTGE NTTAAATLGM GRSTWSENSA NARTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLD

1051 GGGGTGSSDL ANDSFIRQVL DRQHFEPDGK YHLFGSRGEL AERSGHIGLG

1101 KIQSHQLGNL MIQQAAIKGN IGYIVRFSDH GHEVHSPFDN HASHSDSDEA

1151 GSPVDGFSLY RIHWDGYEHH PADGYDGPQG GGYPAPKGAR DIYSYDIKGV

1201 AQNIRLNLTD NRSTGQRLAD RFHNAGSMLT QGVGDGFKRA TRYSPELDRS

1251 GNAAEAFNGT ADIVKNIIGA AGEIVGAGDA VQGISEGSNI AVMHGLGLLS

1301 TENKMARIND LADMAQLKDY AAAAIRDWAV QNPNAAQGIE AVSNIFMAAI

1351 PIKGIGAVRG KYGLGGITAH PIKRSQMGAI ALPKGKSAVS DNFADAAYAK

1401 YPSPYHSRNI RSNLEQRYGK ENITSSTVPP SNGKNVKLAD QRHPKTGVPF

1451 DGKGFPNFEK HVKYDTLEHH HHHH*
```

ΔQ983-741
```
                                              (SEQ ID NO: 19)
ATGACTTCTGCGCCCGACTTCAATGCAGGCGGTACCGGTATCGGCAGCAA

CAGCAGAGCAACAACAGCGAAATCAGCAGCAGTATCTTACGCCGGTATCA

AGAACGAAATGTGCAAAGACAGAAGCATGCTCTGTGCCGGTCGGGATGAC
```

-continued
```
GTTGCGGTTACAGACAGGGATGCCAAAATCAATGCCCCCCCCCGAATCT

GCATACCGGAGACTTTCCAAACCCAAATGACGCATACAAGAATTTGATCA

ACCTCAAACCTGCAATTGAAGCAGGCTATACAGGACGCGGGGTAGAGGTA

GGTATCGTCGACACAGGCGAATCCGTCGGCAGCATATCCTTTCCCGAACT

GTATGGCAGAAAAGAACACGGCTATAACGAAAATTACAAAAACTATACGG

CGTATATGCGGAAGGAAGCGCCTGAAGACGGAGGCGGTAAAGACATTGAA

GCTTCTTTCGACGATGAGGCCGTTATAGAGACTGAAGCAAAGCCGACGGA

TATCCGCCACGTAAAAGAAATCGGACACATCGATTTGGTCTCCCATATTA

TTGGCGGGCGTTCCGTGGACGGCAGACCTGCAGGCGGTATTGCGCCCGAT

GCGACGCTACACATAATGAATACGAATGATGAAACCAAGAACGAAATGAT

GGTTGCAGCCATCCGCAATGCATGGGTCAAGCTGGGCGAACGTGGCGTGC

GCATCGTCAATAACAGTTTTGGAACAACATCGAGGGCAGGCACTGCCGAC

CTTTTCCAAATAGCCAATTCGGAGGAGCAGTACCGCCAAGCGTTGCTCGA

CTATTCCGGCGGTGATAAAACAGACGAGGGTATCCGCCTGATGCAACAGA

GCGATTACGGCAACCTGTCCTACCACATCCGTAATAAAAACATGCTTTTC

ATCTTTTCGACAGGCAATGACGCACAAGCTCAGCCCAACACATATGCCCT

ATTGCCATTTTATGAAAAAGACGCTCAAAAAGGCATTATCACAGTCGCAG

GCGTAGACCGCAGTGGAGAAAAGTTCAAACGGGAAATGTATGGAGAACCG

GGTACAGAACCGCTTGAGTATGGCTCCAACCATTGCGGAATTACTGCCAT

GTGGTGCCTGTCGGCACCCTATGAAGCAAGCGTCCGTTTCACCCGTACAA

ACCCGATTCAAATTGCCGGAACATCCTTTTCCGCACCCATCGTAACCGGC

ACGGCGGCTCTGCTGCTGCAGAAATACCCGTGGATGAGCAACGACAACCT

GCGTACCACGTTGCTGACGACGGCTCAGGACATCGGTGCAGTCGGCGTGG

ACAGCAAGTTCGGCTGGGGACTGCTGGATGCGGGTAAGGCCATGAACGGA

CCCGCGTCCTTTCCGTTCGGCGACTTTACCGCCGATACGAAAGGTACATC

CGATATTGCCTACTCCTTCCGTAACGACATTTCAGGCACGGGCGGCCTGA

TCAAAAAAGGCGGCAGCAACTGCAACTGCACGGCAACAACACCTATACGG

GCAAAACCATTATCGAAGGCGGTTCGCTGGTGTTGTACGGCAACAACAAA

TCGGATATGCGCGTCGAAACCAAAGGTGCGCTGATTTATAACGGGGCGGC

ATCCGGCGGCAGCCTGAACAGCGACGGCATTGTCTATCTGGCAGATACCG

ACCAATCCGGCGCAAACGAAACCGTACACATCAAAGGCAGTCTGCAGCTG

GACGGCAAAGGTACGCTGTACACACGTITGGGCAAACTGCTGAAAGTGGA

CGGTACGGCGATTATCGGCGGCAAGCTGTACATGTCGGCACGCGGCAAGG

GGGCAGGCTATCTCAACAGTACCGGACGACGTGTTCCCTTCCTGAGTGCC

GCCAAAATCGGGCAGGATTATTCTTTCTTCACAAACATCGAAACCGACGG

CGGCCTGCTGGCTTCCCTCGACAGCGTCGAAAAAACAGCGGGCAGTGAAG

GCGACACGCTGTCCTATTATGTCCGTCGCGGCAATGCGGCACGGACTGCT

TCGGCAGCGGCACATTCCGCGCCCGCCGGTCTGAAACACGCCGTAGAACA

GGGCGGCAGCAATCTGGAAAACCTGATGGTCGAACTGGATGCCTCCGAAT

CATCCGCAACACCCGAGACGGTTGAAACTGCGGCAGCCGACCGCACAGAT

ATGCCGGGCATCCGCCCCTACGGCGCAACTTTCCGCGCAGCGGCAGCCGT
```

-continued

```
ACAGCATGCGAATGCCGCCGACGGTGTACGCATCTTCAACAGTCTCGCCG
CTACCGTCTATGCCGACAGTACCGCCGCCCATGCCGATATGCAGGGACGC
CGCCTGAAAGCCGTATCGGACGGGTTGGACCACAACGGCACGGGTCTGCG
CGTCATCGCGCAAACCCAACAGGACGGTGGAACGTGGGAACAGGGCGGTG
TTGAAGGCAAAATGCGCGGCAGTACCCAAACCGTCGGCATTGCCGCGAAA
ACCGGCGAAAATACGACAGCAGCCGCCACACTGGGCATGGGACGCAGCAC
ATGGAGCGAAAACAGTGCAAATGCAAAAACCGACAGCATTAGTCTGTTTG
CAGGCATACGGCACGATGCGGGCGATATCGGCTATCTCAAAGGCCTGTTC
TCCTACGGACGCTACAAAAACAGCATCAGCCGCAGCACCGGTGCGGACGA
ACATGCGGAAGGCAGCGTCAACGGCACGCTGATGCAGCTGGGCGCACTGG
GCGGTGTCAACGTTCCGTTTGCCGCAACGGGAGATTTGACGGTCGAAGGC
GGTCTGCGCTACGACCTGCTCAAACAGGATGCATTCGCCGAAAAAGGCAG
TGCTTTGGGCTGGAGCGGCAACAGCCTCACTGAAGGCACGCTGGTCGGAC
TCGCGGGTCTGAAGCTGTCGCAACCCTTGAGCGATAAAGCCGTCCTGTTT
GCAACGGCGGGCGTGGAACGCGACCTGAACGGACGCGACTACACGGTAAC
GGGCGGCTTTACCGGCGCGACTGCAGCAACCGGCAAGACGGGGCACGCA
ATATGCCGCACACCCGTCTGGTTGCCGGCCTGGGCGCGGATGTCGAATTC
GGCAACGGCTGGAACGGCTTGGCACGTTACAGCTACGCCGGTTCCAAACA
GTACGGCAACCACAGCGGACGAGTCGGCGTAGGCTACCGGTTCCTCGAGG
GATCCGGAGGGGTGGTGTCGCCGCCGACATCGGTGCGGGGCTTGCCGAT
GCACTAACCGCACCGCTCGACCATAAAGACAAAGGTTTGCAGTCTTTGAC
GCTGGATCAGTCCGTCAGGAAAAACGAGAAACTGAAGCTGGCGGCACAAG
GTGCGGAAAAACTTATGGAAACGGTGACAGCCTCAATACGGGCAAATTG
AAGAACGACAAGGTCAGCCGTTTCGACTTTATCCGCCAAATCGAAGTGGA
CGGGCAGCTCATTACCTTGGAGAGTGGAGAGTTCCAAGTATACAAACAAG
CCATTCCGCCTTAACCGCCTTTCAGACCGAGCAAATACAAGATTCGGAGC
ATTCCGGGAAGATGGTTGCGAAACGCCAGTTCAGAATCGGCGACATAGCG
GGCGAACATACATCTTGACAAGCTTCCCGAGGCGGCAGGGCGACATATCG
CGGGACGGCGTTCGGTTCAGACGATGCCGGCGGAAAACTGACCTACACCA
TAGATTTCGCCGCCAAGCAGGGAAACGGCAAAATCGAACATTTGAAATCG
CCAGAACTCAATGTCGACCTGGCCGCCGCCGATATCAAGCCGGATGGAAA
ACGCCATGCCGTCATCAGCGGTTCCGTCCTTTACAACCAAGCCGAAAGGC
AGTTACTCCCTCGGTATCTTTGGCGGAAAGCCCAGGAAGTTGCCGGCAGC
GCGCGGAAGTGAAAACCGTAAACGGCATACGCCATATCGGCCTTGCCGCC
AAGCAACTCGAGCACCACCACCACCACCACTGA
```

(SEQ ID NO: 20)
  1 MTSAPDFNAG GTGIGSNSRA TTAKSAAVSY AGIKNEMCKD RSMLCAGRDD
 51 VAVTDRDAKI NAPPPNLHTG DFPNPNDAYK NLINLKPAIE AGYTGRGVEV
101 GIVDTGESVG SISFPELYGR KEHGYNENYK NYTAYMRKEA PEDGGGKDIE
151 ASFDDEAVIE TEAKPTDIRH VKEIGHIDLV SHIIGGRSVD GRPAGGIAPD
201 ATLHIMNTND ETKNEMMVAA IRNAWVKLGE RGVPIVNNSF GTTSRAGTAD

```
 251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVER GNAARTASAA AHSAPAGLKH AVEQGGSNLE NLMVELDASE

701 SSATPETVET AAADRTDMPG IRPYGATFRA AAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GSGGGGVAAD IGAGLADALT APLDHKDKGL QSLTLDQSVR KNEKLKLAAQ

1101 GAEKTYGNGD SLNTGKLKND KVSRFDFIRQ IEVDGQLITL ESGEFQVYKQ

1151 SHSALTAFQT EQIQDSEHSG KMVAKRQPRI GDIAGEHTSF DKLPEGGRAT

1201 YRGTAFGSDD AGGKLTYTID FAAKQGNGKI EHLKSPELNV DLAAADIKPD

1251 GKRHAVISGS VLYNQAEKGS YSLGIFGGKA QEVAGSAEVK TVNGIRHIGL

1301 AAKQLEHHHH HH*

ΔG983-961
                                                    (SEQ ID NO: 21)
ATGCATTCTGCGCCCGACTTCAATGCAGGCGGTACCGGTATCGGCAGCAA

CAGCAGAGCAACAACAGCGAAATCAGCAGCAGTATCTTACGCCGGTATCA

AGAACGAAATGTGCAAAGACAGAAGCATGCTCTGTGCCGGTCGGGATGAC

GTTGCGGTTACAGACAGGGATGCCAAAATCAATGCCCCCCCCCCGAATCT

GCATACCGGAGACTTTCCAAACCCAAATGACGCATACAAGAATTTGATCA

ACCTCAAACCTGCAATTGAAGCAGGCTATACAGGACGGGGTAGAGGTAGG

TATCGTCGACACACGCGAATCCGTCGGCAGCATATCCTTTCCCGAACTGT

ATGGCAGAAAAGAACACGGCTATAACGAAAATTACAAAAACTATACGGCG

TATATGCGGAAGGAAGCGCCTGAAGACGGAGGCGGTAAAGACATTGAAGC

TTCTTTCGACGATGAGGCCGTTATAGAGACTGAAGCAAAGCCGACGGATA

TCCGCCACGTAAAAGAAATCGGACACATCGATTTGGTCTCCCATATTATT

GGCGGGCGTTCCGTGGACGGCAGACCTGCAGGCGGTSTTGCGCCCGATGC

GACGCTACACATAATGAATACGAATGATGAAACCAAGAACGAAATGATGG

TTGCAGCCATCCGCAATGCATGGGTCAAGCTGGGCGAACGTGGCGTGCGC

ATCGTCAATAACAGTTTGGAACAACATCGAGGGCAGGCACTGCCGACCTT

TTCCAAATAGCCAATTCGGAGGAGCAGTACCGCCAGCGTTGCTCGACTAT

TCCGGCGGTGATAACAGACGAGGGTATCCGCCTGATGCAACAGAGCGATT
```

-continued
```
ACGGCAACCTGTCCTACCACATCCGTAATAAAAACATGCTTTTCATCTTT
TCGACAGGCAATGACCACAAGCTCAGCCCAACACATATGCCCTATTGCCA
TTTTATGAAAAAGACGCTCAAAAAGGCATTATCACAGTCGCAGGCGTAGA
CCGCAGTGGAGAAAAGTTCAAACGGGAAATGTATGGAGAACCGGGTACAG
AACCGCTTGAGTATGGCTCCAACCATTGCGGAATTACTGCCATGTGGTGC
CTGTCGGCACCCTATGAAGCAAGCGTCCGTTTCACCCGTACAAACCCGAT
TCAAATTGCCGGAACATCCTTTTCCGCACCCATCGTAACCGGCACGGCGG
CTCTGCTGCAGAAATACCGTGGATGAGCAACGACAACCTGCGTACCACGT
TGCTGACGACGGCTCAGGACATCGGTGCAGTCGGCGTGGACAGCAAGTTC
GGCTGGGGACTGCTGGATGCGGGTAAGGCCATGAACGGACCCGCGTCCTT
TCCGTTCGGCGACTTTACCGCCGATACGAAAGGTACATCCGATAATGCCT
ACTCCTTCCGTAACGACATTTCAGGCACGGGCGGCCTGATCAAAAAGGC
GGCAGCCAACTGCAACTGCACGGCAACAACACCTATACGGGCAAAACCAT
TATCGAAGGCGGTTCGCTGGTGTTGTACGGCAACAACAAATCGGATATGC
GCGTCGAAACCAAAGGTGCGCTGATTTATAACGGGCGGCATCCGGCGGCA
GCCTGAACAGCGACGGCATTGTCTATCTGGCAGATACCGACCAATCCGGC
GCAAACGAAACCGTACACATCAAAGGCAGTCTGCAGCTGGACGGCAAAGG
TACGCTGTACACACGTTTGGGCAAACTGCTGAAAGTGGACGGTACGGCGA
TTATCGGCGGCAAGCTGTACATGTCGGCACGCGGCAAGGGGGCAGGCTAT
CTCAACAGTACCGGACGACGTGTTCCCTTCCTGAGTGCCGCCAAAATCGG
GCAGGATTATTCTTTCTTCACAAACATCGAAACCGACGGCGGCCTGCTGG
CTTCCCTCGACAGCGTCGAAAAAACAGCGGGCAGTGAAGGCGACACGCTG
TCCTATTATGTCCGTCGCGGCAATGCGGCACGGACTGCTTCGGCAGCGGC
ACATTCCGCGCCCGCCGGTCTGAAACACGCCGTAGAACAGGGCGGCAGCA
ATCTGGAAAACCTGATGGTCGAACTGGATGCCTCCGAATCATCCCATGCG
GAAGGCAGCGTCAACGGCACGCTGATGCAGCTGGGCGCACTGGGCGGTGT
CAACGTTCCGTTTGCCGCAACGGGAGATTTGACGGTCGAAGGCGGTCTGC
GCTACGACCTGCTCAAACAGGATGCATTCGCCGAAAAAGGCAGTGCTTTG
GGCTGGAGCGGCAACAGCCTCACTGAAGGCACGCTGGTCGGACTCGCGGG
TCTGAAGCTGTCGCAACCCTTGAGCGATAAAGCCGTCCTGTTTGCAACGG
CGGGCGTGGAACGCGACCTGAACGGACGCGACTACACGGTAACGGGCGGC
TTTACCGGCGCGACTGCAGCAACCGGCAAGACGGGGGCACGCAATATGCC
GCACACCCGTCTGGTTGCCGGCCTGGGCGCGGATGTCGAATTCGGCAACG
GCTGGAACGGCTTGGCACGTTACAGCTACGCCGGTTCCAAACAGTACGGC
AACCACAGCGGACGAGTCGGCGTAGGCTACCGGTTCCTCGAGGGTGGCGG
AGGCACTGGATCCGCCACAAACGACGACGATGTTAAAAAAGCCACTGTGG
CCATTGCTGCTGCCTACAACAATGGCCAAGAAATCAACGGTTTCAAAGCT
GGAGAGACCATCTACGACATTGATGAAGACGGCACAATTACCAAAAAGA
CGCAACTGCAGCCGATGTTGAAGCCGACGACTTTAAAGGTCTGGGTCTGA
AAAAAGTCGTGACTAACCTGACCAAAACCGTCAATGAAAACAAACAAAAC
GTCGATGCCAAAGTAAAAGCTGCAGAATCTGAAATAGAAAAGTTAACAAC
```

-continued

```
CAAGTTAGCAGACACTGATGCCGCTTTAGCAGATACTGATGCCGCTCTGG
ATGCAACCACCAACGCCTTGAATAAATTGGGAGAAAATATAACGACATTT
GCTGAAGAGACTAAGACAAATATCGTAAAAATTGATGAAAAATTAGAAGC
CGTGGCTGATACCGTCGACAAGCATGCCGAAGCATTCAACGATATCGCCG
ATTCATTGGATGAAACCAACACTAAGGCAGACGAAGCCGTCAAAACCGCC
AATGAAGCCAAACAGACGGCCGAAGAAACCAAACAAAACGTCGATGCCAA
AGTAAAAGCTGCAGAAACTGCAGCAGGCAAAGCCGAAGCTGCCGCTGGCA
CAGCTAATACTGCAGCCGACAAGGCCGAAGCTGTCGCTGCAAAAGTTACC
GACATCAAAGCTGATATCGCTACGAACAAAGATAATATTGCTAAAAAAGC
AAACAGTGCCGACGTGTACACCAGAGAAGAGTCTGACAGCAAATTTGTCA
GAATTGATGGTCTGAACGCTACTACCGAAAAATTGGACACACGCTTGGCT
TCTGCTGAAAAATCCATTGCCGATCACGATACTCGCCTGAACGGTTTGGA
TAAAACAGTGTCAGACCTGCGCAAAGAAACCCGCCAAGGCCTTGCAGAAC
AAGCCGCGCTCTCCGGTCTGTTCCAACCTTACAACGTGGGTCGGTTCAAT
GTAACGGCTGCAGTCGGCGGCTACAAATCCGAATCGGCAGTCGCCATCGG
TACCGGCTTCCGCTTTACCGAAAACTTTGCCGCCAAAGCAGGCGTGGCAG
TCGGCACTTCGTCCGGTTCTTCCGCAGCCTACCATGTCGGCGTCAATTAC
GATGGCTCGAGCACCACCACCACCACTGA
```

(SEQ ID NO: 22)
```
   1 MTSAPDFNAG GTGIGSNSRA TTAKSAAVSY AGIKNEMCKD RSMLCAGRDD
  51 VAVTDRDAKI NAPPPNLHTG DFPNPNDAYK NLINLKPAIE AGYTGRGVEV
 101 GIVDTGESVG SISFPELYGR KEHGYNENYK NYTAYMRKEA PEDGGGKDIE
 151 ASFDDEAVIE TEAKPTDIRH VKEIGHIDLV SHIIGGRSVD GRPAGGIAPD
 201 ATLHIMNTND ETKNEMMVAA IRNAWVKLGE RGVPIVNNSF GTTSRAGTAD
 251 LFQIANSEEQ YRQALLDYSG GDKTDEGIRL MQQSDYGNLS YHIRNKNMLF
 301 IFSTGNDAQA QPNTYALLPF YEKDAQKGII TVAGVDRSGE KFKREMYGEP
 351 GTEPLEYGSN HCGITAMWCL SAPYEASVRF TRTNPIQIAG TSFSAPIVTG
 401 TAALLLQKYP WMSNDNLRTT LLTTAQDIGA VGVDSKFGWG LLDAGKAMNG
 451 PASFPFGDFT ADTKGTSDIA YSFRNDISGT GGLIKKGGSQ LQLHGNNTYT
 501 GKTIIEGGSL VLYGNNKSDM RVETKGALIY NGAASGGSLN SDGIVYLADT
 551 DQSGANETVH IKGSLQLDGK GTLYTRLGKL LKVDGTAIIG GKLYMSARGK
 601 GAGYLNSTGR RVPFLSAAKI GQDYSFFTNI ETDGGLLASL DSVEKTAGSE
 651 GDTLSYYVER GNAARTASAA AHSAPAGLKH AVEQGGSNLE NLMVELDASE
 701 SSATPETVET AAADRTDMPG IRPYGATFRA AAVQHANAA DGVRIFNSLA
 751 ATVYADSTAA HADMQGRRLK AVSDGLDHNG TGLRVIAQTQ QDGGTWEQGG
 801 VEGKMRGSTQ TVGIAAKTGE NTTAAATLGM GRSTWSENSA NAKTDSISLF
 851 AGIRHDAGDI GYLKGLFSYG RYKNSISRST GADEHAEGSV NGTLMQLGAL
 901 GGVNVPFAAT GDLTVEGGLR YDLLKQDAFA EKGSALGWSG NSLTEGTLVG
 951 LAGLKLSQPL SDKAVLFATA GVERDLNGRD YTVTGGFTGA TAATGKTGAR
1001 NMPHTRLVAG LGADVEFGNG WNGLARYSYA GSKQYGNHSG RVGVGYRFLE
1051 GGGGTGSATN DDDVKKAATV AIAAAYNNGQ EINGFKAGET IYDIDEDGTI
```

-continued

```
1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVKTANEA KQTAEETKQN

1251 VDAKVKAAET AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGRFNVTA AVGGYKSESA

1401 VAIGTGFRFT ENFAAKAGVA VGTSSGSSAA YHVGVNYEWL EHHHHHH*
```

ΔG983-961c
(SEQ ID NO: 23)

```
ATGACTTCTGCGCCCGACTTCAATGCAGGCGGTACCGGTATCGGCAGCAA
CAGCAGAGCAACAACAGCGAAATCAGCAGCAGTATCTACGCCGGTATCAA
GAACGAAATGTGCAAAGACAGAAGCATGCTCTGTGCCGGTCGGGATGACG
TTGCGGTTACAGACAGGGATGCCAAAATCAATGCCCCCCCCCCGAATCTG
CATACCGGAGACTTTCCAAACCCAAATGACGCATACAAGAATTTGATCAA
CCTCAAACCTGCAATTGAAGCAGGCTATACAGGACGCGGGGTAGAGGTAG
GTATCGTCGACACAGGCGAATCCGTCGGCAGCATATCCTTTCCCGAACTG
TATGGCAGAAAAGAACACGGCTATAACGAAAATTACAAAAACTATACGGC
GTATATGCGGAAGGAAGCGCCTGAAGACGGAGGCGGTAAAGACATTGAAG
CTTCTTTCGACGATGAGGCCGTTATAGAGACTGAAGCAAAGCCGACGGAT
ATCCGCCACGTAAAAGAAATCGGACACATCGATTTGGTCTCCCATATTAT
TGGCGGGCGTTCCGTGGACAGCAGACCTGCAGGCGGTATTGCGCCCGATG
CGACGCTACACATAATGAATACGAATGATGAAACCAAGAACGAAATGATG
GTTGCAGCCATCCGCAATGCATGGGTCAAGCTGGGCGAACGTGGCGTGCG
CATCGTCAATAACAGTTTTGGACAACATCGAGGGCAGGCACTGCCGACCT
TTTCCAAATAGCCAATTCGGAGGAGCAGTACCGCCAAGCGTTGCTCGACT
ATTCCGGCGGTGATAAAACAGACGAGGGTATCCGCCTGATGCAACAGAGC
GATTACGGCAACCTGTCCTACCACATCCGTAATAAAAACATGCTTTTCAT
CTTTTCGACAGGCAATGACGCACAAGCTCAGCCCAACACATATGCCCTAT
TGCCATTTTATGAAAAAGACGCTCAAAAAGGCATTATCACAGTCGCAGGC
GTAGACCGCAGTGGAGAAAGTTCAAACGGGAAATGTATGGAGAACCGGGT
ACAGAACCGCTTGAGTATGGCTCCAACCATTGCGAATTACTGCCATGTGG
TGCCTGTCGGCACCCTATGAAGCAAGCGTCCGTTTCACCCGTACAAACCC
GATTCAAATTGCCGGAACATCCTTTTCCGCACCCATCGTAACCGGCACGG
CGGCTCTGCTGCTGCAGAAATACCCGTGGATGAGCAACGACAACCTGCGT
ACCACGTTGCTGACGACGGCTCAGGACATCGGTGCAGTCGGCGTGGACAG
CAAGTTCGGCTGGGGACTGCTGGATGCGGGTAAGGCCATGAACGGACCCG
CGTCCTTTCCGTTCGGCGACTTTACCGCCGATACGAAAGGTACATCCGAT
ATTGCCTACTCCTTCCGTAACGACATTTCAGGCACGGGCGGCCTGATCAA
AAAGGCGGCAGCCAACTGCAACTGCACGGCAACAACACCTATACGGGCAA
AACCATTATCGAAGGCGGTTCGCTGGTGTTGTACGGCAACAAATCGGATA
TGCGCGTCGAAACCAAAGGTGCGCTGATTTATAACGGGGCGGCATCCGGC
```

-continued

```
GGCAGCCTGAACAGCGACGGCATTGTCTATCTGGCAGATACCGACCAATC

CGGCGCAAACGAAACCGTACACATCAAAGCAGTCTGCAGCTGGACGGCAA

AGGTACGCTGTACACACGTTTGGGCAAACTGCTGAAAGTGGACGGTACGG

CGATTATCGGCGGCAAGCTGTACATGTCGGCACGCGGCAAGGGGCAGGC

TATCTCAACAGTACCGGACGACGTGTTCCCTTCCTGAGTGCCGCCAAAAT

CGGGCAGGATTATTCTTTCTTCACAAACATCGAAACCGACGGCGGCCTGC

TGGCTTCCCTCGACAGCGTCGAAAAAACAGCGGGCAGTGAAGGCGACACG

CTGTCCTATTATGTCCGTCGCGGCAATGCGGCACGGACTGCTTCGGCAGC

GGCACATTCCGCGCCCGCCGGTCTGAAACACGCCGTAGAACAGGGCGGCA

GCAATCTGGAAACCTGATGGTCGAACTGGATGCCTCCGAATCATCCGCAA

CACCCGAGACGGTTGAAACTGCGGCAGCCGACCGCACAGATATGCCGGGC

ATCCGCCCCTACGGCGCAACTTTCCGCGCAGCGGCAGCCGTACAGCATGC

GAATGCCGCCGACGGTGTACGCATCTTCAACAGTCTCGCCGCTACCGTCT

ATGCCGACAGTACCGCCGCCCATGCCGATATGCAGGGACGCCGCCTGAAA

GCCGTATCGGACGGGTTGGACCACAACGGCACGGGTCTGCGCGTCATCGC

GCAAACCCAACAGGACGGTGGAACGTGGGAACAGGGCGGTGTTGAAGGCA

AAATGCGCGGCAGTACCCAAACCGTCGGCATTGCCGCGAAAACCGGCGAA

AATACGACAGCAGCCGCCACACTGGGCATGGGACGCAGCACATGGAGCGA

AAACATGTCAAATGCAAAAACCGACAGCATTAGTCTGTTTGCAGGCATAC

GGCACGATGCGGGCGATATCGGCTATCTCAAAGGCCTGTTCTCCTACGGA

CGCTACAAAAACAGCATCAGCCGCAGCACCGGTGCGGACGAACATGCGGA

AGGCAGCGTCAACGGCACGCTGATGCAGCTGGGCGCACTGGGCGGTGTCA

ACGTTCCGTTTGCCGCAACGGGAGATTTGACGGTCGAAGGCGGTCTGCGC

TACGACCTGCTCAAACAGGATGCATTCGCCGAAAAAGGCAGTGCTTTGGG

CTGGAGCGGCAACAGCCTCACTGAAGGCACGCTGGTCGGACTCGCGGGTC

TAGCTGTCGAACCCTTGAGCGATAAAGCCGTCCTGTTTGCAACGGCGGGC

GTGGAACGCGACCTGAACGGACGCGACTACACGGTAACGGGCGGCTTTAC

CGGCGCGACTGCAGCAACCGGCAAGACGGGGGCACGCAATATGCCGCACA

CCCGTCTGGTTGCCGGCCTGGGCGCGGATGTCGAATTCGGCAACGGCTGG

AACGGCTTGGCACGTTACAGCTACGCCGGTTCCAAACAGTACGGCAACCA

CAGCGGACGAGTCGGCGTAGGCTACCGGTTCCTCGAGGGTGGCACTGGAT

CCGCCACAAACGACGACGATGTTAAAAAAGCTGCCACTGTGGCCATTGCT

GCTGCCTACAACAATGGCCACAAGAAATCAACGGTTTCAAAGCTGGAGAG

ACCATCTACGACATTGATGAAGACGGCACAATTACCAAAAAAGACGCAAC

TGCAGCCGATGTTGAAGCCGACGACTTTAAAGGTCTGGGTCTGAAAAAAG

TCGTGACTAACCTGACCAAAACCGTCAATGAAACAAACAAAACGTCGAT

GCCAAAGTAAAAGCTGCAGAATCTGAAATAGAAAAGTTAACAACCAAGTT

AGCAGACACTGATGCCGCTTTAGCAGATACTGATGCCGCTCTGGATGCAA

CCACCAACGCCTTGAATAAATTGGGAGAAAATATAACGACATTTGCTGAA

GAGACTAAGACAAATATCGTAAAAATTGATGAAAAATTAGAAAGCCGTGG

CTGATACCGTCGACAAGCATGCCGAAGCATTCAACGATATCGCCGATTCA
```

-continued

```
TTGGATGAAACCAACACTAAGGCAGACGAAGCCGTCAAAACCGCCAATGA
AGCCAAACAGACGGCCGAAGAAACCAAACAAAACGTCGATGCCAAAGTAA
AAGCTGCAGAAACTGCAGCAGGCAAAGCCGAAGCTGCCGCTGGCACAGCT
AATACTGCAGCCGACAAGGCCGAAGCTGTCGCTGCAAAAGTTACCGACAT
CAAAGCTGATATCGCTACGAACAAAGATAATATTGCTAAAAAAGCAAACA
GTGCCGACGTGTACACCAGAGAAGAGTCTGACAGCAAATTTGTCAGAATT
GATGGTCTGAACGCTACTACCGAAAAATTGGACACACGCTTCTGCTGAAA
AATCCATTGCCGATCACGATACTCGCCTGAACGGTTTGGATAAAACAGTG
TCAGACCTGCGCAAAGAAACCCGCCAAGGCCTTGCAGAACAAGCCGCGCT
CTCCGGTCTGTTCCAACCTTACAACGTGGGTCTCGAGCACCACCACCACC
ACCACTGA
```

```
                                               (SEQ ID NO: 24)
   1 MTSAPDFNAG GTGIGSNSRA TTAKSAAVSY AGIKNEMCKD RSMLCAGRDD

51 VAVTDRDAKI NAPPPNLHTG DFPNPNDAYK NLINLKPAIE AGYTGRGVEV

101 GIVDTGESVG SISFPELYGR KEHGYNENYK NYTAYMRKEA PEDGGGKDIE

151 ASFDDEAVIE TEAKPTDIRH VKEIGHIDLV SHIIGGRSVD GRPAGGIAPD

201 ATLHIMNTND ETKNEMMVAA IRNAWVKLGE RGVPIVNNSF GTTSRAGTAD

251 LFQIANSEEQ YRQALLDYSG GDKTDEGIRL MQQSDYGNLS YHIRNKNMLF

301 IFSTGNDAQA QPNTYALLPF YEKDAQKGII TVAGVDRSGE KFKREMYGEP

351 GTEPLEYGSN HCGITAMWCL SAPYEASVRF TRTNPIQIAG TSFSAPIVTG

401 TAALLLQKYP WMSNDNLRTT LLTTAQDIGA VGVDSKFGWG LLDAGKAMNG

451 PASFPFGDFT ADTKGTSDIA YSFRNDISGT GGLIKKGGSQ LQLHGNNTYT

501 GKTIIEGGSL VLYGNNKSDM RVETKGALIY NGAASGGSLN SDGIVYLADT

551 DQSGANETVH IKGSLQLDGK GTLYTRLGKL LKVDGTAIIG GKLYMSARGK

601 GAGYLNSTGR RVPFLSAAKI GQDYSFFTNI ETDGGLLASL DSVEKTAGSE

651 GDTLSYYVER GNAARTASAA AHSAPAGLKH AVEQGGSNLE NLMVELDASE

701 SSATPETVET AAADRTDMPG IRPYGATFRA AAAVQHANAA DGVRIFNSLA

751 ATVYADSTAA HADMQGRRLK AVSDGLDHNG TGLRVIAQTQ QDGGTWEQGG

801 VEGKMRGSTQ TVGIAAKTGE NTTAAATLGM GRSTWSENSA NAKTDSISLF

851 AGIRHDAGDI GYLKGLFSYG RYKNSISRST GADEHAEGSV NGTLMQLGAL

901 GGVNVPFAAT GDLTVEGGLR YDLLKQDAFA EKGSALGWSG NSLTEGTLVG

951 LAGLKLSQPL SDKAVLFATA GVERDLNGRD YTVTGGFTGA TAATGKTGAR

1001 NMPHTRLVAG LGADVEFGNG WNGLARYSYA GSKQYGNHSG RVGVGYRFLE

1051 GGGGTGSATN DDDVKKAATV AIAAAYNNGQ EINGFKAGET IYDIDEDGTI

1101 TKKDATAADV EADDFKGLGL KKVVTNLTKT VNENKQNVDA KVKAAESEIE

1151 KLTTKLADTD AALADTDAAL DATTNALNKL GENITTFAEE TKTNIVKIDE

1201 KLEAVADTVD KHAEAFNDIA DSLDETNTKA DEAVKTANEA KQTAEETKQN

1251 VDAKVKAAET AAGKAEAAAG TANTAADKAE AVAAKVTDIK ADIATNKDNI

1301 AKKANSADVY TREESDSKFV RIDGLNATTE KLDTRLASAE KSIADHDTRL

1351 NGLDKTVSDL RKETRQGLAE QAALSGLFQP YNVGLEHHHH HH*
```

Example 4

Hybrids of ΔG741

Protein 741 has the following sequence (SEQ ID NO: 25):

```
  1 VNRTAFCCLS LTTALILTAC SSGGGGVAAD IGAGLADALT APLDHKDKGL

51 QSLTLDQSVR KNEKLKLAAQ GAEKTYGNGD SLNTGKLKND KVSEFDFIRQ

101 IEVDGQLITL ESGEFQVYKQ SHSALTAFQT EQIQDSEHSG KMVAKRQFRI

151 GDIAGEHTSF DKLPEGGRAT YRGTAFGSDD AGGKLTYTID FAAKQGNGKI

201 EHLKSPELNV DLAAADIKPD GKRHAVISGS VLYNQAEKGS YSLGIFGGKA

251 QEVAGSAEVK TVNGIRHIGL AAKQ*
```

ΔG741 thus has the following basic sequence (SEQ ID NO: 26):

```
                     VAAD IGAGLADALT APLDHKDKGL
QSLTLDQSVR KNEKLKLAAQ GAEKTYGNGD SLNTGKLKND KVSEFDFIRQ
IEVDGQLITL ESGEFQVYKQ SHSALTAFQT EQIQDSEHSG KMVAKRQFRI
GDIAGEHTSF DKLPEGGRAT YRGTAFGSDD AGGKLTYTID FAAKQGNGKI
EHLKSPELNV DLAAADIKPD GKRHAVISGS VLYNQAEKGS YSLGIFGGKA
QEVAGSAEVK TVNGIRHIGL AAKQ*
```

ΔG741 was fused directly in-frame upstream of proteins 961, 961c, 983 and ORF46.1:

ΔG741-961

(SEQ ID NO: 27)

```
ATGGTCGCCGCCGACATCGGTGCGGGGCTTGCCGATGCACTAACCGCACC

GCTCGACCATAAAGACAAAGGTTTGCAGTCTTTGACGCTGGATCAGTCCG

TCAGGAAAAACGAGAAACTGAAGCTGGCGGCACAAGGTGCGGAAAAAACT

TATGGAAACGGTGACAGCCTCAATACGGGCAAATTGAAGAACGACAAGGT

CAGCCGTTTCGACTTTATCCGCCAAATCGAAGTGGACGGGCAGCTCATTA

CCTTGGAGAGTGGAGAGTTCCAAGTATACAAACAAAGCCATTCCGCCTTA

ACCGCCTTTCAGACCGAGCAAATACAAGATTCGGAGCATTCCGGGAAGAT

GGTTGCGAAACGCCAGTTCAGAATCGGCGACATAGCGGGCGAACATACAT

CTTTTGACAAGCTTCCCGAAGGCGGCAGGGCGACATATCGCGGGACGGCG

TTCGGTTCAGACGATGCCGGCGGAAAACTGACCTACACCATAGATTTCGC

CGCCAAGCAGGGAAACGGCAAAATCGAACATTTGAAATCGCCAGAACTCA

ATGTCGACCTGGCCGCCGCCGATATCAAGCCGGATGGAAAACGCCATGCC

GTCATCAGCGGTTCCGTCCTTTACAACCAAGCCGAGAAAGGCAGTTACTC

CCTCGGTATCTTTGGCGGAAAAGCCCAGGAAGTTGCCGGCAGCGCGGAAG

TGAAAACCGTAAACGGCATACGCCATATCGGCCTTGCCGCCAAGCAACTC

GAGGGTGGCGGAGGCACTGGATCCGCCACAAACGACGACGATGTTAAAAA

AGCTGCCACTGTGGCCATTGCTGCTGCCTACAACAATGGCCAAGAAATCA

ACGGTTTCAAGCTGGAGAGACCATCTACGACATTGATGAAGACGGCACAT

TACCAAAAAAGACGCAACTGCAGCCGATGTTGAAGCCGACGACTTTAAAG

GTCTGGGTCTGAAAAAAGTCGTGACTAACCTGACCAAAACCGTCAATGAA

AACAAACAAAACGTCGATGCCAAAGTAAAAGCTGCAGAATCTGAAATAGA

AAAGTTAACAACCAAGTTAGCAGACACTGATGCCGCTTTAGCAGATACTG
```

-continued

```
ATGCCGCTCTGGATGCAACCACCAACGCCTTGAATAAATTGGGAGAAAAT

ATAACGACATTTGCTGAAGAGACTAAGACAAATATCGTAAAAATTGATGA

AAAATTAGAAGCCGTGGCTGATACCGTCGACAAGCATGCCGAAGCATTCA

ACGATATCGCCGATTCATTGGATGAAACCAACACTAAGGCAGACGAAGCC

GTCAAAACCGCCAATGAAGCCAAACAGACGGCCGAAGAAACCAAACAAAA

CGTCGATGCCAAAGTAAAAGCTGCAGAAACTGCAGCAGGCAAAGCCGAAG

CTGCCGCTGGCACAGCTAATACTGCAGCCGACAAGGCCGAAGCTGTCGCT

GCAAAAGTTACCGACATCAAAGCTGATATCGCTACGAACAAAGATAATAT

TGCTAAAAAAGCAAACAGTGCCGACGTGTACACCAGAGAAGAGTCTGACA

GCAAATTTGTCAGAATTATGGTCTGAACGCTACTACCGAAAAATTGGACA

CACGCTTGGCTTCTGCTGAAAAATCCATTGCCGATCACGATACTCGCCTG

AACGGTTTGGATAAAACAGTGTCAGACCTGCGCAAAGAAACCCGCCAAGG

CCTTGCAGAACAAGCCGCGCTCTCCGGTCTGTTCCAACCTTACAACGTGG

GTCGGTTCAATGTAACGGCTGCAGTCGGCGGCTACAAATCCGAATCGGCG

GCAGTCGCCATCGGTACCGGCTTCCGCTTTACCGAAAACTTTGCCGCCAA

AGCAGGCGTGGCAGTCGGCACTTCGTCCGGTTCTTCCGCAGCCTACCATG

TCGGCGTCAATTACGAGTGGCTCGAGCACCACCACCACCACCACTGA
```

(SEQ ID NO: 28)
```
  1 MVAADIGAGL ADALTAPLDH KDKGLQSLTL DQSVRKNEKL KLAAQGAEKT

51 YGNGDSLNTG KLKNDKVSPF DFIRQIEVDG QLITLESGEF QVYKQSHSAL

101 TAFQTEQIQD SEHSGKMVAK RQFRIGDIAG EHTSFDKLPE GGRATYRGTA

151 FGSDDAGGKL TYTIDFAAKQ GNGKIEHLKS PELNVDLAAA DIKPDGKRHA

201 VISGSVLYNQ AEKGSYSLGI FGGKAQEVAG SAEVKTVNGI RHIGLAAKQL

251 EGGGGTGSAT NDDDVKKAAT VAIAAAYNNG QEINGFKAGE TIYDIDEDGT

301 ITKKDATAAD VEADDFKGLG LKKVVTNLTK TVNENKQNVD AKVKAAESEI

351 EKLTTKLADT DAALADTDAA LDATTNALNK LGENITTFAE ETKTNIVKID

401 EKLEAVADTV DKHAEAFNDI ADSLDETNTK ADEAVKTANE AKQTAEETKQ

451 NVDAKVKAAE TAAGKAEAAA GTANTAADKA EAVAAKVTDI KADIATNKDN

501 IAKKANSADV YTREESDSKF VRIDGLNATT EKLDTRLASA EKSIADHDTR

551 LNGLDKTVSD LRKETRQGLA EQAALSGLFQ PYNVGRFNVT AAVGGYKSES

601 AVAIGTGFRF TENFAAKAGV AVGTSSGSSA AYHVGVNYEW LEHHHHHH*
```

ΔG741-961c (SEQ ID NO: 29)
```
ATGGTCGCCGCCGACATCGGTGCGGGGCTTGCCGATGCACTAACCGCACC

GCTCGACCATAAAGACAAAGGTTTGCAGTCTTTGACGCTGGATCAGTCCG

TCAGGAAAAACGAGAAACTGAAGCTGGCGGCACAAGGTGCGGAAAAAACT

TATGGAAACGGTGACAGCCTCAATACGGGCAATTGAGAACGACAAGGTCA

GCCGTTTCGACTTTATCCGCCAAATCGAAGTGGACGGGCAGCTCATTACC

TTGGAGAGTGGAGAGTTCCAGTATACAAACAAAGCCATTCCGCCTTAACC

GCCTTTCAGACCGAGCAAATACAAGATTCGGAGCATTCCGGGAAGATGGT

TGCGAAACGCCAGTTCAGAATCGGCGACATAGCGGGCGAACATACATCTT

TTGACAAGCTTCCCGAAGGCGGCAGGGCGACATATCGCGGGACGGCGTTC
```

-continued

```
GGTTCAGACGATGCCGGCGGAAAACTGACCTACACCATAGATTTCGCCGC

CAAGCAGGGAAACGGCAAAATCGAACATTTGAAATCGCCAGAACTCAATG

TCGACCTGGCCGCCGCCGATATCAAGCCGGATGGAAAACGCCATGCCGTC

ATCAGCGGTTCCGTCCTTTACAACCAAGCCGAGAAAGGCAGTTACTCCCT

CGGTATCTTTGGCGGAAAAGCCCAGGAAGTTGCCGGCAGCGCGGAAGTGA

AAACCGTAAACGGCATACGCCATATCGGCCTTGCCGCCAAGCAACTCGAG

GGTGGCGGAGGCACTGGATCCGCCACAAACGACGACGATGTTAAAAAAGC

TGCCACTGTGGCCATTGCTGCTGCCTACAACAATGGCCAAGAAATCAACG

GTTTCAAAGCTGGAGAGACCATCTACGACATTGATGAAGACGGCACAATT

ACCAAAAAAGACGCAACTGCAGCCGATGTTGAAGCCGACGACTTTAAAGG

TCTGGGTCTGAAAAAAGTCGTGACTAACCTGACCAAAACCGTCAATGAAA

ACAAACAAAACGTCGATGCCAAAGTAAAAGCTGCAGAATCTGAAATAGAA

AAGTTAACAACCAAGTTAGCAGACACTGATGCCGCTTTAGCAGATACTGA

TGCCGCTCTGGATGCAACCACCAACGCCTTGAATAAATTGGGAGAAAATA

TAACGACATTTGCTGAAGAGACTAAGACAAATATCGTAAAAATTGATGAA

AAATTAGAAGCCGTGGCTGATACCGTCGACAAGCATGCCGAAGCATTCAA

CGATATCGCCGATTCATTGGATGAAACCAACACTAAGGCAGACGAAGCCG

TCAAAACCGCCAATGAAGCCAAACAGACGGCCGAAGAAACCAAACAAAAC

GTCGATGCCAAAGTAAAAGCTGCAGAAACTGCAGCAGGCAAAGCCGAAGC

TGCCGCTGGCACAGCTAATACTCAGCCGACAAGGCCGAAGCTGTCGCTGC

AAAAGTTACCGACATCAAAGCTGATATCGCTACGAACAAAGATAATATTG

CTAAAAAAGCAAACAGTGCCGACGTGTACACCAGAGAAGAGTCTGACAGC

AAATTTGTCAGAATTGATGGTCTGAACGCTACTACCGAAAAATTGGACAC

ACGCTTGGCTGCTGAAAAATCCATTGCCGATCACGATACTCGCCTGAACG

GTTTGGATAAAACAGTGTCAGACCTCCGCGCAAAGAAACCCGCCAAGGCC

TTGCAGAACAAGCCGCGCTCTCCGGTCTGTTCCAACCTTACAACGTGGGT

CTCGAGCACCACCACCACCACCACTGA
```

```
                                                  (SEQ ID NO: 30)
  1 MVAADIGAGL ADALTAPLDH KDKGLQSLTL DQSVRKNEKL KLAAQGAEKT

51 YGNGDSLNTG KLKNDKVSPF DFIRQIEVDG QLITLESGEF QVYKQSHSAL

101 TAFQTEQIQD SEHSGKMVAK RQFRIGDIAG EHTSFDKLPE GGRATYRGTA

151 FGSDDAGGKL TYTIDFAAKQ GNGKIEHLKS PELNVDLAAA DIKPDGKRHA

201 VISGSVLYNQ AEKGSYSLGI FGGKAQEVAG SAEVKTVNGI RHIGLAAKQL

251 EGGGGTGSAT NDDDVKKAAT VAIAAAYNNG QEINGFKAGE TIYDIDEDGT

301 ITKKDATAAD VEADDFKGLG LKKVVTNLTK TVNENKQNVD AKVKAAESEI

351 EKLTTKLADT DAALADTAA LDATTNALNK LGENITTFAE ETKTNIVKID

401 EKLEAVADTV DKHAEAFNDI ADSLDETNTK ADEAVKTANE AKQTAEETKQ

451 NVDAKVKAAE TAAGKAEAAA GTANTAADKA EAVAAKVTDI KADIATNKDN
```

-continued

```
501 IAKKANSADV YTREESDSKF VRIDGLNATT EKLDTRLASA EKSIADHDTR

551 LNGLDKTVSD LRKETRQGLA EQAALSGLFQ PYNVGLEHHH HHH*
```

ΔG741-983

(SEQ ID NO: 31)

```
ATGGTCGCCGCCGACATCGGTGCGGGGCTTGCCGATGCACTAACCGCACC

GCTCGACCATAAAGACAAAGGTTTGCAGTCTTTGACGCTGGATCAGTCCG

TCAGGAAAAACGAGAAACTGAAGCTGGCGGCACAAGGTGCGGAAAAAACT

TATGGAAACGGTGACAGCCTCAATACGGGCAATTGAGAACGACAAGGTCA

GCCGTTTCGACTTTATCCGCCAAATCGAAGTGGACGGGCAGCTCATTACC

TTGGAGAGTGGAGAGTTCCAGTATACAAACAAAGCCATTCCGCCTTAACC

GCCTTTCAGACCGAGCAAATACAAGATTCGGAGCATTCCGGGAAGATGGT

TGCGAAACGCCAGTTCAGAATCGGCGACATAGCGGGCGAACATACATCTT

TTGACAAGCTTCCCGAAGGCGGCAGGGCGACATATCGCGGGACGGCGTTC

GGTTCAGACGATGCCGGCGGAAAACTGACCTACACCATAGATTTCGCCGC

CAAGCAGGGAAACGGCAAAATCGAACATTTGAAATCGCCAGAACTCAATG

TCGACCTGGCCGCCGCCGATATCAAGCCGGATGGAAAACGCCATGCCGTC

ATCAGCGGTTCCGTCCTTTACAACCAAGCCGAGAAAGGCAGTTACTCCCT

CGGTATCTTTGGCGGAAAAGCCCAGGAAGTTGCCGGCAGCGCGGAAGTGA

AAACCGTAAACGGCATACGCCATATCGGCCTTGCCGCCAAGCAACTCGAG

GGATCCGCCGGAGGCGGCACTTCTGCGCCCGACTTCATGCAGGCGGTACC

GGTATCGGCAGCAACAGCAGAGCAACAACAGCGAAATCAGCAGCAGTATC

TTACGCCGGTATCAAGAACGAAATGTGCAAAGACAGAAGCATGCTCTGTG

CCGGTCGGGATGACGTTGCGGTTACAGACAGGGATGCCAAAATCATGCCC

CCCCCCCGAATCTGCATACCGGAGACTTTCCAAACCCAAATGAVGCATAC

AAGAATTTGATCAACCTCAAACCTGCAATTGAAGCAGGCTATACAGGACG

CGGGGTAGAGGTAGGTATCGTCGACACAGGCGAATCCGTCGGCAGCATAT

CCTTTCCCGAACTGTATGGCAGAAAAGAACACGGCTATAACGAAAATTAC

AAAAACTATACGGCGTATATGCGGAAGGAAGCGCCTGAAGACGGAGGCGG

TAAAGACATTGAAGCTTCTTTCGACGATGAGGCCGTTATAGAGACTGAAG

CAAAGCCGACGGATATCCGCCACGTAAAAGAAATCGGACACATCGATTTG

GTCTCCCATATTATTGGCGGGCGTTCCGTGGACGGCAGACCTGCAGGCGG

TATTGCGCCCGATGCGACGCTACACATAATGAATACGAATGATGAAACCA

AGAACGAAATGATGGTTGCAGCCATCCGCAATGCATGGGTCAAGCTGGGC

GAACGTGGCGTGCGCGCATCGTCAATAACAGTTTTGGAACAACATCGAGG

GCAGGCACTGCCGACCTTTTCCAAATAGCCAATTCGGAGGAGCAGTACCG

CCAAGCGTTGCTCGACTATCCGGCGGTGATAAAACAGACGAGGGTATCCG

CCTGATGCAACAGAGCGATTACGGCAACCTGTCCTACCACATCCGTAATA

AAAACATGCTTTTCATCTTTTCGACAGGCAATGACGCACAAGCTCAGCCC

AACACATATGCCCTATTGCCATTTTATGAAAAAGACGCTCAAAAAGGCAT

TATCACAGTCGCAGGCGTAGACCGCAGTGGAGAAAAGTTCAAACGGGAAA

TGTATGGAGAACCGGGTACAGAACCGCTTGAGTATGGCTCCAACCATTGC

GGAATTACTGCCATGTGGTGCCTGTCGGCACCCTATGAAGCAAGCGTCCG
```

-continued

```
TTTCACCCGTACAAACCCGATTCAAATTGCCGGAACATCCTTTTCCGCAC
CCATCGTAACCGGCACGGCGGCTCTGCTGCTGCAGAAATACCCGTGGATG
AGCAACGACAACCTGCGTACCACGTTGCTGACGACGGCTCAGGACATCGG
TGCAGTCGGCGTGGACAGCAAGTTCGGCTGGGACTGCTGGATGCGGGTA
AGGCCATGAACGGACCCGCGTCCTTTCCGTTCGGCGACTTTACCGCCGAT
ACGAAAGGTACATCCGATATTGCCTACTCCTTCCGTAACGACATTTCAGG
CACGGGCGGCCTGATCAAAAAAGGCGGCAGCCAACTGCAACTGCACGGCA
ACAACACCTATACGGGCAAAACCATTATCGAAGGCGGTTCGCTGGTGTTG
TACGGCAACAACAAATCGGATATGCGCGTCGAAACCAAAGGTGCGCTGAT
TTATAACGGGGCGGCATCCGGCGGCAGCCTGAACAGCGACGGCATTGTCT
ATCTGGCAGATACCGACCAATCCGGCGCAAACGAAACCGTACACATCAAA
GGCAGTCTGCAGCTGGACGGCAAAGGTACGCTGTACACACGTTTGGGCAA
ACTGCTGAAAGTGGACGGTACGGCGATTATCGGCGGCAAGCTGTACATGT
CGGCACGCGGCAAGGGGGCAGGCTATCTCAACAGTACCGGACGACGTGTT
CCCTTCCTGAGTGCCGCCAAAATCGGGCAGGATTATTCTTTCTTCACAAA
CATCGAAACCGACGGCGGCCTGCTGGCTTCCCTCGACAGCGTCGAAAAAA
CAGCGGGCAGTGAAGGCGACACGCTGTCCTATTATGTCCGTCGCGGCAAT
GCGGCACGGACTGCTTCGGCAGCGGCACATTCCGCGCCCGCCGGTCTGAA
ACACGCCGTAGAACAGGGCGGCAGCAATCTGGAAAACCTGATGGTCGAAC
TGGATGCCTCCGAATCATCCGCAACACCCGAGACGGTTGAAACTGCGGCA
GCCGACCGCACAGATATGCCGGGCATCCGCCCCTACGGCGCAACTTTCCG
CGCAGCGGCAGCCGTACAGCATGCGAATGCCGCCGACGGTGTACGCATCT
CAACAGTCTCGCCGCTACCGTCTATGCCGACAGTACCGCCGCCCATGCCG
ATATGCAGGGACGCCGCCTGAAAGCCGTATCGGACGGGTTGGACCACAAC
GGCACGGGTCTGCGCGTCATCGCGCAAACCCAACAGGACGGTGGAACGTG
GGAACAGGGCGGTGTTGAAGGCAAAATGCGCGGCAGTACCCAAACCGTCG
GCATTGCCGCGAAAACCGGCGAAAATACGACAGCAGCCGCCACACTGGGC
ATGGGACGCAGCACATGGAGCGAAAACAGTGCAAATGCAAAAACCGACAG
CATTAGTCTGTTTGCAGGCATACGGCACGATGCGGGCGATATCGGCTATC
TCAAAGGCCTGTTCTCCTACGGACGCTACAAAAACAGCATCAGCCGCAGC
ACCGGTGCGGACGAACATGCGGAAGGCAGCGTCAACGGCACGCTGATGCA
GCTGGGCGCACTGGGCGGTGTCAACGTTCCGTTTGCCGCAACGGGAGATT
TGACGGTCGAAGGCGGTCTGCGCTACGACCTGCTCAAACAGGATGCATTC
GCCGAAAAAGGCAGTGCTTTGGGCTGGAGCGGCAACAGCCTCACTGAAGG
CACGCTGGTCGGACTCGCGGGTCTGAAGCTGTCGCAACCCTTGAGCGATA
AAGCCGTCCTGTTTGCAACGGCGGGCGTGGAACGCGACCTGAACGGACGC
GACTACACGGTAACGGGCGGCTTTACCGGCGCGACTGCAGCAACCGGCAA
GACGGGGGCACGCAATATGCCGCACACCCGTCTGGTTGCCGGCCTGGGCG
```

-continued
CGGATGTCGAATTCGGCAACGGCTGGAACGGCTTGGCACGTTACAGCTAC

GCCGGTTCCAAACAGTACGGCAACCACAGCGGACGAGTCGGCGTAGGCTA

CCGGTTCCTCGAGCACCACCACCACCACCACTGA (SEQ ID NO: 32)
```
   1 MVAADIGAGL ADALTAPLDH KDKGLQSLTL DQSVRKNEKL KLAAQGAEKT

51 YGNGDSLNTG KLKNDKVSPF DFIRQIEVDG QLITLESGEF QVYKQSHSAL

101 TAFQTEQIQD SEHSGKMVAK RQFRIGDIAG EHTSFDKLPE GGRATYRGTA

151 FGSDDAGGKL TYTIDFAAKQ GNGKIEHLKS PELNVDLAAA DIKPDGKRHA

201 VISGSVLYNQ AEKGSYSLGI FGGKAQEVAG SAEVKTVNGI RHIGLAAKQL

251 EGSGGGGTSA PDFNAGGTGI GSNSRATTAK SAAVSYAGIK NEMCKDRSML

301 CAGRDDVAVT DRDAKINAPP PNLHTGDFPN PNDAYKNLIN LKPAIEAGYT

351 GRGVEVGIVD TGESVGSISF PELYGRKEHG YNENYKNYTA YMRKEAPEDG

401 GGKDIEASFD DEAVIETEAK PTDIRHVKEI GHIDLVSHII GGRSVDGRPA

451 GGIAPDATLH IMNTNDETKN EMMVAAIRNA WVKLGERGVR IVNNSFGTTS

501 RAGTADLFQI ANSEEQYRQA LLDYSGGDKT DEGIRLMQQS DYGNLSYHIR

551 NKNMLFIFST GNDAQAQPNT YALLPFYEKD AQKGIITVAG VDRSGEKFKR

601 EMYGEPGTEP LEYGSNHCGI TAMWCLSAPY EASVRFTRTN PIQIAGTSFS

651 APIVTGTAAL LLQKYPWMSN DNLRTTLLTT AQDIGAVGVD SKFGWGLLDA

701 GKAMNGPASF PFGDFTADTK GTSDIAYSFR NDISGTGGLI KKGGSQLQLH

751 GNNTYTGKTI IEGGSLVLYG NNKSDMRVET KGALIYNGAA SGGSLNSDGI

801 VYLADTDQSG ANETVHIKGS LQLDKGTLY TRLGKLLKVD GTAIIGGKLY

851 MSARGKGAGY LNSTGRRVPF LSAAKIGQDY SFFTNIETDG GLLASLDSVE

901 KTAGSEGDTL SYYVERGNAA RTASAAAHSA PAGLKHAVEQ GGSNLENLMV

951 ELDASESSAT PETVETAAAD RTDMPGIRPY GATFRAAAAV QHANAADGVR

1001 IFNSLAATVY ADSTAAHADM QGRRLKAVSD GLDHNGTGLR VIAQTQQDGG

1051 TWEQGGVEGK MRGSTQTVGI AAKTGENTTA AATLGMGRST WSENSANAKT

1101 DSISLFAGIR HDAGDIGYLK GLFSYGRYKN SISRSTGADE HAEGSVNGTL

1151 MQLGALGGVN VPFAATGDLT VEGGLRYDLL KQDAFAEKGS ALGWSGNSLT

1201 EGTLVQLAGL KLSQPLSDKA VLFATAGVER DLNGRDYTVT GGFTGATAAT

1251 GKTGARNMPH TRLVAGLGAD VEFGNGWNGL ARYSYAGSKQ YGNHSGRVGV

1301 GYRFLEHHHH HH*
```

ΔG741-ORF46.1
(SEQ ID NO: 33)
ATGGTCGCCGCCGACATCGGTGCGGGCTTGCCGATGCACTAACCGCACC

GCTCGACCATAAAGACAAAGGTTTGCAGTCTTTGACGCTGGATCAGTCCG

TCAGGAAAAACGAGAAACTGAAGCTGGCGGCACAAGGTGCGGAAAAAACT

TATGGAAACGGTGACAGCCTCAATACGGGCAATTGAGAACGACAAGGTCA

GCCGTTTCGACTTTATCCGCCAAATCGAAGTGGACGGGCAGCTCATTACC

TTGGAGAGTGGAGAGTTCCAGTATACAAACAAAGCCATTCCGCCTTAACC

GCCTTTCAGACCGAGCAAATACAAGATTCGGAGCATTCCGGGAAGATGGT

TGCGAAACGCCAGTTCAGAATCGGCGACATAGCGGGCGAACATACATCTT

TTGACAAGCTTCCCGAAGGCGGCAGGGCGACATATCGCGGGACGGCGTTC

```
GGTTCAGACGATGCCGGCGGAAAAACTGACCTACACCATAGATTTCGCCGC

CAAGCAGGGAAACGGCAAAATCGAACATTTGAAATCGCCAGAACTCAATG

TCGACCTGGCCGCCGCCGATATCAAGCCGGATGGAAAACGCCATGCCGTC

ATCAGCGGTTCCGTCCTTTACAACCAAGCCGAGAAAGGCAGTTACTCCCT

CGGTATCTTTGGCGGAAAAGCCCAGGAAGTTGCCGGCAGCGCGGAAGTGA

AAACCGTAAACGGCATACGCCATATCGGCCTTGCCGCCAAGCAACTCGAC

GGTGGCGGAGGCACTGGATCCTCAGATTTGGCAAACGATTCTTTTATCCG

GCAGGTTCTCGACCGTCCAGCATTTCGAACCCGACGGGAAATACCACCTA

TTCGGCAGCAGGGGGGAACTTGCCGAGCGCAGCGGCCATATCGGATTGGA

AAAATACAAAGCCATCAGTTGGGCAACCTGATGATTCAACAGGCGGCCAT

TAAAGGAAATATCGGCTACATTGTCCGCTTTTCCGATCACGGGCACGAAG

TCCATTCCCCCTTCGACAACCATGCCTCACATTCCGATTCTGATGAAGCC

GGTAGTCCCGTTGACGGATTTAGCCTTTACCGCATCCATTGGGACGGATA

CGAACACCATCCCGCCGACGGCTATGACGGGCCACAGGGCGGCGGCTATC

CCGCTCCCAAAGGCGCGAGGGATATATACAGCTACGACATAAAAGGCGTT

GCCCAAAATATCCGCCTCAACCTGACCGACAACCGCAGCACCGGACAACG

GCTTGCCGACCGTTTCCACAATGCCGGTAGTATGCTGACGCAAGGAGTAG

GCGACGGATTCAAACGCGCCACCCGATACAGCCCGAGCTGGACAGATCGG

GCAATGCCGCCGAAGCCTTCAACGGCACTGCAGATATCGTTAAAAACATC

ATCGGCGCGGCAGGAGAAATTGTCGGCGCAGGCGATGCCGTGCAGGGCAT

AAGCGAAGGCTCAAACATTGCTGTCATGCACGGCTTGGGTCTGCTTTCCA

CCGAAAACAAGATGGCGCGCATCAACGATTTGGCAGATATGGCGCAACTC

AAAGACTATGCCGCAGCAGCCATCCGCGGGGCAGTCCAAAACCCCAATGC

CGCACAATGCATAGAAGCCGTCAGCAATATCTTTATGGCAGCCATCCCCA

TCAAAGGGATTGGAGCTGTTCGGGGAAAATACGGCTTGGGCGGCATCACG

GCACATCCTATCAAGCGGTCGCAGATGGGCGCGATCGCATTGCCGAAAGG

GAAATCCGCCGTCAGCGACAATTTTGCCGATGCGGCATACGCCAATACCC

GTCCCCTTACCATCCCGAAATATCCGTTCATTGGAGCAGCGTTACGGCAA

AGAAAACATCACCTCCTCAACCGTGCCGCCGTCAAACGGCAAAAATGTCA

AACTGGCAGACCAACGCCACCCGAAGACAGGCGTACCGTTTACGGTAAAG

GGTTTCCGAATTTTGAGAAGCACGTGAAATATGATACGCTCGAGCACCAC

CACCACCACCACTGA
```

(SEQ ID NO: 34)
  1 MVAADIGAGL ADALTAPLDH KDKGLQSLTL DQSVRKNEKL KLAAQGAEKT

51 YGNGDSLNTG KLKNDKVSPF DFIRQIEVDG QLITLESGEF QVYKQSHSAL

101 TAFQTEQIQD SEHSGKMVAK RQFRIGDIAG EHTSFDKLPE GGRATYRGTA

151 FGSDDAGGKL TYTIDFAAKQ GNGKIEHLKS PELNVDLAAA DIKPDGKRHA

201 VISGSVLYNQ AEKGSYSLGI FGGKAQEVAG SAEVKTVNGI RHIGLAAKQL

251 DGGGGTGSSD LANDSFIRQV LDRQHFEPDG KYHLFGSRGE LAERSGHIGL

301 GKIQSHQLGN LMIQQAAIKG NIGYIVRFSD HGHEVESPFD NHASESDSDE

351 AGSPVDGFSL YRIHWDGYEH HPADYDGPQ GGGYPAPKGA RDIYSYDIKG

```
401 VAQNIRLNLT DNRSTGQRLA DRFHNAGSML TQGVGDGFKR ATRYSPELDR

451 SGNAAEAFNG TADIVKNIIG AAGEIVGAGD AVQGISEGSN IAVMHGLGLL

501 STENKHAPIN DLADMAQLKD YAAAAIRDWA VQNPNAAQGI EAVSNIFMAA

551 IPIKGIGAVR GKYGLGGITA HPIKRSQMGA IALPKGKSAV SDNFADAAYA

601 KYPSPYHSRN IRSNLEQRYG KENITSSTVP PSNGKNVKLA DQRHPKTGVP

651 FDGKGFPNFE KHVKYDTLEH HHHHH*
```

Example 5

Hybrids of 287

Expression of 287 as full-length with a C-terminal His-tag, or without its leader peptide but with a C-terminal His-tag, gives fairly low expression levels. Better expression is achieved using a N-terminal GST-fusion. As an alternative to using GST as an N-terminal fusion partner, 287 was placed at the C-terminus of protein 919 ('919-287'), of protein 953 ('953-287'), and of proteins ORF46.1 ('ORF46.1-287'). In both cases, the leader peptides were deleted, and the hybrids were direct in-frame fusions.

To generate the 953-287 hybrid, the leader peptides of the two proteins were omitted by designing the forward primer downstream from the leader of each sequence; the stop codon sequence was omitted in the 953 reverse primer but included in the 287 reverse primer. For the 953 gene, the 5' and the 3' primers used for amplification included a NdeI and a BamHI-restriction sites respectively, whereas for the amplification of the 287 gene the 5' and the 3' primers included a BamHI and a XhoI restriction sites respectively. In this way a sequential directional cloning of the two genes in pET21b+, using NdeI-BamHI (to clone the first gene) and subsequently BamHI-XhoI (to clone the second gene) could be achieved.

The 919-287 hybrid was obtained by cloning the sequence coding for the mature portion of 287 into the XhoI site at the 3'-end of the 919-His clone in pET21b+. The primers used for amplification of the 287 gene were designed for introducing a SalI restriction site at the 5'- and a XhoI site at the 3'- of the PCR fragment. Since the cohesive ends produced by the SalI and XhoI restriction enzymes are compatible, the 287 PCR product digested with SalI-XhoI could be inserted in the pET21b-919 clone cleaved with XhoI.

The ORF46.1-287 hybrid was obtained similarly.

The bactericidal efficacy (homologous strain) of antibodies raised against the hybrid proteins was compared with antibodies raised against simple mixtures of the component antigens:

|  | Mixture with 287 | Hybrid with 287 |
| --- | --- | --- |
| 919 | 32000 | 16000 |
| 953 | 8192 | 8192 |
| ORF46.1 | 128 | 8192 |

Data for bactericidal activity against heterologous MenB strains and against serotypes A and C were also obtained for 919-287 and 953-287:

|  | 919 | | 953 | | ORF46.1 | |
| --- | --- | --- | --- | --- | --- | --- |
| Strain | Mixture | Hybrid | Mixture | Hybrid | Mixture | Hybrid |
| MC58 | 512 | 1024 | 512 | 1024 | — | 1024 |
| NGH38 | 1024 | 2048 | 2048 | 4096 | — | 4096 |
| BZ232 | 512 | 128 | 1024 | 16 | — | — |
| MenA (F6124) | 512 | 2048 | 2048 | 32 | — | 1024 |
| MenC (C11) | >2048 | n.d. | >2048 | n.d. | — | n.d. |
| MenC (BZ133) | >4096 | >8192 | >4096 | <16 | — | 2048 |

Hybrids of ORF46.1 and 919 were also constructed. Best results (four-fold higher titre) were achieved with 919 at the N-terminus.

Hybrids 919-519His, ORF97-225His and 225-ORF97His were also tested. These gave moderate ELISA titres and bactericidal antibody responses.

As hybrids of two proteins A & B may be either NH$_2$-A-B—COOH or NH$_2$-B-A-COOH, the "reverse" hybrids with 287 at the N-terminus were also made, but using ΔG287. A panel of strains was used, including homologous strain 2996. FCA was used as adjuvant:

|  | 287 & 919 | | 287 & 953 | | 287 & ORF46.1 | |
| --- | --- | --- | --- | --- | --- | --- |
| Strain | ΔG287-919 | 919-287 | ΔG287-953 | 953-287 | ΔG287-46.1 | 46.1-287 |
| 2996 | 128000 | 16000 | 65536 | 8192 | 16384 | 8192 |
| BZ232 | 256 | 128 | 128 | <4 | <4 | <4 |
| 1000 | 2048 | <4 | <4 | <4 | <4 | <4 |
| MC58 | 8192 | 1024 | 16384 | 1024 | 512 | 128 |
| NGH38 | 32000 | 2048 | >2048 | 4096 | 16384 | 4096 |
| 394/98 | 4096 | 32 | 256 | 128 | 128 | 16 |
| MenA (F6124) | 32000 | 2048 | >2048 | 32 | 8192 | 1024 |
| MenC (BZ133) | 64000 | >8192 | >8192 | <16 | 8192 | 2048 |

Better bactericidal titres are generally seen with 287 at the N-terminus.

When fused to protein 961 [NH$_2$-ΔG287-961-COOH—sequence shown above], the resulting protein is insoluble and must be denatured and renatured for purification. Following renaturation, around 50% of the protein was found to remain insoluble. The soluble and insoluble proteins were compared, and much better bactericidal titres were obtained with the soluble protein (FCA as adjuvant):

|  | 2996 | BZ232 | MC58 | NGH38 | F6124 | BZ133 |
| --- | --- | --- | --- | --- | --- | --- |
| Soluble | 65536 | 128 | 4096 | >2048 | >2048 | 4096 |
| Insoluble | 8192 | <4 | <4 | 16 | n.d. | n.d. |

Titres with the insoluble form were, however, improved by using alum adjuvant instead:

| Insoluble | 32768 | 128 | 4096 | >2048 | >2048 | 2048 |
|---|---|---|---|---|---|---|

961c was also used in hybrid proteins (see above). As 961 and its domain variants direct efficient expression, they are ideally suited as the N-terminal portion of a hybrid protein.

Example 6

Further Hybrids

Further hybrid proteins of the invention are shown in the drawings and have the sequences set out below. These are advantageous when compared to the individual proteins:

ORF46.1-741

(SEQ ID NO: 35)

```
ATGTCAGATTTGGCAAACGATTCTTTTATCCGGCAGGTTCTCGACCGTCA
GCATTTCGAACCCGACGGGAAATACCACCTATTCGGCAGCAGGGGGGAAC
TTGCCGAGCGCAGCGGCCATATCGGATTGGGAAAAATACAAAGCCATCAG
TTGGGCAACCTGATGATTCAACAGGCGGCCATTAAAGGAAATATCGGCTA
CATTGTCCGCTTGTCCGATCACGGGCACGAAGTCCATTCCCCCTTCGACA
ACCATGCCTCACATTCCGATTCTGATGAAGCCGGTAGTCCCGTTGACGGA
TTTAGCCTTTACCGCATCCATTGGGACGGATACGAACACCATCCCGCCGA
CGGCTATGACGGGCCACAGGGCGGCGGCTATCCCGCTCCCAAAGGCGCGA
GGGATATATACAGCTACGACATAAAAGGCGTTGCCCAAAATATCCGCCTC
AACCTGACCGACAACCGCAGCACCGGACAACGGCTTGCCGACCGTTTCCA
CAATGCCGGTAGTATGCTGACGCAAGGAGTAGGCGACGGATTCAAACGCG
CCACCCGATACAGCCCCGAGCTGGACAGATCGGGCAATGCCGCCGAAGCC
TTCAACGGCACTGCAGATATCGTTAAAAACATCATCGGCGCGGCAGGAGA
AATTGTCGGCGCAGGCGATGCCGTGCAGGGCATAAGCGAAGGCTCAAACA
TTGCTGTCATGCACGGCTTGGGTCTGCTTTCCACCGAAAACAAGATGGCG
CGCATCAACGATTTGGCAGATATGGCGCAACTCAAAGACTATGCCGCAGC
AGCAGCCATCCGCGATTGGGCAGTCCAAAACCCCAATGCCGCACAAGGCA
TAGAAGCCGTCAGCAATATCTTTATGGCAGCCATCCCCATCAAAGGGATT
GGAGCTGTTCGGGGAAAATACGGCTTGGGCGGCATCACGGCACATCCTAT
CAAGCGGTCGCAGATGGGCGCGATCGCATTGCCGAAAGGGAAATCCGCCG
TCAGCGACAATTTTGCCGATGCGGCATACGCCAAATACCCGTCCCCTTAC
CATTCCCGAAATATCCGTTCAAACTTGGAGCAGCGTTACGGCAAAGAAAA
CATCACCTCCTCAACCGTGCCGCCGTCAAACGGCAAAAATGTCAAACTGG
CAGACCAACGCCACCCGAAGACAGGCGTACCGTTTGACGGTAAAGGGTTT
CCGAATTTTGAGAGCACGTGAAATATGATACGGGATCCGGAGGGGTGGT
GTCGCCGCCGACATCGGTGCGGGCTTGCCGATGCACTAACCGCACCGCT
CGACCATAAAGACAAAGGTTTGCAGTCTTTGACGCTGGATCAGTCCGTCA
GGAAAAACGAGAAACTGAAGCTGGCGGCACAAGGTGCAGAAAAACTTATG
GAAACGGTACAGCCTCAATACGGGCAAATTGAGAACGACAAGGTCAGCCG
TTTCGACTTTATCCGCCAAATCGAAGTGGGACGGGCAGCTCATTACCTTG
GAGAGTGGAGAGTTCCAAGTATACAAACAAAGCCATTCCGCCTTAACCGC
CTTTCAGACCGAGCAAATACAAGATTCGGAGCATTCCGGGAAGATGGTTG
CGAAACGCCAGTTCAGAATCGGCGACATAGCGGGCGAACATACATCTTTT
GACAAGCTTCCCGAAGGCGGCAGGGCGACATATCGCGGGACGGCGTTCGG
```

-continued

```
TTCAGACGATGCCGGCGGAAAACTGACCTACACCATAGATTTCGCCGCCA

AGCAGGGAAACGGCAAAATCGAACATTTGAAATCGCCAGAACTCAATGTC

GACCTGGCCGCCGCCGATATCAAGCCGGATGGAAAACGCCATGCCGTCAT

CAGCGGTTCCGTCCTTTACAACCAAGCCGAGAAAGGCAGTTACTCCCTCG

GTATCTTTGGCGGAAAAGCCCAGGAAGTTGCCGGCAGCGCGGAAGTGAAA

ACCGTAAACGCATACGCCATATCGGCCTGCCGCAAGCAACTCGAGCACCA

CCACCACCACCACTGA
```

(SEQ ID NO: 36)
```
  1 MSDLANDSFI RQVLDRQHFE PDGKYHLFGS RGELAERSGH IGLGKIQSHQ

51 LGNLMIQQAA IKGNIGYIVR FSDHGHEVHS PFDNHASHSD SDEAGSPVDG

101 FSLYRIHWDG YEHHPADGYD GPQGGGYPAP KGARDIYSYD IKGVAQNIRL

151 NLTDNRSTGQ RLADRFHNAG SMLTQGVGDG FKRATRYSPE LDRSGNAAEA

201 FNGTADIVKN IIGAAGEIVG AGDAVQGISE GSNIAVMHGL GLLSTENKMA

251 RINDLADMAQ LKDYAAAAIR DWAVQNPNAA QGIEAVSNIF MAAIPIKGIG

301 AVRGKYGLGG ITAHPIKRSQ MGAIALPKGK SAVSDNFADA AYAKYPSPYH

351 SRNIRSNLEQ RYGKENITSS TVPPSNGKNV KLADQRHPKT GVPFDGKGFP

401 NFEKHVKYDT GSGGGGVAAD IGAGLADALT APLDHKDKGL QSLTLDQSVR

451 KNEKLKLAAQ GAEKTYGNGD SLNTGKLKND KVSRFDFIRQ IEVDGQLITL

501 ESGEFQVYKQ SHSALTAFQT EQIQDSEHSG KMVAKRQFRI GDIAGEHTSF

551 DKLPEGGRAT YRGTAFGSDD AGGKLTYTID FAAKQGNGKI EHLKSPELNV

601 DLAAADIKPD GKRHAVISGS VLYNQAEKGS YSLGIFGGKA QEVAGSAEVK

651 TVNGIRHIGL AAKQLEHHHH HH*
```
ORF46.1-961
                                                      (SEQ ID NO: 37)
```
ATGTCAGATTTGGCAAACGATTCTTTTATCCGGCAGGTTCTCGACCGTCA

GCATTTCGAACCCGACGGGAAATACCACCTATTCGGCAGCAGGGGGGAAC

TTGCCGAGCGCAGCGGCCATATCGGATTGGGAAAAATACAAAGCCATCAG

TTGGGCAACCTGATGATTCAACAGGCGGCCATTAAAGGAAATATCGGCTA

CATTGTCCGCTTGTCCGATCACGGGCACGAAGTCCATTCCCCCTTCGACA

ACCATGCCTCACATTCCGATTCTGATGAAGCCGGTAGTCCCGTTGACGGA

TTTAGCCTTTACCGCATCCATTGGGACGGATACGAACACCATCCCGCCGA

CGGCTATGACGGGCCACAGGGCGGCGGCTATCCCGCTCCCAAAGGCGCGA

GGGATATATACAGCTACGACATAAAAGGCGTTGCCCAAAATATCCGCCTC

AACCTGACCGACAACCGCAGCACCGGACAACGGCTTGCCGACCGTTTCCA

CAATGCCGGTAGTATGCTGACGCAAGGAGTAGGCGACGGATTCAAACGCG

CCACCCGATACAGCCCCGAGCTGGACAGATCGGGCAATGCCGCCGAAGCC

TTCAACGGCACTGCAGATATCGTTAAAAACATCATCGGCGCGGCAGGAGA

AATTGTCGGCGCAGGCGATGCCGTGCAGGGCATAAGCGAAGGCTCAAACA

TTGCTGTCATGCACGGCTTGGGTCTGCTTTCCACCGAAAACAAGATGGCG

CGCATCAACGATTTGGCAGATATGGCGCAACTCAAAGACTATGCCGCAGC

AGCAGCCATCCGCGATTGGGCAGTCCAAAACCCCAATGCCGCACAAGGCA

TAGAAGCCGTCAGCAATATCTTTATGGCAGCCATCCCCATCAAAGGGATT
```

-continued

```
GGAGCTGTTCGGGGAAAATACGGCTTGGGCGGCATCACGGCACATCCTAT

CAAGCGGTCGCAGATGGGCGCGATCGCATTGCCGAAAGGGAAATCCGCCG

TCAGCGACAATTTTGCCGATGCGGCATACGCCAAATACCCGTCCCCTTAC

CATTCCCGAAATATCCGTTCAAACTTGGAGCAGCGTTACGGCAAAGAAAA

CATCACCTCCTCAACCGTGCCGCCGTCAAACGGCAAAAATGTCAAACTGG

CAGACCAACGCCACCCGAAGACAGGCGTACCGTTTGACGGTAAAGGGTTT

CCGAATTTTGAGAGCACGTGAAATATGATACGGGATCCGGAGGAGGAGGA

GCCACAAACGACGACGATGTTAAAAAAGCTGCCACTGTGGCCATTGCTGC

TGCCTACAACAATGGCCAAGAAATCAACGGTTTCAAAGCTGGAGAGACCA

TCTACGACATTGATGAAQACGGCACAATTACCAAAAAAGACGCAACTGCA

GCCGATGTTGAAGCCGACGACTTTAAAGGTCTGGGTCTGAAAAAAGTCGT

GACTAACCTGACCAACCGTCAATGAAAACAAACAAAACGTCGATGCCAAA

GTAAAAGCTGCAGAATCTGAAATAGAAAAGTTAACAACCAAGTTAGCAGA

CACTGATGCCGCTTTAGCAGATACTGATGCCGCTCTGGATGCAACCACCA

ACGCCTTGAATAAATTGGGAGAAAATATAACGACATTTGCTGAAGAGACT

AAGACAAATATCGTAAAAATTGATGAAAAATTAGAAGCCGTGGCTGATAC

CGTCGACAAGCATGCCGAAGCATTCAACGATATCGCCGATTCATTGGATG

AAACCAACACTAAGGCAGACGAAGCCGTCAAAACCGCCAATGAAGCCAAA

CAGACGGCCGAAGAAACCAAACAAAACGTCGATGCCAAAGTAAAAGCTGC

AGAAACTGCAGCAGGCAAAGCCGAAGCTGCCGCTGGCACAGCTAATACTG

CAGCCGACAAGGCCGAAGCTGTCGCTGCAAAAGTTACCGACATCAAAGCT

GATATCGCTACGAACAAAGATAATATTGCTAAAAAAGCAAACAGTGCCGA

CGTGTACACCAGAGAAGAGTCTGACAGCAAATTTGTAGAATTGATGGTCT

GAACGCTACTACCGAAAAATTGGACACACGCTTGGCTTCTGCTGAAAAAT

CCATTGCCGATCACGATACTCGCCTGACGGTTTGGATAAAACAGTGTCAG

ACCTGCGCAAAGAAACCCGCCAAGGCCTTGCAGAACAAGCCGCGCTCTCC

GGTCTGTTCCAACCTTACAACGTGGGTCGGTTCAATGTAACGGCTGCAGT

CGGCGGCTACAAATCCGAATCGGCAGTCGCCATCGGTACCGGCTTCCGCT

TTACCGAAAACTTGCCGCCAAAGCAGGCGTGGCAGTCGGCACTTCGTCCG

GTTCTTCCGCAGCCTACCATGTCGGCGTCAATTACGAGTGGCTCGAGCAC

CACCACCACCACCACTGA
```

```
                                          (SEQ ID NO: 38)
   1 MSDLANDSFI RQVLDRQHFE PDGKYHLFGS RGELAERSGH IGLGKIQSHQ
  51 LGNLMIQQAA IKGNIGYIVR FSDHGHEVHS PFDNHASHSD SDEAGSPVDG
 101 FSLYRIHWDG YEHHPADGYD GPQGGGYPAP KGARDIYSYD IKGVAQNIRL
 151 NLTDNRSTGQ RLADRFHNAG SMLTQGVGDG FKRATRYSPE LDRSGNAAEA
 201 FNGTADIVKN IIGAAGEIVG AGDAVQGISE GSNIAVMHGL GLLSTENKMA
 251 RINDLADMAQ LKDYAAAAIR DWAVQNPNAA QGIEAVSNIF MAAIPIKGIG
 301 AVRGKYGLGG ITAHPIKRSQ MGAIALPKGK SAVSDNFADA AYAKYPSPYH
 351 SRNIRSNLEQ RYGKENITSS TVPPSNGKNV KLADQRHPKT GVPFDGKGFP
 401 NFEKHVKYDT GSGGGGATND DDVKKAATVA IAAAYNNGQE INGFKAGETI
```

-continued

```
451 YDIDEDGTIT KKDATAADVE ADDFKGLGLK KVVTNLTKTV NENKQNVDAK

501 VKAAESEIEK LTTKLADTDA ALDATDAALD ATTNALNKLG ENITTFAEET

551 KTNIVKIDEK LEAVADTVDK HAEAFNDIAD SLDETNTKAD EAVKTANEAK

601 QTAEETKQNV DAKVKAAETA AGKAEAAAGT ANTAADKAEA VAAKVTDIKA

651 DIATNKDNIA KKANSADVYT REESDSKFVR IDGLNATTEK LDTRLASAEK

701 SIADHDTRLN GLDKTVSDLR KETRQGLAEQ AALSGLFQPY NVGRFNVTAA

751 VGGYKSESAV AIGTGFRFTE NFAAKAGVAV GTSSGSSAAY HVGVNYEWLE

801 HHHHHH*
```

ORF46.1-961c
(SEQ ID NO: 39)

```
ATGTCAGATTTGGCAAACGATTCTTTTATCCGGCAGGTTCTCGACCGTCA
GCATTTCGAACCCGACGGGAAATACCACCTATTCGGCAGCAGGGGGGAAC
TTGCCGAGCGCAGCGGCCCATATCGGATTGGGAAAAATACAAAGCCATCAG
TTGGGCAACCTGATGATTCAACAGGCGGCCATTAAAGGAAATATCGGCTA
CATTGTCCGCTTGTCCGATCACGGGCACGAAGTCCATTCCCCCTTCGACA
ACCATGCCTCACATTCCGATTCTGATGAAGCCGGTAGTCCCGTTGACGGA
TTTAGCCTTTACCGCATCCATTGGGACGGATACGAACACCATCCCGCCGA
CGGCTATGACGGGCCACAGGGCGGCGGCTATCCCGCTCCCAAAGGCGCGA
GGGATATATACAGCTACGACATAAAAGGCGTTGCCCAAAATATCCGCCTC
AACCTGACCGACAACCGCAGCACCGGACAACGGCTTGCCGACCGTTTCCA
CAATGCCGGTAGTATGCTGACGCAAGGAGTAGGCGACGGATTCAAACGCG
CCACCCGATACAGCCCCGAGCTGGACAGATCGGGCAATGCCGCCGAAGCC
TTCAACGGCACTGCAGATATCGTTAAAAACATCATCGGCGCGGCAGGAGA
AATTGTCGGCGCAGGCGATGCCGTGCAGGGCATAAGCGAAGGCTCAAACA
TTGCTGTCATGCACGGCTTGGGTCTGCTTTCCACCGAAAACAAGATGGCG
CGCATCAACGATTTGGCAGATATGGCGCAACTCAAAGACTATGCCGCAGC
AGCAGCCATCCGCGATTGGGCAGTCCAAAACCCCAATGCCGCACAAGGCA
TAGAAGCCGTCAGCAATATCTTTATGGCAGCCATCCCCATCAAAGGGATT
GGAGCTGTTCGGGAAAATACGGCTTGGGCGGCATCACGGCACATCCTAT
CAAGCGGTCGCAGATGGGCGCGATCGCATTGCCGAAAGGGAAATCCGCCG
TCAGCGACAATTTTGCCGATGCGGCATACGCCAAATACCCGTCCCCTTAC
CATTCCCGAAATATCCGTTCAAACTTGGAGCAGCGTTACGGCAAAGAAAA
CATCACCTCCTCAACCGTGCCGCCGTCAAACGGCAAAAATGTCAAACTGG
CAGACCAACGCCACCCGAAGACAGGCGTACCGTTTGACGGTAAAGGGTTT
CCGAATTTTGAGAGCACGTGAAATATGATACGGGATCCGGAGGAGGAGGA
GCCACAAACGACGACGATGTTAAAAAAGCTGCCACTGTGGCCATTGCTGC
TGCCTACAACAATGGCCAAGAAATCAACGGTTTCAAAGCTGGAGAGACCA
TCTACGACATTGATGAAQACGGCACAATTACCAAAAAAGACGCAACTGCA
GCCGATGTTGAAGCCGACGACTTTAAAGGTCTGGGTCTGAAAAAAGTCGT
GACTAACCTGACCAACCGTCAATGAAAACAAACAAAACGTCGATGCCAAA
GTAAAAGCTGCAGAATCTGAAATAGAAAAGTTAACAACCAAGTTAGCAGA
```

-continued

```
CACTGATGCCGCTTTAGCAGATACTGATGCCGCTCTGGATGCAACCACCA
ACGCCTTGAATAAATTGGGAGAAAATATAACGACATTTGCTGAAGAGACT
AAGACAAATATCGTAAAAATTGATGAAAAATTAGAAGCCGTGGCTGATAC
CGTCGACAAGCATGCCGAAGCATTCAACGATATCGCCGATTCATTGGATG
AAACCAACACTAAGGCAGACGAAGCCGTCAAAACCGCCAATGAAGCCAAA
CAGACGGCCGAAGAAACCAAACAAAACGTCGATGCCAAAGTAAAAGCTGC
AGAAACTGCAGCAGGCAAAGCCGAAGCTGCCGCTGGCACAGCTAATACTG
CAGCCGACAAGGCCGAAGCTGTCGCTGCAAAAGTTACCGACATCAAAGCT
GATATCGCTACGAACAAAGATAATATTGCTAAAAAAGCAAACAGTGCCGA
CGTGTACACCAGAGAAGAGTCTGACAGCAAATTTGTAGAATTGATGGTCT
GAACGCTACTACCGAAAAATTGGACACACGCTTGGCTTCTGCTGAAAAAT
CCATTGCCGATCACGATACTCGCCTGACGGTTTGGATAAAACAGTGTCAG
ACCTGCGCAAGAAACCCGCCAAGGCCTTGCAGAACAAGCCGCGCTCTCC
GGTCTGTTCCAACCTTACAACGTGGGTCTCGAGCACCACCACCACCACCA
CTGA
```

(SEQ ID NO: 40)
```
  1 MSDLANDSFI RQVLDRQHFE PDGKYHLFGS RGELAERSGH IGLGKIQSHQ
 51 LGNLMIQQAA IKGNIGYIVR FSDHGHEVHS PFDNHASHSD SDEAGSPVDG
101 FSLYRIHWDG YEHHPADGYD GPQGGGYPAP KGARDIYSYD IKGVAQNIRL
151 NLTDNRSTGQ RLADRFHNAG SMLTQGVGDG FKRATRYSPE LDRSGNAAEA
201 FNGTADIVKN IIGAAGEIVG AGDAVQGISE GSNIAVMHGL GLLSTENKMA
251 RINDLADMAQ LKDYAAAAIR DWAVQNPNAA QGIEAVSNIF MAAIPIKGIG
301 AVRGKYGLGG ITAHPIKRSQ MGAIALPKGK SAVSDNFADA AYAKYPSPYH
351 SRNIRSNLEQ RYGKENITSS TVPPSNGKNV KLADQRHPKT GVPFDGKGFP
401 NFEKHVKYDT GSGGGGATND DDVKKAATVA IAAAYNNGQE INGFKAGETI
451 YDIDEDGTIT KKDATAADVE ADDFKGLGLK KVVTNLTKTV NENKQNVDAK
501 VKAAESEIEK LTTKLADTDA ALDATDAALD ATTNALNKLG ENITTFAEET
551 KTNIVKIDEK LEAVADTVDK HAEAFNDIAD SLDETNTKAD EAVKTANEAK
601 QTAEETKQNV DAKVKAAETA AGKAEAAAGT ANTAADKAEA VAAKVTDIKA
651 DIATNKDNIA KKANSADVYT REESDSKFVR IDGLNATTEK LDTRLASAEK
701 SIADHDTRLN GLDKTVSDLR KETRQGLAEQ AALSGLFQPY NVGLEHHHHH
751 H*
```

961-ORF46.1

(SEQ ID NO: 41)
```
ATGGCCACAAACGACGACGATGTTAAAAAAGCTGCCACTGTGGCCATTGC
TGCTGCCTACAACAATGGCCAAGAAATCAACGGTTTCAAAGCTGGAGAGA
CCATCTACGACATTGATGAAGACGGCACAATTACCAAAAAAGACGCAACT
GCAGCCGATGTTGAAGCCGACGACTAAAGGTCTGGGTCTGAAAAAGTCG
TGACTAACCTGACCAAAACCGTCTGAAAACAAACAAACGTCGATGCCAAA
GTAAAAGCTGCAGAATCTGAAATAGAAAAGTTAACAACCAAGTTAGCAGA
CACTGATGCCGCTTTAGCAGATACTGATGCCGCTCTGGATGCAACCACCA
ACGCCTGAATAAATTGGGAAAAATATAACGACATTTGCTGAAGAGACTAA
```

-continued

```
GACAAATATCGTAAAAATTGATGAAAAATTAGAAGCCGTGGCTGATACCG
TCGACAAGCATGCCGCTTTAGCAGATACTGATGCCGCTCTGGATGCAACC
ACCAACGCCTTGAATAAATTGGGAGAAAATATAACGACATTTGCTGAAGA
GACTAAGACAAATATCGTAAAAATTGATGAAAAATTAGAAGCCGTGGCTG
ATACCGTCGACAAGCATGCCGAAGCATTCAACGATATCGCCGATTCATTG
GATGAAACCAACACTAAGGCAGACGAAGCCGTCAAAACCGCCAATGCTGA
TATCGCTACGAACAAGATAATATTGCTAAAAAAGCAAACAGTGCCGACGT
GTACACCAGAGAAGAGTCTGACAGCAAATGTCAGAATTGATGGTCTGAAC
GCTACTACCGAAAAATTGGACACACGCTTGGCTTCTGCTGAAAAATCCAT
TGCCGATCACGATACTCGCCTGAACGGTTTGGATAAAAACAGTGTCAGAC
CTGCGCAAAGAAACCCGCCAAGGCCTTGCAGAACAAGCCGCGCTCTCCGG
TCTGTTCCAACCTTACAACGTGGGTCGGTTCAATGTAACGGCTGCAGTCG
GCGGCTACAAATCCGAATCGGCAGTCGCCATCGGTACCGGCTTCCGCTTT
ACCGAAAACTTTGCCGCCAAAGCAGGCGTGGCAGTCGGCACTTCGTCCGG
TTCTTCCGCAGCCTACCATGTCGGCGTCAATTACGAGTGGGGATCCGGAG
GAGGAGGATCAGATTTGGCAAACGATTCTTTTATCCGGCAGGTTCTCGAC
CGTCAGCATTTCGAACCCGACGGGAAATACCACCTATTCGGCAGCAGGGG
GGAACTTGCCGAGCGCAGCGGCCATATCGGATTGGGAAAAATACAAAGCC
ATCAGTTGGGCAACCTGATGATTCAACAGGCGGCCATTAAAGGAAATATC
GGCTACATTGTCCGCTTTTCCGATCACGGGCACGAATCCATTCCCCCTTC
GACAACCATGCCTCACATTCCGATTCTGATGAAGCCGGTAGTCCCGTTGA
CGGATTTAGCCTTTACCGCATCCATTGGGACGGATACGAACACCATCCCG
CCGACGGCTATGACGGGCCACAGGGCGGCGGCTATCCCGCTCCCAAAGGC
GCGAGGGATATATACAGCTACGACATAAAAGGCGTTGCCCAAAATATCCG
CCTCAACCTGACCGACAACCGCAGCACCGGACAACGGCTTGCCGACCGTT
TCCACAATGCCGGTAGTATGCTGACGCAAGGAGTAGGCGACGGATTCAAA
CGCGCCACCCGATACAGCCCCGAGCTGGACAGATCGGGCAATGCCGCCGA
AGCCTTCAACGGCACTGCAGATATCGTTAAAAACATCATCGGCGCGGCAG
GAGAAATGTCGGCGCAGGCGATGCCGTGCAGGGCATAAGCGAAGGCTCAA
ACATTGCTGTCATGCACGGCTTGGGTCTGCTTTCCACCGAAAAOAGATGG
CGCGCATCAACGATTTGATATGGCAACTCAAAGACTATGCCGCAGCAGCC
ATCCGCGATTGGGCAGTCCAAAACCCCAATGCCGCACAAGCATAGAAGCC
GCAATATCTTTATGGCAGCCATCCCCATCAAAGGGATTGGAGCTGTTCGG
GGAAAATACGGCTTGGGCGGCATCACGGCACATCCTATCAAGCGGTCGCA
GATGGGCGCGATCGCATTGCCGAAAGGGAAATCCGCCGTCAGCGACAATT
TTGCCGATGCGGCATACGCCAAATACCCGTCCCCTTACCATTCCCGAAAT
ATCCGTTCAAACTTGGAGCAGCGTTACGGCAAAGAAAACATCACCTCCTC
AACCGTGCCGCCGTCAAACGGCAAAAATGTCAAACTGGCAGACCAACGCC
ACCCGAAGACAGGCGTACCGTTTGACGGTAAAGGGTTTCCGAATTTTGAG
AAGCACGTGAAATATGATACGCTCGAGCACCACCACCACCACCACTGA
```

-continued (SEQ ID NO: 42)

```
  1 MATNDDDVKK AATVAIAAAY NNGQEINGFK AGETIYDIDE DGTITKKDAT
 51 AADVEADDFK GLGLKKVVTN LTKTVNENKQ NVDAKVKAAE SEIEKLTTKL
101 ADTDAALADT DAALDATTNA LNKLGENITT FAEETKTNIV KIDEKLEAVA
151 DTVDKHAEAF NDIADSLDET NTKADEAVKT ANEAKQTAEE TKQNVDAKVK
201 AAETAAGKAE AAAGTANTAA DKAEAVAAKV TDIKADIATN KDNIAKKANS
251 ADVYTREESD SKFVRIDGLN ATTEKLDTRL ASAEKSIADH DTRLNGLDKT
301 VSDLRKETRQ GLAEQAALSG LFQPYNVGRF NVTAAVGGYK SESAVAIGTG
351 FRFTENFAAK AGVAVGTSSG SSAAYHVGVN YEWGSGGGGS DLANDSFIRQ
401 VLDRQHFEPD GKYHLFGSRG ELAERSGHIG LGKIQSHQLG NLMIQQAAIK
451 GNIGYIVRFS DHGHEVHSPF DNHASHSDSD EAGSPVDGFS LYRIHWDGYE
501 HHPADGYDGP QGGGYPAPKG ARDIYSYDIK GVAQNIRLNL TDNRSTGQRL
551 ADRFHNAGSM LTQGVGDGFK RATRYSPELD RSGNAAEAFN GTADIVKNII
601 GAAGEIVGAG DAVQGISEGS NIAVMHGLGL LSTENKMARI NDLADMAQLK
651 DYAAAAIRDW AVQNPNAAQG IEAVSNIFMA AIPIKGIGAV RGKYGLGGIT
701 AHPIKRSQMG AIALPKGKSA VSDNPADAAY AKYPSPYHSR NIRSNLEQRY
751 GKENITSSTV PPSNGKNVKL ADQRHPKTGV PFDGKGFPNF EKHVKYDTLE
801 HHHHHH*
```

961-741

(SEQ ID NO: 43)

ATGGCCACAAACGACGACGATGTTAAAAAAGCTGCCACTGTGGCCATTGC

TGCTGCCTACAACAATGGCCAAGAAATCAACGGTTTCAAAGCTGGAGAGA

CCATCTACGACATTGATGAAGACGGCACAATTACCAAAAAAGACGCAACT

GCAGCCGATGTTGAAGCCGACGACTAAAGGTCTGGGTCTGAAAAAAGTCG

TGACTAACCTGACCAAAACCGTCTGAAAACAAACAAACGTCGATGCCAAA

GTAAAAGCTGCAGAATCTGAAATAGAAAAGTTAACAACCAAGTTAGCAGA

CACTGATGCCGCTTTAGCAGATACTGATGCCGCTCTGGATGCAACCACCA

ACGCCTGAATAAATTGGGAAAAATATAACGACATTTGCTGAAGAGACTAA

GACAAATATCGTAAAAATTGATGAAAAATTAGAAGCCGTGGCTGATACCG

TCGACAAGCATGCCGCTTTAGCAGATACTGATGCCGCTCTGGATGCAACC

ACCAACGCCTTGAATAAATTGGGAGAAAATATAACGACATTTGCTGAAGA

GACTAAGACAAATATCGTAAAAATTGATGAAAAATTAGAAGCCGTGGCTG

ATACCGTCGACAAGCATGCCGAAGCATTCAACGATATCGCCGATTCATTG

GATGAAACCAACACTAAGGCAGACGAAGCCGTCAAAACCGCCAATGCTGA

TATCGCTACGAACAAGATAATATTGCTAAAAAAGCAAACAGTGCCGACGT

GTACACCAGAGAAGAGTCTGACAGCAAATGTCAGAATTGATGGTCTGAAC

GCTACTACCGAAAAATTGGACACACGCTTGGCTTCTGCTGAAAAATCCAT

TGCCGATCACGATACTCGCCTGAACGGTTTGGATAAAACAGTGTCAGAC

CTGCGCAAAGAAACCCGCCAAGGCCTTGCAGAACAAGCCGCGCTCTCCGG

TCTGTTCCAACCTTACAACGTGGGTCGGTTCAATGTAACGGCTGCAGTCG

GCGGCTACAAATCCGAATCGGCAGTCGCCATCGGTACCGGCTTCCGCTTT

ACCGAAAACTTTGCCGCCAAAGCAGGCGTGGCAGTCGGCACTTCGTCCGG

-continued
TTCTTCCGCAGCCTACCATGTCGGCGTCAATTACGAGTGGGGATCCGGAG

GGGGTGGTGTCGCCGCCGACATCGGTGCGGGGTTGCCGATGCACTAACCG

CACCGCTCGACCATAAAGACAAAGGTTTGCAGTCTTGACGCTGGATCAGT

CAGTCCGTCAGGAAAAACGAGAAACTGAAGCTGGCGGCACAAGGTGCGGA

AAAAACTTATGGAAACGGTGACAGCCTCAATACGGGCAATTGAAGAACGA

CAAGGTCAGCCGTTTCGACTTTATCCGCCAAATCGAAGTGGACGGGCAGC

TCATTACCTTGGAGAGTGGAGAGTTCCAAGTATACAAACAAAGCCATTCC

GCCTTAACCGCCTTTCAGACCGAGCAAATACATCGGAGCATTCCGGGAAT

GGTTGCGAAACGCCAGTTCAGAATCGGCGACATAGCGGGCCGAACATACA

TCTTTTGACAAGCTTCCCGAAGGCGGCAGGGCGACATATCGCGGGACGGC

GTTCGGTTCAGATGCCGGCGGAAAACTGACCTACACCATAGATTTCGCCG

CCAAGCAGGGAAACGGCAAAATCGAACATTTGAAATCGCCAGAACTCAAT

GTCGACCTGGCCGCCGCCGATATCAAGCCGGATGGAAAACGCCATGCCGT

CATCAGCGGTTCCGTCCTTTACAACCAAGCCGAGAAAGGCAGTTACTCCC

TCGGTATCTTTGGCGGAAAAGCCCAGGAAGTTGCCGGCAGCGCGGAAGTG

AAAACCGTAAACGGCATACGCCATATCGGCCTTGCCGCCAAGCAACTCGA

GCACCACCACCACCACCACTGA (SEQ ID NO: 44)
  1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGRF NVTAAVGGYK SESAVAIGTG

351 FRFTENFAAK AGVAVGTSSG SSAAYHVGVN YEWGSGGGGV AADIGAGLAD

401 ALTAPLDHKD KGLQSLTLDQ SVRKNEKLKL AAQGAEKTYG NGDSLNTGRL

451 KNDKVSRFDF IRQIEVDGQL ITLESGEFQV YKQSHSALTA FQTEQIQDSE

501 HSGKMVAKRQ FRIGDIAGEH TSFDKLPEGG RATYRGTAFG SDDAGGKLTY

551 TIDFAAKQGN GKIEHLKSPE LNVDLAAADI KPDGKRHAVI SGSVLYNQAE

601 KGSYSLGIFG GKAQEVAGSA EVKTVNGIRH IGLAAKQLEH HHHHH*

961-983
(SEQ ID NO: 45)
ATGGCCACAAACGACGACGATGTTAAAAAAGCTGCCACTGTGGCCATTGC

TGCTGCCTACAACAATGGCCAAGAAATCAACGGTTTCAAAGCTGGAGAGA

CCATCTACGACATTGATGAAGACGGCACAATTACCAAAAAAGACGCAACT

GCAGCCGATGTTGAAGCCGACGACTAAAGGTCTGGGTCTGAAAAAAGTCG

TGACTAACCTGACCAAAACCGTCTGAAAACAAACAAACGTCGATGCCAAA

GTAAAAGCTGCAGAATCTGAAATAGAAAAGTTAACAACCAAGTTAGCAGA

CACTGATGCCGCTTTAGCAGATACTGATGCCGCTCTGGATGCAACCACCA

ACGCCTGAATAAATTGGGAAAAATATAACGACATTTGCTGAAGAGACTAA

GACAAATATCGTAAAAATTGATGAAAAATTAGAAGCCGTGGCTGATACCG

```
-continued
TCGACAAGCATGCCGCTTTAGCAGATACTGATGCCGCTCTGGATGCAACC

ACCAACGCCTTGAATAAATTGGGAGAAAATATAACGACATTTGCTGAAGA

GACTAAGACAAATATCGTAAAAATTGATGAAAAATTAGAAGCCGTGGCTG

ATACCGTCGACAAGCATGCCGAAGCATTCAACGATATCGCCGATTCATTG

GATGAAACCAACACTAAGGCAGACGAAGCCGTCAAAACCGCCAATGCTGA

TATCGCTACGAACAAGATAATATTGCTAAAAAAGCAAACAGTGCCGACGT

GTACACCAGAGAAGAGTCTGACAGCAAATGTCAGAATTGATGGTCTGAAC

GCTACTACCGAAAAATTGGACACACGCTTGGCTTCTGCTGAAAAATCCAT

TGCCGATCACGATACTCGCCTGAACGGTTTGGATAAAAACAGTGTCAGAC

CTGCGCAAAGAAACCCGCCAAGGCCTTGCAGAACAAGCCGCGCTCTCCGG

TCTGTTCCAACCTTACAACGTGGGTCGGTTCAATGTAACGGCTGCAGTCG

GCGGCTACAAATCCGAATCGGCAGTCGCCATCGGTACCGGCTTCCGCTTT

ACCGAAAACTTTGCCGCCAAAGCAGGCGTGGCAGTCGGCACTTCGTCCGG

TTCTTCCGCAGCCTACCATGTCGGCGTCAATTACGAGTGGGGATCCGGCG

GAGGCGGCACTTCTGCGCCCGACTTCAATGCAGGCGGTACCGGTATCGGC

AGCAACAGCAGCAACAACAACAGCGAAATCAGCAGCAGTATCTTACGCCG

GTATCAAGAACGAAATGTGCAAAGACAGAAGCATGCTCTGTGCCGGTCGG

GATGACGTTGCGGTTACAGACAGGGATGCCAAAATCAATGCCCCCCCCCC

GAATCTGCATACCGGAGACTTTCCAAACCCAAATGACGCATACAAGAATT

TGATCAACCTCAAACCTGCAATTGAAGCAGGCTATACAGQACGCGGGGTA

GAGGTAGGTATCGTCGACACAGGCGAATCCGTCGGCAGCATATCCTTTCC

CGAACTGTATGGCAGAAAAGAACACGGCTATAACGAAAATTACAAAAACT

ATACGGCGTATATGCGGAAGGAAGCGCCTGAGACGGAGGCGGTAAAGACA

TTGAAGCTTCTTTCGACGATGAGGCCGTTATAGAGACTGAAGCAAAGCCG

ACGGATATCCGCCACGTAAAAGAAATCGGACACATCGATTTGGTCTCCCA

TATTATTGGCGGGCGTTCCGTGGACGGCAGACCTGCAGGCGGTATTGCGC

CCGATGCGACGCTACACATAATGAATACGAATGATGAAACCAAGAACGAA

ATGATGGTTGCAGCCATCCGCAATGCATGGGTCAAGCTGGGCGAACGTGG

CGTGCGCATCGTCAATAACAGTTTTGGACAACATCGAGGGCAGGCACTGC

CGACCTTTTCCAAATAGCCAATTCGGAGGAGCAGTACCGCCAAGCGTTGC

TCGACTATTCCGGCGGTGATAAAACAGACGAGGGTATCCGCCTGATGCAA

CAGAGCGATTACGGCAACCTGTCCTACCACATCCGTAATAAAAACATGCT

TTTCATTTTTCGACAGGCAATGACGCACAAGCTCAGCCCAACACATATGC

CCTATTGCCATTTTATGAAAAAGACGCTCAAAAAGGCATTATCACAGTCG

CAGGCGTAGACCGCAGTGGAGAAAAGTTAACGGGAAATGTATGGAGAACC

GGGTACAGAACCGCTTGAGTATGGCTCCAACCATTGCGGAATTACTGCCA

TGTGGTGCCTGTCGGCACCCTATGAAGCAAGCGTCCGTTTCACCCGTACA

AACCCGATTCAAATTGCCGGAACATCCTTTTCCGCACCCATCGTAACCGG

CACGGCGGCTCTGCTGCTGCAGAAATACCCGTGGATGAGCAACGACAACG

AACCTGCGTACCACGTTGOTGACGACGGCTCAQGACATCGQTGCAGTCGG

CGTGGACAGCAAGTTCGGCTGGGGACTGGATGCGGGTAAGGCCATGAACG
```

-continued

```
GACCCGCGTCCTTTCCGTTCGGCGACTTTACCGCCGATACGAAAGGTACA
TCCGATATTGCCTACTCCTTCCGTAACGACATTTCAGGCACGGGCGGCCT
GATCAAAAAAGCGGCAGCCAACTGCAACTGCACGGCAACAACACCTATAC
GGGCAAAACCATTATCGAAGGCGGTTCGCTGGTGTTGTACGGCAACAACA
AATCGGATATGCGCGTCGAAACCAAAGGTGCGCTGATTTATAACGGGGCG
GCATCCGGCGGCAGCCTGAACAGCGACGGCATTGTCTATCTGGCAGATAC
CGACCAATCCGGCGCAAACGAAACCGTACACATCAAAGGCAGTCTGCAGC
TGGACGGCAAAGGTACGCTGTACACACGTTTGGGCAAACTGCTGAAAGTG
GACGGTACGGCGATTATCGGCGGCAAGCTGTACATGTCGGCACGCGGCAA
GGGGGCAGGCTATCTCAACAGTACCGGACGACGTGTTCCCTTCCTGAGTG
CCGCCAAAATCGGGCAGGATTATTCTTTCTCACAAACATCGAAACCGACG
GCGGCCTGCTGGCTTCCCTCGACAGCGTCGAAAAAACAGCGGGCAGTGAA
GGCGACACGCTGTCCTATTATGTCCGTCGCGGCAATGCGGCACGGACTGC
TTCGGCAGCGGCACATTCCGCGCCCGCCGGTCTGAAACACGCCGTAGAAC
AGGGCGGCAGCAATCTGGAAAACCTGATGGTCGAACTGGATGCCTCCGAA
TCATCCGCAACACCCGAGACGGTTGAAACTGCGGCAGCCGACCGCACAGA
TATGCCGGGCATCCGCCCCTACGGCGCAACTTTCCGCGCAGCGGCAGCCG
TACAGCATGCGAATGCCGCCGACGGTGTACGCATCTTCAACAGTCTCGCC
GCTACCGTCTATGCCGACAGTACCGCCGCCCATGCCGATATGCAGGGACG
CCGCCTGAAAGCCGTATCGGACGGGGTTGGACCACAACGGCACGGGTCTG
CGCGTCATCGCGCAAACCCAACAGGACGGTGGAACGTGGGAACAGGGCGG
TGTTGAAGGCAAAATGCGCGGCAGTACCCAAACCGTCGGCATTGCCGCGA
AAACCGGCGAAAATACGACAGCAGCCGCCACACTGGGCATGGGACGCAGC
ACATGGAGCGAAAACAGTGCAAATGCAAAAACCGACAGCATTAGTCTGTT
TGCAGGCATACGGCACGATGCGGGCGATATCGGCTATCTCAAAGGCCTGT
TCTCCTACGGACGCTACAAAAACAGCATCAGCCGCAGCACCGGTGCGGAC
GAACATGCGGAAGGCAGCGTCAACGGCACGCTGATGCAGCTGGGCGCACT
GGGCGGTGTCAACGTTCCGTTTGCCGCAACGGGAGATTTGACGGTCGAAG
GCGGTCTGCGCTACGACCTGCTCAAACAGGATGCATTCGCCGAAAAAGGC
AGTGCTTTGGGCTGGAGCGGCAACAGCCTCACTGAAGGCACGCTGGTCGG
ACTCGCGGGTCTGAAGCTGTCGCAACCCTTGAGCGATAAAGCCGTCCTGT
TGCAACGGCGGGCGTGGAACGCGACCTGAACGGACGCGACTACACGGTAA
CGGGCGGCTTTACCGGCGCGACTGCAGCAACCGGCAAGACGGGGCACGC
AATATGCCGCACACCCGTCTGGTTGCCGGCCTGGGCGCGGATGTCGAATT
CGGCAACGGCTGGAACGGCTTGGCACGTTACAGCTACGCCGGTTCCAAAC
AGTACGGCAACCACAGCGGACGAGTCGGCGTAGGCTACCGGTTCCTCGAG
CACCACCACCACCACCACTGA
```

(SEQ ID NO: 46)
  1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

-continued

```
151 DTVDKHAEAF NDIADSLDET NTKADEAVKT ANEAKQTAEE TKQNVDAKVK
201 AAETAAGKAE AAAGTANTAA DKAEAVAAKV TDIKADIATN KDNIAKKANS
251 ADVYTREESD SKFVRIDGLN ATTEKLDTRL ASAEKSIADH DTRLNGLDKT
301 VSDLRKETRQ GLAEQAALSG LFQPYNVGRF NVTAAVGGYK SESAVAIGTG
351 FRFTENFAAK AGVAVGTSSG SSAAYHVGVN YEWGSGGGGT SAPDFNAGGT
401 GIGSNSRATT AKSAAVSYAG IKNEMCKDRS MLCAGRDDVA VTDRDAKINA
451 PPPNLHTGDF PNPNDAYKNL INLKPAIEAG YTGRGVEVGI VDTGESVGSI
501 SFPELYGRKE HGYNENYKNY TAYMRKEAPE DGGGKDIEAS PDDEAVIETE
551 AKPTDIRHVK EIGHIDLVSH IIGGRSVDGR PAGGIAPDAT LHIMNTNDET
601 KNEMMVAAIR NAWVKLGERG VRIVNNSFGT TSRAGTADLF QIANSEEQYR
651 QALLDYSGGD KTDEGIRLMQ QSDYGNLSYH IRNKNMLFIF STGNDAQAQP
701 NTYALLPFYE KDAQKGIITV AGVDRSGEKF KREMYGEPGT EPLEYGSNHC
751 GITAMWCLSA PYEASVRFTR TNPIQIAGTS FSAPIVTGTA ALLLQKYPWM
801 SNDNLRTTLL TTAQDIGAVG VDSKFGWGLL DAGKAMNGPA SFPFGDFTAD
851 TKGTSDIAYS FRNDISGTGG LIKKGGSQLQ LHGNNTYTGK TIIEGGSLVL
901 YGNNKSDMRV ETKGALIYNG AASGGSLNSD GIVYLADTDQ SGANETVHIK
951 GSLQLDGKGT LYTRLGKLLK VDGTAIIGGK LYMSARGRGA GYLNSTGRRV
1001 PFLSAAKIGQ DYSFFTNIET DGGLLASLDS VEKTAGSEGD TLSYYVRRGN
1051 AARTASAAAH SAPAGLKHAV EQGGSNLENL MVELDASESS ATPETVETAA
1101 ADRTDMPGIR PYGATFRAAA AVQHANAADG VRIFNSLAAT VYADSTAAHA
1151 DMQGRRLKAV SDGLDHNGTG LRVIAQTQQD GGTWEQGGVE GKMRGSTQTV
1201 GIAAKTGENT TAAATLGMGR STWSENSANA KTDSISLFAG IRHDAGDIGY
1251 LKGLPSYGRY KNSISRSTGA DEHAEGSVNG TLMQLGALGG VNVPFAATGD
1301 LTVEGGLRYD LLKQDAFAEK GSALGWSGNS LTEGTLVGLA GLKLSQPLSD
1351 KAVLFATAGV ERDLNGRDYT VTGGFTGATA ATGKTGAPNM PHTRLVAGLG
1401 ADVEFGNGWN GLARYSYAGS KQYGNHSGRV GVGYRFLEHH HHHH*
```

961c-ORF46.1
(SEQ ID NO: 47)

```
ATGGCCACAAACGACGACGATGTTAAAAAAGCTGCCACTGTGGCCATTGC
TGCTGCCTACAACAATGGCCAAGAAATCAACGGTTTCAAAGCTGGAGAGA
CCATCTACGACATTGATGAAGACGGCACAATTACCAAAAAAGACGCAACT
GCAGCCGATGTTGAAGCCGACGACTAAAGGTCTGGGTCTGAAAAAAGTCG
TGACTAACCTGACCAAAACCGTCTGAAAACAAACAAACGTCGATGCCAAA
GTAAAAGCTGCAGAATCTGAAATAGAAAGTTAACAACCAAGTTAGCAGA
CACTGATGCCGCTTTAGCAGATACTGATGCCGCTCTGGATGCAACCACCA
ACGCCTGAATAAATTGGGAAAAATATAACGACATTTGCTGAAGAGACTAA
GACAAATATCGTAAAAATTGATGAAAAATTAGAAGCCGTGGCTGATACCG
TCGACAAGCATGCCGCTTTAGCAGATACTGATGCCGCTCTGGATGCAACC
ACCAACGCCTTGAATAAATTGGGAGAAAATATAACGACATTTGCTGAAGA
GACTAAGACAAATATCGTAAAAATTGATGAAAAATTAGAAGCCGTGGCTG
ATACCGTCGACAAGCATGCCGAAGCATTCAACGATATCGCCGATTCATTG
```

-continued

```
GATGAAACCAACACTAAGGCAGACGAAGCCGTCAAAACCGCCAATGCTGA
TATCGCTACGAACAAGATAATATTGCTAAAAAAGCAAACAGTGCCGACGT
GTACACCAGAGAAGAGTCTGACAGCAAATGTCAGAATTGATGGTCTGAAC
GCTACTACCGAAAAATTGGACACACGCTTGGCTTCTGCTGAAAAATCCAT
TGCCGATCACGATACTCGCCTGAACGGTTTGGATAAAAACAGTGTCAGAC
CTGCGCAAAGAAACCCGCCAAGGCCTTGCAGAACAAGCCGCGCTCTCCGG
TCTGTTCCAACCTTACAACGTGGGTGGATCCGGAGGAGGAGGATCAGATT
TGGCAAACGATTCTTTTATCCGGCAGGTTCTCGACCGTCAGCATTTCGAA
CCCGACGGGAAATACCACCTATTCGGCAGCAGGGGGGAACTTGCCGACCG
CAGCGGCCATATCGGATTGGGAAAAATACAAAGCCATCAGTTGGGCAACC
TGATGATTCAACAGGCGGCCATTAAAGGAAATATCGGCTACATTGTCCGC
CGCTTTTCCGATCACGGGCACGAAGTCCATTCCCCCTTCGACAACCATGC
CTCACATTCCGATTCTGATGAAGCCGGTAGTCCCGTTGACGGATTTAGCC
TTTACCGCATCCATTGGGACGGATACGAACACCATCCCGCCGACGGCTAT
GACGGGCCACAGGGCGGCGGCTATCCCGCTCCCAAAGGCGCGAGGGATAT
ATACAGCTACGACATAAAAGGCGTTGCCCAAAATATCCGCCTCAACCTGA
CCGACAACCGCAGCACCGGACAACGGCTTGCCGACCGTTTCCACAATGCC
GGTAGTATGCTGACGCAAGGAGTAGGCGACGGATTCAAACGCGCCACCCG
ATACAGCCCCGAGCTGGACAGATCGGGCAATGCCGCCGAAGCCTTCAACG
GAGTAGGCGACGGATTCAAACGCGCCACCCGATACAGCCCCGAGCTGGAC
AGATCGGGCAATGCCGCCGAAGCCTTCAACGGCACTGCAGATATCGTTAA
AAACATCATCGGCGCGGCAGGAGAAATTGTCGGCGCAGGCCGATGCCGTG
CAGGGCATAAGCGAAGGCTCAAACATTGCTGTCATGCACGGCTTGGGTCT
GCTTTCCACCGAAAACAAGATGGCGCGCATCAACGATTTGGCAGATATGG
CGCAACTCAAAGACTATGCCGCAGCCAGCCATCCGCGATTGGGCAGTCCA
AAACCCCAATGCCGCACAAGGCATAGAACCGTCAGCAATATCTTTCAAGC
GGTCGCAGATGGGCGCGATCGCATTGCCGAAAGGGAAATCCGCCGTCAGC
CAGTTACGGCAAAGAAAACATCACCTCCTCAACCGTGCCGCCGTCAAACG
GCAAAAATGTCAACTGGCAGACCAACGCCACCCGAAGACAGGCGTACCGT
TTGACGGTAAAGGGTTTCCGAATTTTGAGAAGCACGTGAAATATGATACG
CTCAGCACCACCACCACCACCACTGA
```

(SEQ ID NO: 48)

```
  1 MATNDDDVKK AATVAIAAAY NNGQEINGFK AGETIYDIDE DGTITKKDAT
 51 AADVEADDFK GLGLKKVVTN LTKTVNENKQ NVDAKVKAAE SEIEKLTTKL
101 ADTDAALADT DAALDATTNA LNKLGENITT FAEETKTNIV KIDEKLEAVA
151 DTVDKHAEAF NDIADSLDET NTKADEAVKT ANEAKQTAEE TKQNVDAKVK
201 AAETAAGKAE AAAGTANTAA DKAEAVAAKV TDIKADIATN KDNIAKKANS
251 ADVYTREESD SKFVRIDGLN ATTEKLDTRL ASAEKSIADH DTRLNGLDKT
301 VSDLRKETRQ GLAEQAALSG LFQPYNVGGS GGGGSDLAND SFIRQVLDRQ
351 HFEPDGKYHL FGSRGELAER SGHIGLGKIQ SHQLGNLMIQ QAAIKGNIGY
401 IVRFSDHGHE VHSPFDNHAS HSDSDEAGSP VDGFSLYRIH WDGYEHHPAD
```

```
451 GYDGPQGGGY PAPKGARDIY SYDIKGVAQN IRLNLTDNRS TGQRLADRFH

501 NAGSMLTQGV GDGFKRATRY SPELDRSGNA AEAFNGTADI VKNIIGAAGE

551 IVGAGDAVQG ISEGSNIAVM HGLGLLSTEN KMARINDLAD MAQLKDYAAA

601 AIRDWAVQNP NAAQGIEAVS NIFMAAIPIK GIGAVRGKYG LGGITAHPIK

651 RSQMGAIALP KGKSAVSDNF ADAAYAKYPS PYHSRNIRSN LEQRYGKENI

701 TSSTVPPSNG KNVKLADQRH PKTGVPFDGK GFPNFEKHVK YDTLEHHHHH

751 H*
```

961c-741

(SEQ ID NO: 49)

```
ATGGCCACAAACGACGACGATGTTAAAAAAGCTGCCACTGTGGCCATTGC

TGCTGCCTACAACAATGGCCAAGAAATCAACGGTTTCAAAGCTGGAGAGA

CCATCTACGACATTGATGAAGACGGCACAATTACCAAAAAAGACGCAACT

GCAGCCGATGTTGAAGCCGACGACTAAAGGTCTGGGTCTGAAAAAAGTCG

TGACTAACCTGACCAAAACCGTCTGAAAACAAACAAACGTCGATGCCAAA

GTAAAAGCTGCAGAATCTGAAATAGAAAAGTTAACAACCAAGTTAGCAGA

CACTGATGCCGCTTTAGCAGATACTGATGCCGCTCTGGATGCAACCACCA

ACGCCTGAATAAATTGGGAAAAATATAACGACATTTGCTGAAGAGACTAA

GACAAATATCGTAAAAATTGATGAAAAATTAGAAGCCGTGGCTGATACCG

TCGACAAGCATGCCGCTTTAGCAGATACTGATGCCGCTCTGGATGCAACC

ACCAACGCCTTGAATAAATTGGGAGAAAATATAACGACATTTGCTGAAGA

GACTAAGACAAATATCGTAAAAATTGATGAAAAATTAGAAGCCGTGGCTG

ATACCGTCGACAAGCATGCCGAAGCATTCAACGATATCGCCGATTCATTG

GATGAAACCAACACTAAGGCAGACGAAGCCGTCAAAACCGCCAATGCTGA

TATCGCTACGAACAAGATAATATTGCTAAAAAAGCAAACAGTGCCGACGT

GTACACCAGAGAAGAGTCTGACAGCAAATGTCAGAATTGATGGTCTGAAC

GCTACTACCGAAAAATTGGACACACGCTTGGCTTCTGCTGAAAAATCCAT

TGCCGATCACGATACTCGCCTGAACGGTTTGGATAAAAACAGTGTCAGAC

CTGCGCAAAGAAACCCGCCAAGGCCTTGCAGAACAAGCCGCGCTCTCCGG

TCTGTTCCAACCTTACAACGTGGGTGGATCCGGAGGGGTGGTGTCGCCG

CCGACATCGGTGCGGGGCTTGCCGATGCACTAACCGCACCGCTCGACCAT

AAAGACAAAGGTTTGCAGTCTTTGACGCTGGATCAGTCCGTCAGGAAAAA

CGAGAAACTGAAGCTGGCGGCACAAGGTGCGGAAAAAACTTATGGAAACG

GTGACAGCCTCAATACGGGCAAATTGAAGAACGACAAGGTCAGCCGTTTC

GACTTTATCCGCCAAATCGAAGTGGACGGGCAGCTCATTACCTTGGAGAG

TGGAGAGTTCCAAGTATACAAACAAAGCCATTCCGCCTTAACCGCCTTTC

AGACCGAGCAAATACAAGATTCGGAGCATTCCGGGAAGATGGTTGCGAAA

CGCCAGTTCAGAATCGGCGACATAGCGGGCGAACATACATCTTTGACAAG

CTTCCCGAAGGCGGCAGGGCGACATATCGCGGGACGGCGTTCGGTTCAGA

CGATGCCGGCGGAAACTGACCTACACCATAGATTTCGCCGCCAAGCAGGG

AAACGGCAAAATCGAACATTTGAAATCGCCAGAATCAATGTCGACCTGGC

CGCCGCCGATATCAAGCCGGATGGAAAACGCCATGCCGTCATCAGCGGTT

CCGTCCTTTACAACCAAGCCGAGAAAGGCAGTTACTCCCTCGGTATCTTT
```

```
GGCGGAAAAGCCCAGGAAGTTGCCGGCAGCGCGGAAGTGAAAACCGTAAA

CGGCATACGCCATATCGGCCTTGCCGCCAAGCAACTCGAGCACCACCACC

ACCACCACTGA
```

(SEQ ID NO: 50)

```
  1 MATNDDDVKK AATVAIAAAY NNGQEINGFK AGETIYDIDE DGTITKKDAT

51 AADVEADDFK GLGLKKVVTN LTKTVNENKQ NVDAKVKAAE SEIEKLTTKL

101 ADTDAALADT DAALDATTNA LNKLGENITT FAEETKTNIV KIDEKLEAVA

151 DTVDKHAEAF NDIADSLDET NTKADEAVKT ANEAKQTAEE TKQNVDAKVK

201 AAETAAGKAE AAAGTANTAA DKAEAVAAKV TDIKADIATN KDNIAKKANS

251 ADVYTREESD SKFVRIDGLN ATTEKLDTRL ASAEKSIADH DTRLNGLDKT

301 VSDLRKETRQ GLAEQAALSG LFQPYNVGGS GGGGVAADIG AGLADALTAP

351 LDHKDKGLQS LTLDQSVRKN EKLKLAAQGA EKTYGNGDSL NTGKLKNDKV

401 SRFDFIRQIE VDGQLITLES GEFQVYKQSH SALTAFQTEQ IQDSEHSGKM

451 VAKRQFRIGD IAGEHTSFDK LPEGGRATYR GTAFGSDDAG GKLTYTIDFA

501 AKQGNGKIEH LKSPELNVDL AAADIKPDGK RHAVISGSVL YNQAEKGSYS

551 LGIFGGKKQE VAGSAEVKTV NGIRHIGLAA KQLEHHHHHH *
```

961c-983

(SEQ ID NO: 51)

```
ATGGCCACAAACGACGACGATGTTAAAAAAGCTGCCACTGTGGCCATTGC

TGCTGCCTACAACAATGGCCAAGAAATCAACGGTTTCAAAGCTGGAGAGA

CCATCTACGACATTGATGAAGACGGCACAATTACCAAAAAAGACGCAACT

GCAGCCGATGTTGAAGCCGACGACTAAAGGTCTGGGTCTGAAAAAAGTCG

TGACTAACCTGACCAAAACCGTCTGAAAACAAACAAACGTCGATGCCAAA

GTAAAAGCTGCAGAATCTGAAATAGAAAAGTTAACAACCAAGTTAGCAGA

CACTGATGCCGCTTTAGCAGATACTGATGCCGCTCTGGATGCAACCACCA

ACGCCTGAATAAATTGGGAAAAATATAACGACATTTGCTGAAGAGACTAA

GACAAATATCGTAAAAATTGATGAAAAATTAGAAGCCGTGGCTGATACCG

TCGACAAGCATGCCGCTTTAGCAGATACTGATGCCGCTCTGGATGCAACC

ACCAACGCCTTGAATAAATTGGGAGAAAATATAACGACATTTGCTGAAGA

GACTAAGACAAATATCGTAAAAATTGATGAAAAATTAGAAGCCGTGGCTG

ATACCGTCGACAAGCATGCCGAAGCATTCAACGATATCGCCGATTCATTG

GATGAAACCAACACTAAGGCAGACGAAGCCGTCAAAACCGCCAATGCTGA

TATCGCTACGAACAAGATAATATTGCTAAAAAAGCAAACAGTGCCGACGT

GTACACCAGAGAAGAGTCTGACAGCAAATGTCAGAATTGATGGTCTGAAC

GCTACTACCGAAAAATTGGACACACGCTTGGCTTCTGCTGAAAAATCCAT

TGCCGATCACGATACTCGCCTGAACGGTTTGGATAAAAACAGTGTCAGAC

CTGCGCAAAGAAACCCGCCAAGGCCTTGCAGAACAAGCCGCGCTCTCCGG

TCTGTTCCAACCTTACAACGTGGGTGGATCCGGAGGCGGCACTTCTGCGC

CCGACTTCAATGCAGGCGGTACCGGTATCGGCAGCAACAGCAGAcACAAC

AGCGAATCAGCAGCAGTATCTTACGCCGGTATCAAGAACGAAATGTGCAA

AGACAGAAGCATGCTCTGTGCCGGTCGGGATGACGTTGCGGTTACAGACA

GGGATGCCAAAATCAATGCCCCCCCCCCGAATCTGCATACCGGAGACTTT
```

-continued

```
CCAAACCCAAATGACGCATACAAGAATTTGATCAACCTCAACCTGCAATT
GAAGCAGGCTATACAGGACGCGGGGTAGAGGTAGGTATCGTCGACACAGG
CGAATCCGTCGGCAGCATATCCTTTCCCGAACTGTATGGCAGAAAAGAAC
ACGGCGGATAACGAAAATTACAAAAACTATACGGCGTATATGCGGAAGGA
AGCGCCTGAAGACGGAGGCGGTAAAGACATTGAAGCTTCTTTCGACGATG
AGGCCGTTATAGAGACTGAAGCAAAGCCGACGGATATCCGCCACGTAAAA
GAAATCGGACACATCGATTTGGTCTCCCATATTATTGGCGGGCGTTCCGT
GGACGGCAGACCTGCAGGCGGTATTGCGCCCGATGCGACGCTACACATAA
TGAATACGAATGATGAAACCAAGAACGAATGATGGTTGCAGCCATCCGCA
ATGCATGGGTCAAGCTGGGCAACGTGGCGTGCGCATCGTCAATAACAGT
TTTGGAACAACATCGAGGGCAGGCACTGCCGACCTTTTCCAAATAGCCAA
TTCGGAGGAGCAGTACCGCCAAGCGTTGCTCGACTATTCCGGCGGTGATA
AACAGACGAGGGTATCCGCCTGATGCAACAGAGCGATTACGGCAACCTGT
CCTACCACATCCGTAATAAAAACATGCTTTTCATCTTTTCGACAGGCAAT
GACGCACAAGCTCAGCCCAACACATATGCCCTATTGCCATTTTTATGAAA
AAGACGCTCAAAAAGGCATTATCACAGTCGCAGGCGTAGACCGGAGTGGA
GAAAAGTTCAAACGGGAAATGTATGGAGAACCGGGTACAGAACCGCTTGA
GTATGGCTCCAACCATTGCGGAATTACTGCCATGTGGTGCCTGTCGGCAC
CCTATGGCAAGCGTCCGTTTCACCCGTACAAACCCGATTCAAATTGCCGG
AACATCCTTTTCCGCACCCATCGTAACCGGCACGGCGGCTCTGCTGCTGC
AGAAATACCCGTGGATGAGCAACGACAACCTGCGTACCACGTTGCTGACG
ACGGCTCAGGACATCGGTGCAGTCGGCGTGGACAGCAAGTTCGGCTGGGG
ACTGCTGGATGCGGGTAAGGCCATGACGGACCCGCGTCCTTTCCGTTCGG
CGACTTTACCGCCGATACGAAAGTACATCCGATATTGCCTACTCCTTCCG
TAACGACATTTCAGGCACGGGCGGCCTGATCAAAAAAGGCGGCAGCCAAC
TGCAACTGCACGGCAACAACACCTATACGGGCAAAACCATTATCGAAGGC
GGTTCGCTGGTGTTGTACGGCAACAACAAATCGGATATGCGCGTCGAAAC
CAAAGGTGCGCTGATTTATAACGGGGCGGCATCCGGCGGCAGCCTGAACA
GCGACGGCATTGTCTATCTGGCAGATACCGACCAATCCGGCGCAAACGAA
ACCGTACACATCAAAGGCAGTCTGCAGCTGGACGGCAAAGGTACGCTGTA
CACACGTTTGGGCAAACTGCTGAAAGTGGACGGTACGGCGATTATCGGCG
GCAAGCTGTACATGTCGGCACGCGGCAAGGGGGCAGGCTATCTCAACAGT
ACCGGACGACGTGTTCCCTTCCTGAGTGCCGCCAAAATCGGGCAGGATTA
TTCTTTCTTCACAAACATCGAAACCGACGGCGGCCTGCTGGCTTCCCTCG
AAGCGTCGAAAAAACAGCGGGCAGTGAAGGCGACACGCTGTCCTATTATG
TCCGTCGCGGCAATGCGGCACGGACTGCTTCGGCAGCGGCACATTCCGCG
CCCGCCGGTCTGAAACACGCCGTAGAACAGGGCGGCAGCAATCTGGAAAA
CCTGATGGTCGAACTGGATGCCTCCGAATCATCCGCAACACCCGAGACGG
TTGAAACTGCGGCAGCCGACCGCACAGATATGCCGGGCATCCGCCCCTAC
GGCGCAACTTTCCGCGCAGCGGCAGCCGTACAGCATGCGAATGCCGCCGA
```

-continued
```
CGGTGTACGCATCTTCAACAGTCTCGCCGCTACCGTCTATGCCGCCAGTA
CCGCCGCCCATGCCGATATGCAGGGACGCCGCCTGAAAGCCGTATCGGAC
GGGTTGGACCACAACGGCACGGGTCTGCGCGTCATCGCGCAAACCCAACA
GGACGGTGGAACGTGGGAACAGGGCGGTGTTGAAGGCAAAATGCGCGGCA
GTACCCAAACCGTCGGCATTGCCGCGAAAACCGGCGAAAATACGACAGCA
GCCGCCACACTGGGCATGGACGCAGCACATGGAGCGAAAACAGTGCAAA
TGCAAAAACCGACAGCATTAGTCTGTTTGCAGGCATACGGCACGATGCGG
GCGATATCGGCTATCTCAAAGGCCTGTTCTCCTACGGACGCTACAAAAAC
AGCATCAGCCGCAGCACCGGTGCGGACGAACATGCGGAAGGCAGCGTCAA
CGGCACGCTGATGCAGCTGGGCGCACTGGGCGGTGTCAACGTTCCGTTTG
CCGCAACGGGAGATTTGACGGTCGAAGGCGGTCTGCGCTACGACCTGCTC
AAACAGGATGCATTCGCCGAAAAAGGCAGTGCTTTGGGCTGGAGCGGCAA
CAGCCTCACTGAAGGCACGCTGGTCGGACTCGCGGGTCTGAAGCTGTCGC
AACCCTTGAGCGATAAAGCCGTCCTGTTTGCAACGGCGGGCGTGGAACGC
GACCTGAACGGACGCGACTACACGGTAACGGGCGGCTTTACCGGCGCGAC
TGCAGCAACCGGCAAGACGGGGGCACGCAATATGCCGCACACCCGTCTGG
TTGCCGGCCTGGGCGCGGATGTCGAATTCGGCAACGGCTGGAACGGCTTG
GCACGTTACAGCTACGCCGGTTCCAAACAGTACGGCAACCACAGCGGACG
AGTCGGCGTAGGCTACCGGTTCCTCGAGCACCACCACCACCACCACTGA
```
(SEQ ID NO: 52)
```
   1 MATNDDDVKK AATVAIAAAY NNGQEINGFK AGETIYDIDE DGTITKKDAT
  51 AADVEADDFK GLGLKKVVTN LTKTVNENKQ NVDAKVKAAE SEIEKLTTKL
 101 ADTDAALADT DAALDATTNA LNKLGENITT FAEETKTNIV KIDEKLEAVA
 151 DTVDKHAEAF NDIADSLDET NTKADEAVKT ANEAKQTAEE TKQNVDAKVK
 201 AAETAAGKAE AAAGTANTAA DKAEAVAAKV TDIKADIATN KDNIAKKANS
 251 ADVYTREESD SKFVRIDGLN ATTEKLDTRL ASAEKSIADH DTRLNGLDKT
 301 VSDLRKETRQ GLAEQAALSG LFQPYNVGGS GGGGTSAPDF NAGGTGIGSN
 351 SEATTAKSAA VSYAGIKNEM CKDRSMLCAG RDDVAVTDRD AKINAPPPNL
 401 HTGDFPNPND AYKNLINLKP AIEAGYTGRG VEVGIVDTGE SVGSISFPEL
 451 YGRKEHGYNE NYKNYTAYMR KEAPEDGGGK DIEASFDDEA VIETEAKPTD
 501 IRHVKEIGHI DLVSHIIGGR SVDGRPAGGI APDATLHIMN TNDETKNEMM
 551 VAAIRNAWVK LGERGVRIVN NSFGTTSRAG TADLFQIANS EEQYRQALLD
 601 YSGGDKTDEG IRLMQQSDYG NLSYHIRNKN MLFIFSTGND AQAQPNTYAL
 651 LPFYEKDAQK GIITVAGVDR SGEKFKREMY GEPGTEPLEY GSNHCGITAM
 701 WCLSAPYEAS VRFTRTNPIQ IAGTSFSAPI VTGTAALLLQ KYPWMSNDNL
 751 RTTLLTTAQD IGAVGVDSKF GWGLLDAGKA MNGPASFPFG DFTADTKGTS
 801 DIAYSFRNDI SGTGGLIKKG GSQLQLHGNN TYTGKTIIEG GSLVLYGNNK
 851 SDMRVETKGA LIYNGAASGG SLNSDGIVYL ADTDQSQANE TVHIKGSLQL
 901 DGKGTLYTRL GKLLKVDGTA IIGGKLYMSA RGKGAGYLNS TGRRVPFLSA
 951 AKIGQDYSFF TNIETDGGLL ASLDSVEKTA GSEGDTLSYY VRRGNAARTA
1001 SAAAHSAPAG LKHAVEQGGS NLENLMVELD ASESSATPET VETAAADRTD
```

-continued

1051 MPGIRPYGAT FEAAAAVQHA NAADGVRIFN SLAATVYADS TAAHADMQGR

1101 RLKAVSDGLD HNGTGLRVIA QTQQDGGTWE QGGVEGKMRG STQTVGIAAK

1151 TGENTTAAAT LGMGRSTWSE NSANAKTDSI SLFAGIRHDA GDIGYLKGLF

1201 SYGRYKNSIS RSTGADEHAE GSVNGTLMQL GALGGVNVPF AATGDLTVEG

1251 GLRYDLLKQD AFAEKGSALG WSGNSLTEGT LVGLAGLKLS QPLSDKAVLF

1301 ATAGVEEDLN GRDYTVTGGF TGATAATGKT GARNMPHTRL VAGLGADVEF

1351 GNGWNGLARY SYAGSKQYGN HSGRVGVGYR FLEHHHHHH*

961cL-ORF46.1
(SEQ ID NO: 53)
ATGAAACACTTTCCATCCAAAGTACTGACCACAGCCATCCTTGCCACTTT

CTGTAGCGGCGCACTGGCAGCCACAAACGACGACGATGTTAAAAAAGCTG

CCACTGTGGCCATTGCTGCTGCCTACAACAATGGCCAAGAAATCAACGGT

TTCAAAGCTGGAGAGACCATCTACGACATTGATGAAGACGGCACAATTAC

CAAAAAAGACGCAACTGCAGCCGATGTTGAAGCCGACGACTTTAAAGTCT

GGGTCTGAAAAAAGTCGTGACTAACCTGACCAAAACCGTCAATGAAAACA

AACAAAACGTCGATGCCAAAGTAAAAGCTGCAGAATCTGAAATAGAAAAG

TTAACAACCAAGTTAGCAGACACTGATGCCGCTTTAGCAGATACTATGCC

GCTCTGGATGCAACCACCAACGCCTTGAATAAAATTGGGAGAAAATATAA

CGACATTTGCTGAAGAGACTAAGACAAATATCGTAAAAATTGATGAAAAA

TTAGAAGCCGATAGGCTGATACCGTCGkCAAGCATGCCGAAGCATTCAAC

GATATCGCCGATTCATTGGATGAAACCAACACTAAGGCAGACGAAGCCGT

CAAAACCGCCAATGAAGCCAAACAGACGGCCGAAGAAACCAAACAAAACG

TCGATGCCAAAGTAAAAGCTGCAGAAACTGCAGCAGGCAAAGCCGAAGCT

GCCGCTGGCACAGCTAATACTGCAGCCGACAGGCCGAAGCTGTCGCTGCA

AAAGTTACCGACATCAAAGCTGATATCGCTACGACAAAGATAATATTGCT

AAAAAGCAAACAGCCGACGTGTACACCAGAGAAGAGTCTGACAGCAAATT

TGTCAGAATTGATGGTCTGAGCGCTACTACCGAAAAATTGGACACACGCT

TGGCTTCTGCTGAAAAATCCATTGCCGATCACGATACTCGCCTGAACGGT

TTGGATAAAACAGTGTCAGACCTGCGCAAAGAAACCCGCCAAGGCCTTGC

AGAACAAGCCGCGCTCTCCGGTCTGTTCCAACCTTACAACGTGGGTGGAT

CCGGAGGAGGAGGATCAGATTTGGCAAACGATTCTTTTATCCGGCAGGTT

CTCGACCGTCAGCATTTCGAACCCGACGGGAAATACCACCTATTCGGCAG

CAGGGGGGAACTTGCCGAGCGCAGCGGCCATATCGGATTGGGAAAAATAC

AAAGCCATCAGTTGGGCAACCTGATGATTCAACAGGCGGCCATTAAAGGA

AATATCGGCTACACATTGTCCGCTTTTCCGATCACGGGCACGAAGTCCAT

TCCCCCTTCGACAACCATGCCTCACATTCCGATTCTGATGAAGCCGGTAG

TCCCGTTGACGGATTTAGCCTTTACCGCATCCATTGGGACGGATACGAAC

ACCATCCCGCCGACGGCTATGACGGGCCACAGGGCGGCGGCTATCCCGCT

CCCAAAGGCGCGAAAGGATATATACAGCTACGACATAAAAGGCGTTGCCC

AAAATATCCGCCTCAACCTGACCGACAACCGCAGCACCGGACAACGGCTT

GCCGACCGTTTCCACAATGCCGGTAGTATGCTGACGCAAGGAGTAGGCGA

CGGATTCAAACGCGCCACCCGATACAGCCCCGAGCTGGACAGATCGGGCA

-continued

```
ATGCCGCCGCGAAGCCTTCAACGGCACTGCAGATATCGTTAAAAACATCA
TCGGCGCGGCAGGAGAAATTGTCGCCGCAGGCGATGCCGTGCAGGGCATA
AGCGAAGGCTCAAACATTGCTGTCATGCACGGCTTGGGTCTGCTTTCCAC
CGAAAACAAGATGGCGCGCATCAGCGATTTGGCAGATATGGCGCAACTCA
AAGACTATGCCGCAGCAGCCATCCGCGATTGGGCAGTCCAAAACCCCAAT
GCCGCACAAGGCATAGAAGCCGTCAGCAATATCTTTATGGCAGCCATCCC
CATCAAAGGGATTGGAGCTGTTCGGGGAAAATACGGCTTGGGCGGCATCA
CGGCACATCCTATCAAGCGGTCGCAGATGGGCGCGATCGCATTGCCGAAA
GGGAAATCCGCCGTCAGCGACAATTTTGCCGATGCGGCATACGCCAAATA
CCCGTCCCCTTACCATTCCCGAATATCCGTTCAACTTACGGAGCAGCGTT
ACGGCAAAGAAAACATCACCTCCTCAACCGTGCCGCCGTCAAACGGCAAA
AATGTCAAACTGGCAGACCAACGCCACCCGAAGACAGGCGTACCGTTTGA
CGGTAAAGGGTTTCCGAATTTTGAGAAGCACGTGAAATATGATACGTAAC
TCGAG
```

```
                                               (SEQ ID NO: 54)
  1 MKHFPSKVLT TAILATFCSG ALAATNDDDV KKAATVAIAA AYNNGQEING
 51 FKAGETIYDI DEDGTITKKD ATAADVEADD FKGLGLKKVV TNLTKTVNEN
101 KQNVDAKVKA AESEIEKLTT KLADTDAALA DTDAALDATT NALNKLGENI
151 TTFAEETKTN IVKIDEKLEA VADTVDKHAE AFNDIADSLD ETNTKADEAV
201 KTANEAKQTA EETKQNVDAK VKAAETAAGK AEAAAGTANT AADKAEAVAA
251 KVTDIKADIA TNKDNIAKKA NSHDVYTREE SDSKFVRIDG LNATTEKLDT
301 RLASAEKSIA DHDTRLNGLD KTVSDLRKET RQGLAEQAAL SGLPQPYNVG
351 GSGGGGSDLA NDSFIRQVLD RQHFEPDGKY HLFQSRGELA ERSGHIGLGK
401 IQSHQLGNLM IQQAAIKGNI GYIVRFSDHG HEVESPFDNH ASHSDSDEAG
451 SPVDGFSLYR IHWDGYEHHP ADGYDGPQGG GYPAPKGARD IYSYDIRGVA
501 QNIRLNLTDN RSTGQRLADR FHNAGSMLTQ GVGDGFKRAT RYSPELDRSG
551 NAAEAFNGTA DIVKNIIGAA GEIVGAGDAV QGISEGSNIA VMHGLGLLST
601 ENKMARINDL ADMAQLKDYA AAAIRDWAVQ NPNAAQGIEA VSNIFMAAIP
651 IKGIGAVRGK YGLGGITAHP IKRSQMGAIA LPKGKSAVSD NFADAAYAKY
701 PSPYHSRNIR SNLEQRYGKE NITSSTVPPS NGKNVKLADQ RHPKTGVPFD
751 GKGFPNFEKH VKYDT*
```

961cL-741
```
                                               (SEQ ID NO: 55)
ATGAAACACTTTCCATCCAAAGTACTGACCACAGCCATCCTTGCCACTTT
CTGTAGCGGCGCACTGGCAGCCACAAACGACGACGATGTTAAAAAAGCTG
CCACTGTGGCCATTGCTGCTGCCTACAACAATGGCCAAGAAATCAACGGT
TTCAAAGCTGGAGAGACCATCTACGACATTGATGAAGACGGCACAATTAC
CAAAAAAGACGCAACTGCAGCCGATGTTGAAGCCGACTTTAAAGTCTT
GGGTCTGAAAAAAGTCGTGACTAACCTGACCAAAACCGTCAATGAAACA
AACAAAACGTCGATGCCAAAGTAAAAGCTGCAGAATCTGAAATAGAAAAG
TTAACAACCAAGTTAGCAGACACTGATGCCGCTTTAGCAGATACTATGCC
GCTCTGGATGCAACCACCAACGCCTTGAATAAAATTGGGAGAAAATATAA
```

-continued

```
CGACATTTGCTGAAGAGACTAAGACAAATATCGTAAAAATTGATGAAAAA
TTAGAAGCCGATAGGCTGATACCGTCGkCAAGCATGCCGAAGCATTCAAC
GATATCGCCGATTCATTGGATGAAACCAACACTAAGGCAGACGAAGCCGT
CAAAACCGCCAATGAAGCCAAACAGACGGCCGAAGAAACCAAACAAAACG
TCGATGCCAAAGTAAAAGCTGCAGAAACTGCAGCAGGCAAAGCCGAAGCT
GCCGCTGGCACAGCTAATACTGCAGCCGACAGGCCGAAGCTGTCGCTGCA
AAAGTTACCGACATCAAAGCTGATATCGCTACGACAAAGATAATATTGCT
AAAAAGCAAACAGCCGACGTGTACACCAGAGAAGAGTCTGACAGCAAATT
TGTCAGAATTGATGGTCTGAGCGCTACTACCGAAAAATTGGACACACGCT
TGGCTTCTGCTGAAAAATCCATTGCCGATCACGATACTCGCCTGAACGGT
TTGGATAAAACAGTGTCAGACCTGCGCAAAGAAACCCGCCAAGGCCTTGC
AGAACAAGCCGCGCTCTCCGGTCTGTTCCAACCTTACAACGTGGGTGGAT
CCGGAGGGGTGGTGTCGCCGCCGACATCGGTGCGGGGCTTGCCGATGCA
CTAACCGCACCGCTCGACCATAAAGACAAAGGTTTGCAGTCTTTGACGCT
GGATCAGTCCGTCAGGAAAAACGAGAAACTGAAGCTGGCGGCACAAGGTG
CGGAAAAAACTTATGGAAACGGTGACAGCCTCAATACGGGCAAATTGAAG
AACGACAAGGTCAGCCGTTTCGACTTTATCCGCCAAATCGAAGTGGACGG
GCAGCTCATTACCTTGGAGAGTGGAGAGTTCCAAGTATACAAACAAAGCC
ATTCCGCCTTAACCGCCTTTCADACCGAGCAAATACAAATTCGGAGCATT
CCGGGAAGATGGTTGCGAAACGCCAGTTCAGAATCGGCGACATAGCGGGC
GAACATACATCTTTTGACAAGCTTCCCGAAGGCGGCAGGGCGACATATCG
CGGGACGGCGTTCGGTTCAGACGATGCCGGCGGAAAACTGACCTACACCA
TAGATTTCGCCGCCAAGCAGGGAAACGGCAAAATCGAACATTTGAAATCG
CCAGAACTCAATGTCGACCTGGCCGCCGCCGATATCAAGCCGGATGGAAA
ACGCCATGCCGTCATCAGCGGTTCCGTCCTTPACAACCAAGCCGAGAAAG
GCAGTTACTCCCTCGGTATCTTTGGCGGAAAAGCCCAGGAAGTTGCCGGC
AGCGCGGAAGTGAAAACCGTAAACGGCATACGCCATATCGGCCTTGCCGC
CAAGCAACTCGAGCACCACCACCACCACCACTGA
```

```
                                              (SEQ ID NO: 56)
  1 MKHFPSKVLT TAILATFCSG ALAATNDDDV KKAATVAIAA AYNNGQEING

51 FKAGETIYDI DEDGTITKKD ATAADVEADD FKGLGLKKVV TNLTKTVNEN

101 KQNVDAKVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGK AEAAAGTANT AADKAEAVAA

251 KVTDIKADIA TNKDNIAKKA NSHDVYTREE SDSKFVRIDG LNATTEKLDT

301 RLASAEKSIA DHDTRLNGLD KTVSDLRKET RQGLAEQAAL SGLPQPYNVG

351 GSGGGGVAAD IGAGLADALT APLDHKDKGL QSLTLDQSVR KNEKLKLAAQ

401 GAEKTYGNGD SLNTGKLKND KVSRFDFIRQ IEVDGQLITL ESGEFQVYKQ

451 SHSALTAFQT EQIQDSEHSG KMVAKRQFRI GDIAGEHTSF DKLPEGGRAT

501 YRGTAFGSDD AGGKLTYTID FAAKQGNGKI EHLKSPELNV DLAAADIKPD

551 GKRHAVISGS VLYNQAEKGS YSLGIPGGKA QEVAGSAEVK TVNGIRHIGL
```

601 AAKQLEHHHH HH*

961cL-983

(SEQ ID NO: 57)

ATGAAACACTTTCCATCCAAAGTACTGACCACAGCCATCCTTGCCACTTT

CTGTAGCGGCGCACTGGCAGCCACAAACGACGACGATGTTAAAAAAGCTG

CCACTGTGGCCATTGCTGCTGCCTACAACAATGGCCAAGAAATCAACGGT

TTCAAAGCTGGAGAGACCATCTACGACATTGATGAAGACGGCACAATTAC

CAAAAAGACGCAACTGCAGCCGATGTTGAAGCCGACGACTTTAAAGTCT

GGGTCTGAAAAAAGTCGTGACTAACCTGACCAAAACCGTCAATGAAAACA

AACAAAACGTCGATGCCAAAGTAAAAGCTGCAGAATCTGAAATAGAAAG

TTAACAACCAAGTTAGCAGACACTGATGCCGCTTTAGCAGATACTATGCC

GCTCTGGATGCAACCACCAACGCCTTGAATAAAATTGGGAGAAAATATAA

CGACATTTGCTGAAGAGACTAAGACAAATATCGTAAAAATTGATGAAAA

TTAGAAGCCGATAGGCTGATACCGTCGkCAAGCATGCCGAAGCATTCAAC

GATATCGCCGATTCATTGGATGAAACCAACACTAAGGCAGACGAAGCCGT

CAAAACCGCCAATGAAGCCAAACAGACGGCCGAAGAAACCAAACAAAACG

TCGATGCCAAAGTAAAAGCTGCAGAAACTGCAGCAGGCAAAGCCGAAGCT

GCCGCTGGCACAGCTAATACTGCAGCCGACAGGCCGAAGCTGTCGCTGCA

AAAGTTACCGACATCAAAGCTGATATCGCTACGACAAAGATAATATTGCT

AAAAAGCAAACAGCCGACGTGTACACCAGAGAAGAGTCTGACAGCAAATT

TGTCAGAATTGATGGTCTGAGCGCTACTACCGAAAAATTGGACACACGCT

TGGCTTCTGCTGAAAAATCCATTGCCGATCACGATACTCGCCTGAACGGT

TTGGATAAAACAGTGTCAGACCTGCGCAAAGAAACCCGCCAAGGCCTTGC

AGAACAAGCCGCGCTCTCCGGTCTGTTCCAACCTTACAACGTGGGTGGAT

CCGGCGGAGGCGGCACTTCTGCGCCCGACTTCAATGCAGGCGGTACCGGT

CGGCAGCAACAGCAGAGCAACAACAGCGAAATCAGCAGCAGTATCTTACG

CCGGTATCAAGAACGAAATGTGCAAAGACAGAAGCATGCTCTGTGCCGGT

CGGGATGACGTTGCGGTTACAGACAGGGATGCCAAAATCAATGCCCCCCC

CCCGAATCTGCATACCGGAGACTTTCCAAACCCAAATGACGCATACAAGA

ATTTGATCAACCTCAAACCTGCAATTGAAGCAGGCTATACAGGACGCGGG

GTAGAGGTAGGTATCGTCGACACAGGCGAATCCGTCGGCAGCATATCCTT

TCCCGAACTGTATGGCAGAAAAGAACACGGCTATAACGAAAATTACAAAA

ACTATACGGCGTATATGCGGAAGGAAGCGCCTGACGAAGGAGGCGGTAAG

ACATTGAAGCTTCTTTCGACGATGAGGCCGTTATAGAGACTGAAGCAAAG

CCGACGGATATCCGCCACGTAAAAGAAATCGGACACATCGATTTGGTCTC

CCATATTATTGGCGGGCGTTCCGTGGACGGCAGACCTGCAGGCGGTATTG

CGCCCGATGCGACGCTACACATAATGATACGAATGATGAAACCAAGAACG

AAATGATGGTTGCAGCCATCCGCAATGCATGGGTCAAGCTGGGCGAACGT

GGCGTGCGCATCGTCATAACAGTTTTGGAACAACATCGAGGGCAGGCACT

GCCGACCTTTTCCAAATAGCCAATTCGGAGGAGCAGTACCGCCAAGCGTT

GCTCGACTATTCCGGCGGTGATAAAACAGACGAGGGTATCCGCCTGATGC

-continued

```
AACAGAGCGATTACGGCAACCTGTCCTACCACATCCGTAATAAAAACATG

CTTTTCATCTTTTCGACAGGCAATGACGCACAAGCTCAGCCCAACACATA

TGCCCTATTGCCATTTTATGAAAAAGACGCTCAAAAAGGCATATCACAGT

CGCAGGCGTAGACCGCAGTGGAGAAAAGTTCAAACGGGAAATGTATGGAG

AACCGGGTACAGACCGCTTGAGTATGGCTCCAACCATTGCGGAATTACTG

CCATGTGGTGCCTGTCGGCACCCTATGAGCAAGCGTCCGTTCACCCGTAC

AAACCCGATTCAAATTGCCGGAACATCCTTTTCCGCACCCATCGTAACCG

GCACGGCGGCTCTGCTGCTGCAGAAATACCCGTGGATGAGCAACGACAAC

CTGCGTACCACGTTGCTGACGACGGCTCAGGACATCGGTGCAGTCGGCGT

GGACAGCAAGTTCGGCTGGGGACTGCTGGATGCGGGTAAGGCCATGAACG

GACCCGCGTCCTTTCCGTTCGGCGACTTTACCGCCGATACGAAAGGTACA

TCCGATATTGCCTACTCCTTCCGTAACGACATTTCAGGCACGGGCGGCCT

GATCAAAAAGGCGGCAGCCAACTGCAACTGCACGGCAACAACACCTATA

CGGGCAAAACCATTATCGAAGGCGGTTCGCTGGTGTTGTACGGCAACAAC

AAATCGGATATGCGCGTCGAAACCAAAGGTGCGCTGATTTATAACGGGGC

GGCATCCGGCGGCAGCCTGAACAGCGACGGCATTGTCTATCTGGCAGATA

CCGACCAATCCGGCGCAAACGAAACCGTACACATCAAAGGCAGTCTGCAG

CTGGACGGCAAAGGTACGCTGTACACACGTTTGGGCAAACTGCTGAAAGT

GGACGGTACGGCGATTATCGGCGGCAAGCTGTACATGTCGGCACGCGGCA

AGGGGGCAGGCTATCTCAACAGTACCGGACGACGTGTTCCCTTCCTGAGT

GCCGCCAAAATCGGGCAGGATTATTCTTTCTTCACAAACATCGAAACCGA

CGGCGGCCTGCTGGCTTCCCTCGACAGCGTCGAAAAAACAGCGGGCAGTG

AAGGCGACACGCTGTCCTATTATGTCCGTCGCGGCAATGCGGCACGGACT

GCTTCGGCAGCGGCACATTCCGCGCCCGCCGGTCTGAAACACGCCGTAGA

ACAGGGCGGCAGCAATCTGGAAAACCTGATGGTCGAACTGGATGCCTCCG

AATCATCCGCAACACCCQAGACGGTTGAAACTGCGGCAGCCGACCGCACA

GATATGCCGGGCATCCGCCCCTACGGCGCAACTTTCCGCGCAGCGGCAGC

CGTACAGCATGCGAATGCCGCCGACGGTGTACGCATCTATCAACAGTCTC

GCCGCAGTACCGTCTATGCCGACAGTACCGCCGCCCATGCCGATATGCAG

GGACGCCGCCTGAAAGCCGTATCGGACGGGTTGGACCACAACGGCACGGG

TCTGCGCGTCATCGCGCAAACCCAACAGGACGGTGGAACGTGGGAACAGG

GCGGTGTTGAAGGCAAAATGCGCGGCAGTACCCAAACCGTCGGCATTGCC

GCGAAAACCGGCGAAAATACGACAGCAGCCGCCACACTGGGCATGGGACG

CAGCACATGGAGCGAAAACAGTGCAAATGCAAAAACCGACAGCATTAGTC

TGTTTGCAGGCATACGGCACGATGCGGGCGATATCGGCTATCTCAAAGGC

CTGTTCTCCTACGGACGCTACAAAAACAGCATCAGCCGCAGCACCGGTGC

GGACGAACATGCGGAAGGCAGCGTCAACGGCACGCTGATGCAGCTGGGCG

CACTGGGCGGTGTCACGTTCCGTTTGCCGCAACGGGAGATTTGACGGTCG

AAGGCGGTCTGCGCTACGACCTGCTCAAACAGGATGCATTCGCCGAAAAA

GGCAGTGCTTTGGGCTGGAGCGGCAACAGCCTCACTGAAGGCACGCTGGT

CGGACTCGCGGGTCTGAAGCTGTCGCAACCCTTGAGCGATAAAGCCGTCC
```

-continued

```
TGTTTGCAACGGCGGGCGTGGAACGCGACCTGAACGGACGCGACTACACG

GTAACGGGCGGCTTTACCGGCGCGACTGCAGCAACCGGCAAGACGGGGGC

ACGCAATATGCCGCACACCCGTCTGGTTGCCGGCCTGGGCGCGGATGTCG

AATTCGGCAACGGCTGGAACGGCTTGGCACGTTACAGCTACGCCGGTTCC

AAACAGTACGGCAACCACAGCGGACGAGTCGGCGTAGGCTACCGGTTCTG

ACTCGAG
```

(SEQ ID NO: 58)

```
   1 MKHFPSKVLT TAILATFCSG ALAATNDDDV KKAATVAIAA AYNNGQEING

51 FKAGETIYDI DEDGTITKKD ATAADVEADD FKGLGLKKVV TNLTKTVNEN

101 KQNVDAKVKA AESEIEKLTT KLADTDAALA DTDAALDATT NALNKLGENI

151 TTFAEETKTN IVKIDEKLEA VADTVDKHAE AFNDIADSLD ETNTKADEAV

201 KTANEAKQTA EETKQNVDAK VKAAETAAGK AEAAAGTANT AADKAEAVAA

251 KVTDIKADIA TNKDNIAKKA NSHDVYTREE SDSKFVRIDG LNATTEKLDT

301 RLASAEKSIA DHDTRLNGLD KTVSDLRKET RQGLAEQAAL SGLPQPYNVG

351 GSGGGGTSAP DFNAGGTGIG SNSRATTAKS AAVSYAGIKN EMCKDRSMLC

401 AGRDDVAVTD RDAKINAPPP NLHTGDFPNP NDAYKNLINL KPAIEAGYTG

451 RGVEVGIVDT GESVGSISFP ELYGRKEHGY NENYKNYTAY MRKEAPEDGG

501 GKDIEASFDD EAVIETEAKP TDIRHVKEIG HIDLVSHIIG GRSVDGRPAG

551 GIAPDATLHI MNTNDETKNE MMVAAIRNAW VKLGERGVRI VNNSFGTTSR

601 AGTADLFQIA NSEEQYRQAL LDYSGGDKTD EGIRLHQQSD YGNLSYHIRN

651 KNMLFIFSTG NDAQAQPNTY ALLPFYEKDA QKGIITVAGV DRSGEKFKRE

701 MYGEPGTEPL EYGSNHCGIT AMWCLSAPYE ASVEPTRTNP IQIAGTSFSA

751 PIVTGTAALL LQKYPWMSND NLRTTLLTTA QDIGAVGVDS KFGWGLLDAG

801 KAMNGPASFP FGDFTADTKG TEDIAYSFRN DISGTGGLIK KGGSQLQLHG

851 NNTYTGKTII EGGSLVLYGN NKSDMRVETK GALIYNGAAS GGSLNSDGIV

901 YLADTDQSGA NETVHIKGSL QLDGKGTLYT RLGKLLKVDG TAIIGGKLYM

951 SARGKGAGYL NSTGRRVPFL SAAKIGQDYS FFTNIETDGG LLASLDSVEK

1001 TAGSEGDTLS YYVRRGNAAR TASAAAHSAP AGLKHAVEQG GSNLENLMVE

1051 LDASESSATP ETVETAAADR TDMPGIRPYG ATFRAAAAVQ HANAADGVRI

1101 FNSLAATVYA DSTAAHADMQ GRRLKAVSDG LDHNGTGLRV IAQTQQDGGT

1151 WEQGGVEGKM RGSTQTVGIA AKTGENTTAA ATLGMGRSTW SENSANAKTD

1201 SISLFAGIRH DAGDIGYLKG LFSYGRYKNS ISRSTGADEH AEGSVNGTLM

1251 QLGALGGVNV PFAATGDLTV EGGLRYDLLK QDAFAEKGSA LGWSGNSLTE

1301 GTLVGLAGLK LSQPLSDKAV LFATAGVERD LNGRDYTVTG GFTGATAATG

1351 KTGARNMPHT RLVAQLQADV EFGNGWNGLA RYSYAGSKQY QNHSGRVGVG

1401 YRF*
```

It will be understood that the invention has been described by way of example only and modifications may be made whilst remaining within the scope and spirit of the invention. For instance, the use of proteins from other strains is envisaged [e.g. see WO00/66741 for polymorphic sequences for ORF4, ORF40, ORF46, 225, 235, 287, 519, 726, 919 and 953].

EXPERIMENTAL DETAILS

Cloning Strategy and Oligonucleotide Design

Genes coding for antigens of interest were amplified by PCR, using oligonucleotides designed on the basis of the genomic sequence of *N. meningitidis* B MC58. Genomic DNA from strain 2996 was always used as a template in PCR reactions, unless otherwise specified, and the amplified fragments were cloned in the expression vector pET21b+ (Novagen) to express the protein as C-terminal His-tagged product, or in pET-24b+(Novagen) to express the protein in 'untagged' form (e.g. ΔG 287K).

Where a protein was expressed without a fusion partner and with its own leader peptide (if present), amplification of the open reading frame (ATG to STOP codons) was performed.

Where a protein was expressed in 'untagged' form, the leader peptide was omitted by designing the 5'-end amplification primer downstream from the predicted leader sequence.

The melting temperature of the primers used in PCR depended on the number and type of hybridising nucleotides in the whole primer, and was determined using the formulae:

$$T_{m1} = 4(G+C) + 2(A+T) \quad \text{(tail excluded)}$$

$$T_{m2} = 64.9 + 0.41(\% GC) - 600/N \quad \text{(whole primer)}$$

The melting temperatures of the selected oligonucleotides were usually 65-70° C. for the whole oligo and 50-60° C. for the hybridising region alone.

Oligonucleotides were synthesised using a Perkin Elmer 394 DNA/RNA Synthesizer, eluted from the columns in 2.0 ml NH$_4$OH, and deprotected by 5 hours incubation at 56° C. The oligos were precipitated by addition of 0.3M Na-Acetate and 2 volumes ethanol. The samples were centrifuged and the pellets resuspended in water.

|  | | Sequences | SEQ ID NO | Restriction site |
|---|---|---|---|---|
| fu (961)-741(MC58)-His | Fwd | CGCGGATCC-GGAGGGGGTGGTGTCG | 59 | BamHI |
|  | Rev | CCCGCTCGAG-TTGCTTGGCGGCAAGGC | 60 | XhoI |
| fu (961)-983-His | Fwd | CGCGGATCC-GGCGGAGGCGGCACTT | 61 | BamHI |
|  | Rev | CCCGCTCGAGG-GAACCGGTAGCCTACG | 62 | XhoI |
| fu (961)-Orf46.1-His | Fwd | CGCGGATCCGGTGGTGGTGGT-TCAGATTTGGCAAACGATTC | 63 | BamHI |
|  | Rev | CCCGCTCGAG-CGTATCATATTTCACGTGC | 64 | XhoI |
| fu (961 c-L)-741(MC58) | Fwd | CGCGGATCCC-GGAGGGGGTGGTGTCG | 65 | BamHI |
|  | Rev | CCCGCTCGAG-TTATTGCTTGGCGGCAAG | 66 | XhoI |
| fu (961c-L)-983 | Fwd | CGCGGATCC-GGCGGAGGCGGCACTT | 67 | BamHI |
|  | Rev | CCCGCTCGAG-TCAGAACCGGTAGCCTAC | 68 | XhoI |
| fu (961c.L)-Orf46.1 | Fwd | CGCGGATCCGGTGGTGGTGGT-TCAGATTTGGCAAACGATTC | 69 | BamHl |
|  | Rev | CCCGCTCGAG-TTACGTATCATATTTCACGTGC | 70 | XhoI |
| fu-(ΔG287)-919-His | Fwd | CGCGGATCCGGTGGTGGTGGT-CAAAGCAAGAGCATCCAAACC | 71 | BamHI |
|  | Rev | CCCAAGCTT-TTCGGGCGGTATTCGGGCTTC | 72 | HindIII |
| fu(ΔG287)-953-His | Fwd | CGCGGATCCGGTGGTGGTGGT-GCCACCTACAAAGTGGAC | 73 | BamHI |
|  | Rev | GCCCAAGCTT-TTGTTGGCTGCCCTCGAT | 74 | HindIII |
| fu-(ΔG287)-961- | Fwd | CGCGGATCCGGTGGTGGTGGT-ACAAGCGACGACG | 75 | BamHI |
|  | Rev | GCCCAAGCTT-CCACTCGTAATTGACGCC | 76 | HindIII |
| fu-(ΔG287)-Orf46.1-His | Fwd | CGCGGATCCGGTGGTGGTGGT-TCAGATTTGGCAAACGATTC | 77 | BamHI |
|  | Rev | CCCAAGCTT-CGTATCATATTTCACGTGC | 78 | HindIII |
| fu-(ΔG287-919)-Orf46.1-His | Fwd | CCCAAGCTTGGTGGTGGTGGTGGT-TCAGATTTGGCAAACGATTC | 79 | HindIII |
|  | Rev | CCCGCTCGAG-CGTATCATATTTCACGTGC | 80 | XhoI |
| fu-(ΔG287-Orf46.1)-919-His | Fwd | CCCAAGCTTGGTGGTGGTGGTGGT-CAAAGCAAGAGCATCCAAACC | 81 | HindIII |
|  | Rev | CCCGCTCGAG-CGGGCGGTATTCGGGCTT | 82 | XhoI |
| fu ΔG287(394.98)-... | Fwd | CGCGGATCCGCTAGC-CCCGATGTTAAATCGGC | 83 | NbeI |
|  | Rev | CGGGGATCC-ATCCTGCTCTTTTTTGCCGG | 84 | BamHI |
| fu Orf1-(Orf46.1)-His | Fwd | CGCGGATCCGCTAGC-GGACACACTTATTTCGGCATC | 85 | NheI |
|  | Rev | CGCGGATCC-CCAGCGGTAGCCTAATTTTGAT | 86 |  |
| fu (Orf1)-Orf46.1-His | Fwd | CGCGGATCCGGTGGTGGTGGT-TCAGATTTGGCAAACGATTC | 87 | BamHI |
|  | Rev | CCCAAGCTT-CGTATCATATTTCACGTGC | 88 | HindIII |
| fu (919)-Orf46.1-His | Fwd1 | GCGGCGTCGACGGTGGCGGAGGCACTGGATCCTCAG | 89 | SalI |
|  | Fwd2 | GGAGGCACTGGATCCTCAGATTTGGCAAACGATTC | 90 |  |
|  | Rev | CCCGCTCGAG-CGTATCATATTTCACGTGC | 91 | XhoI |

-continued

| Sequences | | | SEQ ID NO | Restriction site |
|---|---|---|---|---|
| fu (orf46)-287-His | Fwd | CGGGGATCCGGGGGCGGCGGTGGCG | 92 | BamHI |
| | Rev | CCCAAGCTTATCCTGCTCTTTTTGCCGGC | 93 | HindIII |
| Fu (orf46)-919-His | Fwd | CGCGGATCCGGTGGTGGTGGTCAAAGCAAGAGCATCCAAACC | 94 | BamHI |
| | Rev | CCCAAGCTTCGGGCGGTATTCGGGCTTC | 95 | HindIII |
| Fu (orf46-919)-287-His | Fwd | CCCCAAGCTTGGGGGCGGCGGTGGCG | 96 | HindIII |
| | Rev | CCCGCTCGAGATCCTGCTCTTTTTGCCGGC | 97 | XhoI |
| Fu (orf46-287)-919-His | Fwd | CCCAAGCTTGGTGGTGGTGGTGGTCAAAGCAAGAGCATCCAAACC | 98 | HindIII |
| | Rev | CCCGCTCGAGCGGGCGGTATTCGGGCTT | 99 | XhoI |
| (ΔG741)-961c-His | Fwd1 | GGAGGCACTGGATCCGCAGCCACAAACGACGACGA | 100 | XhoI |
| | Fwd2 | GCGGCCTCGAG-GGTGGCGGAGGCACTGGATCCGCAG | 101 | |
| | Rev | CCCGCTCGAG-ACCCAGCTTGTAAGGTTG | 102 | XhoI |
| (ΔG741)-961-His | Fwd1 | GGAGGCACTGGATCCGCAGCCACAAACGACGACGA | 103 | XhoI |
| | Fwd2 | GCGGCCTCGAG-GGTGGCGGAGGCACTGGATCCGCAG | 104 | |
| | Rev | CCCGCTCGAG-CCACTCGTAATTGACGC | 105 | XhoI |
| (ΔG741)-983-His | Fwd | GCGGCCTCGAG-GGATCCGGCGGAGGCGGCACTTCTGCG | 106 | XhoI |
| | Rev | CCCGCTCGAG-GAACCGGTAGCCTACG | 107 | XhoI |
| (ΔG741)-orf46.1-His | Fwd1 | GGAGGCACTGGATCCTCAGATTTGGCAAACGATTC | 108 | SalI |
| | Fwd2 | GCGGCGTCGACGGTGGCGGAGGCACTGGATCCTCAGA | 109 | |
| | Rev | CCCGCTCGAG-CGTATCATATTTCACGTGC | 110 | XhoI |
| (ΔG983)-741(MC58)-His | Fwd | GCGGCCTCGAG-GGATCCGGAGGGGGTGGTGTCGCC | 111 | XhoI |
| | Rev | CCCGCTCGAG-TTGCTTGGCGGCAAG | 112 | XhoI |
| (ΔG983)-961c-His | Fwd1 | GGAGGCACTGGATCCGCAGCCACAAACGACGACGA | 113 | XhoI |
| | Fwd2 | GCGGCCTCGAG-GGTGGCGGAGGCACTGGATCCGCAG | 114 | |
| | Rev | CCCGCTCGAG-ACCCAGCTTGTAAGGTTG | 115 | XhoI |
| (ΔG983)-961-His | Fwd1 | GGAGGCACTGGATCCGCAGCCACAAACGACGACGA | 116 | XhoI |
| | Fwd2 | GCGGCCTCGAG-GGTGGCGGAGGCACTGGATCCGCAG | 117 | |
| | Rev | CCCGCTCGAG-CCACTCGTAATTGACGCC | 118 | XhoI |
| (ΔG983)-Orf46.1-His | Fwd1 | GGAGGCACTGGATCCTCAGATTTGGCAAACGATC | 119 | SalI |
| | Fwd2 | GCGGCGTCGACGGTGGCGGAGGCACTGGATCCTCAGA | 120 | |
| | Rev | CCCGCTCGAG-CGTATCATATTTCACGTGC | 121 | XhoI |

\* This primer was used as a Reverse primer for all the C terminal fusions of 287 to the His-tag.
§Forward primers used in combination with the 287-His Reverse primer.
NB - All PCR reactions use strain 2996 unless otherwise specified (e.g. strain MC58)

In all constructs starting with an ATG not followed by a unique NheI site, the ATG codon is part of the NdeI site used for cloning. The constructs made using NheI as a cloning site at the 5' end (e.g. all those containing 287 at the N-terminus) have two additional codons (GCT AGC) fused to the coding sequence of the antigen.

Preparation of Chromosomal DNA Templates

*N. meningitidis* strains 2996, MC58, 394.98, 1000 and BZ232 (and others) were grown to exponential phase in 100 ml of GC medium, harvested by centrifugation, and resuspended in 5 ml buffer (20% w/v sucrose, 50 mM Tris-HCl, 50 mM EDTA, pH 8). After 10 minutes incubation on ice, the bacteria were lysed by adding 10 ml of lysis solution (50 mM NaCl, 1% Na-Sarkosyl, 50 μg/ml Proteinase K), and the suspension incubated at 37° C. for 2 hours. Two phenol extractions (equilibrated to pH 8) and one CHCl$_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading OD$_{260}$.

PCR Amplification

The standard PCR protocol was as follows: 200 ng of genomic DNA from 2996, MC581000, or BZ232 strains or 10 ng of plasmid DNA preparation of recombinant clones were used as template in the presence of 40 μM of each oligonucleotide primer, 400-800 μM dNTPs solution, 1×PCR buffer (including 1.5 mM MgCl$_2$), 2.5 units TaqI DNA polymerase (using Perkin-Elmer AmpliTaQ, Boerhingher Mannheim Expand™ Long Template).

After a preliminary 3 minute incubation of the whole mix at 95° C., each sample underwent a two-step amplification: the first 5 cycles were performed using the hybridisation temperature that excluded the restriction enzyme tail of the primer (T$_{m1}$). This was followed by 30 cycles according to the hybridisation temperature calculated for the whole length oligos (T$_{m2}$). Elongation times, performed at 68° C. or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

Digestion of PCR Fragments and of the Cloning Vectors

The purified DNA corresponding to the amplified fragment was digested with the appropriate restriction enzymes for cloning into pET-21b+, pET22b+ or pET-24b+. Digested fragments were purified using the QIAquick PCR purification kit (following the manufacturer's instructions) and eluted with either H$_2$O or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

Cloning

The fragments corresponding to each gene, previously digested and purified, were ligated into pET21b+, pET22b+ or pET-24b+. A molar ratio of 3:1 fragment/vector was used with T4 DNA ligase in the ligation buffer supplied by the manufacturer.

Recombinant plasmid was transformed into competent *E. coli* DH5 or HB101 by incubating the ligase reaction solution and bacteria for 40 minutes on ice, then at 37° C. for 3 minutes. This was followed by the addition of 800 µl LB broth and incubation at 37° C. for 20 minutes. The cells were centrifuged at maximum speed in an Eppendorf microfuge, resuspended in approximately 200 µl of the supernatant and plated onto LB ampiclllin (100 mg/ml) agar.

Screening for recombinant clones was performed by growing randomly selected colonies overnight at 37° C. in 4.0 ml of LB broth+100 µg/ml ampicillin. Cells were pelleted and plasmid DNA extracted using the Qiagen QIAprep Spin Miniprep Kit, following the manufacturer's instructions. Approximately 1 µg of each individual miniprep was digested with the appropriate restriction enzymes and the digest loaded onto a 1-1.5% agarose gel (depending on the expected insert size), in parallel with the molecular weight marker (1 kb DNA Ladder, GIBCO). Positive clones were selected on the basis of the size of insert.

Expression

After cloning each gene into the expression vector, recombinant plasmids were transformed into *E. coli* strains suitable for expression of the recombinant protein. 1 µl of each construct was used to transform *E. coli* BL21-DE3 as described above. Single recombinant colonies were inoculated into 2 ml LB+Amp (100 µg/ml), incubated at 37° C. overnight, then diluted 1:30 in 20 ml of LB+Amp (100 µg/ml) in 100 ml flasks, to give an OD$_{600}$ between 0.1 and 0.2. The flasks were incubated at 30° C. or at 37° C. in a gyratory water bath shaker until OD$_{600}$ indicated exponential growth suitable for induction of expression (0.4-0.8 OD). Protein expression was induced by addition of 1.0 mM IPTG. After 3 hours incubation at 30° C. or 37° C. the OD$_{600}$ was measured and expression examined. 1.0 ml of each sample was centrifuged in a microfuge, the pellet resuspended in PBS and analysed by SDS-PAGE and Coomassie Blue staining.

Purification of His-Tagged Proteins

Various forms of 287 were cloned from strains 2996 and MC58. They were constructed with a C-terminus His-tagged fusion and included a mature form (aa 18-427), constructs with deletions (Δ1, Δ2, Δ3 and Δ4) and clones composed of either B or C domains. For each clone purified as a His-fusion, a single colony was streaked and grown overnight at 37° C. on a LB/Amp (100 µg/ml) agar plate. An isolated colony from this plate was inoculated into 20 ml of LB/Amp (100 µg/ml) liquid medium and grown overnight at 37° C. with shaking. The overnight culture was diluted 1:30 into 1.0 L LB/Amp (100 µg/ml) liquid medium and allowed to grow at the optimal temperature (30 or 37° C.) until the OD$_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of either (i) cold buffer A (300 mM NaCl, 50 mM phosphate buffer, 10 mM imidazole, pH 8.0) for soluble proteins or (ii) buffer B (10 mM Tris-HCl, 100 mM phosphate buffer, pH 8.8 and, optionally, 8M urea) for insoluble proteins. Proteins purified in a soluble form included 287-His, Δ1, Δ2, Δ3 and Δ4287-His, Δ4287MC58-His, 287c-His and 287cMC58-His. Protein 287bMC58-His was insoluble and purified accordingly. Cells were disrupted by sonication on ice four times for 30 sec at 40 W using a Branson sonifier 450 and centrifuged at 13000×g for 30 min at 4° C. For insoluble proteins, pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants for both soluble and insoluble preparations were mixed with 150 µl Ni$^{2+}$-resin (previously equilibrated with either buffer A or buffer B, as appropriate) and incubated at room temperature with gentle agitation for 30 min. The resin was Chelating Sepharose Fast Flow (Pharmacia), prepared according to the manufacturer's protocol. The batch-wise preparation was centrifuged at 700 g for 5 min at 4° C. and the supernatant discarded. The resin was washed twice (batch-wise) with 10 ml buffer A or B for 10 min, resuspended in 1.0 ml buffer A or B and loaded onto a disposable column. The resin continued to be washed with either (i) buffer A at 4° C. or (ii) buffer B at room temperature, until the OD$_{280}$ of the flow-through reached 0.02-0.01. The resin was further washed with either (i) cold buffer C (300 mM NaCl, 50 mM phosphate buffer, 20 mM imidazole, pH 8.0) or (ii) buffer D (10 mM Tris-HCl, 100 mM phosphate buffer, pH 6.3 and, optionally, 8M urea) until OD$_{280}$ of the flow-through reached 0.02-0.01. The His-fusion protein was eluted by addition of 700 µl of either (i) cold elution buffer A (300 mM NaCl, 50 mM phosphate buffer, 250 mM imidazole, pH 8.0) or (ii) elution buffer B (10 mM Tris-HCl, 100 mM phosphate buffer, pH 4.5 and, optionally, 8M urea) and fractions collected until the OD$_{280}$ indicated all the recombinant protein was obtained 20 µl aliquots of each elution fraction were analysed by SDS-PAGE. Protein concentrations were estimated using the Bradford assay.

Renaturation of Denatured His-Fusion Proteins.

Denaturation was required to solubilize 287bMC8, so a renaturation step was employed prior to immunisation. Glycerol was added to the denatured fractions obtained above to give a final concentration of 10% v/v. The proteins were diluted to 200 µg/ml using dialysis buffer I (10% v/v glycerol, 0.5M arginine, 50 mM phosphate buffer, 5.0 mM reduced glutathione, 0.5 mM oxidised glutathione, 2.0M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

$$\text{Protein (mg/ml)} = (1.55 \times OD_{280}) - (0.76 \times OD_{260})$$

Immunization

Balb/C mice were immunized with antigens on days 0, 21 and 35 and sera analyzed at day 49.

Sera Analysis—ELISA

The acapsulated MenB M7 and the capsulated strains were plated on chocolate agar plates and incubated overnight at 37° C. with 5% CO$_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 4000 rpm. The supernatant was discarded and bacteria were washed twice with PBS, resuspended in PBS containing 0.025% formaldehyde, and incubated for 1 hour at 37° C. and then overnight at 4° C. with stirring. 100 µl bacterial cells were added to each well of a 96 well Greiner plate and incubated overnight at 4° C. The wells were then washed three times with PBT washing buffer (0.1% Tween-20 in PBS). 200 µl of saturation buffer (2.7% polyvinylpyrrolidone 10 in water) was added to each well and the plates incubated for 2 hours at 37° C. Wells were washed three times with PBT. 200 µl of diluted sera (Dilution buffer. 1% BSA, 0.1% Tween-20, 0.1% $NaN_3$ in PBS) were added to each well and the plates incubated for 2 hours at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH 5, 10 mg of O-phenildiamine and 10 µl of $H_2O_2$) were added to each well and the plates were left at room temperature for 20 minutes. 100 µl 12.5% $H_2SO_4$ was added to each well and $OD_{490}$ was followed. The ELISA titers were calculated abitrarely as the dilution of sera which gave an $OD_{490}$ value of 0.4 above the level of preimmune sera. The ELISA was considered positive when the dilution of sera with $OD_{490}$ of 0.4 was higher than 1:400.

Sera Analysis—FACS Scan Bacteria Binding Assay

The acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA in PBS, 0.4% $NaN_3$) and centrifuged for 5 minutes at 4000 rpm. Cells were resuspended in blocking buffer to reach $OD_{620}$ of 0.05. 100 µl bacterial cells were added to each well of a Costar 96 well plate. 100 µl of diluted (1:100, 1:200, 1:400) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated $F(ab)_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan (Laser Power 15 mW) setting were: FL2 on; FSC-H threshold: 92; FSC PMT Voltage: E 01; SSC PMT: 474; Amp. Gains 6.1; FL-2 PMT: 586; compensation values: 0.

Sera Analysis—Bactericidal Assay

N. meningitidis strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 10 mM $MgCl_2$, 10 mM $CaCl_2$ and 0.5% (w/v) BSA (assay buffer) at the working dilution of $10^5$ CFU/ml. The total volume of the final reaction mixture was 50 µl with 25 µl of serial two fold dilution of test serum, 12.5 µl of bacteria at the working dilution, 12.5 µl of baby rabbit complement (final concentration 25%).

Controls included bacteria incubated with complement serum, immune sera incubated with bacteria and with complement inactivated by heating at 56° C. for 30'. Immediately after the addition of the baby rabbit complement, 10 µl of the controls were plated on Mueller-Hinton agar plates using the tilt method (time 0). The 96-wells plate was incubated for 1 hour at 37° C. with rotation. 7 µl of each sample were plated on Mueller-Hinton agar plates as spots, whereas 10 µl of the controls were plated on Mueller-Hinton agar plates using the tilt method (time 1). Agar plates were incubated for 18 hours at 37 degrees and the colonies corresponding to time 0 and time 1 were counted.

Sera Analysis—Western Blots

Purified proteins (500 ng/lane), outer membrane vesicles (5 µg) and total cell extracts (25 µg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: N. meningitidis strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson sonifier 3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilise the inner membranes. The suspension was centrifuged at 1000 g for 10 minutes to remove aggregates, the supernatant was further centrifuged at 50000 g for 3 hours. The pellet, containing the outer membranes was washed in PBS and resuspended in the same buffer. Protein concentration was measured by the D.C. Bio-Rad Protein assay (Modified Lowry method), using BSA as a standard.

Total cell extracts were prepared as follows: N. meningitidis strain 2996 was grown overnight on a GC plate, harvested with a loop and resuspended in 1 ml of 20 mM Tris-HCl. Heat inactivation was performed at 56° C. for 30 minutes.

The invention claimed is:

1. A hybrid protein of formula NH$_2$-A-B—COOH, wherein A and B are different Neisserial proteins and are each selected from orf1, orf4, orf25, orf40, orf46, orf83, 233, 287, 2921, 564, 687, 741, 907, 919, 953, 961 and 983, wherein when the different Neisserial proteins are 953 and 287, A is 953 and B is 287.

2. The protein of claim 1, wherein A and B are each selected from ORF46, 287, 741, 919, 953, 961 and 983.

3. The protein of claim 2, wherein at least one of said ORF46, 287, 741, 919, 953, 961 and 983 consists essentially of the full-length form of the protein.

4. The protein of claim 2, wherein at least one of said ORF46, 287, 741, 919, 953, 961 and 983 has a deletion.

5. The protein of claim 4, wherein A and/or B has a poly-glycine deletion ('ΔG').

6. The protein of claim 5, wherein A and/or B is ΔG741 or ΔG983 or B is ΔG-287.

7. The protein of claim 4, wherein A and/or B is a truncated protein.

8. The protein of claim 7, wherein B is Δ1-287, Δ2-287, Δ3-287 or Δ4-287.

9. The protein of claim 1, wherein A and B are: (a) 919 and 287; (b) 953 and 287; (c) 287 and ORF46; (d) ORF1 and ORF46; (e) 919 and ORF46; (f) ORF46 and 919; (g) ORF46 and 741; (h) ORF46 and 961; (i) 961 and ORF46; (j) 961 and 741; or (k) 961 and 983.

10. The protein of claim 4, wherein the protein is ΔG287-919, ΔG287-961, ΔG983-ORF46, ΔG983-741, ΔG983-961, ΔG983-961C, ΔG741-961, ΔG741-961C, ΔG741-983, ΔG741-ORF46, ORF46-961C, 961C-ORF46, 961C-741, 961C-983, 961CL-ORF46, 961CL-741 or 961CL-983.

11. The protein of claim 2, wherein B is 287.

12. The protein of claim 1, wherein B is ΔG-287.

13. The protein of claim 12, wherein A is ORF46, 919, 953 or 961.

14. The protein of claim 11, wherein 287 is from strain 2996 or 394/98.

15. The protein of claim 2, wherein A is 961.

16. The protein of claim 1, wherein A and B are from the same strain.

17. The protein of claim 1, wherein A and B are joined directly.

18. The protein of claim 1, wherein A and B are joined via a linker peptide.

19. The protein of claim 18, wherein the linker peptide is a poly-glycine linker, with the proviso that B is not a AG protein.

20. The protein of claim 11, wherein 287 is from strain 2996 or 394/98.

21. The protein of claim 12, wherein 287 is from strain 2996 or 394/98.

22. The protein of claim 13, wherein 287 is from strain 2996 or 394/98.

23. The protein of claim 9, wherein A and B are from the same strain.

24. The protein of claim 10, wherein A and B are from the same strain.

25. The protein of claim 9, wherein A and B are joined directly.

26. The protein of claim 10, wherein A and B are joined directly.

27. The protein of claim 9, wherein A and B are joined via a linker peptide.

28. The protein of claim 10, wherein A and B are joined via a linker peptide.

29. A method for producing the hybrid protein of claim 1 comprising expressing in a cell a nucleic acid encoding the hybrid protein of claim 1.

30. The method of claim 29, wherein A and B are: (a) 919 and 287; (b) 953 and 287; (c) 287 and ORF46; (d) ORF1 and ORF46; (e) 919 and ORF46; (f) ORF46 and 919; (g) ORF46 and 741; (h) ORF46 and 961; (i) 961 and ORF46; (j) 961 and 741; or (k) 961 and 983.

31. The method of claim 29, in which the cell is an *E. coli* cell.

32. The method of claim 30, in which the cell is an *E. coli* cell.

33. A composition comprising the hybrid protein of claim 1 and an aluminum salt.

34. The composition of claim 33, wherein A and B are: (a) 919 and 287; (b) 953 and 287; (c) 287 and ORF46; (d) ORF1 and ORF46; (e) 919 and ORF46; (f) ORF46 and 919; (g) ORF46 and 741; (h) ORF46 and 961; (i) 961 and ORF46; (j) 961 and 741; or (k) 961 and 983.

* * * * *

SEQUENCE LISTING

<160> NUMBER OF SEQ ID NOS: 121

<210> SEQ ID NO 1
<211> LENGTH: 608
<212> TYPE: PRT
<213> ORGANISM: Neisseria meningitidis (group B)
<220> FEATURE:
<221> NAME/KEY: MISC_FEATURE
<222> LOCATION: (1)..(24)
<223> OTHER INFORMATION: Leader peptide

<400> SEQUENCE: 1

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
                35                  40                  45

His Leu Phe Gly Ser Arg Gly Glu Leu Ala Glu Arg Ser Gly His Ile
        50                  55                  60

Gly Leu Gly Lys Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ser Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
210                 215                 220

Asn Gly Thr Ala Asp Ile Val Lys Asn Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
        290                 295                 300

Gly Ile Glu Ala Val Ser Asn Ile Phe Met Ala Ile Pro Ile Lys
305                 310                 315                 320

Gly Ile Gly Ala Val Arg Gly Lys Tyr Gly Leu Gly Gly Ile Thr Ala
                325                 330                 335

His Pro Ile Lys Arg Ser Gln Met Gly Ala Ile Ala Leu Pro Lys Gly
            340                 345                 350

```
Lys Ser Ala Val Ser Asp Asn Phe Ala Asp Ala Ala Tyr Ala Lys Tyr
            355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Ile Pro Lys Ala
            435                 440                 445

Lys Pro Val Ser Asp Ala Lys Pro Arg Trp Glu Val Asp Arg Lys Leu
    450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
            500                 505                 510

Gly Met Gly Lys Phe Thr Asp Ser Met Asn Asp Lys Ala Phe Ser Arg
            515                 520                 525

Leu Val Lys Ser Val Lys Glu Asn Gly Phe Thr Asn Pro Val Val Glu
    530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
            580                 585                 590

Val Leu Asn Glu Ser Gly Asn Val Lys Arg Pro Arg Tyr Arg Ser Lys
    595                 600                 605

<210> SEQ ID NO 2
<211> LENGTH: 464
<212> TYPE: PRT
<213> ORGANISM: Artificial
<220> FEATURE:
<223> OTHER INFORMATION: deletion G287 in strain MC58

<400> SEQUENCE: 2

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
                20                  25                  30

Gly Ser Gln Gly Gln Gly Ala Pro Ser Ala Gln Gly Ser Gln Asp Met
            35                  40                  45

Ala Ala Val Ser Glu Glu Asn Thr Gly Asn Gly Gly Ala Val Thr Ala
    50                  55                  60

Asp Asn Pro Lys Asn Glu Asp Glu Val Ala Gln Asn Asp Met Pro Gln
65                  70                  75                  80

Asn Ala Ala Gly Thr Asp Ser Ser Thr Pro Asn His Thr Pro Asp Pro
                85                  90                  95

Asn Met Leu Ala Gly Asn Met Glu Asn Gln Ala Thr Asp Ala Gly Glu
            100                 105                 110
```

Ser Ser Gln Pro Ala Asn Gln Pro Asp Met Ala Asn Ala Ala Asp Gly
        115                 120                 125

Met Gln Gly Asp Asp Pro Ser Ala Gly Gly Gln Asn Ala Gly Asn Thr
    130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
            165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
        195                 200                 205

Asn Asn Phe Leu Asp Glu Glu Val Gln Leu Lys Ser Glu Phe Glu Lys
    210                 215                 220

Leu Ser Asp Ala Asp Lys Ile Ser Asn Tyr Lys Lys Asp Gly Lys Asn
225                 230                 235                 240

Asp Lys Phe Val Gly Leu Val Ala Asp Ser Val Gln Met Lys Gly Ile
            245                 250                 255

Asn Gln Tyr Ile Ile Phe Tyr Lys Pro Lys Pro Thr Ser Phe Ala Arg
            260                 265                 270

Phe Arg Arg Ser Ala Arg Ser Arg Arg Ser Leu Pro Ala Glu Met Pro
        275                 280                 285

Leu Ile Pro Val Asn Gln Ala Asp Thr Leu Ile Val Asp Gly Glu Ala
    290                 295                 300

Val Ser Leu Thr Gly His Ser Gly Asn Ile Phe Ala Pro Glu Gly Asn
305                 310                 315                 320

Tyr Arg Tyr Leu Thr Tyr Gly Ala Glu Lys Leu Pro Gly Gly Ser Tyr
            325                 330                 335

Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
        355                 360                 365

Arg Pro Tyr Pro Thr Arg Gly Arg Phe Ala Ala Lys Val Asp Phe Gly
    370                 375                 380

Ser Lys Ser Val Asp Gly Ile Ile Asp Ser Gly Asp Asp Leu His Met
385                 390                 395                 400

Gly Thr Gln Lys Phe Lys Ala Ala Ile Asp Gly Asn Gly Phe Lys Gly
            405                 410                 415

Thr Trp Thr Glu Asn Gly Ser Gly Asp Val Ser Gly Lys Phe Tyr Gly
            420                 425                 430

Pro Ala Gly Glu Glu Val Ala Gly Lys Tyr Ser Tyr Arg Pro Thr Asp
        435                 440                 445

Ala Glu Lys Gly Gly Phe Gly Val Phe Ala Gly Lys Lys Glu Gln Asp
450                 455                 460

<210> SEQ ID NO 3
<211> LENGTH: 2505
<212> TYPE: DNA
<213> ORGANISM: Artificial
<220> FEATURE:
<223> OTHER INFORMATION: deletion G287-919

<400> SEQUENCE: 3
atggctagcc ccgatgttaa atcggcggac acgctgtcaa aaccggccgc tcctgttgtt     60

-continued

```
gctgaaaaag agacagaggt aaaagaagat gcgccacagg caggttctca aggacagggc      120
gcgccatcca cacaaggcag ccaagatatg cggcagtttt cggcagaaaa tacaggcaat      180
ggcggtgcgg caacaacgga caaacccaaa aatgaagacg agggaccgca aaatgatatg      240
ccgcaaaatt ccgccgaatc cgcaaatcaa acagggaaca accaacccgc cgattcttca      300
gattccgccc ccgcgtcaaa ccctgcacct gcgaatggcg gtagcaattt tggaagggtt      360
gatttggcta atggcgtttt gattgatggg ccgtcgcaaa atataacgtt gacccactgt      420
aaaggcgatt cttgtaatgg tgataattta ttggatgaag aagcaccgtc aaaatcagaa      480
tttgaaaatt taaatgagtc tgaacgaatt gagaaatata agaaagatgg gaaaagcgat      540
aaatttacta atttggttgc gacagcagtt caagctaatg gaactaacaa atatgtcatc      600
atttataaag acaagtccgc ttcatcttca tctgcgcgat tcaggcgttc tgcacggtcg      660
aggaggtcgc ttcctgccga gatgccgcta atccccgtca atcaggcgga tacgctgatt      720
gtcgatgggg aagcggtcag cctgacgggg cattccggca atatcttcgc gcccgaaggg      780
aattaccggt atctgactta cggggcgaaa aaattgcccg gcggatcgta tgccctccgt      840
gtgcaaggcg aaccgcaaa aggcgaaatg cttgctggca cggccgtgta caacggcgaa      900
gtgctgcatt ttcatacgga aaacggccgt ccgtacccga ctagaggcag gtttgccgca      960
aaagtcgatt tcggcagcaa atctgtggac ggcattatcg acagcggcga tgatttgcat     1020
atgggtacga aaaattcaa agccgccatc gatggaaacg gctttaaggg gacttggacg     1080
gaaaatggcg gcggggatgt tccggaagg ttttacggcc cggccggcga ggaagtggcg     1140
ggaaaataca gctatcgccc gacagatgcg gaaaagggcg gattcggcgt gtttgccggc     1200
aaaaaagagc aggatggatc cggaggagga ggatgccaaa gcaagagcat ccaaaccttt     1260
ccgcaacccg acacatccgt catcaacggc ccggaccggc cggtcggcat ccccgacccc     1320
gccggaacga cggtcggcgg cggcggggcc gtctataccg ttgtaccgca cctgtccctg     1380
ccccactggg cggcgcagga tttgccaaaa agcctgcaat ccttccgcct cggctgcgcc     1440
aatttgaaaa accgccaagg ctggcaggat gtgtgcgccc aagcctttca acccccgtc     1500 cattcctttc aggcaaaaca gttttttgaa cgctatttca cgccgtggca ggttgcaggc     1560
aacggaagcc ttgccggtac ggttaccggc tattacgagc cggtgctgaa gggcgacgac     1620
aggcggacgg cacaagcccg cttcccgatt acggtattc ccgacgattt tatctccgtc     1680
cccctgcctg ccggtttgcg gagcggaaaa gcccttgtcc gcatcaggca gacggaaaa     1740 aacagcggca caatcgacaa taccggcggc acacataccg ccgacctctc ccgattcccc     1800
atcaccgcgc gcacaacggc aatcaaaggc aggttttgaag gaagccgctt cctcccctac     1860
cacacgcgca accaaatcaa cggcggcgcg cttgacggca agcccccgat actcggttac     1920
gccgaagacc ccgtcgaact ttttttttatg cacatccaag gctcgggccg tctgaaaacc     1980
ccgtccggca aatacatccg catcggctat gccgacaaaa acgaacatcc ctacgttttcc     2040 atcggacgct atatggcgga caaaggctac ctcaagctcg gcagacctc gatgcagggc     2100 atcaaagcct atatgcggca aaatccgcaa cgcctcgccg aagttttggg tcaaaacccc     2160
agctatatct ttttccgcga gcttgccgga agcagcaatg acgtcccgt cggcgcactg     2220 ggcacgccgt tgatggggga atatgccggc gcagtcgacc ggcactacat taccttgggc     2280
gcgcccttat ttgtcgccac cgcccatccg gttacccgca aagccctcaa ccgcctgatt     2340
atggcgcagg ataccggcag cgcgattaaa ggcgcggtgc gcgtggatta ttttttgggga     2400 tacggcgacg aagccggcga acttgccggc aaacagaaaa ccacgggtta cgtctggcag     2460
```

```
ctcctaccca acggtatgaa gcccgaatac cgcccgtaac tcgag                    2505
```

<210> SEQ ID NO 4
<211> LENGTH: 832
<212> TYPE: PRT
<213> ORGANISM: Artificial
<220> FEATURE:
<223> OTHER INFORMATION: deletion G287-919

<400> SEQUENCE: 4

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350
```

```
Asn Gly Phe Lys Gly Thr Trp Thr Glu Asn Gly Gly Asp Val Ser
            355                 360                 365
Gly Arg Phe Tyr Gly Pro Ala Gly Glu Val Ala Gly Lys Tyr Ser
    370                 375                 380
Tyr Arg Pro Thr Asp Ala Glu Lys Gly Phe Gly Val Phe Ala Gly
385                 390                 395                 400
Lys Lys Glu Gln Asp Gly Ser Gly Gly Gly Cys Gln Ser Lys Ser
                405                 410                 415
Ile Gln Thr Phe Pro Gln Pro Asp Thr Ser Val Ile Asn Gly Pro Asp
            420                 425                 430
Arg Pro Val Gly Ile Pro Asp Pro Ala Gly Thr Thr Val Gly Gly Gly
            435                 440                 445
Gly Ala Val Tyr Thr Val Val Pro His Leu Ser Leu Pro His Trp Ala
    450                 455                 460
Ala Gln Asp Phe Ala Lys Ser Leu Gln Ser Phe Arg Leu Gly Cys Ala
465                 470                 475                 480
Asn Leu Lys Asn Arg Gln Gly Trp Gln Asp Val Cys Ala Gln Ala Phe
                485                 490                 495
Gln Thr Pro Val His Ser Phe Gln Ala Lys Gln Phe Phe Glu Arg Tyr
            500                 505                 510
Phe Thr Pro Trp Gln Val Ala Gly Asn Gly Ser Leu Ala Gly Thr Val
            515                 520                 525
Thr Gly Tyr Tyr Glu Pro Val Leu Lys Gly Asp Asp Arg Arg Thr Ala
    530                 535                 540
Gln Ala Arg Phe Pro Ile Tyr Gly Ile Pro Asp Asp Phe Ile Ser Val
545                 550                 555                 560
Pro Leu Pro Ala Gly Leu Arg Ser Gly Lys Ala Leu Val Arg Ile Arg
                565                 570                 575
Gln Thr Gly Lys Asn Ser Gly Thr Ile Asp Asn Thr Gly Gly Thr His
            580                 585                 590
Thr Ala Asp Leu Ser Arg Phe Pro Ile Thr Ala Arg Thr Thr Ala Ile
            595                 600                 605
Lys Gly Arg Phe Glu Gly Ser Arg Phe Leu Pro Tyr His Thr Arg Asn
610                 615                 620
Gln Ile Asn Gly Gly Ala Leu Asp Gly Lys Ala Pro Ile Leu Gly Tyr
625                 630                 635                 640
Ala Glu Asp Pro Val Glu Leu Phe Phe Met His Ile Gln Gly Ser Gly
                645                 650                 655
Arg Leu Lys Thr Pro Ser Gly Lys Tyr Ile Arg Ile Gly Tyr Ala Asp
            660                 665                 670
Lys Asn Glu His Pro Tyr Val Ser Ile Gly Arg Tyr Met Ala Asp Lys
            675                 680                 685
Gly Tyr Leu Lys Leu Gly Gln Thr Ser Met Gln Gly Ile Lys Ala Tyr
    690                 695                 700
Met Arg Gln Asn Pro Gln Arg Leu Ala Glu Val Leu Gly Gln Asn Pro
705                 710                 715                 720
Ser Tyr Ile Phe Phe Arg Glu Leu Ala Gly Ser Ser Asn Asp Gly Pro
            725                 730                 735
Val Gly Ala Leu Gly Thr Pro Leu Met Gly Glu Tyr Ala Gly Ala Val
            740                 745                 750
Asp Arg His Tyr Ile Thr Leu Gly Ala Pro Leu Phe Val Ala Thr Ala
            755                 760                 765
His Pro Val Thr Arg Lys Ala Leu Asn Arg Leu Ile Met Ala Gln Asp
```

```
                770                 775                 780
Thr Gly Ser Ala Ile Lys Gly Ala Val Arg Val Asp Tyr Phe Trp Gly
785                 790                 795                 800

Tyr Gly Asp Glu Ala Gly Glu Leu Ala Gly Lys Gln Lys Thr Thr Gly
                805                 810                 815

Tyr Val Trp Gln Leu Leu Pro Asn Gly Met Lys Pro Glu Tyr Arg Pro
            820                 825                 830
```

<210> SEQ ID NO 5
<211> LENGTH: 1746
<212> TYPE: DNA
<213> ORGANISM: Artificial
<220> FEATURE:
<223> OTHER INFORMATION: deletion G287-953

<400> SEQUENCE: 5

```
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaacccgc cgattcttca     300
gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg aaaaagcgat     540
aaatttacta atttggttgc gacagcagtt caagctaatg aactaacaa atatgtcatc     600
atttataaag acaagtccgc ttcatcttca tctgcgcgat tcaggcgttc tgcacggtcg     660
aggaggtcgc ttcctgccga gatgccgcta atccccgtca atcaggcgga tacgctgatt     720
gtcgatgggg aagcggtcag cctgacgggg cattccggca atatcttcgc gcccgaaggg     780
aattaccggt atctgactta cggggcgaa aaattgcccg gcggatcgta tgccctccgt     840
gtgcaaggcg aaccggcaaa aggcgaaatg cttgctggca cggccgtgta caacggcgaa     900
gtgctgcatt tcatacgga aaacggccgt ccgtacccga ctagaggcag gtttgccgca     960
aaagtcgatt cggcagcaa atctgtggac ggcattatcg acagcggcga tgatttgcat    1020
atgggtacgc aaaaattcaa agccgccatc gatggaaacg ctttaaggg acttggacg     1080
gaaaatggcg gcggggatgt ttccggaagg ttttacggcc cggccggcga ggaagtggcg    1140
ggaaaataca gctatcgccc gacagatgcg gaaaagggcg gattcggcgt gtttgccggc    1200
aaaaagagc aggatggatc cggaggagga ggagccacct acaaagtgga cgaatatcac    1260
gccaacgccc gtttcgccat cgaccatttc aacaccagca ccaacgtcgg cggtttttac    1320
ggtctgaccg gttccgtcga gttcgaccaa gcaaaacgcg acggtaaaat cgacatcacc    1380
atccccgttg ccaacctgca aagcggttcg caacactta ccgaccacct gaaatcagcc    1440
gacatcttcg atgccgccca atatccggac atccgctttg tttccaccaa attcaacttc    1500
aacggcaaaa aactggtttc cgttgacggc aacctgacca tgcacggcaa accgccccc    1560
gtcaaactca agccgaaaaa attcaactgc taccaaagcc cgatggcgaa accgaagtt    1620
tgcggcggcg acttcagcac caccatcgac cgcaccaaat ggggcgtgga ctacctcgtt    1680
aacgttggta tgaccaaaag cgtccgcatc gacatccaaa tcgaggcagc caaacaataa    1740
```

```
ctcgag                                                                 1746
```

<210> SEQ ID NO 6
<211> LENGTH: 579
<212> TYPE: PRT
<213> ORGANISM: Artificial
<220> FEATURE:
<223> OTHER INFORMATION: deletion G287-953

<400> SEQUENCE: 6

| Met | Ala | Ser | Pro | Asp | Val | Lys | Ser | Ala | Asp | Thr | Leu | Ser | Lys | Pro | Ala |
|---|---|---|---|---|---|---|---|---|---|---|---|---|---|---|---|
| 1 | | | | 5 | | | | | 10 | | | | | 15 | |

| Ala | Pro | Val | Val | Ala | Glu | Lys | Glu | Thr | Glu | Val | Lys | Glu | Asp | Ala | Pro |
| | | | 20 | | | | | 25 | | | | | 30 | | |

| Gln | Ala | Gly | Ser | Gln | Gly | Gln | Gly | Ala | Pro | Ser | Thr | Gln | Gly | Ser | Gln |
| | | 35 | | | | | 40 | | | | | 45 | | | |

| Asp | Met | Ala | Ala | Val | Ser | Ala | Glu | Asn | Thr | Gly | Asn | Gly | Gly | Ala | Ala |
| | 50 | | | | 55 | | | | | 60 | | | | | |

| Thr | Thr | Asp | Lys | Pro | Lys | Asn | Glu | Asp | Glu | Gly | Pro | Gln | Asn | Asp | Met |
| 65 | | | | | 70 | | | | | 75 | | | | | 80 |

| Pro | Gln | Asn | Ser | Ala | Glu | Ser | Ala | Asn | Gln | Thr | Gly | Asn | Asn | Gln | Pro |
| | | | | 85 | | | | | 90 | | | | | 95 | |

| Ala | Asp | Ser | Ser | Asp | Ser | Ala | Pro | Ala | Ser | Asn | Pro | Ala | Pro | Ala | Asn |
| | | | 100 | | | | | 105 | | | | | 110 | | |

| Gly | Gly | Ser | Asn | Phe | Gly | Arg | Val | Asp | Leu | Ala | Asn | Gly | Val | Leu | Ile |
| | | | 115 | | | | | 120 | | | | | 125 | | |

| Asp | Gly | Pro | Ser | Gln | Asn | Ile | Thr | Leu | Thr | His | Cys | Lys | Gly | Asp | Ser |
| | 130 | | | | | 135 | | | | | 140 | | | | |

| Cys | Asn | Gly | Asp | Asn | Leu | Leu | Asp | Glu | Glu | Ala | Pro | Ser | Lys | Ser | Glu |
| 145 | | | | | 150 | | | | | 155 | | | | | 160 |

| Phe | Glu | Asn | Leu | Asn | Glu | Ser | Glu | Arg | Ile | Glu | Lys | Tyr | Lys | Lys | Asp |
| | | | | 165 | | | | | 170 | | | | | 175 | |

| Gly | Lys | Ser | Asp | Lys | Phe | Thr | Asn | Leu | Val | Ala | Thr | Ala | Val | Gln | Ala |
| | | | 180 | | | | | 185 | | | | | 190 | | |

| Asn | Gly | Thr | Asn | Lys | Tyr | Val | Ile | Ile | Tyr | Lys | Asp | Lys | Ser | Ala | Ser |
| | | 195 | | | | | 200 | | | | | 205 | | | |

| Ser | Ser | Ser | Ala | Arg | Phe | Arg | Arg | Ser | Ala | Arg | Ser | Arg | Arg | Ser | Leu |
| | 210 | | | | | 215 | | | | | 220 | | | | |

| Pro | Ala | Glu | Met | Pro | Leu | Ile | Pro | Val | Asn | Gln | Ala | Asp | Thr | Leu | Ile |
| 225 | | | | | 230 | | | | | 235 | | | | | 240 |

| Val | Asp | Gly | Glu | Ala | Val | Ser | Leu | Thr | Gly | His | Ser | Gly | Asn | Ile | Phe |
| | | | | 245 | | | | | 250 | | | | | 255 | |

| Ala | Pro | Glu | Gly | Asn | Tyr | Arg | Tyr | Leu | Thr | Tyr | Gly | Ala | Glu | Lys | Leu |
| | | | 260 | | | | | 265 | | | | | 270 | | |

| Pro | Gly | Gly | Ser | Tyr | Ala | Leu | Arg | Val | Gln | Gly | Glu | Pro | Ala | Lys | Gly |
| | | 275 | | | | | 280 | | | | | 285 | | | |

| Glu | Met | Leu | Ala | Gly | Thr | Ala | Val | Tyr | Asn | Gly | Glu | Val | Leu | His | Phe |
| | 290 | | | | | 295 | | | | | 300 | | | | |

| His | Thr | Glu | Asn | Gly | Arg | Pro | Tyr | Pro | Thr | Arg | Gly | Arg | Phe | Ala | Ala |
| 305 | | | | | 310 | | | | | 315 | | | | | 320 |

| Lys | Val | Asp | Phe | Gly | Ser | Lys | Ser | Val | Asp | Gly | Ile | Ile | Asp | Ser | Gly |
| | | | | 325 | | | | | 330 | | | | | 335 | |

| Asp | Asp | Leu | His | Met | Gly | Thr | Gln | Lys | Phe | Lys | Ala | Ala | Ile | Asp | Gly |
| | | | 340 | | | | | 345 | | | | | 350 | | |

| Asn | Gly | Phe | Lys | Gly | Thr | Trp | Thr | Glu | Asn | Gly | Gly | Gly | Asp | Val | Ser |

|  |  | 355 |  |  | 360 |  |  | 365 |  |  |  |
|---|---|---|---|---|---|---|---|---|---|---|---|

Gly Arg Phe Tyr Gly Pro Ala Gly Glu Glu Val Ala Gly Lys Tyr Ser
    370                            375                    380

Tyr Arg Pro Thr Asp Ala Glu Lys Gly Gly Phe Gly Val Phe Ala Gly
385                            390                        395                  400

Lys Lys Glu Gln Asp Gly Ser Gly Gly Gly Ala Thr Tyr Lys Val
                  405                        410                        415

Asp Glu Tyr His Ala Asn Ala Arg Phe Ala Ile Asp His Phe Asn Thr
            420                      425                        430

Ser Thr Asn Val Gly Gly Phe Tyr Gly Leu Thr Gly Ser Val Glu Phe
         435                      440                    445

Asp Gln Ala Lys Arg Asp Gly Lys Ile Asp Ile Thr Ile Pro Val Ala
     450                        455                      460

Asn Leu Gln Ser Gly Ser Gln His Phe Thr Asp His Leu Lys Ser Ala
465                            470                        475                  480

Asp Ile Phe Asp Ala Ala Gln Tyr Pro Asp Ile Arg Phe Val Ser Thr
                  485                        490                    495

Lys Phe Asn Phe Asn Gly Lys Lys Leu Val Ser Val Asp Gly Asn Leu
            500                      505                        510

Thr Met His Gly Lys Thr Ala Pro Val Lys Leu Lys Ala Glu Lys Phe
         515                      520                    525

Asn Cys Tyr Gln Ser Pro Met Ala Lys Thr Glu Val Cys Gly Gly Asp
     530                        535                      540

Phe Ser Thr Thr Ile Asp Arg Thr Lys Trp Gly Val Asp Tyr Leu Val
545                            550                        555                  560

Asn Val Gly Met Thr Lys Ser Val Arg Ile Asp Ile Gln Ile Glu Ala
                  565                        570                    575

Ala Lys Gln

<210> SEQ ID NO 7
<211> LENGTH: 2388
<212> TYPE: DNA
<213> ORGANISM: Artificial
<220> FEATURE:
<223> OTHER INFORMATION: deletion 287-961

<400> SEQUENCE: 7

| | | | | | |
|---|---|---|---|---|---|
| atggctagcc | ccgatgttaa | atcggcggac | acgctgtcaa | aaccggccgc | tcctgttgtt | 60 |
| gctgaaaaag | agacagaggt | aaaagaagat | gcgccacagg | caggttctca | aggacagggc | 120 |
| gcgccatcca | cacaaggcag | ccaagatatg | gcggcagttt | cggcagaaaa | tacaggcaat | 180 |
| ggcggtgcgg | caacaacgga | caaacccaaa | aatgaagacg | agggaccgca | aaatgatatg | 240 |
| ccgcaaaatt | ccgccgaatc | cgcaaatcaa | acagggaaca | accaacccgc | cgattcttca | 300 |
| gattccgccc | ccgcgtcaaa | ccctgcacct | gcgaatggcg | gtagcaattt | tggaagggtt | 360 |
| gatttggcta | atggcgtttt | gattgatggg | ccgtcgcaaa | atataacgtt | gacccactgt | 420 |
| aaaggcgatt | cttgtaatgg | tgataattta | ttggatgaag | aagcaccgtc | aaaatcagaa | 480 |
| tttgaaaatt | taaatgagtc | tgaacgaatt | gagaaatata | agaaagatgg | gaaaagcgat | 540 |
| aaatttacta | atttggttgc | gacagcagtt | caagctaatg | gaactaacaa | atatgtcatc | 600 |
| atttataaag | acaagtccgc | ttcatcttca | tctgcgcgat | tcaggcgttc | tgcacggtcg | 660 |
| aggaggtcgc | ttcctgccga | gatgccgcta | atccccgtca | atcaggcgga | tacgctgatt | 720 |
| gtcgatgggg | aagcggtcag | cctgacgggg | cattccggca | atatcttcgc | gcccgaaggg | 780 |

```
aattaccggt atctgactta cggggcggaa aaattgcccg gcggatcgta tgccctccgt    840
gtgcaaggcg aaccggcaaa aggcgaaatg cttgctggca cggccgtgta caacggcgaa    900
gtgctgcatt ttcatacgga aaacggccgt ccgtacccga ctagaggcag gtttgccgca    960
aaagtcgatt tcggcagcaa atctgtggac ggcattatcg acagcggcga tgatttgcat   1020
atgggtacgc aaaaattcaa agccgccatc gatggaaacg gctttaaggg gacttggacg   1080
gaaaatggcg gcggggatgt ttccggaagg ttttacggcc cggccggcga ggaagtggcg   1140
ggaaaataca gctatcgccc gacagatgcg gaaaagggcg gattcggcgt gtttgccggc   1200
aaaaaagagc aggatggatc cggaggagga ggagccacaa acgacgacga tgttaaaaaa   1260
gctgccactg tggccattgc tgctgcctac aacaatggcc aagaaatcaa cggtttcaaa   1320
gctggagaga ccatctacga cattgatgaa gacggcacaa ttaccaaaaa agacgcaact   1380
gcagccgatg ttgaagccga cgactttaaa ggtctgggtc tgaaaaaagt cgtgactaac   1440
ctgaccaaaa ccgtcaatga aaacaaacaa acgtcgatg ccaaagtaaa agctgcagaa   1500
tctgaaatag aaaagttaac aaccaagtta gcagacactg atgccgcttt agcagatact   1560
gatgccgctc tggatgcaac caccaacgcc ttgaataaat tgggagaaaa tataacgaca   1620
tttgctgaag agactaagac aaatatcgta aaaattgatg aaaaattaga agccgtggct   1680
gataccgtcg acaagcatgc cgaagcattc aacgatatcg ccgattcatt ggatgaaacc   1740
aacactaagg cagacgaagc cgtcaaaacc gccaatgaag ccaaacagac ggccgaagaa   1800
accaaacaaa acgtcgatgc caaagtaaaa gctgcagaaa ctgcagcagg caaagccgaa   1860
gctgccgctg gcacagctaa tactgcagcc gacaaggccg aagctgtcgc tgcaaaagtt   1920
accgacatca agctgatat cgctacgaac aaagataata ttgctaaaaa agcaaacagt   1980
gccgacgtgt acaccagaga agagtctgac agcaaatttg tcagaattga tggtctgaac   2040
gctactaccg aaaaattgga cacacgcttg gcttctgctg aaaaatccat tgccgatcac   2100
gatactcgcc tgaacggttt ggataaaaca gtgtcagacc tgcgcaaaga aacccgccaa   2160
ggccttgcag aacaagccgc gctctccggt ctgttccaac cttacaacgt gggtcggttc   2220
aatgtaacgg ctgcagtcgg cggctacaaa tccgaatcgg cagtcgccat cggtaccggc   2280
ttccgcttta ccgaaaactt tgccgccaaa gcaggcgtgg cagtcggcac ttcgtccggt   2340
tcttccgcag cctaccatgt cggcgtcaat tacgagtggt aactcgag              2388
```

<210> SEQ ID NO 8
<211> LENGTH: 793
<212> TYPE: PRT
<213> ORGANISM: Artificial
<220> FEATURE:
<223> OTHER INFORMATION: deletion G287-961

<400> SEQUENCE: 8

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
                20                  25                  30

Gln Ala Gly Ser Gln Gly Gln Gly Ala Pro Ser Thr Gln Gly Ser Gln
            35                  40                  45

Asp Met Ala Ala Val Ser Ala Glu Asn Thr Gly Asn Gly Gly Ala Ala
        50                  55                  60

Thr Thr Asp Lys Pro Lys Asn Glu Asp Glu Gly Pro Gln Asn Asp Met
65                  70                  75                  80
```

```
Pro Gln Asn Ser Ala Glu Ser Ala Asn Gln Thr Gly Asn Asn Gln Pro
                85                  90                  95
Ala Asp Ser Ser Asp Ser Ala Pro Ala Ser Asn Pro Ala Pro Ala Asn
            100                 105                 110
Gly Gly Ser Asn Phe Gly Arg Val Asp Leu Ala Asn Gly Val Leu Ile
            115                 120                 125
Asp Gly Pro Ser Gln Asn Ile Thr Leu Thr His Cys Lys Gly Asp Ser
            130                 135                 140
Cys Asn Gly Asp Asn Leu Leu Asp Glu Glu Ala Pro Ser Lys Ser Glu
145                 150                 155                 160
Phe Glu Asn Leu Asn Glu Ser Glu Arg Ile Glu Lys Tyr Lys Lys Asp
                165                 170                 175
Gly Lys Ser Asp Lys Phe Thr Asn Leu Val Ala Thr Ala Val Gln Ala
            180                 185                 190
Asn Gly Thr Asn Lys Tyr Val Ile Ile Tyr Lys Asp Lys Ser Ala Ser
            195                 200                 205
Ser Ser Ser Ala Arg Phe Arg Arg Ser Ala Arg Ser Arg Arg Ser Leu
        210                 215                 220
Pro Ala Glu Met Pro Leu Ile Pro Val Asn Gln Ala Asp Thr Leu Ile
225                 230                 235                 240
Val Asp Gly Glu Ala Val Ser Leu Thr Gly His Ser Gly Asn Ile Phe
                245                 250                 255
Ala Pro Glu Gly Asn Tyr Arg Tyr Leu Thr Tyr Gly Ala Glu Lys Leu
            260                 265                 270
Pro Gly Gly Ser Tyr Ala Leu Arg Val Gln Gly Glu Pro Ala Lys Gly
            275                 280                 285
Glu Met Leu Ala Gly Thr Ala Val Tyr Asn Gly Glu Val Leu His Phe
        290                 295                 300
His Thr Glu Asn Gly Arg Pro Tyr Pro Thr Arg Gly Arg Phe Ala Ala
305                 310                 315                 320
Lys Val Asp Phe Gly Ser Lys Ser Val Asp Gly Ile Ile Asp Ser Gly
                325                 330                 335
Asp Asp Leu His Met Gly Thr Gln Lys Phe Lys Ala Ala Ile Asp Gly
            340                 345                 350
Asn Gly Phe Lys Gly Thr Trp Thr Glu Asn Gly Gly Gly Asp Val Ser
            355                 360                 365
Gly Arg Phe Tyr Gly Pro Ala Gly Glu Glu Val Ala Gly Lys Tyr Ser
        370                 375                 380
Tyr Arg Pro Thr Asp Ala Glu Lys Gly Gly Phe Gly Val Phe Ala Gly
385                 390                 395                 400
Lys Lys Glu Gln Asp Gly Ser Gly Gly Gly Ala Thr Asn Asp Asp
                405                 410                 415
Asp Val Lys Lys Ala Ala Thr Val Ala Ile Ala Ala Ala Tyr Asn Asn
            420                 425                 430
Gly Gln Glu Ile Asn Gly Phe Lys Ala Gly Glu Thr Ile Tyr Asp Ile
            435                 440                 445
Asp Glu Asp Gly Thr Ile Thr Lys Lys Asp Ala Thr Ala Ala Asp Val
            450                 455                 460
Glu Ala Asp Asp Phe Lys Gly Leu Gly Leu Lys Val Val Thr Asn
465                 470                 475                 480
Leu Thr Lys Thr Val Asn Glu Asn Lys Gln Asn Val Asp Ala Lys Val
                485                 490                 495
Lys Ala Ala Glu Ser Glu Ile Glu Lys Leu Thr Thr Lys Leu Ala Asp
```

```
                 500                 505                 510
Thr Asp Ala Ala Leu Ala Asp Thr Asp Ala Ala Leu Asp Ala Thr Thr
                515                 520                 525
Asn Ala Leu Asn Lys Leu Gly Glu Asn Ile Thr Thr Phe Ala Glu Glu
                530                 535                 540
Thr Lys Thr Asn Ile Val Lys Ile Asp Glu Lys Leu Glu Ala Val Ala
545                 550                 555                 560
Asp Thr Val Asp Lys His Ala Glu Ala Phe Asn Asp Ile Ala Asp Ser
                565                 570                 575
Leu Asp Glu Thr Asn Thr Lys Ala Asp Glu Ala Val Lys Thr Ala Asn
                580                 585                 590
Glu Ala Lys Gln Thr Ala Glu Glu Thr Lys Gln Asn Val Asp Ala Lys
                595                 600                 605
Val Lys Ala Ala Glu Thr Ala Ala Gly Lys Ala Glu Ala Ala Ala Gly
                610                 615                 620
Thr Ala Asn Thr Ala Ala Asp Lys Ala Glu Ala Val Ala Ala Lys Val
625                 630                 635                 640
Thr Asp Ile Lys Ala Asp Ile Ala Thr Asn Lys Asp Asn Ile Ala Lys
                645                 650                 655
Lys Ala Asn Ser Ala Asp Val Tyr Thr Arg Glu Ser Asp Ser Lys
                660                 665                 670
Phe Val Arg Ile Asp Gly Leu Asn Ala Thr Thr Glu Lys Leu Asp Thr
                675                 680                 685
Arg Leu Ala Ser Ala Glu Lys Ser Ile Ala Asp His Asp Thr Arg Leu
                690                 695                 700
Asn Gly Leu Asp Lys Thr Val Ser Asp Leu Arg Lys Glu Thr Arg Gln
705                 710                 715                 720
Gly Leu Ala Glu Gln Ala Ala Leu Ser Gly Leu Phe Gln Pro Tyr Asn
                725                 730                 735
Val Gly Arg Phe Asn Val Thr Ala Ala Val Gly Gly Tyr Lys Ser Glu
                740                 745                 750
Ser Ala Val Ala Ile Gly Thr Gly Phe Arg Phe Thr Glu Asn Phe Ala
                755                 760                 765
Ala Lys Ala Gly Val Ala Val Gly Thr Ser Ser Gly Ser Ser Ala Ala
                770                 775                 780
Tyr His Val Gly Val Asn Tyr Glu Trp
785                 790

<210> SEQ ID NO 9
<211> LENGTH: 2700
<212> TYPE: DNA
<213> ORGANISM: Artificial
<220> FEATURE:
<223> OTHER INFORMATION: deletion G287NZ-919

<400> SEQUENCE: 9
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
gcgccatccg cacaaggcgg tcaagatatg cggcggtttt cggaagaaaa tacaggcaat     180
ggcggtgcgg cagcaacgga caaacccaaa aatgaagacg agggggcgca aaatgatatg     240
ccgcaaaatg ccgccgatac agatagtttg acaccgaatc acaccccggc ttcgaatatg     300
ccggccggaa atatggaaaa ccaagcaccg gatgccgggg aatcggagca gccggcaaac     360
caaccggata tggcaaatac ggcggacgga atgcagggtg acgatccgtc ggcaggcggg     420
```

```
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgc tgattgtcga tggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaggcg aaatgctcgc gggcacggca   1080
gtgtacaacg gcgaagtgct gcattttcat acggaaaacg gccgtccgtc cccgtccaga   1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggatg ccaaagcaag   1440
agcatccaaa cctttccgca acccgacaca tccgtcatca acggcccgga ccggccggtc   1500
ggcatccccg acccgccgg aacgacggtc ggcggcggcg gggccgtcta taccgttgta   1560
ccgcacctgt ccctgcccca ctgggcggcg caggatttcg ccaaaagcct gcaatccttc   1620
cgcctcggct gcgccaattt gaaaaaccgc caaggctggc aggatgtgtg cgcccaagcc   1680
tttcaaaccc ccgtccattc ctttcaggca aaacagtttt ttgaacgcta tttcacgccg   1740
tggcaggttg caggcaacgg aagccttgcc ggtacggtta ccggctatta cgagccggtg   1800
ctgaagggcg acgacaggcg gacggcacaa gcccgcttcc cgatttacgg tattcccgac   1860
gattttatct ccgtccccct gcctgccggt ttgcggagcg gaaaagccct tgtccgcatc   1920
aggcagacgg gaaaaaacag cggcacaatc gacaataccg gcggcacaca taccgccgac   1980
ctctcccgat tccccatcac cgcgcgcaca acggcaatca aaggcaggtt tgaaggaagc   2040
cgcttcctcc cctaccacac gcgcaaccaa atcaacggcg gcgcgcttga cggcaaagcc   2100
ccgatactcg gttacgccga agaccccgtc gaacttttt tatgcacat ccaaggctcg   2160 ggccgtctga aaccccgtc cggcaaatac atccgcatcg gctatgccga caaaaacgaa   2220
catccctacg tttccatcgg acgctatatg gcggacaaag gctacctcaa gctcgggcag   2280
acctcgatgc agggcatcaa agcctatatg cggcaaaatc cgcaacgcct cgccgaagtt   2340
ttgggtcaaa accccagcta tatctttttc cgcgagcttg ccggaagcag caatgacggt   2400
cccgtcggcg cactgggcac gccgttgatg ggggaatatg ccggcgcagt cgaccggcac   2460
tacattacct tgggcgcgcc cttatttgtc gccaccgccc atccggttac ccgcaaagcc   2520
ctcaaccgcc tgattatggc gcaggatacc ggcagcgcga ttaaaggcgc ggtgcgcgtg   2580
gattattttt ggggatacgg cgacgaagcc ggcgaacttg ccggcaaaca gaaaaccacg   2640
ggttacgtct ggcagctcct acccaacggt atgaagcccg aataccgccc gtaaaagctt   2700
```

<210> SEQ ID NO 10

<211> LENGTH: 897
<212> TYPE: PRT
<213> ORGANISM: Artificial
<220> FEATURE:
<223> OTHER INFORMATION: deletion G287NZ-919

<400> SEQUENCE: 10

```
Met Ala Ser Pro Asp Val Lys Ser Ala Asp Thr Leu Ser Lys Pro Ala
1               5                   10                  15
Ala Pro Val Val Ser Glu Lys Glu Thr Glu Ala Lys Glu Asp Ala Pro
            20                  25                  30
Gln Ala Gly Ser Gln Gly Gln Gly Ala Pro Ser Ala Gln Gly Gly Gln
        35                  40                  45
Asp Met Ala Ala Val Ser Glu Glu Asn Thr Gly Asn Gly Gly Ala Ala
    50                  55                  60
Ala Thr Asp Lys Pro Lys Asn Glu Asp Glu Gly Ala Gln Asn Asp Met
65                  70                  75                  80
Pro Gln Asn Ala Ala Asp Thr Asp Ser Leu Thr Pro Asn His Thr Pro
                85                  90                  95
Ala Ser Asn Met Pro Ala Gly Asn Met Glu Asn Gln Ala Pro Asp Ala
            100                 105                 110
Gly Glu Ser Glu Gln Pro Ala Asn Gln Pro Asp Met Ala Asn Thr Ala
        115                 120                 125
Asp Gly Met Gln Gly Asp Pro Ser Ala Gly Glu Asn Ala Gly
    130                 135                 140
Asn Thr Ala Ala Gln Gly Thr Asn Gln Ala Glu Asn Asn Gln Thr Ala
145                 150                 155                 160
Gly Ser Gln Asn Pro Ala Ser Ser Thr Asn Pro Ser Ala Thr Asn Ser
                165                 170                 175
Gly Gly Asp Phe Gly Arg Thr Asn Val Gly Asn Ser Val Val Ile Asp
            180                 185                 190
Gly Pro Ser Gln Asn Ile Thr Leu Thr His Cys Lys Gly Asp Ser Cys
        195                 200                 205
Ser Gly Asn Asn Phe Leu Asp Glu Glu Val Gln Leu Lys Ser Glu Phe
    210                 215                 220
Glu Lys Leu Ser Asp Ala Asp Lys Ile Ser Asn Tyr Lys Lys Asp Gly
225                 230                 235                 240
Lys Asn Asp Gly Lys Asn Asp Lys Phe Val Gly Leu Val Ala Asp Ser
                245                 250                 255
Val Gln Met Lys Gly Ile Asn Gln Tyr Ile Ile Phe Tyr Lys Pro Lys
            260                 265                 270
Pro Thr Ser Phe Ala Arg Phe Arg Arg Ser Ala Arg Ser Arg Ser
        275                 280                 285
Leu Pro Ala Glu Met Pro Leu Ile Pro Val Asn Gln Ala Asp Thr Leu
    290                 295                 300
Ile Val Asp Gly Glu Ala Val Ser Leu Thr Gly His Ser Gly Asn Ile
305                 310                 315                 320
Phe Ala Pro Glu Gly Asn Tyr Arg Tyr Leu Thr Tyr Gly Ala Glu Lys
                325                 330                 335
Leu Pro Gly Gly Ser Tyr Ala Leu Arg Val Gln Gly Glu Pro Ser Lys
            340                 345                 350
Gly Glu Met Leu Ala Gly Thr Ala Val Tyr Asn Gly Glu Val Leu His
        355                 360                 365
Phe His Thr Glu Asn Gly Arg Pro Ser Pro Ser Arg Gly Arg Phe Ala
    370                 375                 380
```

```
Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                    405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Val Ala Gly Lys Tyr
                435                 440                 445

Ser Tyr Arg Pro Thr Asp Ala Glu Lys Gly Gly Phe Gly Val Phe Ala
450                 455                 460

Gly Lys Lys Glu Gln Asp Gly Ser Gly Gly Gly Cys Gln Ser Lys
465                 470                 475                 480

Ser Ile Gln Thr Phe Pro Gln Pro Asp Thr Ser Val Ile Asn Gly Pro
                485                 490                 495

Asp Arg Pro Val Gly Ile Pro Asp Pro Ala Gly Thr Thr Val Gly Gly
                500                 505                 510

Gly Gly Ala Val Tyr Thr Val Val Pro His Leu Ser Leu Pro His Trp
                515                 520                 525

Ala Ala Gln Asp Phe Ala Lys Ser Leu Gln Ser Phe Arg Leu Gly Cys
530                 535                 540

Ala Asn Leu Lys Asn Arg Gln Gly Trp Gln Asp Val Cys Ala Gln Ala
545                 550                 555                 560

Phe Gln Thr Pro Val His Ser Phe Gln Ala Lys Gln Phe Phe Glu Arg
                565                 570                 575

Tyr Phe Thr Pro Trp Gln Val Ala Gly Asn Gly Ser Leu Ala Gly Thr
                580                 585                 590

Val Thr Gly Tyr Tyr Glu Pro Val Leu Lys Gly Asp Asp Arg Arg Thr
                595                 600                 605

Ala Gln Ala Arg Phe Pro Ile Tyr Gly Ile Pro Asp Asp Phe Ile Ser
610                 615                 620

Val Pro Leu Pro Ala Gly Leu Arg Ser Gly Lys Ala Leu Val Arg Ile
625                 630                 635                 640

Arg Gln Thr Gly Lys Asn Ser Gly Thr Ile Asp Asn Thr Gly Gly Thr
                645                 650                 655

His Thr Ala Asp Leu Ser Arg Phe Pro Ile Thr Ala Arg Thr Thr Ala
                660                 665                 670

Ile Lys Gly Arg Phe Glu Gly Ser Arg Phe Leu Pro Tyr His Thr Arg
                675                 680                 685

Asn Gln Ile Asn Gly Gly Ala Leu Asp Gly Lys Ala Pro Ile Leu Gly
                690                 695                 700

Tyr Ala Glu Asp Pro Val Glu Leu Phe Phe Met His Ile Gln Gly Ser
705                 710                 715                 720

Gly Arg Leu Lys Thr Pro Ser Gly Lys Tyr Ile Arg Ile Gly Tyr Ala
                725                 730                 735

Asp Lys Asn Glu His Pro Tyr Val Ser Ile Gly Arg Tyr Met Ala Asp
                740                 745                 750

Lys Gly Tyr Leu Lys Leu Gly Gln Thr Ser Met Gln Gly Ile Lys Ala
                755                 760                 765

Tyr Met Arg Gln Asn Pro Gln Arg Leu Ala Glu Val Leu Gly Gln Asn
                770                 775                 780

Pro Ser Tyr Ile Phe Phe Arg Glu Leu Ala Gly Ser Ser Asn Asp Gly
785                 790                 795                 800
```

```
Pro Val Gly Ala Leu Gly Thr Pro Leu Met Gly Glu Tyr Ala Gly Ala
                805                 810                 815

Val Asp Arg His Tyr Ile Thr Leu Gly Ala Pro Leu Phe Val Ala Thr
            820                 825                 830

Ala His Pro Val Thr Arg Lys Ala Leu Asn Arg Leu Ile Met Ala Gln
        835                 840                 845

Asp Thr Gly Ser Ala Ile Lys Gly Ala Val Arg Val Asp Tyr Phe Trp
    850                 855                 860

Gly Tyr Gly Asp Glu Ala Gly Glu Leu Ala Gly Lys Gln Lys Thr Thr
865                 870                 875                 880

Gly Tyr Val Trp Gln Leu Leu Pro Asn Gly Met Lys Pro Glu Tyr Arg
                885                 890                 895

Pro
```

<210> SEQ ID NO 11
<211> LENGTH: 1941
<212> TYPE: DNA
<213> ORGANISM: Artificial
<220> FEATURE:
<223> OTHER INFORMATION: deletion G287NZ-953

<400> SEQUENCE: 11

```
atggctagcc ccgatgtcaa gtcggcggac acgctgtcaa aacctgccgc ccctgttgtt    60
tctgaaaaag agacagaggc aaaggaagat gcgccacagg caggttctca aggacagggc   120
gcgccatccg cacaaggcgg tcaagatatg gcggcggttt cggaagaaaa tacaggcaat   180
ggcggtgcgg cagcaacgga caaacccaaa atgaagacg aggggggcgca aaatgatatg   240 ccgcaaaatg ccgccgatac agatagtttg acaccgaatc acaccccggc ttcgaatatg   300
ccggccggaa atatggaaaa ccaagcaccg gatgccgggg aatcggagca gccggcaaac   360
caaccggata tggcaaatac ggcggacgga atgcagggtg acgatccgtc ggcaggcggg   420
gaaaatgccg gcaatacggc tgcccaaggt acaaatcaag ccgaaaacaa tcaaaccgcc   480
ggttctcaaa tcctgcctc ttcaaccaat cctagcgcca cgaatagcgg tggtgatttt   540
ggaaggacga acgtgggcaa ttctgttgtg attgacgggc gtcgcaaaa tataacgttg    600 acccactgta aaggcgattc ttgtagtggc aataatttct tggatgaaga agtacagcta   660
aaatcagaat ttgaaaaatt aagtgatgca gacaaaataa gtaattacaa gaaagatggg   720
aagaatgacg ggaagaatga taaatttgtc ggtttggttg ccgatagtgt gcagatgaag   780
ggaatcaatc aatatattat cttttataaa cctaaaccca cttcatttgc gcgatttagg   840
cgttctgcac ggtcgaggcg gtcgcttccg gccgagatgc cgctgattcc cgtcaatcag   900
gcggatacgc tgattgtcga tggggaagcg gtcagcctga cggggcattc cggcaatatc   960
ttcgcgcccg aagggaatta ccggtatctg acttacgggg cggaaaaatt gcccggcgga  1020
tcgtatgccc tccgtgttca aggcgaacct tcaaaaggcg aaatgctcgc gggcacggca  1080
gtgtacaacg gcgaagtgct gcattttcat acggaaaacg gccgtccgtc cccgtccaga  1140
ggcaggtttg ccgcaaaagt cgatttcggc agcaaatctg tggacggcat tatcgacagc  1200
ggcgatggtt tgcatatggg tacgcaaaaa ttcaaggccg ccatcgatgg aaacggcttt  1260
aaggggactt ggacggaaaa tggcggcggg gatgtttccg aaagttttta cggcccggcc  1320
ggcgaggaag tggcgggaaa atacagctat cgcccaacag atgcggaaaa gggcggattc  1380
ggcgtgtttg ccggcaaaaa agagcaggat ggatccggag gaggaggagc cacctacaaa  1440
gtggacgaat atcacgccaa cgcccgtttc gccatcgacc atttcaacac cagcaccaac  1500
```

```
gtcggcggtt tttacggtct gaccggttcc gtcgagttcg accaagcaaa acgcgacggt   1560
aaaatcgaca tcaccatccc cgttgccaac ctgcaaagcg gttcgcaaca ctttaccgac   1620
cacctgaaat cagccgacat cttcgatgcc gcccaatatc cggacatccg ctttgtttcc   1680
accaaattca acttcaacgg caaaaaactg gtttccgttg acggcaacct gaccatgcac   1740
ggcaaaaccg cccccgtcaa actcaaagcc gaaaaattca actgctacca agcccgatg    1800 gcgaaaaccg aagtttgcgg cggcgacttc agcaccacca tcgaccgcac caaatggggc   1860
gtggactacc tcgttaacgt tggtatgacc aaaagcgtcc gcatcgacat ccaaatcgag   1920
gcagccaaac aataaaagct t                                             1941
```

<210> SEQ ID NO 12
<211> LENGTH: 644
<212> TYPE: PRT
<213> ORGANISM: Artificial
<220> FEATURE:
<223> OTHER INFORMATION: deletion G287NZ-953

<400> SEQUENCE: 12

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Ala Pro Ser Ala Gln Gly Gly Gln
        35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
```

```
                275                 280                 285
Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln

<210> SEQ ID NO 13
<211> LENGTH: 2583
<212> TYPE: DNA
<213> ORGANISM: Artificial
<220> FEATURE:
<223> OTHER INFORMATION: deletion G287NZ-961

<400> SEQUENCE: 13
```

-continued

```
atggctagcc ccgatgtcaa gtcggcggac acgctgtcaa aacctgccgc ccctgttgtt     60
tctgaaaaag agacagaggc aaaggaagat gcgccacagg caggttctca aggacagggc    120
gcgccatccg cacaaggcgg tcaagatatg gcggcggttt cggaagaaaa tacaggcaat    180
ggcggtgcgc agcaacggac aaacccaaaa atgaagacg aggggcgca aaatgatatg     240
ccgcaaaatg ccgccgatac agatagtttg acaccgaatc acaccccggc ttcgaatatg    300
ccggccggaa atatggaaaa ccaagcaccg gatgccgggg aatcggagca gccggcaaac    360
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgc tgattgtcga tggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaaggcg aaatgctcgc gggcacggca   1080
gtgtacaacg gcgaagtgct gcatttcat acggaaaacg gccgtccgtc cccgtccaga    1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcgaaaaa gggcggattc   1380
ggcgtgtttg ccggcaaaaa agagcaggat ggatccggag gaggaggagc cacaaacgac   1440
gacgatgtta aaaagctgc cactgtggcc attgctgctg cctacaacaa tggccaagaa    1500
atcaacggtt caaagctgg agagaccatc tacgacattg atgaagacgg cacaattacc   1560
aaaaaagacg caactgcagc cgatgttgaa gccgacgact ttaaaggtct gggtctgaaa   1620
aaagtcgtga ctaacctgac caaaaccgtc aatgaaaaca acaaaacgt cgatgccaaa   1680
gtaaaagctg cagaatctga aatagaaaag ttaacaacca agttagcaga cactgatgcc   1740
gctttagcag atactgatgc cgctctggat gcaaccacca acgccttgaa taaattggga   1800
gaaaatataa cgacatttgc tgaagagact aagacaaata tcgtaaaaat tgatgaaaaa   1860
ttagaagccg tggctgatac cgtcgacaag catgccgaag cattcaacga tatcgccgat   1920
tcattggatg aaaccaacac taaggcagac gaagccgtca aaaccgccaa tgaagccaaa   1980
cagacggccg aagaaccaa acaaaacgtc gatgccaaag taaaagctgc agaaactgca   2040
gcaggcaaag ccgaagctgc cgctggcaca gctaatactg cagccgacaa ggccgaagct   2100
gtcgctgcaa aagttaccga catcaaagct gatatcgcta cgaacaaaga taatattgct   2160
aaaaaagcaa acagtgccga cgtgtacacc agagaagagt ctgacagcaa atttgtcaga   2220
attgatggtc tgaacgctac taccgaaaaa ttggacacac gcttggcttc tgctgaaaaa   2280
tccattgccg atcacgatac tcgcctgaac ggtttggata aaacagtgtc agacctgcgc   2340
```

```
aaagaaaccc gccaaggcct tgcagaacaa gccgcgctct ccggtctgtt ccaaccttac    2400
aacgtgggtc ggttcaatgt aacggctgca gtcggcggct acaaatccga atcggcagtc    2460
gccatcggta ccggcttccg ctttaccgaa aactttgccg ccaaagcagg cgtggcagtc    2520
ggcacttcgt ccggttcttc cgcagcctac catgtcggcg tcaattacga gtggtaaaag    2580
ctt                                                                  2583
```

<210> SEQ ID NO 14
<211> LENGTH: 858
<212> TYPE: PRT
<213> ORGANISM: Artificial
<220> FEATURE:
<223> OTHER INFORMATION: deletion G287NZ-961

<400> SEQUENCE: 14

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320
```

```
Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
                420                 425                 430

Ser Gly Lys Phe Tyr Gly Pro Ala Gly Glu Glu Val Ala Gly Lys Tyr
            435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Asn Asp
465                 470                 475                 480

Asp Asp Val Lys Lys Ala Ala Thr Val Ala Ile Ala Ala Ala Tyr Asn
                485                 490                 495

Asn Gly Gln Glu Ile Asn Gly Phe Lys Ala Gly Glu Thr Ile Tyr Asp
            500                 505                 510

Ile Asp Glu Asp Gly Thr Ile Thr Lys Lys Asp Ala Thr Ala Ala Asp
    515                 520                 525

Val Glu Ala Asp Asp Phe Lys Gly Leu Gly Leu Lys Lys Val Val Thr
530                 535                 540

Asn Leu Thr Lys Thr Val Asn Glu Asn Lys Gln Asn Val Asp Ala Lys
545                 550                 555                 560

Val Lys Ala Ala Glu Ser Glu Ile Glu Lys Leu Thr Thr Lys Leu Ala
                565                 570                 575

Asp Thr Asp Ala Ala Leu Ala Asp Thr Asp Ala Ala Leu Asp Ala Thr
            580                 585                 590

Thr Asn Ala Leu Asn Lys Leu Gly Glu Asn Ile Thr Thr Phe Ala Glu
    595                 600                 605

Glu Thr Lys Thr Asn Ile Val Lys Ile Asp Glu Lys Leu Glu Ala Val
        610                 615                 620

Ala Asp Thr Val Asp Lys His Ala Glu Ala Phe Asn Asp Ile Ala Asp
625                 630                 635                 640

Ser Leu Asp Glu Thr Asn Thr Lys Ala Asp Glu Ala Val Lys Thr Ala
                645                 650                 655

Asn Glu Ala Lys Gln Thr Ala Glu Glu Thr Lys Gln Asn Val Asp Ala
            660                 665                 670

Lys Val Lys Ala Ala Glu Thr Ala Ala Gly Lys Ala Glu Ala Ala Ala
    675                 680                 685

Gly Thr Ala Asn Thr Ala Ala Asp Lys Ala Glu Ala Val Ala Ala Lys
690                 695                 700

Val Thr Asp Ile Lys Ala Asp Ile Ala Thr Asn Lys Asp Asn Ile Ala
705                 710                 715                 720

Lys Lys Ala Asn Ser Ala Asp Val Tyr Thr Arg Glu Glu Ser Asp Ser
                725                 730                 735
```

```
Lys Phe Val Arg Ile Asp Gly Leu Asn Ala Thr Thr Glu Lys Leu Asp
                740                 745                 750

Thr Arg Leu Ala Ser Ala Glu Lys Ser Ile Ala Asp His Asp Thr Arg
            755                 760                 765

Leu Asn Gly Leu Asp Lys Thr Val Ser Asp Leu Arg Lys Glu Thr Arg
        770                 775                 780

Gln Gly Leu Ala Glu Gln Ala Ala Leu Ser Gly Leu Phe Gln Pro Tyr
785                 790                 795                 800

Asn Val Gly Arg Phe Asn Val Thr Ala Ala Val Gly Gly Tyr Lys Ser
                805                 810                 815

Glu Ser Ala Val Ala Ile Gly Thr Gly Phe Arg Phe Thr Glu Asn Phe
            820                 825                 830

Ala Ala Lys Ala Gly Val Ala Val Gly Thr Ser Ser Gly Ser Ser Ala
        835                 840                 845

Ala Tyr His Val Gly Val Asn Tyr Glu Trp
    850                 855

<210> SEQ ID NO 15
<211> LENGTH: 1082
<212> TYPE: PRT
<213> ORGANISM: Artificial
<220> FEATURE:
<223> OTHER INFORMATION: Protein 983

<400> SEQUENCE: 15

Met Arg Thr Thr Pro Thr Phe Pro Thr Lys Thr Phe Lys Pro Thr Ala
1               5                   10                  15

Met Ala Leu Ala Val Ala Thr Thr Leu Ser Ala Cys Leu Gly Gly Gly
            20                  25                  30

Gly Gly Gly Thr Ser Ala Pro Asp Phe Asn Ala Gly Gly Thr Gly Ile
        35                  40                  45

Gly Ser Asn Ser Arg Ala Thr Thr Ala Lys Ser Ala Ala Val Ser Tyr
    50                  55                  60

Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
        115                 120                 125

Gly Arg Gly Val Glu Val Gly Ile Val Asp Thr Gly Glu Ser Val Gly
    130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Gly Lys Asp Ile Glu Ala Ser Phe Asp Asp Glu Ala Val
            180                 185                 190

Ile Glu Thr Glu Ala Lys Pro Thr Asp Ile Arg His Val Lys Glu Ile
        195                 200                 205

Gly His Ile Asp Leu Val Ser His Ile Ile Gly Gly Arg Ser Val Asp
    210                 215                 220

Gly Arg Pro Ala Gly Gly Ile Ala Pro Asp Ala Thr Leu His Ile Met
225                 230                 235                 240
```

-continued

```
Asn Thr Asn Asp Glu Thr Lys Asn Glu Met Val Ala Ala Ile Arg
                245                 250                 255
Asn Ala Trp Val Lys Leu Gly Glu Arg Gly Val Arg Ile Val Asn Asn
            260                 265                 270
Ser Phe Gly Thr Thr Ser Arg Ala Gly Thr Ala Asp Leu Phe Gln Ile
        275                 280                 285
Ala Asn Ser Glu Glu Gln Tyr Arg Gln Ala Leu Leu Asp Tyr Ser Gly
    290                 295                 300
Gly Asp Lys Thr Asp Glu Gly Ile Arg Leu Met Gln Gln Ser Asp Tyr
305                 310                 315                 320
Gly Asn Leu Ser Tyr His Ile Arg Asn Lys Asn Met Leu Phe Ile Phe
                325                 330                 335
Ser Thr Gly Asn Asp Ala Gln Ala Gln Pro Asn Thr Tyr Ala Leu Leu
            340                 345                 350
Pro Phe Tyr Glu Lys Asp Ala Gln Lys Gly Ile Ile Thr Val Ala Gly
        355                 360                 365
Val Asp Arg Ser Gly Glu Lys Phe Lys Arg Glu Met Tyr Gly Glu Pro
    370                 375                 380
Gly Thr Glu Pro Leu Glu Tyr Gly Ser Asn His Cys Gly Ile Thr Ala
385                 390                 395                 400
Met Trp Cys Leu Ser Ala Pro Tyr Glu Ala Ser Val Arg Phe Thr Arg
                405                 410                 415
Thr Asn Pro Ile Gln Ile Ala Gly Thr Ser Phe Ser Ala Pro Ile Val
            420                 425                 430
Thr Gly Thr Ala Ala Leu Leu Leu Gln Lys Tyr Pro Trp Met Ser Asn
        435                 440                 445
Asp Asn Leu Arg Thr Thr Leu Leu Thr Thr Ala Gln Asp Ile Gly Ala
    450                 455                 460
Val Gly Val Asp Ser Lys Phe Gly Trp Gly Leu Leu Asp Ala Gly Lys
465                 470                 475                 480
Ala Met Asn Gly Pro Ala Ser Phe Pro Phe Gly Asp Phe Thr Ala Asp
                485                 490                 495
Thr Lys Gly Thr Ser Asp Ile Ala Tyr Ser Phe Arg Asn Asp Ile Ser
            500                 505                 510
Gly Thr Gly Gly Leu Ile Lys Lys Gly Gly Ser Gln Leu Gln Leu His
        515                 520                 525
Gly Asn Asn Thr Tyr Thr Gly Lys Thr Ile Ile Glu Gly Gly Ser Leu
    530                 535                 540
Val Leu Tyr Gly Asn Asn Lys Ser Asp Met Arg Val Glu Thr Lys Gly
545                 550                 555                 560
Ala Leu Ile Tyr Asn Gly Ala Ala Ser Gly Gly Ser Leu Asn Ser Asp
                565                 570                 575
Gly Ile Val Tyr Leu Ala Asp Thr Asp Gln Ser Gly Ala Asn Glu Thr
            580                 585                 590
Val His Ile Lys Gly Ser Leu Gln Leu Asp Gly Lys Gly Thr Leu Tyr
        595                 600                 605
Thr Arg Leu Gly Lys Leu Leu Lys Val Asp Gly Thr Ala Ile Ile Gly
    610                 615                 620
Gly Lys Leu Tyr Met Ser Ala Arg Gly Lys Gly Ala Gly Tyr Leu Asn
625                 630                 635                 640
Ser Thr Gly Arg Arg Val Pro Phe Leu Ser Ala Ala Lys Ile Gly Gln
                645                 650                 655
Asp Tyr Ser Phe Phe Thr Asn Ile Glu Thr Asp Gly Gly Leu Leu Ala
```

```
                    660                 665                 670
Ser Leu Asp Ser Val Glu Lys Thr Ala Gly Ser Glu Gly Asp Thr Leu
            675                 680                 685

Ser Tyr Tyr Val Arg Arg Gly Asn Ala Ala Arg Thr Ala Ser Ala Ala
    690                 695                 700

Ala His Ser Ala Pro Ala Gly Leu Lys His Ala Val Glu Gln Gly Gly
705                 710                 715                 720

Ser Asn Leu Glu Asn Leu Met Val Glu Leu Asp Ala Ser Glu Ser Ser
            725                 730                 735

Ala Thr Pro Glu Thr Val Glu Thr Ala Ala Asp Arg Thr Asp Met
        740                 745                 750

Pro Gly Ile Arg Pro Tyr Gly Ala Thr Phe Arg Ala Ala Ala Val
            755                 760                 765

Gln His Ala Asn Ala Ala Asp Gly Val Arg Ile Phe Asn Ser Leu Ala
        770                 775                 780

Ala Thr Val Tyr Ala Asp Ser Thr Ala Ala His Ala Asp Met Gln Gly
785                 790                 795                 800

Arg Arg Leu Lys Ala Val Ser Asp Gly Leu Asp His Asn Gly Thr Gly
            805                 810                 815

Leu Arg Val Ile Ala Gln Thr Gln Gln Asp Gly Gly Thr Trp Glu Gln
            820                 825                 830

Gly Gly Val Glu Gly Lys Met Arg Gly Ser Thr Gln Thr Val Gly Ile
            835                 840                 845

Ala Ala Lys Thr Gly Glu Asn Thr Thr Ala Ala Thr Leu Gly Met
850                 855                 860

Gly Arg Ser Thr Trp Ser Glu Asn Ser Ala Asn Ala Lys Thr Asp Ser
865                 870                 875                 880

Ile Ser Leu Phe Ala Gly Ile Arg His Asp Ala Gly Asp Ile Gly Tyr
            885                 890                 895

Leu Lys Gly Leu Phe Ser Tyr Gly Arg Tyr Lys Asn Ser Ile Ser Arg
            900                 905                 910

Ser Thr Gly Ala Asp Glu His Ala Glu Gly Ser Val Asn Gly Thr Leu
            915                 920                 925

Met Gln Leu Gly Ala Leu Gly Gly Val Asn Val Pro Phe Ala Ala Thr
            930                 935                 940

Gly Asp Leu Thr Val Glu Gly Gly Leu Arg Tyr Asp Leu Leu Lys Gln
945                 950                 955                 960

Asp Ala Phe Ala Glu Lys Gly Ser Ala Leu Gly Trp Ser Gly Asn Ser
            965                 970                 975

Leu Thr Glu Gly Thr Leu Val Gly Leu Ala Gly Leu Lys Leu Ser Gln
            980                 985                 990

Pro Leu Ser Asp Lys Ala Val Leu Phe Ala Thr Ala Gly Val Glu Arg
        995                 1000                1005

Asp Leu Asn Gly Arg Asp Tyr Thr Val Thr Gly Gly Phe Thr Gly
    1010                1015                1020

Ala Thr Ala Ala Thr Gly Lys Thr Gly Ala Arg Asn Met Pro His
    1025                1030                1035

Thr Arg Leu Val Ala Gly Leu Gly Ala Asp Val Glu Phe Gly Asn
    1040                1045                1050

Gly Trp Asn Gly Leu Ala Arg Tyr Ser Tyr Ala Gly Ser Lys Gln
    1055                1060                1065

Tyr Gly Asn His Ser Gly Arg Val Gly Val Gly Tyr Arg Phe
    1070                1075                1080
```

<210> SEQ ID NO 16
<211> LENGTH: 1047
<212> TYPE: PRT
<213> ORGANISM: Artificial
<220> FEATURE:
<223> OTHER INFORMATION: deletion G983

<400> SEQUENCE: 16

```
Thr Ser Ala Pro Asp Phe Asn Ala Gly Gly Thr Gly Ile Gly Ser Asn
1               5                   10                  15

Ser Arg Ala Thr Thr Ala Lys Ser Ala Ala Val Ser Tyr Ala Gly Ile
            20                  25                  30

Lys Asn Glu Met Cys Lys Asp Arg Ser Met Leu Cys Ala Gly Arg Asp
                35                  40                  45

Asp Val Ala Val Thr Asp Arg Asp Ala Lys Ile Asn Ala Pro Pro Pro
 50                  55                  60

Asn Leu His Thr Gly Asp Phe Pro Asn Pro Asn Asp Ala Tyr Lys Asn
 65                  70                  75                  80

Leu Ile Asn Leu Lys Pro Ala Ile Glu Ala Gly Tyr Thr Gly Arg Gly
                85                  90                  95

Val Glu Val Gly Ile Val Asp Thr Gly Glu Ser Val Gly Ser Ile Ser
            100                 105                 110

Phe Pro Glu Leu Tyr Gly Arg Lys Glu His Gly Tyr Asn Glu Asn Tyr
        115                 120                 125

Lys Asn Tyr Thr Ala Tyr Met Arg Lys Glu Ala Pro Glu Asp Gly Gly
    130                 135                 140

Gly Lys Asp Ile Glu Ala Ser Phe Asp Asp Glu Ala Val Ile Glu Thr
145                 150                 155                 160

Glu Ala Lys Pro Thr Asp Ile Arg His Val Lys Glu Ile Gly His Ile
                165                 170                 175

Asp Leu Val Ser His Ile Ile Gly Gly Arg Ser Val Asp Gly Arg Pro
            180                 185                 190

Ala Gly Gly Ile Ala Pro Asp Ala Thr Leu His Ile Met Asn Thr Asn
        195                 200                 205

Asp Glu Thr Lys Asn Glu Met Met Val Ala Ala Ile Arg Asn Ala Trp
    210                 215                 220

Val Lys Leu Gly Glu Arg Gly Val Arg Ile Val Asn Asn Ser Phe Gly
225                 230                 235                 240

Thr Thr Ser Arg Ala Gly Thr Ala Asp Leu Phe Gln Ile Ala Asn Ser
                245                 250                 255

Glu Glu Gln Tyr Arg Gln Ala Leu Leu Asp Tyr Ser Gly Gly Asp Lys
            260                 265                 270

Thr Asp Glu Gly Ile Arg Leu Met Gln Gln Ser Asp Tyr Gly Asn Leu
        275                 280                 285

Ser Tyr His Ile Arg Asn Lys Asn Met Leu Phe Ile Phe Ser Thr Gly
    290                 295                 300

Asn Asp Ala Gln Ala Gln Pro Asn Thr Tyr Ala Leu Leu Pro Phe Tyr
305                 310                 315                 320

Glu Lys Asp Ala Gln Lys Gly Ile Ile Thr Val Ala Gly Val Asp Arg
                325                 330                 335

Ser Gly Glu Lys Phe Lys Arg Glu Met Tyr Gly Glu Pro Gly Thr Glu
            340                 345                 350

Pro Leu Glu Tyr Gly Ser Asn His Cys Gly Ile Thr Ala Met Trp Cys
        355                 360                 365
```

```
Leu Ser Ala Pro Tyr Glu Ala Ser Val Arg Phe Thr Arg Thr Asn Pro
    370                 375                 380

Ile Gln Ile Ala Gly Thr Ser Phe Ser Ala Pro Ile Val Thr Gly Thr
385                 390                 395                 400

Ala Ala Leu Leu Leu Gln Lys Tyr Pro Trp Met Ser Asn Asp Asn Leu
                405                 410                 415

Arg Thr Thr Leu Leu Thr Thr Ala Gln Asp Ile Gly Ala Val Gly Val
                420                 425                 430

Asp Ser Lys Phe Gly Trp Gly Leu Leu Asp Ala Gly Lys Ala Met Asn
            435                 440                 445

Gly Pro Ala Ser Phe Pro Phe Gly Asp Phe Thr Ala Asp Thr Lys Gly
        450                 455                 460

Thr Ser Asp Ile Ala Tyr Ser Phe Arg Asn Asp Ile Ser Gly Thr Gly
465                 470                 475                 480

Gly Leu Ile Lys Lys Gly Gly Ser Gln Leu Gln Leu His Gly Asn Asn
                485                 490                 495

Thr Tyr Thr Gly Lys Thr Ile Ile Glu Gly Gly Ser Leu Val Leu Tyr
                500                 505                 510

Gly Asn Asn Lys Ser Asp Met Arg Val Glu Thr Lys Gly Ala Leu Ile
            515                 520                 525

Tyr Asn Gly Ala Ala Ser Gly Gly Ser Leu Asn Ser Asp Gly Ile Val
        530                 535                 540

Tyr Leu Ala Asp Thr Asp Gln Ser Gly Ala Asn Glu Thr Val His Ile
545                 550                 555                 560

Lys Gly Ser Leu Gln Leu Asp Gly Lys Gly Thr Leu Tyr Thr Arg Leu
                565                 570                 575

Gly Lys Leu Leu Lys Val Asp Gly Thr Ala Ile Ile Gly Gly Lys Leu
            580                 585                 590

Tyr Met Ser Ala Arg Gly Lys Gly Ala Gly Tyr Leu Asn Ser Thr Gly
        595                 600                 605

Arg Arg Val Pro Phe Leu Ser Ala Ala Lys Ile Gly Gln Asp Tyr Ser
610                 615                 620

Phe Phe Thr Asn Ile Glu Thr Asp Gly Gly Leu Leu Ala Ser Leu Asp
625                 630                 635                 640

Ser Val Glu Lys Thr Ala Gly Ser Glu Gly Asp Thr Leu Ser Tyr Tyr
                645                 650                 655

Val Arg Arg Gly Asn Ala Ala Arg Thr Ala Ser Ala Ala Ala His Ser
            660                 665                 670

Ala Pro Ala Gly Leu Lys His Ala Val Glu Gln Gly Gly Ser Asn Leu
        675                 680                 685

Glu Asn Leu Met Val Glu Leu Asp Ala Ser Glu Ser Ser Ala Thr Pro
690                 695                 700

Glu Thr Val Glu Thr Ala Ala Ala Asp Arg Thr Asp Met Pro Gly Ile
705                 710                 715                 720

Arg Pro Tyr Gly Ala Thr Phe Arg Ala Ala Ala Val Gln His Ala
            725                 730                 735

Asn Ala Ala Asp Gly Val Arg Ile Phe Asn Ser Leu Ala Ala Thr Val
            740                 745                 750

Tyr Ala Asp Ser Thr Ala Ala His Ala Asp Met Gln Gly Arg Arg Leu
        755                 760                 765

Lys Ala Val Ser Asp Gly Leu Asp His Asn Gly Thr Gly Leu Arg Val
770                 775                 780
```

Ile Ala Gln Thr Gln Gln Asp Gly Gly Thr Trp Glu Gln Gly Gly Val
785                 790                 795                 800

Glu Gly Lys Met Arg Gly Ser Thr Gln Thr Val Gly Ile Ala Ala Lys
            805                 810                 815

Thr Gly Glu Asn Thr Thr Ala Ala Ala Thr Leu Gly Met Gly Arg Ser
            820                 825                 830

Thr Trp Ser Glu Asn Ser Ala Asn Ala Lys Thr Asp Ser Ile Ser Leu
        835                 840                 845

Phe Ala Gly Ile Arg His Asp Ala Gly Asp Ile Gly Tyr Leu Lys Gly
850                 855                 860

Leu Phe Ser Tyr Gly Arg Tyr Lys Asn Ser Ile Ser Arg Ser Thr Gly
865                 870                 875                 880

Ala Asp Glu His Ala Glu Gly Ser Val Asn Gly Thr Leu Met Gln Leu
            885                 890                 895

Gly Ala Leu Gly Gly Val Asn Val Pro Phe Ala Ala Thr Gly Asp Leu
            900                 905                 910

Thr Val Glu Gly Gly Leu Arg Tyr Asp Leu Leu Lys Gln Asp Ala Phe
        915                 920                 925

Ala Glu Lys Gly Ser Ala Leu Gly Trp Ser Gly Asn Ser Leu Thr Glu
    930                 935                 940

Gly Thr Leu Val Gly Leu Ala Gly Leu Lys Leu Ser Gln Pro Leu Ser
945                 950                 955                 960

Asp Lys Ala Val Leu Phe Ala Thr Ala Gly Val Glu Arg Asp Leu Asn
            965                 970                 975

Gly Arg Asp Tyr Thr Val Thr Gly Phe Thr Gly Ala Thr Ala Ala
            980                 985                 990

Thr Gly Lys Thr Gly Ala Arg Asn  Met Pro His Thr Arg Leu Val Ala
        995                 1000                1005

Gly Leu  Gly Ala Asp Val Glu  Phe Gly Asn Gly Trp  Asn Gly Leu
    1010                1015                1020

Ala Arg  Tyr Ser Tyr Ala Gly  Ser Lys Gln Tyr Gly  Asn His Ser
    1025                1030                1035

Gly Arg  Val Gly Val Gly Tyr  Arg Phe
    1040                1045

<210> SEQ ID NO 17
<211> LENGTH: 4425
<212> TYPE: DNA
<213> ORGANISM: Artificial
<220> FEATURE:
<223> OTHER INFORMATION: deletion G983-ORF46.1

<400> SEQUENCE: 17
atgacttctg cgcccgactt caatgcaggc ggtaccggta tcggcagcaa cagcagagca    60
acaacagcga aatcagcagc agtatcttac gccggtatca agaacgaaat gtgcaaagac   120
agaagcatgc tctgtgccgg tcgggatgac gttgcggtta cagacaggga tgccaaaatc   180
aatgcccccc ccccgaatct gcataccgga gactttccaa acccaaatga cgcatacaag   240
aatttgatca acctcaaacc tgcaattgaa gcaggctata caggacgcgg ggtagaggta   300
ggtatcgtcg acacaggcga atccgtcggc agcatatcct ttcccgaact gtatggcaga   360
aaagaacacg gctataacga aaattacaaa actatacggg cgtatatgcg aaggaagcg   420 cctgaagacg gaggcggtaa agacattgaa gcttctttcg acgatgaggc cgttatagag   480
actgaagcaa agccgacgga tatccgccac gtaaaagaaa tcggacacat cgatttggtc   540

|  |  |  |  |  |  |
|---|---|---|---|---|---|
| tcccatatta | ttggcgggcg | ttccgtggac | ggcagacctg | caggcggtat | tgcgcccgat | 600 |
| gcgacgctac | acataatgaa | tacgaatgat | gaaaccaaga | acgaaatgat | ggttgcagcc | 660 |
| atccgcaatg | catgggtcaa | gctgggcgaa | cgtggcgtgc | gcatcgtcaa | taacagtttt | 720 |
| ggaacaacat | cgagggcagg | cactgccgac | cttttccaaa | tagccaattc | ggaggagcag | 780 |
| taccgccaag | cgttgctcga | ctattccggc | ggtgataaaa | cagacgaggg | tatccgcctg | 840 |
| atgcaacaga | gcgattacgg | caacctgtcc | taccacatcc | gtaataaaaa | catgcttttc | 900 |
| atcttttcga | caggcaatga | cgcacaagct | cagcccaaca | catatgccct | attgccattt | 960 |
| tatgaaaaag | acgctcaaaa | aggcattatc | acagtcgcag | gcgtagaccg | cagtggagaa | 1020 |
| aagttcaaac | gggaaatgta | tggagaaccg | ggtacagaac | cgcttgagta | tggctccaac | 1080 |
| cattgcggaa | ttactgccat | gtggtgcctg | tcggcaccct | atgaagcaag | cgtccgtttc | 1140 |
| acccgtacaa | acccgattca | aattgccgga | acatcctttt | ccgcacccat | cgtaaccggc | 1200 |
| acggcggctc | tgctgctgca | gaaatacccg | tggatgagca | cgacaacct | gcgtaccacg | 1260 |
| ttgctgacga | cggctcagga | catcggtgca | gtcggcgtgg | acagcaagtt | cggctgggga | 1320 |
| ctgctggatg | cgggtaaggc | catgaacgga | cccgcgtcct | ttccgttcgg | cgactttacc | 1380 |
| gccgatacga | aaggtacatc | cgatattgcc | tactccttcc | gtaacgacat | ttcaggcacg | 1440 |
| ggcggcctga | tcaaaaaagg | cggcagccaa | ctgcaactgc | acggcaacaa | cacctatacg | 1500 |
| ggcaaaacca | ttatcgaagg | cggttcgctg | gtgttgtacg | gcaacaacaa | atcggatatg | 1560 |
| cgcgtcgaaa | ccaaaggtgc | gctgatttat | aacggggcgg | catccggcgg | cagcctgaac | 1620 |
| agcgacggca | ttgtctatct | ggcagatacc | gaccaatccg | gcgcaaacga | aaccgtacac | 1680 |
| atcaaaggca | gtctgcagct | ggacggcaaa | ggtacgctgt | acacacgttt | gggcaaactg | 1740 |
| ctgaaagtgg | acgtacggc | gattatcggc | ggcaagctgt | acatgtcggc | acgcggcaag | 1800 |
| ggggcaggct | atctcaacag | taccggacga | cgtgttccct | tcctgagtgc | cgccaaaatc | 1860 |
| gggcaggatt | attctttctt | cacaaacatc | gaaaccgacg | cgcggcctgct | ggcttccctc | 1920 |
| gacagcgtcg | aaaaaacagc | gggcagtgaa | ggcgacacgc | tgtcctatta | tgtccgtcgc | 1980 |
| ggcaatgcgg | cacggactgc | ttcggcagcg | gcacattccg | cgcccgccgg | tctgaaacac | 2040 |
| gccgtagaac | agggcggcag | caatctggaa | aacctgatgg | tcgaactgga | tgcctccgaa | 2100 |
| tcatccgcaa | cacccgagac | ggttgaaact | gcggcagccg | accgcacaga | tatgccgggc | 2160 |
| atccgcccct | acggcgcaac | tttccgcgca | gcggcagccg | tacagcatgc | gaatgccgcc | 2220 |
| gacggtgtac | gcatcttcaa | cagtctcgcc | gctaccgtct | atgccgacag | taccgccgcc | 2280 |
| catgccgata | tgcagggacg | ccgcctgaaa | gccgtatcgg | acgggttgga | ccacaacggc | 2340 |
| acgggtctgc | gcgtcatcgc | gcaaacccaa | caggacggtg | gaacgtggga | cagggcggt | 2400 |
| gttgaaggca | aaatgcgcgg | cagtacccaa | accgtcggca | ttgccgcgaa | aaccggcgaa | 2460 |
| aatacgacag | cagccgccac | actgggcatg | ggacgcagca | catggagcga | aaacagtgca | 2520 |
| aatgcaaaaa | ccgacagcat | tagtctgttt | gcaggcatac | ggcacgatgc | gggcgatatc | 2580 |
| ggctatctca | aaggcctgtt | ctcctacgga | cgctacaaaa | acagcatcag | ccgcagcacc | 2640 |
| ggtgcggacg | aacatgcgga | aggcagcgtc | aacggcacgc | tgatgcagct | gggcgcactg | 2700 |
| ggcggtgtca | acgttccgtt | tgccgcaacg | ggagatttga | cggtcgaagg | cggtctgcgc | 2760 |
| tacgacctgc | tcaaacagga | tgcattcgcc | gaaaaaggca | gtgctttggg | ctggagcggc | 2820 |
| aacagcctca | ctgaaggcac | gctggtcgga | ctcgcgggtc | tgaagctgtc | gcaacccttg | 2880 |
| agcgataaag | ccgtcctgtt | tgcaacggcg | ggcgtggaac | gcgacctgaa | cggacgcgac | 2940 |

-continued

```
tacacggtaa cgggcggctt taccggcgcg actgcagcaa ccggcaagac gggggcacgc    3000
aatatgccgc acaccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgac ggtggcggag gcactggatc ctcagatttg    3180
gcaaacgatt cttttatccg gcaggttctc gaccgtcagc atttcgaacc cgacgggaaa    3240
taccacctat tcggcagcag gggggaactt gccgagcgca gcggccatat cggattggga    3300
aaaatacaaa gccatcagtt gggcaacctg atgattcaac aggcggccat taaaggaaat    3360
atcggctaca ttgtccgctt ttccgatcac gggcacgaag tccattcccc cttcgacaac    3420
catgcctcac attccgattc tgatgaagcc ggtagtcccg ttgacggatt tagcctttac    3480
cgcatccatt gggacggata cgaacaccat cccgccgacg gctatgacgg ccacagggc    3540 ggcggctatc ccgctcccaa aggcgcgagg gatatataca gctacgacat aaaaggcgtt    3600
gcccaaaata tccgcctcaa cctgaccgac aaccgcagca ccggacaacg gcttgccgac    3660
cgtttccaca atgccggtag tatgctgacg caaggagtag gcgacggatt caaacgcgcc    3720
acccgataca gccccgagct ggacagatcg ggcaatgccg ccgaagcctt caacggcact    3780
gcagatatcg ttaaaaacat catcggcgcg gcaggagaaa ttgtcggcgc aggcgatgcc    3840
gtgcagggca taagcgaagg ctcaaacatt gctgtcatgc acggcttggg tctgctttcc    3900
accgaaaaca agatggcgcg catcaacgat ttggcagata tggcgcaact caaagactat    3960
gccgcagcag ccatccgcga ttgggcagtc caaaacccca atgccgcaca aggcatagaa    4020
gccgtcagca atatctttat ggcagccatc cccatcaaag ggattggagc tgttcgggga    4080
aaatacggct tgggcggcat cacggcacat cctatcaagc ggtcgcagat gggcgcgatc    4140
gcattgccga aagggaaatc cgccgtcagc gacaattttg ccgatgcggc atacgccaaa    4200
tacccgtccc cttaccattc ccgaaatatc cgttcaaact tggagcagcg ttacggcaaa    4260
gaaaacatca cctcctcaac cgtgccgccg tcaaacggca aaaatgtcaa actggcagac    4320
caacgccacc cgaagacagg cgtaccgttt gacggtaaag ggtttccgaa ttttgagaag    4380
cacgtgaaat atgatacgct cgagcaccac caccaccacc actga                    4425
```

<210> SEQ ID NO 18
<211> LENGTH: 1474
<212> TYPE: PRT
<213> ORGANISM: Artificial
<220> FEATURE:
<223> OTHER INFORMATION: deletion G983-ORF46.1

<400> SEQUENCE: 18

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95
```

```
Gly Val Glu Val Gly Ile Val Asp Thr Gly Glu Ser Val Gly Ser Ile
                100                 105                 110

Ser Phe Pro Glu Leu Tyr Gly Arg Lys Glu His Gly Tyr Asn Glu Asn
            115                 120                 125

Tyr Lys Asn Tyr Thr Ala Tyr Met Arg Lys Glu Ala Pro Glu Asp Gly
        130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
```

-continued

```
            515                 520                 525
Ile Tyr Asn Gly Ala Ala Ser Gly Gly Ser Leu Asn Ser Asp Gly Ile
            530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
                580                 585                 590

Leu Tyr Met Ser Ala Arg Gly Lys Gly Ala Gly Tyr Leu Asn Ser Thr
                595                 600                 605

Gly Arg Arg Val Pro Phe Leu Ser Ala Ala Lys Ile Gly Gln Asp Tyr
            610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
                660                 665                 670

Ser Ala Pro Ala Gly Leu Lys His Ala Val Glu Gln Gly Gly Ser Asn
                675                 680                 685

Leu Glu Asn Leu Met Val Glu Leu Asp Ala Ser Glu Ser Ser Ala Thr
            690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
                740                 745                 750

Val Tyr Ala Asp Ser Thr Ala Ala His Ala Asp Met Gln Gly Arg Arg
                755                 760                 765

Leu Lys Ala Val Ser Asp Gly Leu Asp His Asn Gly Thr Gly Leu Arg
            770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
                820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
            850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
                900                 905                 910

Leu Thr Val Glu Gly Gly Leu Arg Tyr Asp Leu Leu Lys Gln Asp Ala
                915                 920                 925

Phe Ala Glu Lys Gly Ser Ala Leu Gly Trp Ser Gly Asn Ser Leu Thr
            930                 935                 940
```

```
Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly
    1010                1015                1020

Leu Ala Arg Tyr Ser Tyr Ala Gly Ser Lys Gln Tyr Gly Asn His
    1025                1030                1035

Ser Gly Arg Val Gly Val Gly Tyr Arg Phe Leu Asp Gly Gly Gly
    1040                1045                1050

Gly Thr Gly Ser Ser Asp Leu Ala Asn Asp Ser Phe Ile Arg Gln
    1055                1060                1065

Val Leu Asp Arg Gln His Phe Glu Pro Asp Gly Lys Tyr His Leu
    1070                1075                1080

Phe Gly Ser Arg Gly Glu Leu Ala Glu Arg Ser Gly His Ile Gly
    1085                1090                1095

Leu Gly Lys Ile Gln Ser His Gln Leu Gly Asn Leu Met Ile Gln
    1100                1105                1110

Gln Ala Ala Ile Lys Gly Asn Ile Gly Tyr Ile Val Arg Phe Ser
    1115                1120                1125

Asp His Gly His Glu Val His Ser Pro Phe Asp Asn His Ala Ser
    1130                1135                1140

His Ser Asp Ser Asp Glu Ala Gly Ser Pro Val Asp Gly Phe Ser
    1145                1150                1155

Leu Tyr Arg Ile His Trp Asp Gly Tyr Glu His His Pro Ala Asp
    1160                1165                1170

Gly Tyr Asp Gly Pro Gln Gly Gly Gly Tyr Pro Ala Pro Lys Gly
    1175                1180                1185

Ala Arg Asp Ile Tyr Ser Tyr Asp Ile Lys Gly Val Ala Gln Asn
    1190                1195                1200

Ile Arg Leu Asn Leu Thr Asp Asn Arg Ser Thr Gly Gln Arg Leu
    1205                1210                1215

Ala Asp Arg Phe His Asn Ala Gly Ser Met Leu Thr Gln Gly Val
    1220                1225                1230

Gly Asp Gly Phe Lys Arg Ala Thr Arg Tyr Ser Pro Glu Leu Asp
    1235                1240                1245

Arg Ser Gly Asn Ala Ala Glu Ala Phe Asn Gly Thr Ala Asp Ile
    1250                1255                1260

Val Lys Asn Ile Ile Gly Ala Ala Gly Glu Ile Val Gly Ala Gly
    1265                1270                1275

Asp Ala Val Gln Gly Ile Ser Glu Gly Ser Asn Ile Ala Val Met
    1280                1285                1290

His Gly Leu Gly Leu Leu Ser Thr Glu Asn Lys Met Ala Arg Ile
    1295                1300                1305

Asn Asp Leu Ala Asp Met Ala Gln Leu Lys Asp Tyr Ala Ala Ala
    1310                1315                1320

Ala Ile Arg Asp Trp Ala Val Gln Asn Pro Asn Ala Ala Gln Gly
    1325                1330                1335
```

```
Ile Glu Ala Val Ser Asn Ile Phe Met Ala Ala Ile Pro Ile Lys
    1340            1345                1350

Gly Ile Gly Ala Val Arg Gly Lys Tyr Gly Leu Gly Gly Ile Thr
1355            1360                1365

Ala His Pro Ile Lys Arg Ser Gln Met Gly Ala Ile Ala Leu Pro
    1370            1375                1380

Lys Gly Lys Ser Ala Val Ser Asp Asn Phe Ala Asp Ala Ala Tyr
1385            1390                1395

Ala Lys Tyr Pro Ser Pro Tyr His Ser Arg Asn Ile Arg Ser Asn
    1400            1405                1410

Leu Glu Gln Arg Tyr Gly Lys Glu Asn Ile Thr Ser Ser Thr Val
1415            1420                1425

Pro Pro Ser Asn Gly Lys Asn Val Lys Leu Ala Asp Gln Arg His
    1430            1435                1440

Pro Lys Thr Gly Val Pro Phe Asp Gly Lys Gly Phe Pro Asn Phe
1445            1450                1455

Glu Lys His Val Lys Tyr Asp Thr Leu Glu His His His His
    1460            1465                1470

His
```

<210> SEQ ID NO 19
<211> LENGTH: 3939
<212> TYPE: DNA
<213> ORGANISM: Artificial
<220> FEATURE:
<223> OTHER INFORMATION: deletion G983-741

<400> SEQUENCE: 19

| | | |
|---|---|---|
| atgacttctg cgcccgactt caatgcaggc ggtaccggta tcggcagcaa cagcagagca | 60 |
| acaacagcga atcagcagc agtatcttac gccggtatca agaacgaaat gtgcaaagac | 120 |
| agaagcatgc tctgtgccgg tcgggatgac gttgcggtta cagacaggga tgccaaaatc | 180 |
| aatgccccc ccccgaatct gcataccgga gactttccaa acccaaatga cgcatacaag | 240 |
| aatttgatca acctcaaacc tgcaattgaa gcaggctata caggacgcgg gtagaggta | 300 |
| ggtatcgtcg acacaggcga atccgtcggc agcatatcct ttcccgaact gtatggcaga | 360 |
| aaagaacacg gctataacga aaattacaaa aactatacgg cgtatatgcg aaggaagcg | 420 |
| cctgaagacg gaggcggtaa agacattgaa gcttctttcg acgatgaggc cgttatagag | 480 |
| actgaagcaa agccgacgga tatccgccac gtaaagaaaa tcggacacat cgatttggtc | 540 |
| tcccatatta ttggcgggcg ttccgtggac ggcagacctg caggcggtat tgcgcccgat | 600 |
| gcgacgctac acataatgaa tacgaatgat gaaaccaaga cgaaatgat ggttgcagcc | 660 |
| atccgcaatg catgggtcaa gctgggcgaa cgtggcgtgc gcatcgtcaa taacagtttt | 720 |
| ggaacaacat cgagggcagg cactgccgac cttttccaaa tagccaattc ggaggagcag | 780 |
| taccgccaag cgttgctcga ctattccggc ggtgataaaa cagacgaggg tatccgcctg | 840 |
| atgcaacaga gcgattacgg caacctgtcc taccacatcc gtaataaaaa catgcttttc | 900 |
| atcttttcga caggcaatga cgcacaagct cagcccaaca catatgccct attgccattt | 960 |
| tatgaaaaag acgctcaaaa aggcattatc acagtcgcag gcgtagaccg cagtggagaa | 1020 |
| aagttcaaac gggaaatgta tggagaaccg gtacagaac cgcttgagta tggctccaac | 1080 |
| cattgcggaa ttactgccat gtggtgcctg tcggcaccct atgaagcaag cgtccgtttc | 1140 |
| acccgtacaa acccgattca aattgccgga acatcctttt ccgcacccat cgtaaccggc | 1200 |

```
acggcggctc tgctgctgca gaaatacccg tggatgagca acgacaacct gcgtaccacg    1260
ttgctgacga cggctcagga catcggtgca gtcggcgtgg acagcaagtt cggctgggga    1320
ctgctggatg cgggtaaggc catgaacgga cccgcgtcct ttccgttcgg cgactttacc    1380
gccgatacga aaggtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg gtgttgtacg gcaacaacaa atcggatatg    1560
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acgtacggc gattatcggc ggcaagctgt acatgtcggc acgcggcaag    1800
ggggcaggct atctcaacag taccggacga cgtgttccct tcctgagtgc cgccaaaatc    1860
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acgcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg gaacgtggga acagggcggt    2400
gttgaaggca aaatgcgcgg cagtacccaa accgtcggca ttgccgcgaa aaccggcgaa    2460
aatacgacag cagccgccac actgggcatg ggacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640 ggtgcggacaa acatgcggaa aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtgaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggatccggag ggggtggtgt cgccgccgac    3180
atcggtgcgg ggcttgccga tgcactaacc gcaccgctcg accataaaga caaaggtttg    3240
cagtctttga cgctggatca gtccgtcagg aaaaacgaga actgaagct ggcggcacaa    3300 ggtgcggaaa aaactatgg aaacggtgac agcctcaata cggcaaatt gaagaacgac    3360 aaggtcagcc gtttcgactt tatccgccaa atcgaagtgg acgggcagct cattaccttg    3420
gagagtggag agttccaagt atacaaacaa agccattccg ccttaaccgc ctttcagacc    3480
gagcaaatac aagattcgga gcattccggg aagatggttg cgaaacgcca gttcagaatc    3540
ggcgacatag cgggcgaaca tacatctttt gacaagcttc ccgaaggcgg cagggcgaca    3600
```

```
tatcgcggga cggcgttcgg ttcagacgat gccggcggaa aactgaccta caccatagat    3660
ttcgccgcca agcagggaaa cggcaaaatc gaacatttga atcgccaga actcaatgtc    3720 gacctggccg ccgccgatat caagccggat ggaaaacgcc atgccgtcat cagcggttcc    3780
gtcctttaca accaagccga aaaggcagt tactccctcg gtatctttgg cggaaaagcc    3840
caggaagttg ccggcagcgc ggaagtgaaa accgtaaacg catacgcca tatcggcctt    3900 gccgccaagc aactcgagca ccaccaccac caccactga                           3939
```

<210> SEQ ID NO 20
<211> LENGTH: 1312
<212> TYPE: PRT
<213> ORGANISM: Artificial
<220> FEATURE:
<223> OTHER INFORMATION: deletion G983-741

<400> SEQUENCE: 20

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300
```

```
Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
690                 695                 700

Pro Glu Thr Val Glu Thr Ala Ala Ala Asp Arg Thr Asp Met Pro Gly
705                 710                 715                 720
```

```
Ile Arg Pro Tyr Gly Ala Thr Phe Arg Ala Ala Ala Val Gln His
            725                 730                 735
Ala Asn Ala Ala Asp Gly Val Arg Ile Phe Asn Ser Leu Ala Ala Thr
            740                 745                 750
Val Tyr Ala Asp Ser Thr Ala Ala His Ala Asp Met Gln Gly Arg Arg
            755                 760                 765
Leu Lys Ala Val Ser Asp Gly Leu Asp His Asn Gly Thr Gly Leu Arg
            770                 775                 780
Val Ile Ala Gln Thr Gln Asp Gly Gly Thr Trp Glu Gln Gly Gly
785                 790                 795                 800
Val Glu Gly Lys Met Arg Gly Ser Thr Gln Thr Val Gly Ile Ala Ala
                805                 810                 815
Lys Thr Gly Glu Asn Thr Thr Ala Ala Ala Thr Leu Gly Met Gly Arg
            820                 825                 830
Ser Thr Trp Ser Glu Asn Ser Ala Asn Ala Lys Thr Asp Ser Ile Ser
            835                 840                 845
Leu Phe Ala Gly Ile Arg His Asp Ala Gly Asp Ile Gly Tyr Leu Lys
            850                 855                 860
Gly Leu Phe Ser Tyr Gly Arg Tyr Lys Asn Ser Ile Ser Arg Ser Thr
865                 870                 875                 880
Gly Ala Asp Glu His Ala Glu Gly Ser Val Asn Gly Thr Leu Met Gln
                885                 890                 895
Leu Gly Ala Leu Gly Gly Val Asn Val Pro Phe Ala Ala Thr Gly Asp
                900                 905                 910
Leu Thr Val Glu Gly Gly Leu Arg Tyr Asp Leu Leu Lys Gln Asp Ala
            915                 920                 925
Phe Ala Glu Lys Gly Ser Ala Leu Gly Trp Ser Gly Asn Ser Leu Thr
930                 935                 940
Glu Gly Thr Leu Val Gly Leu Ala Gly Leu Lys Leu Ser Gln Pro Leu
945                 950                 955                 960
Ser Asp Lys Ala Val Leu Phe Ala Thr Ala Gly Val Glu Arg Asp Leu
            965                 970                 975
Asn Gly Arg Asp Tyr Thr Val Thr Gly Gly Phe Thr Gly Ala Thr Ala
            980                 985                 990
Ala Thr Gly Lys Thr Gly Ala Arg Asn Met Pro His Thr Arg Leu Val
            995                 1000                1005
Ala Gly Leu Gly Ala Asp Val Glu Phe Gly Asn Gly Trp Asn Gly
            1010                1015                1020
Leu Ala Arg Tyr Ser Tyr Ala Gly Ser Lys Gln Tyr Gly Asn His
            1025                1030                1035
Ser Gly Arg Val Gly Val Gly Tyr Arg Phe Leu Glu Gly Ser Gly
            1040                1045                1050
Gly Gly Gly Val Ala Ala Asp Ile Gly Ala Gly Leu Ala Asp Ala
            1055                1060                1065
Leu Thr Ala Pro Leu Asp His Lys Asp Lys Gly Leu Gln Ser Leu
            1070                1075                1080
Thr Leu Asp Gln Ser Val Arg Lys Asn Glu Lys Leu Lys Leu Ala
            1085                1090                1095
Ala Gln Gly Ala Glu Lys Thr Tyr Gly Asn Gly Asp Ser Leu Asn
            1100                1105                1110
Thr Gly Lys Leu Lys Asn Asp Lys Val Ser Arg Phe Asp Phe Ile
            1115                1120                1125
Arg Gln Ile Glu Val Asp Gly Gln Leu Ile Thr Leu Glu Ser Gly
```

| | | | | | | | | | | |
|---|---|---|---|---|---|---|---|---|---|---|
| | | 1130 | | | 1135 | | | 1140 | | |
| Glu | Phe | Gln | Val | Tyr | Lys | Gln | Ser | His | Ser | Ala | Leu | Thr | Ala | Phe |
| | | 1145 | | | | 1150 | | | | 1155 | | | | |
| Gln | Thr | Glu | Gln | Ile | Gln | Asp | Ser | Glu | His | Ser | Gly | Lys | Met | Val |
| | | 1160 | | | | 1165 | | | | 1170 | | | | |
| Ala | Lys | Arg | Gln | Phe | Arg | Ile | Gly | Asp | Ile | Ala | Gly | Glu | His | Thr |
| | | 1175 | | | | 1180 | | | | 1185 | | | | |
| Ser | Phe | Asp | Lys | Leu | Pro | Glu | Gly | Gly | Arg | Ala | Thr | Tyr | Arg | Gly |
| | | 1190 | | | | 1195 | | | | 1200 | | | | |
| Thr | Ala | Phe | Gly | Ser | Asp | Asp | Ala | Gly | Gly | Lys | Leu | Thr | Tyr | Thr |
| | | 1205 | | | | 1210 | | | | 1215 | | | | |
| Ile | Asp | Phe | Ala | Ala | Lys | Gln | Gly | Asn | Gly | Lys | Ile | Glu | His | Leu |
| | | 1220 | | | | 1225 | | | | 1230 | | | | |
| Lys | Ser | Pro | Glu | Leu | Asn | Val | Asp | Leu | Ala | Ala | Ala | Asp | Ile | Lys |
| | | 1235 | | | | 1240 | | | | 1245 | | | | |
| Pro | Asp | Gly | Lys | Arg | His | Ala | Val | Ile | Ser | Gly | Ser | Val | Leu | Tyr |
| | | 1250 | | | | 1255 | | | | 1260 | | | | |
| Asn | Gln | Ala | Glu | Lys | Gly | Ser | Tyr | Ser | Leu | Gly | Ile | Phe | Gly | Gly |
| | | 1265 | | | | 1270 | | | | 1275 | | | | |
| Lys | Ala | Gln | Glu | Val | Ala | Gly | Ser | Ala | Glu | Val | Lys | Thr | Val | Asn |
| | | 1280 | | | | 1285 | | | | 1290 | | | | |
| Gly | Ile | Arg | His | Ile | Gly | Leu | Ala | Ala | Lys | Gln | Leu | Glu | His | His |
| | | 1295 | | | | 1300 | | | | 1305 | | | | |
| His | His | His | His | | | | | | | | | | | |
| | | 1310 | | | | | | | | | | | | |

<210> SEQ ID NO 21
<211> LENGTH: 4344
<212> TYPE: DNA
<213> ORGANISM: Artificial
<220> FEATURE:
<223> OTHER INFORMATION: deletion G983-961

<400> SEQUENCE: 21

| | | | | | |
|---|---|---|---|---|---|
| atgacttctg | cgcccgactt | caatgcaggc | ggtaccggta | tcggcagcaa | cagcagagca | 60 |
| acaacagcga | aatcagcagc | agtatcttac | gccggtatca | agaacgaaat | gtgcaaagac | 120 |
| agaagcatgc | tctgtgccgg | tcgggatgac | gttgcggtta | cagacaggga | tgccaaaatc | 180 |
| aatgccccc | ccccgaatct | gcataccgga | gactttccaa | acccaaatga | cgcatacaag | 240 |
| aatttgatca | acctcaaacc | tgcaattgaa | gcaggctata | caggacgcgg | ggtagaggta | 300 |
| ggtatcgtcg | acacaggcga | atccgtcggc | agcatatcct | ttcccgaact | gtatggcaga | 360 |
| aaagaacacg | gctataacga | aaattacaaa | aactatacgg | cgtatatgcg | gaaggaagcg | 420 |
| cctgaagacg | gaggcggtaa | agacattgaa | gcttctttcg | acgatgaggc | cgttatagag | 480 |
| actgaagcaa | agccgacgga | tatccgccac | gtaaaagaaa | tcggacacat | cgatttggtc | 540 |
| tcccatatta | ttggcgggcg | ttccgtggac | ggcagacctg | caggcggtat | tgcgcccgat | 600 |
| gcgacgctac | acataatgaa | tacgaatgat | gaaaccaaga | cgaaatgat | ggttgcagcc | 660 |
| atccgcaatg | catgggtcaa | gctgggcgaa | cgtggcgtgc | gcatcgtcaa | taacagtttt | 720 |
| ggaacaacat | cgagggcagg | cactgccgac | cttttccaaa | tagccaattc | ggaggagcag | 780 |
| taccgccaag | cgttgctcga | ctattccggc | ggtgataaaa | cagacgaggg | tatccgcctg | 840 |
| atgcaacaga | gcgattacgg | caacctgtcc | taccacatcc | gtaataaaaa | catgcttttc | 900 |
| atcttttcga | caggcaatga | cgcacaagct | cagcccaaca | catatgccct | attgccattt | 960 |

```
tatgaaaaag acgctcaaaa aggcattatc acagtcgcag gcgtagaccg cagtggagaa    1020
aagttcaaac gggaaatgta tggagaaccg ggtacagaac cgcttgagta tggctccaac    1080
cattgcggaa ttactgccat gtggtgcctg tcggcaccct atgaagcaag cgtccgtttc    1140
acccgtacaa acccgattca aattgccgga acatccttt ccgcacccat cgtaaccggc    1200
acggcggctc tgctgctgca gaaatacccg tggatgagca cgacaacct gcgtaccacg    1260 ttgctgacga cggctcagga catcggtgca gtcggcgtgg acagcaagtt cggctgggga    1320
ctgctggatg cgggtaaggc catgaacgga cccgcgtcct ttccgttcgg cgactttacc    1380
gccgatacga aagtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg gtgttgtacg gcaacaacaa atcggatatg    1560
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acggtacggc gattatcggc ggcaagctgt acatgtcggc acgcggcaag    1800
ggggcaggct atctcaacag taccggacga cgtgttccct tcctgagtgc cgccaaaatc    1860
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acggcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg gaacgtggga cagggcggt    2400 gttgaaggca aaatgcgcgg cagtacccaa accgtcggca ttgccgcgaa aaccggcgaa    2460
aatacgacag cagccgccac actgggcatg ggacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg gcgtggaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
```

```
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaccgc  caatgaagcc    3720 aaacagacgg ccgaagaaac caaacaaaac gtcgatgcca agtaaaagc  tgcagaaact    3780 gcagcaggca agccgaagc  tgccgctggc acagctaata ctgcagccga caaggccgaa    3840
gctgtcgctg caaaagttac cgacatcaaa gctgatatcg ctacgaacaa agataatatt    3900
gctaaaaaag caaacagtgc cgacgtgtac accagagaag agtctgacag caaatttgtc    3960
agaattgatg gtctgaacgc tactaccgaa aaattggaca cacgcttggc ttctgctgaa    4020
aaatccattg ccgatcacga tactcgcctg aacggtttgg ataaaacagt gtcagacctg    4080
cgcaaagaaa cccgccaagg ccttgcagaa caagccgcgc tctccggtct gttccaacct    4140
tacaacgtgg tcggttcaa  tgtaacggct gcagtcggcg gctacaaatc cgaatcggca    4200
gtcgccatcg gtaccggctt ccgctttacc gaaactttg  ccgccaaagc aggcgtggca    4260
gtcggcactt cgtccggttc ttccgcagcc taccatgtcg gcgtcaatta cgagtggctc    4320
gagcaccacc accaccacca ctga                                           4344
```

<210> SEQ ID NO 22
<211> LENGTH: 1447
<212> TYPE: PRT
<213> ORGANISM: Artificial
<220> FEATURE:
<223> OTHER INFORMATION: deletion G983-961

<400> SEQUENCE: 22

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175
```

```
Ile Asp Leu Val Ser His Ile Ile Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
```

```
                595                 600                 605
Gly Arg Arg Val Pro Phe Leu Ser Ala Ala Lys Ile Gly Gln Asp Tyr
610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
                660                 665                 670

Ser Ala Pro Ala Gly Leu Lys His Ala Val Glu Gln Gly Gly Ser Asn
            675                 680                 685

Leu Glu Asn Leu Met Val Glu Leu Asp Ala Ser Glu Ser Ser Ala Thr
690                 695                 700

Pro Glu Thr Val Glu Thr Ala Ala Asp Arg Thr Asp Met Pro Gly
705                 710                 715                 720

Ile Arg Pro Tyr Gly Ala Thr Phe Arg Ala Ala Ala Val Gln His
                725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
                755                 760                 765

Leu Lys Ala Val Ser Asp Gly Leu Asp His Asn Gly Thr Gly Leu Arg
770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Thr Leu Gly Met Gly Arg
                820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Thr Gly Asp
            900                 905                 910

Leu Thr Val Glu Gly Gly Leu Arg Tyr Asp Leu Leu Lys Gln Asp Ala
            915                 920                 925

Phe Ala Glu Lys Gly Ser Ala Leu Gly Trp Ser Gly Asn Ser Leu Thr
930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Thr Ala
            980                 985                 990

Ala Thr Gly Lys Thr Gly Ala Arg  Asn Met Pro His Thr  Arg Leu Val
            995                 1000                1005

Ala Gly  Leu Gly Ala Asp Val  Glu Phe Gly Asn Gly  Trp Asn Gly
        1010                1015                1020
```

```
Leu Ala Arg Tyr Ser Tyr Ala Gly Ser Lys Gln Tyr Gly Asn His
    1025            1030                1035
Ser Gly Arg Val Gly Val Gly Tyr Arg Phe Leu Glu Gly Gly Gly
    1040            1045                1050
Gly Thr Gly Ser Ala Thr Asn Asp Asp Val Lys Lys Ala Ala
    1055            1060                1065
Thr Val Ala Ile Ala Ala Tyr Asn Asn Gly Gln Glu Ile Asn
    1070            1075                1080
Gly Phe Lys Ala Gly Glu Thr Ile Tyr Asp Ile Asp Glu Asp Gly
    1085            1090                1095
Thr Ile Thr Lys Lys Asp Ala Thr Ala Ala Asp Val Glu Ala Asp
    1100            1105                1110
Asp Phe Lys Gly Leu Gly Leu Lys Lys Val Val Thr Asn Leu Thr
    1115            1120                1125
Lys Thr Val Asn Glu Asn Lys Gln Asn Val Asp Ala Lys Val Lys
    1130            1135                1140
Ala Ala Glu Ser Glu Ile Glu Lys Leu Thr Thr Lys Leu Ala Asp
    1145            1150                1155
Thr Asp Ala Ala Leu Ala Asp Thr Asp Ala Ala Leu Asp Ala Thr
    1160            1165                1170
Thr Asn Ala Leu Asn Lys Leu Gly Glu Asn Ile Thr Thr Phe Ala
    1175            1180                1185
Glu Glu Thr Lys Thr Asn Ile Val Lys Ile Asp Glu Lys Leu Glu
    1190            1195                1200
Ala Val Ala Asp Thr Val Asp Lys His Ala Glu Ala Phe Asn Asp
    1205            1210                1215
Ile Ala Asp Ser Leu Asp Glu Thr Asn Thr Lys Ala Asp Glu Ala
    1220            1225                1230
Val Lys Thr Ala Asn Glu Ala Lys Gln Thr Ala Glu Glu Thr Lys
    1235            1240                1245
Gln Asn Val Asp Ala Lys Val Lys Ala Ala Glu Thr Ala Ala Gly
    1250            1255                1260
Lys Ala Glu Ala Ala Ala Gly Thr Ala Asn Thr Ala Ala Asp Lys
    1265            1270                1275
Ala Glu Ala Val Ala Ala Lys Val Thr Asp Ile Lys Ala Asp Ile
    1280            1285                1290
Ala Thr Asn Lys Asp Asn Ile Ala Lys Lys Ala Asn Ser Ala Asp
    1295            1300                1305
Val Tyr Thr Arg Glu Glu Ser Asp Ser Lys Phe Val Arg Ile Asp
    1310            1315                1320
Gly Leu Asn Ala Thr Thr Glu Lys Leu Asp Thr Arg Leu Ala Ser
    1325            1330                1335
Ala Glu Lys Ser Ile Ala Asp His Asp Thr Arg Leu Asn Gly Leu
    1340            1345                1350
Asp Lys Thr Val Ser Asp Leu Arg Lys Glu Thr Arg Gln Gly Leu
    1355            1360                1365
Ala Glu Gln Ala Ala Leu Ser Gly Leu Phe Gln Pro Tyr Asn Val
    1370            1375                1380
Gly Arg Phe Asn Val Thr Ala Ala Val Gly Gly Tyr Lys Ser Glu
    1385            1390                1395
Ser Ala Val Ala Ile Gly Thr Gly Phe Arg Phe Thr Glu Asn Phe
    1400            1405                1410
```

Ala Ala Lys Ala Gly Val Ala Val Gly Thr Ser Ser Gly Ser Ser
     1415                1420                1425

Ala Ala Tyr His Val Gly Val Asn Tyr Glu Trp Leu Glu His His
     1430                1435                1440

His His His His
     1445

<210> SEQ ID NO 23
<211> LENGTH: 4179
<212> TYPE: DNA
<213> ORGANISM: Artificial
<220> FEATURE:
<223> OTHER INFORMATION: deletion G983-961c

<400> SEQUENCE: 23

| | | | | | |
|---|---|---|---|---|---|
| atgacttctg | cgcccgactt | caatgcaggc | ggtaccggta | tcggcagcaa | cagcagagca | 60 |
| acaacagcga | aatcagcagc | agtatcttac | gccggtatca | agaacgaaat | gtgcaaagac | 120 |
| agaagcatgc | tctgtgccgg | tcgggatgac | gttgcggtta | cagacaggga | tgccaaaatc | 180 |
| aatgccccc | ccccgaatct | gcataccgga | gactttccaa | acccaaatga | cgcatacaag | 240 |
| aatttgatca | acctcaaacc | tgcaattgaa | gcaggctata | caggacgcgg | ggtagaggta | 300 |
| ggtatcgtcg | acacaggcga | atccgtcggc | agcatatcct | ttcccgaact | gtatggcaga | 360 |
| aaagaacacg | gctataacga | aaattacaaa | aactatacgg | cgtatatgcg | gaaggaagcg | 420 |
| cctgaagacg | gaggcggtaa | agacattgaa | gcttctttcg | acgatgaggc | cgttatagag | 480 |
| actgaagcaa | agccgacgga | tatccgccac | gtaaaagaaa | tcggacacat | cgatttggtc | 540 |
| tcccatatta | ttggcgggcg | ttccgtggac | ggcagacctg | caggcggtat | tgcgcccgat | 600 |
| gcgacgctac | acataatgaa | tacgaatgat | gaaaccaaga | cgaaatgat | ggttgcagcc | 660 |
| atccgcaatg | catgggtcaa | gctgggcgaa | cgtggcgtgc | gcatcgtcaa | taacagtttt | 720 |
| ggaacaacat | cgagggcagg | cactgccgac | cttttccaaa | tagccaattc | ggaggagcag | 780 |
| taccgccaag | cgttgctcga | ctattccggc | ggtgataaaa | cagacgaggg | tatccgcctg | 840 |
| atgcaacaga | gcgattacgg | caacctgtcc | taccacatcc | gtaataaaaa | catgcttttc | 900 |
| atcttttcga | caggcaatga | cgcacaagct | cagcccaaca | catatgccct | attgccattt | 960 |
| tatgaaaaag | acgctcaaaa | aggcattatc | acagtcgcag | gcgtagaccg | cagtggagaa | 1020 |
| aagttcaaac | gggaaatgta | tggagaaccg | ggtacagaac | cgcttgagta | tggctccaac | 1080 |
| cattgcggaa | ttactgccat | gtggtgcctg | tcggcaccct | atgaagcaag | cgtccgtttc | 1140 |
| acccgtacaa | acccgattca | aattgccgga | acatcctttt | ccgcacccat | cgtaaccggc | 1200 |
| acggcggctc | tgctgctgca | gaaatacccg | tggatgagca | cgacaacct | gcgtaccacg | 1260 |
| ttgctgacga | cggctcagga | catcggtgca | gtcggcgtgg | acagcaagtt | cggctgggga | 1320 |
| ctgctggatg | cgggtaaggc | catgaacgga | cccgcgtcct | ttccgttcgg | cgactttacc | 1380 |
| gccgatacga | aagtacatc | cgatattgcc | tactccttcc | gtaacgacat | ttcaggcacg | 1440 |
| ggcggcctga | tcaaaaaagg | cggcagccaa | ctgcaactgc | acggcaacaa | cacctatacg | 1500 |
| ggcaaaacca | ttatcgaagg | cggttcgctg | tgttgtacg | gcaacaacaa | atcggatatg | 1560 |
| cgcgtcgaaa | ccaaaggtgc | gctgatttat | aacggggcgg | catccggcgg | cagcctgaac | 1620 |
| agcgacggca | ttgtctatct | ggcagatacc | gaccaatccg | gcgcaaacga | aaccgtacac | 1680 |
| atcaaaggca | gtctgcagct | ggacggcaaa | ggtacgctgt | acacacgttt | gggcaaactg | 1740 |
| ctgaaagtgg | acggtacggc | gattatcggc | ggcaagctgt | acatgtcggc | acgcggcaag | 1800 |

```
ggggcaggct atctcaacag taccggacga cgtgttccct tcctgagtgc cgccaaaatc    1860
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acggcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg aacgtgggga cagggcggt     2400
gttgaaggca aaatgcgcgg cagtacccaa accgtcggca ttgccgcgaa accggcgaa     2460
aatacgacag cagccgccac actgggcatg gacgcagca catggagcga aaacagtgca     2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacgcgc ggcgtggaac gcgacctgaa cggacgcgac    2940
tacacggtaa cgggcggctt taccggcgcg actgcagcaa ccggcaagac gggggcacgc    3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaccgc caatgaagcc     3720
aaacagacgg ccgaagaaac caaacaaaac gtcgatgcca agtaaaagc tgcagaaact     3780
gcagcaggca aagccgaagc tgccgctggc acagctaata ctgcagccga caaggccgaa    3840
gctgtcgctg caaagttac cgacatcaaa gctgatatcg ctacgaacaa agataatatt     3900
gctaaaaaag caaacagtgc cgacgtgtac accagagaag agtctgacag caaatttgtc    3960
agaattgatg gtctgaacgc tactaccgaa aaattggaca cacgcttggc ttctgctgaa    4020
aaatccattg ccgatcacga tactcgcctg aacggtttgg ataaaacagt gtcagacctg    4080
cgcaaagaaa cccgccaagg ccttgcagaa caagccgcgc tctccggtct gttccaacct    4140
tacaacgtgg gtctcgagca ccaccaccac caccactga                          4179
```

<210> SEQ ID NO 24
<211> LENGTH: 1392
<212> TYPE: PRT
<213> ORGANISM: Artificial
<220> FEATURE:
<223> OTHER INFORMATION: deletion G983-961c

<400> SEQUENCE: 24

| | | | | | | | | | | | | | | |
|---|---|---|---|---|---|---|---|---|---|---|---|---|---|---|
| Met | Thr | Ser | Ala | Pro | Asp | Phe | Asn | Ala | Gly | Gly | Thr | Gly | Ile | Gly | Ser |
| 1 | | | | 5 | | | | | 10 | | | | | 15 | |
| Asn | Ser | Arg | Ala | Thr | Thr | Ala | Lys | Ser | Ala | Ala | Val | Ser | Tyr | Ala | Gly |
| | | | 20 | | | | | 25 | | | | | 30 | | |
| Ile | Lys | Asn | Glu | Met | Cys | Lys | Asp | Arg | Ser | Met | Leu | Cys | Ala | Gly | Arg |
| | | | | 35 | | | | | 40 | | | | | 45 | |
| Asp | Asp | Val | Ala | Val | Thr | Asp | Arg | Asp | Ala | Lys | Ile | Asn | Ala | Pro | Pro |
| | 50 | | | | | 55 | | | | | 60 | | | | |
| Pro | Asn | Leu | His | Thr | Gly | Asp | Phe | Pro | Asn | Pro | Asn | Asp | Ala | Tyr | Lys |
| 65 | | | | | 70 | | | | | 75 | | | | | 80 |
| Asn | Leu | Ile | Asn | Leu | Lys | Pro | Ala | Ile | Glu | Ala | Gly | Tyr | Thr | Gly | Arg |
| | | | | 85 | | | | | 90 | | | | | 95 | |
| Gly | Val | Glu | Val | Gly | Ile | Val | Asp | Thr | Gly | Glu | Ser | Val | Gly | Ser | Ile |
| | | | 100 | | | | | 105 | | | | | 110 | | |
| Ser | Phe | Pro | Glu | Leu | Tyr | Gly | Arg | Lys | Glu | His | Gly | Tyr | Asn | Glu | Asn |
| | | | | 115 | | | | | 120 | | | | | 125 | |
| Tyr | Lys | Asn | Tyr | Thr | Ala | Tyr | Met | Arg | Lys | Glu | Ala | Pro | Glu | Asp | Gly |
| | 130 | | | | | 135 | | | | | 140 | | | | |
| Gly | Gly | Lys | Asp | Ile | Glu | Ala | Ser | Phe | Asp | Asp | Glu | Ala | Val | Ile | Glu |
| 145 | | | | | 150 | | | | | 155 | | | | | 160 |
| Thr | Glu | Ala | Lys | Pro | Thr | Asp | Ile | Arg | His | Val | Lys | Glu | Ile | Gly | His |
| | | | | 165 | | | | | 170 | | | | | 175 | |
| Ile | Asp | Leu | Val | Ser | His | Ile | Ile | Gly | Gly | Arg | Ser | Val | Asp | Gly | Arg |
| | | | 180 | | | | | 185 | | | | | 190 | | |
| Pro | Ala | Gly | Gly | Ile | Ala | Pro | Asp | Ala | Thr | Leu | His | Ile | Met | Asn | Thr |
| | | | | 195 | | | | | 200 | | | | | 205 | |
| Asn | Asp | Glu | Thr | Lys | Asn | Glu | Met | Met | Val | Ala | Ala | Ile | Arg | Asn | Ala |
| | 210 | | | | | 215 | | | | | 220 | | | | |
| Trp | Val | Lys | Leu | Gly | Glu | Arg | Gly | Val | Arg | Ile | Val | Asn | Asn | Ser | Phe |
| 225 | | | | | 230 | | | | | 235 | | | | | 240 |
| Gly | Thr | Thr | Ser | Arg | Ala | Gly | Thr | Ala | Asp | Leu | Phe | Gln | Ile | Ala | Asn |
| | | | | 245 | | | | | 250 | | | | | 255 | |
| Ser | Glu | Glu | Gln | Tyr | Arg | Gln | Ala | Leu | Leu | Asp | Tyr | Ser | Gly | Gly | Asp |
| | | | 260 | | | | | 265 | | | | | 270 | | |
| Lys | Thr | Asp | Glu | Gly | Ile | Arg | Leu | Met | Gln | Gln | Ser | Asp | Tyr | Gly | Asn |
| | | | | 275 | | | | | 280 | | | | | 285 | |
| Leu | Ser | Tyr | His | Ile | Arg | Asn | Lys | Asn | Met | Leu | Phe | Ile | Phe | Ser | Thr |
| | 290 | | | | | 295 | | | | | 300 | | | | |
| Gly | Asn | Asp | Ala | Gln | Ala | Gln | Pro | Asn | Thr | Tyr | Ala | Leu | Leu | Pro | Phe |
| 305 | | | | | 310 | | | | | 315 | | | | | 320 |
| Tyr | Glu | Lys | Asp | Ala | Gln | Lys | Gly | Ile | Ile | Thr | Val | Ala | Gly | Val | Asp |
| | | | | 325 | | | | | 330 | | | | | 335 | |
| Arg | Ser | Gly | Glu | Lys | Phe | Lys | Arg | Glu | Met | Tyr | Gly | Glu | Pro | Gly | Thr |
| | | | 340 | | | | | 345 | | | | | 350 | | |
| Glu | Pro | Leu | Glu | Tyr | Gly | Ser | Asn | His | Cys | Gly | Ile | Thr | Ala | Met | Trp |
| | | | | 355 | | | | | 360 | | | | | 365 | |

```
Cys Leu Ser Ala Pro Tyr Glu Ala Ser Val Arg Phe Thr Arg Thr Asn
        370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
                420                 425                 430

Val Asp Ser Lys Phe Gly Trp Gly Leu Leu Asp Ala Gly Lys Ala Met
            435                 440                 445

Asn Gly Pro Ala Ser Phe Pro Phe Gly Asp Phe Thr Ala Asp Thr Lys
        450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
                500                 505                 510

Tyr Gly Asn Asn Lys Ser Asp Met Arg Val Glu Thr Lys Gly Ala Leu
            515                 520                 525

Ile Tyr Asn Gly Ala Ala Ser Gly Gly Ser Leu Asn Ser Asp Gly Ile
        530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
        610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
        690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Val Gln His
            725                 730                 735

Ala Asn Ala Ala Asp Gly Val Arg Ile Phe Asn Ser Leu Ala Ala Thr
                740                 745                 750

Val Tyr Ala Asp Ser Thr Ala Ala His Ala Asp Met Gln Gly Arg Arg
            755                 760                 765

Leu Lys Ala Val Ser Asp Gly Leu Asp His Asn Gly Thr Gly Leu Arg
        770                 775                 780
```

-continued

```
Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
        835                 840                 845

Leu Phe Ala Gly Ile Arg His Asp Ala Gly Asp Ile Gly Tyr Leu Lys
850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
        915                 920                 925

Phe Ala Glu Lys Gly Ser Ala Leu Gly Trp Ser Gly Asn Ser Leu Thr
930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly
        1010                1015                1020

Leu Ala Arg Tyr Ser Tyr Ala Gly Ser Lys Gln Tyr Gly Asn His
        1025                1030                1035

Ser Gly Arg Val Gly Val Gly Tyr Arg Phe Leu Glu Gly Gly Gly
        1040                1045                1050

Gly Thr Gly Ser Ala Thr Asn Asp Asp Asp Val Lys Lys Ala Ala
        1055                1060                1065

Thr Val Ala Ile Ala Ala Tyr Asn Asn Gly Gln Glu Ile Asn
        1070                1075                1080

Gly Phe Lys Ala Gly Glu Thr Ile Tyr Asp Ile Asp Glu Asp Gly
        1085                1090                1095

Thr Ile Thr Lys Lys Asp Ala Thr Ala Ala Asp Val Glu Ala Asp
        1100                1105                1110

Asp Phe Lys Gly Leu Gly Leu Lys Lys Val Val Thr Asn Leu Thr
        1115                1120                1125

Lys Thr Val Asn Glu Asn Lys Gln Asn Val Asp Ala Lys Val Lys
        1130                1135                1140

Ala Ala Glu Ser Glu Ile Glu Lys Leu Thr Thr Lys Leu Ala Asp
        1145                1150                1155

Thr Asp Ala Ala Leu Ala Asp Thr Asp Ala Ala Leu Asp Ala Thr
        1160                1165                1170

Thr Asn Ala Leu Asn Lys Leu Gly Glu Asn Ile Thr Thr Phe Ala
        1175                1180                1185

Glu Glu Thr Lys Thr Asn Ile Val Lys Ile Asp Glu Lys Leu Glu
```

```
                  1190                1195                1200

Ala Val  Ala Asp Thr Val  Asp Lys His Ala  Glu Ala Phe Asn Asp
    1205             1210                 1215

Ile Ala  Asp Ser Leu Asp  Glu Thr Asn Thr  Lys Ala Asp Glu Ala
    1220             1225                 1230

Val Lys  Thr Ala Asn Glu  Ala Lys Gln Thr  Ala Glu Glu Thr Lys
    1235             1240                 1245

Gln Asn  Val Asp Ala Lys  Val Lys Ala Ala  Glu Thr Ala Ala Gly
    1250             1255                 1260

Lys Ala  Glu Ala Ala Ala  Gly Thr Ala Asn  Thr Ala Ala Asp Lys
    1265             1270                 1275

Ala Glu  Ala Val Ala Ala  Lys Val Thr Asp  Ile Lys Ala Asp Ile
    1280             1285                 1290

Ala Thr  Asn Lys Asp Asn  Ile Ala Lys Lys  Ala Asn Ser Ala Asp
    1295             1300                 1305

Val Tyr  Thr Arg Glu Glu  Ser Asp Ser Lys  Phe Val Arg Ile Asp
    1310             1315                 1320

Gly Leu  Asn Ala Thr Thr  Glu Lys Leu Asp  Thr Arg Leu Ala Ser
    1325             1330                 1335

Ala Glu  Lys Ser Ile Ala  Asp His Asp Thr  Arg Leu Asn Gly Leu
    1340             1345                 1350

Asp Lys  Thr Val Ser Asp  Leu Arg Lys Glu  Thr Arg Gln Gly Leu
    1355             1360                 1365

Ala Glu  Gln Ala Ala Leu  Ser Gly Leu Phe  Gln Pro Tyr Asn Val
    1370             1375                 1380

Gly Leu  Glu His His His  His His His
    1385             1390

<210> SEQ ID NO 25
<211> LENGTH: 274
<212> TYPE: PRT
<213> ORGANISM: Artificial
<220> FEATURE:
<223> OTHER INFORMATION: Protein 741

<400> SEQUENCE: 25

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
```

```
            145                 150                 155                 160
Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly Asn Gly Lys Ile Glu His Leu Lys Ser Pro Glu Leu
                195                 200                 205

Asn Val Asp Leu Ala Ala Ala Asp Ile Lys Pro Asp Gly Lys Arg His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
                260                 265                 270

Lys Gln

<210> SEQ ID NO 26
<211> LENGTH: 248
<212> TYPE: PRT
<213> ORGANISM: Artificial
<220> FEATURE:
<223> OTHER INFORMATION: deletion G741

<400> SEQUENCE: 26

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
            50                  55                  60

Lys Val Ser Arg Phe Asp Phe Ile Arg Gln Ile Glu Val Asp Gly Gln
65              70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240
```

His Ile Gly Leu Ala Ala Lys Gln
            245

<210> SEQ ID NO 27
<211> LENGTH: 1947
<212> TYPE: DNA
<213> ORGANISM: Artificial
<220> FEATURE:
<223> OTHER INFORMATION: deletion G741-961

<400> SEQUENCE: 27

| | | |
|---|---|---:|
| atggtcgccg ccgacatcgg tgcggggctt gccgatgcac taaccgcacc gctcgaccat | | 60 |
| aaagacaaag gtttgcagtc tttgacgctg gatcagtccg tcaggaaaaa cgagaaactg | | 120 |
| aagctggcgg cacaaggtgc ggaaaaaact tatggaaacg gtgacagcct caatacgggc | | 180 |
| aaattgaaga acgacaaggt cagccgtttc gactttatcc gccaaatcga agtggacggg | | 240 |
| cagctcatta ccttggagag tggagagttc aagtataca aacaaagcca ttccgcctta | | 300 |
| accgcctttc agaccgagca atacaagat tcggagcatt ccgggaagat ggttgcgaaa | | 360 |
| cgccagttca gaatcggcga catagcgggc gaacatacat cttttgacaa gcttcccgaa | | 420 |
| ggcggcaggg cgacatatcg cgggacgcg ttcggttcag acgatgccgg cggaaaactg | | 480 |
| acctacacca tagatttcgc cgccaagcag ggaaacggca aaatcgaaca tttgaaatcg | | 540 |
| ccagaactca atgtcgacct ggccgccgcc gatatcaagc cggatggaaa acgccatgcc | | 600 |
| gtcatcagcg gttccgtcct ttacaaccaa gccgagaaag gcagttactc cctcggtatc | | 660 |
| tttggcggaa aagcccagga agttgccggc agcgcgaag tgaaaaccgt aaacggcata | | 720 |
| cgccatatcg gccttgccgc caagcaactc gagggtggcg gaggcactgg atccgccaca | | 780 |
| aacgacgacg atgttaaaaa agctgccact gtggccattg ctgctgccta acaatggc | | 840 |
| caagaaatca acggtttcaa agctggagag accatctacg acattgatga agacggcaca | | 900 |
| attaccaaaa aagacgcaac tgcagccgat gttgaagccg acgactttaa aggtctgggt | | 960 |
| ctgaaaaaag tcgtgactaa cctgaccaaa accgtcaatg aaaacaaaca aaacgtcgat | | 1020 |
| gccaaagtaa aagctgcaga atctgaaata gaaaagttaa caaccaagtt agcagacact | | 1080 |
| gatgccgctt tagcagatac tgatgccgct ctggatgcaa ccaccaacgc cttgaataaa | | 1140 |
| ttgggagaaa atataacgac attgctgaa gagactaaga caaatatcgt aaaaattgat | | 1200 |
| gaaaaattag aagccgtggc tgataccgtc gacaagcatg ccgaagcatt caacgatatc | | 1260 |
| gccgattcat tggatgaaac caacactaag gcagacgaag ccgtcaaaac cgccaatgaa | | 1320 |
| gccaaacaga cggccgaaga accaaacaa aacgtcgatg ccaaagtaaa agctgcagaa | | 1380 |
| actgcagcag gcaaagccga agctgccgct ggcacagcta atactgcagc cgacaaggcc | | 1440 |
| gaagctgtcg ctgcaaaagt taccgacatc aaagctgata tcgctacgaa caaagataat | | 1500 |
| attgctaaaa aagcaaacag tgccgacgtg tacaccagag aagagtctga cagcaaattt | | 1560 |
| gtcagaattg atggtctgaa cgctactacc gaaaaattgg acacacgctt ggcttctgct | | 1620 |
| gaaaaatcca ttgccgatca cgatactcgc ctgaacggtt tggataaaac agtgtcagac | | 1680 |
| ctgcgcaaag aaacccgcca aggccttgca gaacaagccg cgctctccgg tctgttccaa | | 1740 |
| ccttacaacg tgggtcggtt caatgtaacg gctgcagtcg gcggctacaa atccgaatcg | | 1800 |
| gcagtcgcca tcggtaccgg cttccgcttt accgaaaaact ttgccgccaa agcaggcgtg | | 1860 |
| gcagtcggca cttcgtccgg ttcttccgca gcctaccatg tcggcgtcaa ttacgagtgg | | 1920 |
| ctcgagcacc accaccacca ccactga | | 1947 |

<210> SEQ ID NO 28
<211> LENGTH: 648
<212> TYPE: PRT
<213> ORGANISM: Artificial
<220> FEATURE:
<223> OTHER INFORMATION: deletion G741-961

<400> SEQUENCE: 28

| | | | | | | | | | | | | | | |
|---|---|---|---|---|---|---|---|---|---|---|---|---|---|---|
| Met | Val | Ala | Ala | Asp | Ile | Gly | Ala | Gly | Leu | Ala | Asp | Ala | Leu | Thr | Ala |
| 1 | | | | 5 | | | | | 10 | | | | | 15 | |
| Pro | Leu | Asp | His | Lys | Asp | Lys | Gly | Leu | Gln | Ser | Leu | Thr | Leu | Asp | Gln |
| | | | 20 | | | | | 25 | | | | | 30 | | |
| Ser | Val | Arg | Lys | Asn | Glu | Lys | Leu | Lys | Leu | Ala | Ala | Gln | Gly | Ala | Glu |
| | | 35 | | | | | 40 | | | | | 45 | | | |
| Lys | Thr | Tyr | Gly | Asn | Gly | Asp | Ser | Leu | Asn | Thr | Gly | Lys | Leu | Lys | Asn |
| | 50 | | | | | 55 | | | | | 60 | | | | |
| Asp | Lys | Val | Ser | Arg | Phe | Asp | Phe | Ile | Arg | Gln | Ile | Glu | Val | Asp | Gly |
| 65 | | | | | 70 | | | | | 75 | | | | | 80 |
| Gln | Leu | Ile | Thr | Leu | Glu | Ser | Gly | Glu | Phe | Gln | Val | Tyr | Lys | Gln | Ser |
| | | | | 85 | | | | | 90 | | | | | 95 | |
| His | Ser | Ala | Leu | Thr | Ala | Phe | Gln | Thr | Glu | Gln | Ile | Gln | Asp | Ser | Glu |
| | | | 100 | | | | | 105 | | | | | 110 | | |
| His | Ser | Gly | Lys | Met | Val | Ala | Lys | Arg | Gln | Phe | Arg | Ile | Gly | Asp | Ile |
| | | 115 | | | | | 120 | | | | | 125 | | | |
| Ala | Gly | Glu | His | Thr | Ser | Phe | Asp | Lys | Leu | Pro | Glu | Gly | Gly | Arg | Ala |
| | 130 | | | | | 135 | | | | | 140 | | | | |
| Thr | Tyr | Arg | Gly | Thr | Ala | Phe | Gly | Ser | Asp | Asp | Ala | Gly | Gly | Lys | Leu |
| 145 | | | | | 150 | | | | | 155 | | | | | 160 |
| Thr | Tyr | Thr | Ile | Asp | Phe | Ala | Ala | Lys | Gln | Gly | Asn | Gly | Lys | Ile | Glu |
| | | | | 165 | | | | | 170 | | | | | 175 | |
| His | Leu | Lys | Ser | Pro | Glu | Leu | Asn | Val | Asp | Leu | Ala | Ala | Ala | Asp | Ile |
| | | | 180 | | | | | 185 | | | | | 190 | | |
| Lys | Pro | Asp | Gly | Lys | Arg | His | Ala | Val | Ile | Ser | Gly | Ser | Val | Leu | Tyr |
| | | 195 | | | | | 200 | | | | | 205 | | | |
| Asn | Gln | Ala | Glu | Lys | Gly | Ser | Tyr | Ser | Leu | Gly | Ile | Phe | Gly | Gly | Lys |
| | 210 | | | | | 215 | | | | | 220 | | | | |
| Ala | Gln | Glu | Val | Ala | Gly | Ser | Ala | Glu | Val | Lys | Thr | Val | Asn | Gly | Ile |
| 225 | | | | | 230 | | | | | 235 | | | | | 240 |
| Arg | His | Ile | Gly | Leu | Ala | Ala | Lys | Gln | Leu | Glu | Gly | Gly | Gly | Gly | Thr |
| | | | | 245 | | | | | 250 | | | | | 255 | |
| Gly | Ser | Ala | Thr | Asn | Asp | Asp | Val | Lys | Lys | Ala | Ala | Thr | Val | Ala | Ala |
| | | | 260 | | | | | 265 | | | | | 270 | | |
| Ile | Ala | Ala | Ala | Tyr | Asn | Asn | Gly | Gln | Glu | Ile | Asn | Gly | Phe | Lys | Ala |
| | | 275 | | | | | 280 | | | | | 285 | | | |
| Gly | Glu | Thr | Ile | Tyr | Asp | Ile | Asp | Glu | Asp | Gly | Thr | Ile | Thr | Lys | Lys |
| | 290 | | | | | 295 | | | | | 300 | | | | |
| Asp | Ala | Thr | Ala | Ala | Asp | Val | Glu | Ala | Asp | Asp | Phe | Lys | Gly | Leu | Gly |
| 305 | | | | | 310 | | | | | 315 | | | | | 320 |
| Leu | Lys | Lys | Val | Val | Thr | Asn | Leu | Thr | Lys | Thr | Val | Asn | Glu | Asn | Lys |
| | | | | 325 | | | | | 330 | | | | | 335 | |
| Gln | Asn | Val | Asp | Ala | Lys | Val | Lys | Ala | Ala | Glu | Ser | Glu | Ile | Glu | Lys |
| | | | 340 | | | | | 345 | | | | | 350 | | |
| Leu | Thr | Thr | Lys | Leu | Ala | Asp | Thr | Asp | Ala | Ala | Leu | Ala | Asp | Thr | Asp |
| | | 355 | | | | | 360 | | | | | 365 | | | |

```
Ala Ala Leu Asp Ala Thr Thr Asn Ala Leu Asn Lys Leu Gly Glu Asn
        370                 375                 380
Ile Thr Thr Phe Ala Glu Glu Thr Lys Thr Asn Ile Val Lys Ile Asp
385                 390                 395                 400
Glu Lys Leu Glu Ala Val Ala Asp Thr Val Asp Lys His Ala Glu Ala
                405                 410                 415
Phe Asn Asp Ile Ala Asp Ser Leu Asp Glu Thr Asn Thr Lys Ala Asp
            420                 425                 430
Glu Ala Val Lys Thr Ala Asn Glu Ala Lys Gln Thr Ala Glu Glu Thr
        435                 440                 445
Lys Gln Asn Val Asp Ala Lys Val Lys Ala Ala Glu Thr Ala Ala Gly
    450                 455                 460
Lys Ala Glu Ala Ala Ala Gly Thr Ala Asn Thr Ala Ala Asp Lys Ala
465                 470                 475                 480
Glu Ala Val Ala Ala Lys Val Thr Asp Ile Lys Ala Asp Ile Ala Thr
                485                 490                 495
Asn Lys Asp Asn Ile Ala Lys Lys Ala Asn Ser Ala Asp Val Tyr Thr
            500                 505                 510
Arg Glu Glu Ser Asp Ser Lys Phe Val Arg Ile Asp Gly Leu Asn Ala
        515                 520                 525
Thr Thr Glu Lys Leu Asp Thr Arg Leu Ala Ser Ala Glu Lys Ser Ile
    530                 535                 540
Ala Asp His Asp Thr Arg Leu Asn Gly Leu Asp Lys Thr Val Ser Asp
545                 550                 555                 560
Leu Arg Lys Glu Thr Arg Gln Gly Leu Ala Glu Gln Ala Ala Leu Ser
                565                 570                 575
Gly Leu Phe Gln Pro Tyr Asn Val Gly Arg Phe Asn Val Thr Ala Ala
            580                 585                 590
Val Gly Gly Tyr Lys Ser Glu Ser Ala Val Ala Ile Gly Thr Gly Phe
        595                 600                 605
Arg Phe Thr Glu Asn Phe Ala Ala Lys Ala Gly Val Ala Val Gly Thr
    610                 615                 620
Ser Ser Gly Ser Ser Ala Ala Tyr His Val Gly Val Asn Tyr Glu Trp
625                 630                 635                 640
Leu Glu His His His His His His
                645

<210> SEQ ID NO 29
<211> LENGTH: 1782
<212> TYPE: DNA
<213> ORGANISM: Artificial
<220> FEATURE:
<223> OTHER INFORMATION: deletion G741-961c

<400> SEQUENCE: 29
atggtcgccg ccgacatcgg tgcggggctt gccgatgcac taaccgcacc gctcgaccat      60
aaagacaaag gtttgcagtc tttgacgctg gatcagtccg tcaggaaaaa cgagaaactg     120
aagctggcgg cacaaggtgc ggaaaaaact tatggaaacg gtgacagcct caatacgggc     180
aaattgaaga cgacaaggt cagccgtttc gactttatcc gccaaatcga agtgacgggg     240
cagctcatta ccttggagag tggagagttc aagtataca aacaaagcca ttccgcctta     300
accgcctttc agaccgagca aatacaagat tcggagcatt ccggaagat ggttgcgaaa     360 cgccagttca gaatcggcga catagcgggc gaacatatac ttttgacaa gcttcccgaa     420
```

-continued

| | |
|---|---|
| ggcggcaggg cgacatatcg cgggacggcg ttcggttcag acgatgccgg cggaaaactg | 480 |
| acctacacca tagatttcgc cgccaagcag ggaaacggca aaatcgaaca tttgaaatcg | 540 |
| ccagaactca atgtcgacct ggccgccgcc gatatcaagc cggatggaaa acgccatgcc | 600 |
| gtcatcagcg gttccgtcct ttacaaccaa gccgagaaag cagttactc cctcggtatc | 660 |
| tttgcggaa aagcccagga agttgccggc agcgcggaag tgaaaaccgt aaacggcata | 720 |
| cgccatatcg gccttgccgc caagcaactc gagggtggcg gaggcactgg atccgccaca | 780 |
| aacgacgacg atgttaaaaa agctgccact gtggccattg ctgctgccta acaatggc | 840 |
| caagaaatca acggtttcaa agctggagag accatctacg acattgatga agacggcaca | 900 |
| attaccaaaa aagacgcaac tgcagccgat gttgaagccg acgactttaa aggtctgggt | 960 |
| ctgaaaaaag tcgtgactaa cctgaccaaa accgtcaatg aaaacaaaca aaacgtcgat | 1020 |
| gccaaagtaa aagctgcaga atctgaaata gaaaagttaa caaccaagtt agcagacact | 1080 |
| gatgccgctt tagcagatac tgatgccgct ctggatgcaa ccaccaacgc cttgaataaa | 1140 |
| ttgggagaaa atataacgac atttgctgaa gagactaaga caaatatcgt aaaaattgat | 1200 |
| gaaaaattag aagccgtggc tgataccgtc gacaagcatg ccgaagcatt caacgatatc | 1260 |
| gccgattcat tggatgaaac caacactaag gcagacgaag ccgtcaaaac cgccaatgaa | 1320 |
| gccaaacaga cggccgaaga aaccaaacaa aacgtcgatg ccaaagtaaa agctgcagaa | 1380 |
| actgcagcag gcaaagccga agctgccgct ggcacagcta atactgcagc cgacaaggcc | 1440 |
| gaagctgtcg ctgcaaaagt taccgacatc aaagctgata tcgctacgaa caaagataat | 1500 |
| attgctaaaa aagcaaacag tgccgacgtg tacaccagag aagagtctga cagcaaattt | 1560 |
| gtcagaattg atggtctgaa cgctactacc gaaaaattgg acacacgctt ggcttctgct | 1620 |
| gaaaaatcca ttgccgatca cgatactcgc ctgaacggtt tggataaaac agtgtcagac | 1680 |
| ctgcgcaaag aaacccgcca aggccttgca gaacaagccg cgctctccgg tctgttccaa | 1740 |
| ccttacaacg tgggtctcga gcaccaccac caccaccact ga | 1782 |

<210> SEQ ID NO 30
<211> LENGTH: 593
<212> TYPE: PRT
<213> ORGANISM: Artificial
<220> FEATURE:
<223> OTHER INFORMATION: deletion G741-961c

<400> SEQUENCE: 30

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
                20                  25                  30

Ser Val Arg Lys Asn Glu Lys Leu Leu Ala Ala Gln Gly Ala Glu
            35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

```
Ala Gly Glu His Thr Ser Phe Asp Lys Leu Pro Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Gly Gly Thr
                245                 250                 255

Gly Ser Ala Thr Asn Asp Asp Val Lys Lys Ala Ala Thr Val Ala
                260                 265                 270

Ile Ala Ala Ala Tyr Asn Asn Gly Gln Glu Ile Asn Gly Phe Lys Ala
                275                 280                 285

Gly Glu Thr Ile Tyr Asp Ile Asp Glu Asp Gly Thr Ile Thr Lys Lys
    290                 295                 300

Asp Ala Thr Ala Ala Asp Val Glu Ala Asp Asp Phe Lys Gly Leu Gly
305                 310                 315                 320

Leu Lys Lys Val Val Thr Asn Leu Thr Lys Thr Val Asn Glu Asn Lys
                325                 330                 335

Gln Asn Val Asp Ala Lys Val Lys Ala Ala Glu Ser Glu Ile Glu Lys
                340                 345                 350

Leu Thr Thr Lys Leu Ala Asp Thr Asp Ala Ala Leu Ala Asp Thr Asp
            355                 360                 365

Ala Ala Leu Asp Ala Thr Thr Asn Ala Leu Asn Lys Leu Gly Glu Asn
370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
                420                 425                 430

Glu Ala Val Lys Thr Ala Asn Glu Ala Lys Gln Thr Ala Glu Glu Thr
                435                 440                 445

Lys Gln Asn Val Asp Ala Lys Val Lys Ala Ala Glu Thr Ala Ala Gly
    450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
        515                 520                 525

Thr Thr Glu Lys Leu Asp Thr Arg Leu Ala Ser Ala Glu Lys Ser Ile
    530                 535                 540
```

```
Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Leu Glu His His His His His
            580                 585                 590

His

<210> SEQ ID NO 31
<211> LENGTH: 3939
<212> TYPE: DNA
<213> ORGANISM: Artificial
<220> FEATURE:
<223> OTHER INFORMATION: deletion G741-983

<400> SEQUENCE: 31
atggtcgccg ccgacatcgg tgcggggctt gccgatgcac taaccgcacc gctcgaccat      60
aaagacaaag gtttgcagtc tttgacgctg gatcagtccg tcaggaaaaa cgagaaactg     120
aagctggcgg cacaaggtgc ggaaaaaact tatggaaacg gtgacagcct caatacgggc     180
aaattgaaga cgacaaggt cagccgtttc gactttatcc gccaaatcga agtggacggg      240
cagctcatta ccttggagag tggagagttc caagtataca aacaaagcca ttccgcctta     300
accgcctttc agaccgagca aatacaagat tcggagcatt ccggaagat ggttgcgaaa      360 cgccagttca gaatcggcga catagcgggc gaacatacat cttttgacaa gcttcccgaa     420
ggcggcaggg cgacatatcg cgggacggcg ttcggttcag acgatgccgg cggaaaactg     480
acctacacca tagatttcgc cgccaagcag ggaaacggca aaatcgaaca tttgaaatcg     540
ccagaactca atgtcgacct ggccgccgcc gatatcaagc cggatggaaa acgccatgcc     600
gtcatcagcg gttccgtcct ttacaaccaa gccgagaaag gcagttactc cctcggtatc     660
tttggcggaa aagcccagga agttgccggc agcgcggaag tgaaaaccgt aaacggcata     720
cgccatatcg gccttgccgc caagcaactc gagggatccg gcggaggcgg cacttctgcg     780
cccgacttca atgcaggcgg taccggtatc ggcagcaaca gcagagcaac aacagcgaaa     840
tcagcagcag tatcttacgc cggtatcaag aacgaaatgt gcaaagacag aagcatgctc     900
tgtgccggtc gggatgacgt tgcggttaca gacagggatg ccaaaatcaa tgccccccc      960 ccgaatctgc ataccggaga cttcccaaac ccaaatgacg catacaagaa tttgatcaac    1020
ctcaaacctg caattgaagc aggctataca ggacgcgggg tagaggtagg tatcgtcgac    1080
acaggcgaat ccgtcggcag catatccttt cccgaactgt atggcagaaa agaacacggc    1140
tataacgaaa attacaaaaa ctatacggcg tatatgcgga aggaagcgcc tgaagacgga    1200 ggcgtaaag acattgaagc ttctttcgac gatgaggccg ttatagagac tgaagcaaag    1260
ccgacggata tccgccacgt aaaagaaatc ggacacatcg atttggtctc ccatattatt    1320
ggcgggcgtt ccgtgacgg cagacctgca ggcggtattg cgcccgatgc gacgctacac    1380
ataatgaata cgaatgatga aaccaagaac gaaatgatgg ttgcagccat ccgcaatgca    1440
tgggtcaagc tggcgaacg tggcgtgcgc atcgtcaata acagttttgg aacaacatcg    1500
agggcaggca ctgccgacct tttccaaata gccaattcgg aggagcagta ccgccaagcg    1560
ttgctcgact attccggcgg tgataaaaca gacgagggta tccgcctgat gcaacagagc    1620
gattacggca acctgtccta ccacatccgt aataaaaaca tgcttttcat cttttcgaca    1680
ggcaatgacg cacaagctca gcccaacaca tatgcctat tgccattta tgaaaaagac    1740
```

-continued

```
gctcaaaaag gcattatcac agtcgcaggc gtagaccgca gtggagaaaa gttcaaacgg  1800
gaaatgtatg gagaaccggg tacagaaccg cttgagtatg gctccaacca ttgcggaatt  1860
actgccatgt ggtgcctgtc ggcaccctat gaagcaagcg tccgtttcac ccgtacaaac  1920
ccgattcaaa ttgccggaac atccttttcc gcacccatcg taaccggcac ggcggctctg  1980
ctgctgcaga ataccegtg gatgagcaac gacaacctgc gtaccacgtt gctgacgacg  2040
gctcaggaca tcggtgcagt cggcgtggac agcaagttcg gctggggact gctggatgcg  2100
ggtaaggcca tgaacggacc cgcgtccttt ccgttcggcg actttaccgc cgatacgaaa  2160
ggtacatccg atattgccta ctccttccgt aacgacattt caggcacggg cggcctgatc  2220
aaaaaaggcg gcagccaact gcaactgcac ggcaacaaca cctatacggg caaaaccatt  2280
atcgaaggcg gttcgctggt gttgtacggc aacaacaaat cggatatgcg cgtcgaaacc  2340
aaaggtgcgc tgatttataa cggggcggca tccggcggca gcctgaacag cgacggcatt  2400
gtctatctgg cagataccga ccaatccggc gcaaacgaaa ccgtacacat caaaggcagt  2460
ctgcagctgg acggcaaagg tacgctgtac acacgtttgg gcaaactgct gaaagtggac  2520
ggtacggcga ttatcggcgg caagctgtac atgtcggcac gcggcaaggg ggcaggctat  2580
ctcaacagta ccgacgacg tgttcccttc ctgagtgccg ccaaaatcgg gcaggattat  2640
tctttcttca caaacatcga aaccgacggc ggcctgctgg cttccctcga cagcgtcgaa  2700
aaaacagcgg gcagtgaagg cgacacgctg tcctattatg tccgtcgcgg caatgcggca  2760
cggactgctt cggcagcggc acattccgcg cccgccggtc tgaaacacgc cgtagaacag  2820
ggcggcagca atctgaaaaa cctgatggtc gaactggatg cctccgaatc atccgcaaca  2880
cccgagacgg ttgaaactgc ggcagccgac cgcacagata tgccgggcat ccgcccctac  2940
ggcgcaactt ccgcgcagc ggcagccgta cagcatgcga atgccgccga cggtgtacgc  3000
atcttcaaca gtctcgccgc taccgtctat gccgacagta ccgccgccca tgccgatatg  3060
cagggacgcc gcctgaaagc cgtatcggac gggttggacc acaacggcac gggtctgcgc  3120
gtcatcgcgc aaacccaaca ggacggtgga acgtgggaac agggcggtgt tgaaggcaaa  3180
atgcgcggca gtacccaaac cgtcggcatt ccgcgcaaaa ccggcgaaaa tacgacagca  3240
gccgccacac tgggcatggg acgcagcaca tggagcgaaa acagtgcaaa tgcaaaaacc  3300
gacagcatta gtctgtttgc aggcatacgg cacgatgcgg gcgatatcgg ctatctcaaa  3360
ggcctgttct cctacggacg ctacaaaaac agcatcagcc gcagcaccgg tgcggacgaa  3420
catgcggaag gcagcgtcaa cggcacgctg atgcagctgg gcgcactggg cggtgtcaac  3480
gttccgtttg ccgcaacggg agatttgacg gtcgaaggcg gtctgcgcta cgacctgctc  3540
aaacaggatg cattcgccga aaaaggcagt gctttgggct ggagcggcaa cagcctcact  3600
gaaggcacgc tggtcggact cgcgggtctg aagctgtcgc aacccttgag cgataaagcc  3660
gtcctgtttg caacgcgggg cgtggaacgc gacctgaacg gacgcgacta cacggtaacg  3720
ggcggcttta ccgcgcgac tgcagcaacc ggcaagacgg gggcacgcaa tatgccgcac  3780
acccgtctgg ttgccggcct gggcgcggat gtcgaattcg gcaacggctg gaacggcttg  3840
gcacgttaca gctacgccgg ttccaaacag tacggcaacc acagcggacg agtcggcgta  3900
ggctaccggt tcctcgagca ccaccaccac caccactga                          3939
```

<210> SEQ ID NO 32
<211> LENGTH: 1312
<212> TYPE: PRT
<213> ORGANISM: Artificial
<220> FEATURE:
<223> OTHER INFORMATION: deletion G741-983

<400> SEQUENCE: 32

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
                20                  25                  30

Ser Val Arg Lys Asn Glu Lys Leu Lys Leu Ala Ala Gln Gly Ala Glu
            35                  40                  45

Lys Thr Tyr Gly Asn Gly Asp Ser Leu Asn Thr Gly Lys Leu Lys Asn
        50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
                100                 105                 110

His Ser Gly Lys Met Val Ala Lys Arg Gln Phe Arg Ile Gly Asp Ile
            115                 120                 125

Ala Gly Glu His Thr Ser Phe Asp Lys Leu Pro Glu Gly Gly Arg Ala
        130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
                180                 185                 190

Lys Pro Asp Gly Lys Arg His Ala Val Ile Ser Gly Ser Val Leu Tyr
            195                 200                 205

Asn Gln Ala Glu Lys Gly Ser Tyr Ser Leu Gly Ile Phe Gly Gly Lys
        210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Ser Gly Gly Gly
                245                 250                 255

Gly Thr Ser Ala Pro Asp Phe Asn Ala Gly Thr Gly Ile Gly Ser
                260                 265                 270

Asn Ser Arg Ala Thr Thr Ala Lys Ser Ala Ala Val Ser Tyr Ala Gly
            275                 280                 285

Ile Lys Asn Glu Met Cys Lys Asp Arg Ser Met Leu Cys Ala Gly Arg
        290                 295                 300

Asp Asp Val Ala Val Thr Asp Arg Asp Ala Lys Ile Asn Ala Pro Pro
305                 310                 315                 320

Pro Asn Leu His Thr Gly Asp Phe Pro Asn Pro Asn Asp Ala Tyr Lys
                325                 330                 335

Asn Leu Ile Asn Leu Lys Pro Ala Ile Glu Ala Gly Tyr Thr Gly Arg
                340                 345                 350

Gly Val Glu Val Gly Ile Val Asp Thr Gly Ser Val Gly Ser Ile
            355                 360                 365

Ser Phe Pro Glu Leu Tyr Gly Arg Lys Glu His Gly Tyr Asn Glu Asn
        370                 375                 380

Tyr Lys Asn Tyr Thr Ala Tyr Met Arg Lys Glu Ala Pro Glu Asp Gly
385                 390                 395                 400
```

```
Gly Gly Lys Asp Ile Glu Ala Ser Phe Asp Asp Gly Ala Val Ile Glu
                    405                 410                 415
Thr Glu Ala Lys Pro Thr Asp Ile Arg His Val Lys Glu Ile Gly His
                420                 425                 430
Ile Asp Leu Val Ser His Ile Ile Gly Gly Arg Ser Val Asp Gly Arg
                435                 440                 445
Pro Ala Gly Gly Ile Ala Pro Asp Ala Thr Leu His Ile Met Asn Thr
            450                 455                 460
Asn Asp Glu Thr Lys Asn Glu Met Met Val Ala Ala Ile Arg Asn Ala
465                 470                 475                 480
Trp Val Lys Leu Gly Glu Arg Gly Val Arg Ile Val Asn Asn Ser Phe
                    485                 490                 495
Gly Thr Thr Ser Arg Ala Gly Thr Ala Asp Leu Phe Gln Ile Ala Asn
                500                 505                 510
Ser Glu Glu Gln Tyr Arg Gln Ala Leu Leu Asp Tyr Ser Gly Gly Asp
                515                 520                 525
Lys Thr Asp Glu Gly Ile Arg Leu Met Gln Gln Ser Asp Tyr Gly Asn
            530                 535                 540
Leu Ser Tyr His Ile Arg Asn Lys Asn Met Leu Phe Ile Phe Ser Thr
545                 550                 555                 560
Gly Asn Asp Ala Gln Ala Gln Pro Asn Thr Tyr Ala Leu Leu Pro Phe
                565                 570                 575
Tyr Glu Lys Asp Ala Gln Lys Gly Ile Ile Thr Val Ala Gly Val Asp
                580                 585                 590
Arg Ser Gly Glu Lys Phe Lys Arg Glu Met Tyr Gly Glu Pro Gly Thr
            595                 600                 605
Glu Pro Leu Glu Tyr Gly Ser Asn His Cys Gly Ile Thr Ala Met Trp
            610                 615                 620
Cys Leu Ser Ala Pro Tyr Glu Ala Ser Val Arg Phe Thr Arg Thr Asn
625                 630                 635                 640
Pro Ile Gln Ile Ala Gly Thr Ser Phe Ser Ala Pro Ile Val Thr Gly
                    645                 650                 655
Thr Ala Ala Leu Leu Leu Gln Lys Tyr Pro Trp Met Ser Asn Asp Asn
                660                 665                 670
Leu Arg Thr Thr Leu Leu Thr Thr Ala Gln Asp Ile Gly Ala Val Gly
            675                 680                 685
Val Asp Ser Lys Phe Gly Trp Gly Leu Leu Asp Ala Gly Lys Ala Met
            690                 695                 700
Asn Gly Pro Ala Ser Phe Pro Phe Gly Asp Phe Thr Ala Asp Thr Lys
705                 710                 715                 720
Gly Thr Ser Asp Ile Ala Tyr Ser Phe Arg Asn Asp Ile Ser Gly Thr
                    725                 730                 735
Gly Gly Leu Ile Lys Lys Gly Gly Ser Gln Leu Gln Leu His Gly Asn
                740                 745                 750
Asn Thr Tyr Thr Gly Lys Thr Ile Ile Glu Gly Gly Ser Leu Val Leu
                755                 760                 765
Tyr Gly Asn Asn Lys Ser Asp Met Arg Val Glu Thr Lys Gly Ala Leu
            770                 775                 780
Ile Tyr Asn Gly Ala Ala Ser Gly Gly Ser Leu Asn Ser Asp Gly Ile
785                 790                 795                 800
Val Tyr Leu Ala Asp Thr Asp Gln Ser Gly Ala Asn Glu Thr Val His
                    805                 810                 815
```

Ile Lys Gly Ser Leu Gln Leu Asp Gly Lys Gly Thr Leu Tyr Thr Arg
            820                 825                 830

Leu Gly Lys Leu Leu Lys Val Asp Gly Thr Ala Ile Ile Gly Gly Lys
            835                 840                 845

Leu Tyr Met Ser Ala Arg Gly Lys Gly Ala Gly Tyr Leu Asn Ser Thr
            850                 855                 860

Gly Arg Arg Val Pro Phe Leu Ser Ala Ala Lys Ile Gly Gln Asp Tyr
865                 870                 875                 880

Ser Phe Phe Thr Asn Ile Glu Thr Asp Gly Gly Leu Leu Ala Ser Leu
                885                 890                 895

Asp Ser Val Glu Lys Thr Ala Gly Ser Glu Gly Asp Thr Leu Ser Tyr
            900                 905                 910

Tyr Val Arg Arg Gly Asn Ala Ala Arg Thr Ala Ser Ala Ala Ala His
            915                 920                 925

Ser Ala Pro Ala Gly Leu Lys His Ala Val Glu Gln Gly Gly Ser Asn
            930                 935                 940

Leu Glu Asn Leu Met Val Glu Leu Asp Ala Ser Glu Ser Ser Ala Thr
945                 950                 955                 960

Pro Glu Thr Val Glu Thr Ala Ala Ala Asp Arg Thr Asp Met Pro Gly
                965                 970                 975

Ile Arg Pro Tyr Gly Ala Thr Phe Arg Ala Ala Ala Val Gln His
            980                 985                 990

Ala Asn Ala Ala Asp Gly Val Arg Ile Phe Asn Ser Leu Ala Ala Thr
            995                 1000                1005

Val Tyr Ala Asp Ser Thr Ala Ala His Ala Asp Met Gln Gly Arg
    1010                1015                1020

Arg Leu Lys Ala Val Ser Asp Gly Leu Asp His Asn Gly Thr Gly
    1025                1030                1035

Leu Arg Val Ile Ala Gln Thr Gln Gln Asp Gly Gly Thr Trp Glu
    1040                1045                1050

Gln Gly Gly Val Glu Gly Lys Met Arg Gly Ser Thr Gln Thr Val
    1055                1060                1065

Gly Ile Ala Ala Lys Thr Gly Glu Asn Thr Thr Ala Ala Ala Thr
    1070                1075                1080

Leu Gly Met Gly Arg Ser Thr Trp Ser Glu Asn Ser Ala Asn Ala
    1085                1090                1095

Lys Thr Asp Ser Ile Ser Leu Phe Ala Gly Ile Arg His Asp Ala
    1100                1105                1110

Gly Asp Ile Gly Tyr Leu Lys Gly Leu Phe Ser Tyr Gly Arg Tyr
    1115                1120                1125

Lys Asn Ser Ile Ser Arg Ser Thr Gly Ala Asp Glu His Ala Glu
    1130                1135                1140

Gly Ser Val Asn Gly Thr Leu Met Gln Leu Gly Ala Leu Gly Gly
    1145                1150                1155

Val Asn Val Pro Phe Ala Ala Thr Gly Asp Leu Thr Val Glu Gly
    1160                1165                1170

Gly Leu Arg Tyr Asp Leu Leu Lys Gln Asp Ala Phe Ala Glu Lys
    1175                1180                1185

Gly Ser Ala Leu Gly Trp Ser Gly Asn Ser Leu Thr Glu Gly Thr
    1190                1195                1200

Leu Val Gly Leu Ala Gly Leu Lys Leu Ser Gln Pro Leu Ser Asp
    1205                1210                1215

Lys Ala Val Leu Phe Ala Thr Ala Gly Val Glu Arg Asp Leu Asn

```
               1220              1225              1230
Gly Arg Asp Tyr Thr Val Thr Gly Gly Phe Thr Gly Ala Thr Ala
        1235              1240              1245

Ala Thr Gly Lys Thr Gly Ala Arg Asn Met Pro His Thr Arg Leu
1250              1255              1260

Val Ala Gly Leu Gly Ala Asp Val Glu Phe Gly Asn Gly Trp Asn
        1265              1270              1275

Gly Leu Ala Arg Tyr Ser Tyr Ala Gly Ser Lys Gln Tyr Gly Asn
        1280              1285              1290

His Ser Gly Arg Val Gly Val Gly Tyr Arg Phe Leu Glu His His
        1295              1300              1305

His His His His
        1310

<210> SEQ ID NO 33
<211> LENGTH: 2028
<212> TYPE: DNA
<213> ORGANISM: Artificial
<220> FEATURE:
<223> OTHER INFORMATION: deletion G741-ORF46.1

<400> SEQUENCE: 33
atggtcgccg ccgacatcgg tgcggggctt gccgatgcac taaccgcacc gctcgaccat    60
aaagacaaag gtttgcagtc tttgacgctg gatcagtccg tcaggaaaaa cgagaaactg   120
aagctggcgg cacaaggtgc ggaaaaaact tatggaaacg gtgacagcct caatacgggc   180
aaattgaaga acgacaaggt cagccgtttc gactttatcc gccaaatcga agtgacgggg   240
cagctcatta ccttggagag tggagagttc aagtataca aacaaagcca ttccgcctta   300
accgcctttc agaccgagca aatacaagat tcggagcatt ccgggaagat ggttgcgaaa   360
cgccagttca gaatcggcga catagcgggc gaacatacat cttttgacaa gcttcccgaa   420
ggcggcaggg cgacatatcg cgggacgcg ttcggttcag acgatgccgg cggaaaactg   480
acctacacca tagatttcgc cgccaagcag ggaaacggca aaatcgaaca tttgaaatcg   540
ccagaactca atgtcgacct ggccgccgcc gatatcaagc cggatggaaa acgccatgcc   600
gtcatcagcg gttccgtcct ttacaaccaa gccgagaaag gcagttactc cctcggtatc   660
tttggcggaa aagcccagga agttgccggc agcgcgaaag tgaaaaccgt aaacggcata   720
cgccatatcg gccttgccgc caagcaactc gacggtggcg gaggcactgg atcctcagat   780
ttggcaaacg attcttttat ccggcaggtt ctcgaccgtc agcatttcga acccgacggg   840
aaataccacc tattcggcag cagggggga cttgccgagc gcagcggcca tatcggattg   900
ggaaaaatac aaagccatca gttgggcaac ctgatgattc aacaggcggc cattaaagga   960
atatcggct acattgtccg cttttccgat cacgggcacg aagtccattc ccccttcgac  1020
aaccatgcct cacattccga ttctgatgaa gccggtagtc ccgttgacgg atttagcctt  1080
taccgcatcc attgggacgg atacgaacac catcccgccg acggctatga cgggccacag  1140
ggcggcggct atcccgctcc caaaggcgcg aggatatat acagctacga cataaaaggc  1200
gttgcccaaa atatccgcct caacctgacc gacaaccgca gcaccggaca acggcttgcc  1260
gaccgttttcc acaatgccgg tagtatgctg acgcaaggag taggcgacgg attcaaacgc  1320
gccacccgat acagccccga gctggacaga tcgggcaatg ccgccgaagc cttcaacggc  1380
actgcagata tcgttaaaaa catcatcggc gcggcaggag aaattgtcgg cgcaggcgat  1440
gccgtgcagg gcataagcga aggctcaaac attgctgtca tgcacggctt gggtctgctt  1500
```

```
tccaccgaaa acaagatggc gcgcatcaac gatttggcag atatggcgca actcaaagac    1560
tatgccgcag cagccatccg cgattgggca gtccaaaacc ccaatgccgc acaaggcata    1620
gaagccgtca gcaatatctt tatggcagcc atccccatca aagggattgg agctgttcgg    1680
ggaaaatacg gcttgggcgg catcacggca catcctatca gcggtcgca gatgggcgcg     1740 atcgcattgc cgaaagggaa atccgccgtc agcgacaatt ttgccgatgc ggcatacgcc    1800 aaataccgt ccccttacca ttcccgaaat atccgttcaa acttggagca gcgttacggc     1860
aaagaaaaca tcacctcctc aaccgtgccg ccgtcaaacg gcaaaaatgt caaactggca    1920
gaccaacgcc acccgaagac aggcgtaccg tttgacggta aagggtttcc gaattttgag    1980
aagcacgtga aatatgatac gctcgagcac caccaccacc accactga                2028
```

<210> SEQ ID NO 34
<211> LENGTH: 675
<212> TYPE: PRT
<213> ORGANISM: Artificial
<220> FEATURE:
<223> OTHER INFORMATION: deletion G741-ORF46.1

<400> SEQUENCE: 34

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Asp Gly Gly Gly Thr
                245                 250                 255

Gly Ser Ser Asp Leu Ala Asn Asp Ser Phe Ile Arg Gln Val Leu Asp
            260                 265                 270
```

```
Arg Gln His Phe Glu Pro Asp Gly Lys Tyr His Leu Phe Gly Ser Arg
        275                 280                 285

Gly Glu Leu Ala Glu Arg Ser Gly His Ile Gly Leu Gly Lys Ile Gln
290                 295                 300

Ser His Gln Leu Gly Asn Leu Met Ile Gln Gln Ala Ala Ile Lys Gly
305                 310                 315                 320

Asn Ile Gly Tyr Ile Val Arg Phe Ser Asp His Gly His Glu Val His
                325                 330                 335

Ser Pro Phe Asp Asn His Ala Ser His Ser Asp Ser Asp Glu Ala Gly
                340                 345                 350

Ser Pro Val Asp Gly Phe Ser Leu Tyr Arg Ile His Trp Asp Gly Tyr
                355                 360                 365

Glu His His Pro Ala Asp Gly Tyr Asp Gly Pro Gln Gly Gly Gly Tyr
            370                 375                 380

Pro Ala Pro Lys Gly Ala Arg Asp Ile Tyr Ser Tyr Asp Ile Lys Gly
385                 390                 395                 400

Val Ala Gln Asn Ile Arg Leu Asn Leu Thr Asp Asn Arg Ser Thr Gly
                405                 410                 415

Gln Arg Leu Ala Asp Arg Phe His Asn Ala Gly Ser Met Leu Thr Gln
            420                 425                 430

Gly Val Gly Asp Gly Phe Lys Arg Ala Thr Arg Tyr Ser Pro Glu Leu
        435                 440                 445

Asp Arg Ser Gly Asn Ala Ala Glu Ala Phe Asn Gly Thr Ala Asp Ile
450                 455                 460

Val Lys Asn Ile Ile Gly Ala Ala Gly Glu Ile Val Gly Ala Gly Asp
465                 470                 475                 480

Ala Val Gln Gly Ile Ser Glu Gly Ser Asn Ile Ala Val Met His Gly
                485                 490                 495

Leu Gly Leu Leu Ser Thr Glu Asn Lys Met Ala Arg Ile Asn Asp Leu
                500                 505                 510

Ala Asp Met Ala Gln Leu Lys Asp Tyr Ala Ala Ala Ile Arg Asp
            515                 520                 525

Trp Ala Val Gln Asn Pro Asn Ala Ala Gln Gly Ile Glu Ala Val Ser
        530                 535                 540

Asn Ile Phe Met Ala Ala Ile Pro Ile Lys Gly Ile Gly Ala Val Arg
545                 550                 555                 560

Gly Lys Tyr Gly Leu Gly Gly Ile Thr Ala His Pro Ile Lys Arg Ser
                565                 570                 575

Gln Met Gly Ala Ile Ala Leu Pro Lys Gly Lys Ser Ala Val Ser Asp
            580                 585                 590

Asn Phe Ala Asp Ala Ala Tyr Ala Lys Tyr Pro Ser Pro Tyr His Ser
            595                 600                 605

Arg Asn Ile Arg Ser Asn Leu Glu Gln Arg Tyr Gly Lys Glu Asn Ile
610                 615                 620

Thr Ser Ser Thr Val Pro Pro Ser Asn Gly Lys Asn Val Lys Leu Ala
625                 630                 635                 640

Asp Gln Arg His Pro Lys Thr Gly Val Pro Phe Asp Gly Lys Gly Phe
            645                 650                 655

Pro Asn Phe Glu Lys His Val Lys Tyr Asp Thr Leu Glu His His His
            660                 665                 670

His His His
    675
```

<210> SEQ ID NO 35
<211> LENGTH: 2019
<212> TYPE: DNA
<213> ORGANISM: Artificial
<220> FEATURE:
<223> OTHER INFORMATION: ORF46.1-741

<400> SEQUENCE: 35

```
atgtcagatt tggcaaacga ttctttatc cggcaggttc tcgaccgtca gcatttcgaa      60
cccgacggga ataccacct attcggcagc agggggaac ttgccgagcg cagcggccat     120
atcggattgg gaaaatacaa aagccatcag ttgggcaacc tgatgattca acaggcggcc     180
attaaaggaa atatcggcta cattgtccgc ttttccgatc acgggcacga agtccattcc     240
cccttcgaca accatgcctc acattccgat tctgatgaag ccggtagtcc cgttgacgga     300
tttagccttt accgcatcca ttgggacgga tacgaacacc atcccgccga cggctatgac     360
gggccacagg gcggcggcta tcccgctccc aaaggcgcga gggatatata cagctacgac     420
ataaaaggcg ttgcccaaaa tatccgcctc aacctgaccg acaaccgcag caccggacaa     480
cggcttgccg accgttttcca caatgccggt agtatgctga cgcaaggagt aggcgacgga     540
ttcaaacgcg ccacccgata cagccccgag ctggacagat cgggcaatgc cgccgaagcc     600
ttcaacggca ctgcagatat cgttaaaaac atcatcggcg cggcaggaga aattgtcggc     660
gcaggcgatg ccgtgcaggg cataagcgaa ggctcaaaca ttgctgtcat gcacggcttg     720
ggtctgcttt ccaccgaaaa caagatggcg cgcatcaacg atttggcaga tatggcgcaa     780
ctcaaagact atgccgcagc agccatccgc gattgggcag tccaaaaccc caatgccgca     840
caaggcatag aagccgtcag caatatcttt atggcagcca tccccatcaa agggattgga     900
gctgttcggg gaaaatacgg cttggccggc atcacgcac atcctatcaa gcggtcgcag     960
atgggcgcga tcgcattgcc gaaagggaaa tccgccgtca gcgacaattt tgccgatgcg    1020
gcatacgcca ataccccgtc cccttaccat tcccgaaata tccgttcaaa cttggagcag    1080
cgttacggca agaaaacat cacctcctca accgtgccgc cgtcaaacgg caaaaatgtc    1140
aaactggcag accaacgcca cccgaagaca ggcgtaccgt ttgacggtaa agggtttccg    1200
aatttttgaga agcacgtgaa atatgatacg ggatccggag ggggtggtgt cgccgccgac    1260
atcggtgcgg ggcttgccga tgcactaacc gcaccgctcg accataaaga caaaggtttg    1320
cagtctttga cgctggatca gtccgtcagg aaaaacgaga aactgaagct ggcggcacaa    1380
ggtgcggaaa aaacttatgg aaacggtgac agcctcaata cggcaaatt gaagaacgac    1440
aaggtcagcc gtttcgactt tatccgccaa atcgaagtgg acgggcagct cattaccttg    1500
gagagtggag agttccaagt atacaaacaa agccattccg ccttaaccgc ctttcagacc    1560
gagcaaatac aagattcgga gcattccggg aagatggttg cgaaacgcca gttcagaatc    1620
ggcgacatag cgggcgaaca tacatctttt gacaagcttc ccgaaggcgg cagggcgaca    1680
tatcgcggga cggcgttcgg ttcagacgat gccggcggaa aactgaccta caccatagat    1740
ttcgccgcca agcagggaaa cggcaaaatc gaacatttga atcgccaga actcaatgtc    1800
gacctggccg ccgccgatat caagccggat ggaaaacgcc atgccgtcat cagcggttcc    1860
gtccttaca accaagccga aaaggcagt tactccctcg gtatctttgg cggaaaagcc    1920
caggaagttg ccggcagcgc ggaagtgaaa accgtaaacg gcatacgcca tatcggcctt    1980
gccgccaagc aactcgagca ccaccaccac caccactga                           2019
```

<210> SEQ ID NO 36
<211> LENGTH: 672
<212> TYPE: PRT
<213> ORGANISM: Artificial
<220> FEATURE:
<223> OTHER INFORMATION: ORF46.1-741

<400> SEQUENCE: 36

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
```

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
            405                 410                 415

Val Ala Ala Asp Ile Gly Ala Gly Leu Ala Asp Ala Leu Thr Ala Pro
                420                 425                 430

Leu Asp His Lys Asp Lys Gly Leu Gln Ser Leu Thr Leu Asp Gln Ser
            435                 440                 445

Val Arg Lys Asn Glu Lys Leu Lys Leu Ala Ala Gln Gly Ala Glu Lys
        450                 455                 460

Thr Tyr Gly Asn Gly Asp Ser Leu Asn Thr Gly Lys Leu Lys Asn Asp
465                 470                 475                 480

Lys Val Ser Arg Phe Asp Phe Ile Arg Gln Ile Glu Val Asp Gly Gln
                485                 490                 495

Leu Ile Thr Leu Glu Ser Gly Glu Phe Gln Val Tyr Lys Gln Ser His
            500                 505                 510

Ser Ala Leu Thr Ala Phe Gln Thr Glu Gln Ile Gln Asp Ser Glu His
            515                 520                 525

Ser Gly Lys Met Val Ala Lys Arg Gln Phe Arg Ile Gly Asp Ile Ala
            530                 535                 540

Gly Glu His Thr Ser Phe Asp Lys Leu Pro Glu Gly Gly Arg Ala Thr
545                 550                 555                 560

Tyr Arg Gly Thr Ala Phe Gly Ser Asp Ala Gly Gly Lys Leu Thr
                565                 570                 575

Tyr Thr Ile Asp Phe Ala Ala Lys Gln Gly Asn Gly Lys Ile Glu His
            580                 585                 590

Leu Lys Ser Pro Glu Leu Asn Val Asp Leu Ala Ala Asp Ile Lys
            595                 600                 605

Pro Asp Gly Lys Arg His Ala Val Ile Ser Gly Ser Val Leu Tyr Asn
610                 615                 620

Gln Ala Glu Lys Gly Ser Tyr Ser Leu Gly Ile Phe Gly Gly Lys Ala
625                 630                 635                 640

Gln Glu Val Ala Gly Ser Ala Glu Val Lys Thr Val Asn Gly Ile Arg
                645                 650                 655

His Ile Gly Leu Ala Ala Lys Gln Leu Glu His His His His
            660                 665                 670

<210> SEQ ID NO 37
<211> LENGTH: 2421
<212> TYPE: DNA
<213> ORGANISM: Artificial
<220> FEATURE:
<223> OTHER INFORMATION: ORF46.1-961

<400> SEQUENCE: 37
atgtcagatt tggcaaacga ttctttatc cggcaggttc tcgaccgtca gcatttcgaa      60
cccgacggga ataccaccct attcggcagc agggggaac ttgccgagcg cagcggccat     120
atcggattgg gaaaaataca aagccatcag ttgggcaacc tgatgattca acaggcggcc    180 attaaggaa atatcggcta cattgtccgc ttttccgatc acgggcacga agtccattcc     240
cccttcgaca accatgcctc acattccgat tctgatgaag ccggtagtcc cgttgacgga    300
tttagccttt accgcatcca ttgggacgga tacgaacacc atcccgccga cggctatgac    360
gggccacagg gcggcggcta tcccgctccc aaaggcgcga gggatatata cagctacgac    420

```
ataaaaggcg ttgcccaaaa tatccgcctc aacctgaccg acaaccgcag caccggacaa    480
cggcttgccg accgtttcca caatgccggt agtatgctga cgcaaggagt aggcgacgga    540
ttcaaacgcg ccacccgata cagccccgag ctggacagat cgggcaatgc cgccgaagcc    600
ttcaacggca ctgcagatat cgttaaaaac atcatcggcg cggcaggaga aattgtcggc    660
gcaggcgatg ccgtgcaggg cataagcgaa ggctcaaaca ttgctgtcat gcacggcttg    720
ggtctgcttt ccaccgaaaa caagatggcg cgcatcaacg atttggcaga tatggcgcaa    780
ctcaaagact atgccgcagc agccatccgc gattgggcag tccaaaaccc caatgccgca    840
caaggcatag aagccgtcag caatatcttt atggcagcca tccccatcaa agggattgga    900
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca ataccccgtc cccttaccat tcccgaaata tccgttcaaa cttggagcag   1080
cgttacggca aagaaaacat cacctcctca accgtgccgc cgtcaaacgg caaaaatgtc   1140
aaactggcag accaacgcca cccgaagaca ggcgtaccgt ttgacggtaa agggtttccg   1200
aattttgaga agcacgtgaa atatgatacg ggatccggag gaggaggagc cacaaacgac   1260
gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca acaaaacgt cgatgccaaa    1500 gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaaccgccaa tgaagccaaa   1800
cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aaacagtgtc agacctgcgc   2160
aaagaaaccc gccaaggcct tgcagaacaa gccgcgctct ccggtctgtt ccaaccttac   2220
aacgtgggtc ggttcaatgt aacggctgca gtcggcggct acaaatccga atcggcagtc   2280
gccatcggta ccggcttccg ctttaccgaa aactttgccg ccaaagcagg cgtggcagtc   2340
ggcacttcgt ccggttcttc cgcagcctac catgtcggcg tcaattacga gtggctcgag   2400
caccaccacc accaccactg a                                             2421
```

<210> SEQ ID NO 38
<211> LENGTH: 806
<212> TYPE: PRT
<213> ORGANISM: Artificial
<220> FEATURE:
<223> OTHER INFORMATION: ORF46.1-961

<400> SEQUENCE: 38

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
                20                  25                  30

Glu Leu Ala Glu Arg Ser Gly His Ile Gly Leu Gly Lys Ile Gln Ser
            35                  40                  45

His Gln Leu Gly Asn Leu Met Ile Gln Gln Ala Ala Ile Lys Gly Asn
        50                  55                  60

Ile Gly Tyr Ile Val Arg Phe Ser Asp His His Glu Val His Ser
65                      70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Asp Val Lys Lys Ala Ala Thr Val Ala Ile Ala
```

```
                    420                 425                 430
Ala Ala Tyr Asn Asn Gly Gln Glu Ile Asn Gly Phe Lys Ala Gly Glu
            435                 440                 445

Thr Ile Tyr Asp Ile Asp Glu Asp Gly Thr Ile Thr Lys Lys Asp Ala
450                 455                 460

Thr Ala Ala Asp Val Glu Ala Asp Phe Lys Gly Leu Gly Leu Lys
465                 470                 475                 480

Lys Val Val Thr Asn Leu Thr Lys Thr Val Asn Glu Asn Lys Gln Asn
            485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
            515                 520                 525

Leu Asp Ala Thr Thr Asn Ala Leu Asn Lys Leu Gly Glu Asn Ile Thr
            530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
            565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln
            595                 600                 605

Asn Val Asp Ala Lys Val Lys Ala Ala Glu Thr Ala Ala Gly Lys Ala
            610                 615                 620

Glu Ala Ala Ala Gly Thr Ala Asn Thr Ala Ala Asp Lys Ala Glu Ala
625                 630                 635                 640

Val Ala Ala Lys Val Thr Asp Ile Lys Ala Asp Ile Ala Thr Asn Lys
            645                 650                 655

Asp Asn Ile Ala Lys Lys Ala Asn Ser Ala Asp Val Tyr Thr Arg Glu
            660                 665                 670

Glu Ser Asp Ser Lys Phe Val Arg Ile Asp Gly Leu Asn Ala Thr Thr
            675                 680                 685

Glu Lys Leu Asp Thr Arg Leu Ala Ser Ala Glu Lys Ser Ile Ala Asp
            690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
            725                 730                 735

Phe Gln Pro Tyr Asn Val Gly Arg Phe Asn Val Thr Ala Ala Val Gly
            740                 745                 750

Gly Tyr Lys Ser Glu Ser Ala Val Ala Ile Gly Thr Gly Phe Arg Phe
            755                 760                 765

Thr Glu Asn Phe Ala Ala Lys Ala Gly Val Ala Val Gly Thr Ser Ser
            770                 775                 780

Gly Ser Ser Ala Ala Tyr His Val Gly Val Asn Tyr Glu Trp Leu Glu
785                 790                 795                 800

His His His His His His
            805

<210> SEQ ID NO 39
<211> LENGTH: 2256
<212> TYPE: DNA
<213> ORGANISM: Artificial
```

<220> FEATURE:
<223> OTHER INFORMATION: ORF-46.1-961c

<400> SEQUENCE: 39

```
atgtcagatt tggcaaacga ttcttttatc cggcaggttc tcgaccgtca gcatttcgaa      60
cccgacggga ataccacct attcggcagc aggggggaac ttgccgagcg cagcggccat      120
atcggattgg gaaaaataca aagccatcag ttgggcaacc tgatgattca acaggcggcc      180
attaaaggaa atatcggcta cattgtccgc ttttccgatc acgggcacga agtccattcc      240
cccttcgaca accatgcctc acattccgat tctgatgaag ccggtagtcc cgttgacgga      300
tttagccttt accgcatcca ttgggacgga tacgaacacc atcccgccga cggctatgac      360
gggccacagg gcggcggcta tcccgctccc aaaggcgcga gggatatata cagctacgac      420
ataaaaggcg ttgcccaaaa tatccgcctc aacctgaccg acaaccgcag caccggacaa      480
cggcttgccg accgtttcca caatgccggt agtatgctga cgcaaggagt aggcgacgga      540
ttcaaacgcg ccacccgata cagccccgag ctggacagat cggcaatgc cgccgaagcc      600
ttcaacggca ctgcagatat cgttaaaaac atcatcggcg cggcaggaga attgtcggc      660
gcaggcgatg ccgtgcaggg cataagcgaa ggctcaaaca ttgctgtcat gcacggcttg      720
ggtctgcttt ccaccgaaaa caagatggcg cgcatcaacg atttggcaga tatggcgcaa      780
ctcaaagact atgccgcagc agccatccgc gattgggcag tccaaaaccc caatgccgca      840
caaggcatag aagccgtcag caatatcttt atggcagcca tccccatcaa agggattgga      900
gctgttcggg gaaaatacgg cttgggcggc atcacggcac atcctatcaa gcggtcgcag      960
atgggcgcga tcgcattgcc gaaagggaaa tccgccgtca gcgacaattt tgccgatgcg     1020
gcatacgcca aataccccgtc cccttaccat tcccgaaata tccgttcaaa cttggagcag     1080
cgttacggca agaaaacat cacctcctca accgtgccgc cgtcaaacgg caaaaatgtc     1140
aaactggcag accaacgcca cccgaagaca ggcgtaccgt ttgacggtaa aggggtttccg    1200
aattttgaga agcacgtgaa atatgatacg ggatccggag gaggaggagc cacaaacgac    1260
gacgatgtta aaaagctgc cactgtggcc attgctgctg cctacaacaa tggccaagaa    1320
atcaacggtt tcaaagctgg agagaccatc tacgacattg atgaagacgg cacaattacc    1380
aaaaaagacg caactgcagc cgatgttgaa gccgacgact ttaaaggtct gggtctgaaa    1440
aaagtcgtga ctaacctgac caaaaccgtc aatgaaaaca acaaaacgt cgatgccaaa    1500
gtaaaagctg cagaatctga aatagaaaag ttaacaacca agttagcaga cactgatgcc    1560
gctttagcag atactgatgc cgctctggat gcaaccacca acgccttgaa taaattggga    1620
gaaaatataa cgacatttgc tgaagagact aagacaaata tcgtaaaaat tgatgaaaaa    1680
ttagaagccg tggctgatac cgtcgacaag catgccgaag cattcaacga tatcgccgat    1740
tcattggatg aaaccaacac taaggcagac gaagccgtca aaaccgccaa tgaagccaaa    1800
cagacggccg aagaaccaa acaaaacgtc gatgccaaag taaaagctgc agaaactgca    1860
gcaggcaaag ccgaagctgc cgctggcaca gctaatactg cagccgacaa ggccgaagct    1920
gtcgctgcaa aagttaccga catcaaagct gatatcgcta cgaacaaaga taatattgct    1980
aaaaaagcaa acagtgccga cgtgtacacc agagaagagt ctgacagcaa atttgtcaga    2040
attgatggtc tgaacgctac taccgaaaaa ttggacacac gcttggcttc tgctgaaaaa    2100
tccattgccg atcacgatac tcgcctgaac ggttttggata aacagtgtc agacctgcgc    2160
aaagaaaccc gccaaggcct tgcagaacaa gccgcgctct ccggtctgtt ccaaccttac    2220
```

```
aacgtgggtc tcgagcacca ccaccaccac cactga                              2256
```

<210> SEQ ID NO 40
<211> LENGTH: 751
<212> TYPE: PRT
<213> ORGANISM: Artificial
<220> FEATURE:
<223> OTHER INFORMATION: ORF46.1-961c

<400> SEQUENCE: 40

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Tyr Pro
        115                 120                 125

Ala Pro Lys Gly Ala Arg Asp Ile Tyr Ser Tyr Asp Ile Lys Gly Val
130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
```

```
            355                 360                 365
Ser Ser Thr Val Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Val Lys Lys Ala Thr Val Ala Ile Ala
            420                 425                 430

Ala Ala Tyr Asn Asn Gly Gln Glu Ile Asn Gly Phe Lys Ala Gly Glu
            435                 440                 445

Thr Ile Tyr Asp Ile Asp Glu Asp Gly Thr Ile Thr Lys Lys Asp Ala
            450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
                485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
            515                 520                 525

Leu Asp Ala Thr Thr Asn Ala Leu Asn Lys Leu Gly Glu Asn Ile Thr
            530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
                565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln
            595                 600                 605

Asn Val Asp Ala Lys Val Lys Ala Ala Glu Thr Ala Ala Gly Lys Ala
            610                 615                 620

Glu Ala Ala Ala Gly Thr Ala Asn Thr Ala Ala Asp Lys Ala Glu Ala
625                 630                 635                 640

Val Ala Ala Lys Val Thr Asp Ile Lys Ala Asp Ile Ala Thr Asn Lys
                645                 650                 655

Asp Asn Ile Ala Lys Lys Ala Asn Ser Ala Asp Val Tyr Thr Arg Glu
            660                 665                 670

Glu Ser Asp Ser Lys Phe Val Arg Ile Asp Gly Leu Asn Ala Thr Thr
            675                 680                 685

Glu Lys Leu Asp Thr Arg Leu Ala Ser Ala Glu Lys Ser Ile Ala Asp
            690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
                725                 730                 735

Phe Gln Pro Tyr Asn Val Gly Leu Glu His His His His His His
            740                 745                 750

<210> SEQ ID NO 41
<211> LENGTH: 2421
<212> TYPE: DNA
<213> ORGANISM: Artificial
```

<220> FEATURE:
<223> OTHER INFORMATION: 961-ORF46.1

<400> SEQUENCE: 41

```
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aaacaaacaa     240
aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat tgggagaaaa tataacgaca tttgctgaag agactaagac aaatatcgta     420
aaaattgatg aaaaattaga agccgtggct gataccgtcg acaagcatgc cgaagcattc     480
aacgatatcg ccgattcatt ggatgaaacc aacactaagg cagacgaagc cgtcaaaacc     540
gccaatgaag ccaaacagac ggccgaagaa accaaacaaa acgtcgatgc caaagtaaaa     600
gctgcagaaa ctgcagcagg caaagccgaa gctgccgctg cacagctaa tactgcagcc     660
gacaaggccg aagctgtcgc tgcaaaagtt accgacatca agctgatat cgctacgaac     720
aaagataata ttgctaaaaa agcaaacagt gccgacgtgt acaccagaga agagtctgac     780
agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag aacaagccgc gctctccggt     960
ctgttccaac cttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggagg aggaggatca gatttggcaa acgattcttt tatccggcag    1200
gttctcgacc gtcagcattt cgaacccgac gggaaatacc acctattcgg cagcagggg    1260
gaacttgccg agcgcagcgg ccatatcgga ttgggaaaaa tacaaagcca tcagttgggc    1320
aacctgatga ttcaacaggc ggccattaaa ggaaatatcg gctacattgt ccgcttttcc    1380
gatcacgggc acgaagtcca ttcccccttc gacaaccatg cctcacattc cgattctgat    1440
gaagccggta gtcccgttga cggatttagc ctttaccgca tccattggga cggatacgaa    1500
caccatcccg ccgacggcta tgacgggcca cagggcggcg gctatccgc tcccaaaggc    1560
gcgagggata tatacagcta cgacataaaa ggcgttgccc aaaatatccg cctcaacctg    1620
accgacaacc gcagcaccgg acaacggctt gccgaccgtt tccacaatgc cggtagtatg    1680
ctgacgcaag gagtaggcga cggattcaaa cgcgccaccc gatacagccc cgagctggac    1740
agatcgggca atgccgccga agccttcaac ggcactgcag atatcgttaa aaacatcatc    1800
ggcgcggcag gagaaattgt cggcgcaggc gatgccgtgc agggcataag cgaaggctca    1860
aacattgctg tcatgcacgg cttgggtctg ctttccaccg aaaacaagat ggcgcgcatc    1920
aacgatttgg cagatatggc gcaactcaaa gactatgccg cagcagccat ccgcgattgg    1980
gcagtccaaa accccaatgc cgcacaaggc atagaagccg tcagcaatat ctttatggca    2040
gccatcccca tcaagggat tggagctgtt cggggaaaat acggcttggg cggcatcacg    2100
gcacatccta tcaagcggtc gcagatggc gcgatcgcat tgccgaaagg gaaatccgcc    2160
gtcagcgaca attttgccga tgcggcatac gccaaatacc cgtcccctta ccattcccga    2220
```

```
aatatccgtt caaacttgga gcagcgttac ggcaaagaaa acatcaccctc ctcaaccgtg     2280 ccgccgtcaa acggcaaaaa tgtcaaactg gcagaccaac gccacccgaa gacaggcgta     2340
ccgtttgacg gtaaagggtt tccgaatttt gagaagcacg tgaaatatga tacgctcgag     2400
caccaccacc accaccactg a                                               2421
```

<210> SEQ ID NO 42
<211> LENGTH: 806
<212> TYPE: PRT
<213> ORGANISM: Artificial
<220> FEATURE:
<223> OTHER INFORMATION: 961-ORF46.1

<400> SEQUENCE: 42

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
```

-continued

```
                325                 330                 335
Gly Gly Tyr Lys Ser Glu Ser Ala Val Ala Ile Gly Thr Gly Phe Arg
                340                 345                 350
Phe Thr Glu Asn Phe Ala Ala Lys Ala Gly Val Ala Val Gly Thr Ser
                355                 360                 365
Ser Gly Ser Ser Ala Ala Tyr His Val Gly Val Asn Tyr Glu Trp Gly
                370                 375                 380
Ser Gly Gly Gly Ser Asp Leu Ala Asn Asp Ser Phe Ile Arg Gln
385                 390                 395                 400
Val Leu Asp Arg Gln His Phe Glu Pro Asp Gly Lys Tyr His Leu Phe
                405                 410                 415
Gly Ser Arg Gly Glu Leu Ala Glu Arg Ser Gly His Ile Gly Leu Gly
                420                 425                 430
Lys Ile Gln Ser His Gln Leu Gly Asn Leu Met Ile Gln Gln Ala Ala
                435                 440                 445
Ile Lys Gly Asn Ile Gly Tyr Ile Val Arg Phe Ser Asp His Gly His
                450                 455                 460
Glu Val His Ser Pro Phe Asp Asn His Ala Ser His Ser Asp Ser Asp
465                 470                 475                 480
Glu Ala Gly Ser Pro Val Asp Gly Phe Ser Leu Tyr Arg Ile His Trp
                485                 490                 495
Asp Gly Tyr Glu His His Pro Ala Asp Gly Tyr Asp Gly Pro Gln Gly
                500                 505                 510
Gly Gly Tyr Pro Ala Pro Lys Gly Ala Arg Asp Ile Tyr Ser Tyr Asp
                515                 520                 525
Ile Lys Gly Val Ala Gln Asn Ile Arg Leu Asn Leu Thr Asp Asn Arg
                530                 535                 540
Ser Thr Gly Gln Arg Leu Ala Asp Arg Phe His Asn Ala Gly Ser Met
545                 550                 555                 560
Leu Thr Gln Gly Val Gly Asp Gly Phe Lys Arg Ala Thr Arg Tyr Ser
                565                 570                 575
Pro Glu Leu Asp Arg Ser Gly Asn Ala Ala Glu Ala Phe Asn Gly Thr
                580                 585                 590
Ala Asp Ile Val Lys Asn Ile Ile Gly Ala Ala Gly Glu Ile Val Gly
                595                 600                 605
Ala Gly Asp Ala Val Gln Gly Ile Ser Glu Gly Ser Asn Ile Ala Val
                610                 615                 620
Met His Gly Leu Gly Leu Leu Ser Thr Glu Asn Lys Met Ala Arg Ile
625                 630                 635                 640
Asn Asp Leu Ala Asp Met Ala Gln Leu Lys Asp Tyr Ala Ala Ala Ala
                645                 650                 655
Ile Arg Asp Trp Ala Val Gln Asn Pro Asn Ala Ala Gln Gly Ile Glu
                660                 665                 670
Ala Val Ser Asn Ile Phe Met Ala Ala Ile Pro Ile Lys Gly Ile Gly
                675                 680                 685
Ala Val Arg Gly Lys Tyr Gly Leu Gly Gly Ile Thr Ala His Pro Ile
                690                 695                 700
Lys Arg Ser Gln Met Gly Ala Ile Ala Leu Pro Lys Gly Lys Ser Ala
705                 710                 715                 720
Val Ser Asp Asn Phe Ala Asp Ala Ala Tyr Ala Lys Tyr Pro Ser Pro
                725                 730                 735
Tyr His Ser Arg Asn Ile Arg Ser Asn Leu Glu Gln Arg Tyr Gly Lys
                740                 745                 750
```

```
Glu Asn Ile Thr Ser Ser Thr Val Pro Pro Ser Asn Gly Lys Asn Val
        755                 760                 765

Lys Leu Ala Asp Gln Arg His Pro Lys Thr Gly Val Pro Phe Asp Gly
    770                 775                 780

Lys Gly Phe Pro Asn Phe Glu Lys His Val Lys Tyr Asp Thr Leu Glu
785                 790                 795                 800

His His His His His His
            805

<210> SEQ ID NO 43
<211> LENGTH: 1938
<212> TYPE: DNA
<213> ORGANISM: Artificial
<220> FEATURE:
<223> OTHER INFORMATION: 961-741

<400> SEQUENCE: 43
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa     240
aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat gggagaaaaa tataacgaca tttgctgaag agactaagac aaatatcgta     420
aaaattgatg aaaaattaga gccgtggct gataccgtcg acaagcatgc cgaagcattc     480
aacgatatcg ccgattcatt ggatgaaacc aacactaagg cagacgaagc cgtcaaaacc     540
gccaatgaag ccaaacagac ggccgaagaa accaaacaaa acgtcgatgc caaagtaaaa     600
gctgcagaaa ctgcagcagg caaagccgaa gctgccgctg gcacagctaa tactgcagcc     660
gacaaggccg aagctgtcgc tgcaaaagtt accgacatca agctgatat cgctacgaac     720
aaagataata ttgctaaaaa agcaaacagt gccgacgtgt acaccagaga agagtctgac     780
agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag aacaagccgc gctctccggt     960
ctgttccaac ttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggagg gggtggtgtc gccgccgaca tcggtgcggg gcttgccgat    1200
gcactaaccg caccgctcga ccataaagac aaaggtttgc agtctttgac gctggatcag    1260
tccgtcagga aaacgagaa actgaagctg cggcacaag gtgcggaaaa aacttatgga    1320
aacggtgaca gcctcaatac gggcaaattg aagaacgaca aggtcagccg tttcgacttt    1380
atccgccaaa tcgaagtgga cgggcagctc attaccttgg agagtggaga gttccaagta    1440
tacaaacaaa gccattccgc cttaaccgcc tttcagaccg agcaaataca agattcggag    1500
cattccggga agatggttgc gaaacgccag ttcagaatcg gcgacatagc gggcgaacat    1560
acatctttg acaagcttcc cgaaggcggc agggcgacat atcgcgggac ggcgttcggt    1620
tcagacgatg ccggcggaaa actgacctac accatagatt tcgccgccaa gcagggaaac    1680
```

```
ggcaaaatcg aacatttgaa atcgccagaa ctcaatgtcg acctggccgc cgccgatatc      1740
aagccggatg aaaacgcca tgccgtcatc agcggttccg tcctttacaa ccaagccgag      1800
aaaggcagtt actccctcgg tatctttggc ggaaaagccc aggaagttgc cggcagcgcg      1860
gaagtgaaaa ccgtaaacgg catacgccat atcggccttg ccgccaagca actcgagcac      1920
caccaccacc accactga                                                    1938
```

\<210\> SEQ ID NO 44
\<211\> LENGTH: 645
\<212\> TYPE: PRT
\<213\> ORGANISM: Artificial
\<220\> FEATURE:
\<223\> OTHER INFORMATION: 961-741

\<400\> SEQUENCE: 44

```
Met Ala Thr Asn Asp Asp Asp Val Lys Lys Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320
```

```
Leu Phe Gln Pro Tyr Asn Val Gly Arg Phe Asn Val Thr Ala Ala Val
            325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
            355                 360                 365

Ser Gly Ser Ser Ala Ala Tyr His Val Gly Val Asn Tyr Glu Trp Gly
370                 375                 380

Ser Gly Gly Gly Val Ala Ala Asp Ile Gly Ala Gly Leu Ala Asp
385                 390                 395                 400

Ala Leu Thr Ala Pro Leu Asp His Lys Asp Lys Gly Leu Gln Ser Leu
            405                 410                 415

Thr Leu Asp Gln Ser Val Arg Lys Asn Glu Lys Leu Lys Leu Ala Ala
            420                 425                 430

Gln Gly Ala Glu Lys Thr Tyr Gly Asn Gly Asp Ser Leu Asn Thr Gly
            435                 440                 445

Lys Leu Lys Asn Asp Lys Val Ser Arg Phe Asp Phe Ile Arg Gln Ile
    450                 455                 460

Glu Val Asp Gly Gln Leu Ile Thr Leu Glu Ser Gly Glu Phe Gln Val
465                 470                 475                 480

Tyr Lys Gln Ser His Ser Ala Leu Thr Ala Phe Gln Thr Glu Gln Ile
            485                 490                 495

Gln Asp Ser Glu His Ser Gly Lys Met Val Ala Lys Arg Gln Phe Arg
            500                 505                 510

Ile Gly Asp Ile Ala Gly Glu His Thr Ser Phe Asp Lys Leu Pro Glu
            515                 520                 525

Gly Gly Arg Ala Thr Tyr Arg Gly Thr Ala Phe Gly Ser Asp Asp Ala
            530                 535                 540

Gly Gly Lys Leu Thr Tyr Thr Ile Asp Phe Ala Ala Lys Gln Gly Asn
545                 550                 555                 560

Gly Lys Ile Glu His Leu Lys Ser Pro Glu Leu Asn Val Asp Leu Ala
            565                 570                 575

Ala Ala Asp Ile Lys Pro Asp Gly Lys Arg His Ala Val Ile Ser Gly
            580                 585                 590

Ser Val Leu Tyr Asn Gln Ala Glu Lys Gly Ser Tyr Ser Leu Gly Ile
            595                 600                 605

Phe Gly Gly Lys Ala Gln Glu Val Ala Gly Ser Ala Glu Val Lys Thr
            610                 615                 620

Val Asn Gly Ile Arg His Ile Gly Leu Ala Ala Lys Gln Leu Glu His
625                 630                 635                 640

His His His His
            645

<210> SEQ ID NO 45
<211> LENGTH: 4335
<212> TYPE: DNA
<213> ORGANISM: Artificial
<220> FEATURE:
<223> OTHER INFORMATION: 961-983

<400> SEQUENCE: 45
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
```

```
ggtctgggtc tgaaaaaagt cgtgactaac ctgaccaaaa ccgtcaatga aaacaaacaa    240
aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca agctgatatc gctacgaac     720
aaagataata ttgctaaaaa agcaaacagt gccgacgtgt acaccagaga agtctgac      780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtcggttc aatgtaacgg ctgcagtcgg cggctacaaa   1020
tccgaatcgg cagtcgccat cggtaccggc ttccgcttta ccgaaaactt tgccgccaaa   1080
gcaggcgtgg cagtcggcac ttcgtccggt tcttccgcag cctaccatgt cggcgtcaat   1140
tacgagtggg atccggcgg aggcggcact tctgcgcccg acttcaatgc aggcggtacc   1200
ggtatcggca gcaacagcag agcaacaaca gcgaaatcag cagcagtatc ttacgccggt   1260
atcaagaacg aaatgtgcaa agacagaagc atgctctgtg ccggtcggga tgacgttgcg   1320
gttacagaca gggatgccaa aatcaatgcc ccccccccga atctgcatac cggagacttt   1380
ccaaacccaa atgacgcata caagaatttg atcaacctca aacctgcaat tgaagcaggc   1440
tatacaggac gcggggtaga ggtaggtatc gtcgacacag gcgaatccgt cggcagcata   1500
tcctttcccg aactgtatgg cagaaaagaa cacggctata cgaaaattaa caaaaactat   1560
acggcgtata tgcggaagga agcgcctgaa gacggaggcg gtaaagacat tgaagcttct   1620
ttcgacgatg aggccgttat agagactgaa gcaaagccga cggatatccg ccacgtaaaa   1680
gaaatcggac acatcgattt ggtctcccat attattggcg ggcgttccgt ggacggcaga   1740
cctgcaggcg gtattgcgcc cgatgcgacg ctacacataa tgaatacgaa tgatgaaacc   1800
aagaacgaaa tgatggttgc agccatccgc aatgcatggg tcaagctggg cgaacgtggc   1860
gtgcgcatcg tcaataacag ttttggaaca acatcgaggg caggcactgc cgacctttc    1920
caaatagcca attcggagga gcagtaccgc caagcgttgc tcgactattc cggcggtgat   1980
aaaacagacg agggtatccg cctgatgcaa cagagcgatt acggcaacct gtcctaccac   2040
atccgtaata aaaacatgct tttcatcttt tcgacaggca atgacgcaca agctcagccc   2100
aacacatatg ccctattgcc attttatgaa aagacgctc aaaaggcat tatcacagtc     2160
gcaggcgtag accgcagtgg agaaaagttc aaacgggaaa tgtatggaga accgggtaca   2220
gaaccgcttg agtatggctc caaccattgc ggaattactg ccatgtggtg cctgtcggca   2280
ccctatgaag caagcgtccg tttcacccgt acaaacccga ttcaaattgc cggaacatcc   2340
ttttccgcac ccatcgtaac cggcacggcg gctctgctgc tgcagaaata cccgtggatg   2400
agcaacgaca acctgcgtac cacgttgctg acgacggctc aggacatcgg tgcagtcggc   2460
gtggacagca agttcggctg gggactgctg gatgcgggta aggccatgaa cggacccgcg   2520
```

```
tcctttccgt tcggcgactt taccgccgat acgaaaggta catccgatat tgcctactcc    2580
ttccgtaacg acatttcagg cacgggcggc ctgatcaaaa aaggcggcag ccaactgcaa    2640
ctgcacggca acaacaccta tacgggcaaa accattatcg aaggcggttc gctggtgttg    2700
tacggcaaca caaatcgga tatgcgcgtc gaaaccaaag gtgcgctgat ttataacggg    2760
gcggcatccg gcggcagcct gaacagcgac ggcattgtct atctggcaga taccgaccaa    2820
tccggcgcaa acgaaaccgt cacatcaaa ggcagtctgc agctggacgg caaaggtacg    2880
ctgtacacac gtttgggcaa actgctgaaa gtggacggta cggcgattat cggcggcaag    2940
ctgtacatgt cggcacgcgg caaggggca ggctatctca acagtaccgg acgacgtgtt    3000
cccttcctga gtgccgccaa aatcgggcag gattattctt tcttcacaaa catcgaaacc    3060
gacggcggcc tgctggcttc cctcgacagc gtcgaaaaaa cagcgggcag tgaaggcgac    3120
acgctgtcct attatgtccg tcgcggcaat gcggcacgga ctgcttcggc agcggcacat    3180
tccgcgcccg ccgtctgaa acacgccgta gaacagggcg gcagcaatct ggaaaacctg    3240
atggtcgaac tggatgcctc cgaatcatcc gcaacacccg agacggttga aactgcggca    3300
gccgaccgca cagatatgcc gggcatccgc ccctacggcg caactttccg cgcagcggca    3360
gccgtacagc atgcgaatgc cgccgacggt gtacgcatct tcaacagtct cgccgctacc    3420
gtctatgccg acagtaccgc cgcccatgcc gatatgcagg acgccgcct gaaagccgta    3480
tcggacgggt tggaccacaa cggcacgggt ctgcgcgtca tcgcgcaaac ccaacaggac    3540
ggtggaacgt gggaacaggg cggtgttgaa ggcaaaatgc gcggcagtac ccaaaccgtc    3600
ggcattgccg cgaaaaccgg cgaaaatacg acagcagccg ccacactggg catgggacgc    3660
agcacatgga gcgaaaacag tgcaaatgca aaaaccgaca gcattagtct gtttgcaggc    3720
atacggcacg atgcgggcga tatcggctat ctcaaaggcc tgttctccta cggacgctac    3780
aaaaacagca tcagccgcag caccggtgcg gacgaacatg cggaaggcag cgtcaacggc    3840
acgctgatgc agctgggcgc actgggcggt gtcaacgttc cgtttgccgc aacgggagat    3900
ttgacggtcg aaggcggtct gcgctacgac ctgctcaaac aggatgcatt cgccgaaaaa    3960
ggcagtgctt tgggctggag cggcaacagc ctcactgaag gcacgctggt cggactcgcg    4020
ggtctgaagc tgtcgcaacc cttgagcgat aaagccgtcc tgtttgcaac ggcgggcgtg    4080
gaacgcgacc tgaacggacg cgactacacg gtaacgggcg gctttaccgg cgcgactgca    4140
gcaaccggca agacggggc acgcaatatg ccgcacaccc gtctggttgc cggcctgggc    4200
gcggatgtcg aattcggcaa cggctggaac ggcttggcac gttacagcta cgccggttcc    4260
aaacagtacg gcaaccacag cggacgagtc ggcgtaggct accggttcct cgagcaccac    4320
caccaccacc actga                                                    4335
```

<210> SEQ ID NO 46
<211> LENGTH: 1444
<212> TYPE: PRT
<213> ORGANISM: Artificial
<220> FEATURE:
<223> OTHER INFORMATION: 961-983

<400> SEQUENCE: 46

Met Ala Thr Asn Asp Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp

```
                35                  40                  45
Ala Thr Ala Ala Asp Val Glu Ala Asp Phe Lys Gly Leu Gly Leu
 50                  55                  60
Lys Lys Val Val Thr Asn Leu Thr Lys Thr Val Asn Glu Asn Lys Gln
 65                  70                  75                  80
Asn Val Asp Ala Lys Val Lys Ala Ala Glu Ser Glu Ile Glu Lys Leu
                 85                  90                  95
Thr Thr Lys Leu Ala Asp Thr Asp Ala Leu Ala Asp Thr Asp Ala
                100                 105                 110
Ala Leu Asp Ala Thr Thr Asn Ala Leu Asn Lys Leu Gly Glu Asn Ile
            115                 120                 125
Thr Thr Phe Ala Glu Glu Thr Lys Thr Asn Ile Val Lys Ile Asp Glu
        130                 135                 140
Lys Leu Glu Ala Val Ala Asp Thr Val Asp Lys His Ala Glu Ala Phe
145                 150                 155                 160
Asn Asp Ile Ala Asp Ser Leu Asp Glu Thr Asn Thr Lys Ala Asp Glu
                165                 170                 175
Ala Val Lys Thr Ala Asn Glu Ala Lys Gln Thr Ala Glu Glu Thr Lys
            180                 185                 190
Gln Asn Val Asp Ala Lys Val Lys Ala Ala Glu Thr Ala Ala Gly Lys
        195                 200                 205
Ala Glu Ala Ala Ala Gly Thr Ala Asn Thr Ala Ala Asp Lys Ala Glu
210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
            260                 265                 270
Thr Glu Lys Leu Asp Thr Arg Leu Ala Ser Ala Glu Lys Ser Ile Ala
        275                 280                 285
Asp His Asp Thr Arg Leu Asn Gly Leu Asp Lys Thr Val Ser Asp Leu
        290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Arg Phe Asn Val Thr Ala Ala Val
                325                 330                 335
Gly Gly Tyr Lys Ser Glu Ser Ala Val Ala Ile Gly Thr Gly Phe Arg
            340                 345                 350
Phe Thr Glu Asn Phe Ala Ala Lys Ala Gly Val Ala Val Gly Thr Ser
        355                 360                 365
Ser Gly Ser Ser Ala Ala Tyr His Val Gly Val Asn Tyr Glu Trp Gly
        370                 375                 380
Ser Gly Gly Gly Thr Ser Ala Pro Asp Phe Asn Ala Gly Gly Thr
385                 390                 395                 400
Gly Ile Gly Ser Asn Ser Arg Ala Thr Thr Ala Lys Ser Ala Ala Val
                405                 410                 415
Ser Tyr Ala Gly Ile Lys Asn Glu Met Cys Lys Asp Arg Ser Met Leu
            420                 425                 430
Cys Ala Gly Arg Asp Asp Val Ala Val Thr Asp Arg Asp Ala Lys Ile
        435                 440                 445
Asn Ala Pro Pro Pro Asn Leu His Thr Gly Asp Phe Pro Asn Pro Asn
        450                 455                 460
```

```
Asp Ala Tyr Lys Asn Leu Ile Asn Leu Lys Pro Ala Ile Glu Ala Gly
465                 470                 475                 480

Tyr Thr Gly Arg Gly Val Glu Val Gly Ile Val Asp Thr Gly Glu Ser
                485                 490                 495

Val Gly Ser Ile Ser Phe Pro Glu Leu Tyr Gly Arg Lys Glu His Gly
                500                 505                 510

Tyr Asn Glu Asn Tyr Lys Asn Tyr Thr Ala Tyr Met Arg Lys Glu Ala
                515                 520                 525

Pro Glu Asp Gly Gly Lys Asp Ile Glu Ala Ser Phe Asp Asp Glu
530                 535                 540

Ala Val Ile Glu Thr Glu Ala Lys Pro Thr Asp Ile Arg His Val Lys
545                 550                 555                 560

Glu Ile Gly His Ile Asp Leu Val Ser His Ile Ile Gly Gly Arg Ser
                565                 570                 575

Val Asp Gly Arg Pro Ala Gly Gly Ile Ala Pro Asp Ala Thr Leu His
                580                 585                 590

Ile Met Asn Thr Asn Asp Glu Thr Lys Asn Glu Met Met Val Ala Ala
                595                 600                 605

Ile Arg Asn Ala Trp Val Lys Leu Gly Glu Arg Gly Val Arg Ile Val
610                 615                 620

Asn Asn Ser Phe Gly Thr Thr Ser Arg Ala Gly Thr Ala Asp Leu Phe
625                 630                 635                 640

Gln Ile Ala Asn Ser Glu Glu Gln Tyr Arg Gln Ala Leu Leu Asp Tyr
                645                 650                 655

Ser Gly Gly Asp Lys Thr Asp Glu Gly Ile Arg Leu Met Gln Gln Ser
                660                 665                 670

Asp Tyr Gly Asn Leu Ser Tyr His Ile Arg Asn Lys Asn Met Leu Phe
                675                 680                 685

Ile Phe Ser Thr Gly Asn Asp Ala Gln Ala Gln Pro Asn Thr Tyr Ala
                690                 695                 700

Leu Leu Pro Phe Tyr Glu Lys Asp Ala Gln Lys Gly Ile Ile Thr Val
705                 710                 715                 720

Ala Gly Val Asp Arg Ser Gly Glu Lys Phe Lys Arg Glu Met Tyr Gly
                725                 730                 735

Glu Pro Gly Thr Glu Pro Leu Tyr Gly Ser Asn His Cys Gly Ile
                740                 745                 750

Thr Ala Met Trp Cys Leu Ser Ala Pro Tyr Glu Ala Ser Val Arg Phe
                755                 760                 765

Thr Arg Thr Asn Pro Ile Gln Ile Ala Gly Thr Ser Phe Ser Ala Pro
                770                 775                 780

Ile Val Thr Gly Thr Ala Ala Leu Leu Leu Gln Lys Tyr Pro Trp Met
785                 790                 795                 800

Ser Asn Asp Asn Leu Arg Thr Thr Leu Leu Thr Thr Ala Gln Asp Ile
                805                 810                 815

Gly Ala Val Gly Val Asp Ser Lys Phe Gly Trp Gly Leu Leu Asp Ala
                820                 825                 830

Gly Lys Ala Met Asn Gly Pro Ala Ser Phe Pro Phe Gly Asp Phe Thr
                835                 840                 845

Ala Asp Thr Lys Gly Thr Ser Asp Ile Ala Tyr Ser Phe Arg Asn Asp
                850                 855                 860

Ile Ser Gly Thr Gly Gly Leu Ile Lys Lys Gly Gly Ser Gln Leu Gln
865                 870                 875                 880
```

```
Leu His Gly Asn Asn Thr Tyr Thr Gly Lys Thr Ile Ile Glu Gly Gly
            885                 890                 895

Ser Leu Val Leu Tyr Gly Asn Asn Lys Ser Asp Met Arg Val Glu Thr
        900                 905                 910

Lys Gly Ala Leu Ile Tyr Asn Gly Ala Ala Ser Gly Gly Ser Leu Asn
        915                 920                 925

Ser Asp Gly Ile Val Tyr Leu Ala Asp Thr Asp Gln Ser Gly Ala Asn
930                 935                 940

Glu Thr Val His Ile Lys Gly Ser Leu Gln Leu Asp Gly Lys Gly Thr
945                 950                 955                 960

Leu Tyr Thr Arg Leu Gly Lys Leu Leu Lys Val Asp Gly Thr Ala Ile
            965                 970                 975

Ile Gly Gly Lys Leu Tyr Met Ser Ala Arg Gly Lys Gly Ala Gly Tyr
            980                 985                 990

Leu Asn Ser Thr Gly Arg Arg Val Pro Phe Leu Ser Ala Ala Lys Ile
            995                 1000                1005

Gly Gln Asp Tyr Ser Phe Phe Thr Asn Ile Glu Thr Asp Gly Gly
    1010                1015                1020

Leu Leu Ala Ser Leu Asp Ser Val Glu Lys Thr Ala Gly Ser Glu
    1025                1030                1035

Gly Asp Thr Leu Ser Tyr Tyr Val Arg Arg Gly Asn Ala Ala Arg
    1040                1045                1050

Thr Ala Ser Ala Ala Ala His Ser Ala Pro Ala Gly Leu Lys His
    1055                1060                1065

Ala Val Glu Gln Gly Gly Ser Asn Leu Glu Asn Leu Met Val Glu
    1070                1075                1080

Leu Asp Ala Ser Glu Ser Ser Ala Thr Pro Glu Thr Val Glu Thr
    1085                1090                1095

Ala Ala Ala Asp Arg Thr Asp Met Pro Gly Ile Arg Pro Tyr Gly
    1100                1105                1110

Ala Thr Phe Arg Ala Ala Ala Ala Val Gln His Ala Asn Ala Ala
    1115                1120                1125

Asp Gly Val Arg Ile Phe Asn Ser Leu Ala Ala Thr Val Tyr Ala
    1130                1135                1140

Asp Ser Thr Ala Ala His Ala Asp Met Gln Gly Arg Arg Leu Lys
    1145                1150                1155

Ala Val Ser Asp Gly Leu Asp His Asn Gly Thr Gly Leu Arg Val
    1160                1165                1170

Ile Ala Gln Thr Gln Gln Asp Gly Gly Thr Trp Glu Gln Gly Gly
    1175                1180                1185

Val Glu Gly Lys Met Arg Gly Ser Thr Gln Thr Val Gly Ile Ala
    1190                1195                1200

Ala Lys Thr Gly Glu Asn Thr Thr Ala Ala Ala Thr Leu Gly Met
    1205                1210                1215

Gly Arg Ser Thr Trp Ser Glu Asn Ser Ala Asn Ala Lys Thr Asp
    1220                1225                1230

Ser Ile Ser Leu Phe Ala Gly Ile Arg His Asp Ala Gly Asp Ile
    1235                1240                1245

Gly Tyr Leu Lys Gly Leu Phe Ser Tyr Gly Arg Tyr Lys Asn Ser
    1250                1255                1260

Ile Ser Arg Ser Thr Gly Ala Asp Glu His Ala Glu Gly Ser Val
    1265                1270                1275

Asn Gly Thr Leu Met Gln Leu Gly Ala Leu Gly Gly Val Asn Val
```

```
                1280                1285                1290
Pro Phe Ala Ala Thr Gly Asp Leu Thr Val Glu Gly Gly Leu Arg
    1295                1300                1305
Tyr Asp Leu Leu Lys Gln Asp Ala Phe Ala Glu Lys Gly Ser Ala
    1310                1315                1320
Leu Gly Trp Ser Gly Asn Ser Leu Thr Glu Gly Thr Leu Val Gly
    1325                1330                1335
Leu Ala Gly Leu Lys Leu Ser Gln Pro Leu Ser Asp Lys Ala Val
    1340                1345                1350
Leu Phe Ala Thr Ala Gly Val Glu Arg Asp Leu Asn Gly Arg Asp
    1355                1360                1365
Tyr Thr Val Thr Gly Gly Phe Thr Gly Ala Thr Ala Ala Thr Gly
    1370                1375                1380
Lys Thr Gly Ala Arg Asn Met Pro His Thr Arg Leu Val Ala Gly
    1385                1390                1395
Leu Gly Ala Asp Val Glu Phe Gly Asn Gly Trp Asn Gly Leu Ala
    1400                1405                1410
Arg Tyr Ser Tyr Ala Gly Ser Lys Gln Tyr Gly Asn His Ser Gly
    1415                1420                1425
Arg Val Gly Val Gly Tyr Arg Phe Leu Glu His His His His His
    1430                1435                1440
His

<210> SEQ ID NO 47
<211> LENGTH: 2256
<212> TYPE: DNA
<213> ORGANISM: Artificial
<220> FEATURE:
<223> OTHER INFORMATION: 961c-ORF46.1

<400> SEQUENCE: 47
atggccacaa acgacgacga tgttaaaaaa gctgccactg tggccattgc tgctgcctac        60
aacaatggcc aagaaatcaa cggtttcaaa gctggagaga ccatctacga cattgatgaa       120
gacggcacaa ttaccaaaaa agacgcaact gcagccgatg ttgaagccga cgactttaaa       180
ggtctgggtc tgaaaaaagt cgtgactaac ctgaccaaaa ccgtcaatga aacaaacaa        240
aacgtcgatg ccaaagtaaa agctgcagaa tctgaaatag aaagttaac aaccaagtta       300
gcagacactg atgccgcttt agcagatact gatgccgctc tggatgcaac caccaacgcc       360
ttgaataaat tgggagaaaa tataacgaca tttgctgaag agactaagac aaatatcgta       420
aaaattgatg aaaaattaga gccgtggct gataccgtcg acaagcatgc cgaagcattc       480
aacgatatcg ccgattcatt ggatgaaacc aacactaagg cagacgaagc cgtcaaaacc       540
gccaatgaag ccaaacagac ggccgaagaa accaaacaaa acgtcgatgc caaagtaaaa       600
gctgcagaaa ctgcagcagg caaagccgaa gctgccgctg gcacagctaa tactgcagcc       660
gacaaggccg aagctgtcgc tgcaaaagtt accgacatca agctgatat cgctacgaac       720
aaagataata ttgctaaaaa agcaaacagt gccgacgtgt acaccagaga gagtctgac        780
agcaaatttg tcagaattga tggtctgaac gctactaccg aaaaattgga cacacgcttg       840
gcttctgctg aaaaatccat tgccgatcac gatactcgcc tgaacggttt ggataaaaca       900
gtgtcagacc tgcgcaaaga aaccgccaa ggccttgcag acaagccgc gctctccggt        960
ctgttccaac cttacaacgt gggtggatcc ggaggaggag gatcagattt ggcaaacgat      1020
tctttttatcc ggcaggttct cgaccgtcag catttcgaac ccgacgggaa ataccaccta     1080
```

```
ttcggcagca gggggggaact tgccgagcgc agcggccata tcggattggg aaaaatacaa    1140
agccatcagt tgggcaacct gatgattcaa caggcggcca ttaaaggaaa tatcggctac    1200
attgtccgct tttccgatca cgggcacgaa gtccattccc ccttcgacaa ccatgcctca    1260
cattccgatt ctgatgaagc cggtagtccc gttgacggat ttagccttta ccgcatccat    1320
tgggacggat acgaacacca tcccgccgac ggctatgacg ggccacaggg cggcggctat    1380
cccgctccca aggcgcgag ggatatatac agctacgaca taaaaggcgt tgcccaaaat     1440
atccgcctca acctgaccga caaccgcagc accggacaac ggcttgccga ccgtttccac    1500
aatgccggta gtatgctgac gcaaggagta ggcgacggat tcaaacgcgc cacccgatac    1560
agccccgagc tggacagatc gggcaatgcc gccgaagcct tcaacggcac tgcagatatc    1620
gttaaaaaca tcatcggcgc ggcaggagaa attgtcggcg caggcgatgc cgtgcagggc    1680
ataagcgaag gctcaaacat tgctgtcatg cacggcttgg gtctgctttc caccgaaaac    1740
aagatggcgc gcatcaacga tttggcagat atggcgcaac tcaaagacta tgccgcagca    1800
gccatccgcg attgggcagt ccaaaacccc aatgccgcac aaggcataga gccgtcagc     1860 aatatcttta tggcagccat ccccatcaaa gggattggag ctgttcgggg aaaatacggc    1920
ttgggcggca tcacggcaca tcctatcaag cggtcgcaga tgggcgcgat cgcattgccg    1980
aaagggaaat ccgccgtcag cgacaatttt gccgatgcgg catacgccaa atacccgtcc    2040
ccttaccatt cccgaaatat ccgttcaaac ttggagcagc gttacggcaa agaaaacatc    2100
acctcctcaa ccgtgccgcc gtcaaacggc aaaaatgtca aactggcaga ccaacgccac    2160
ccgaagacag gcgtaccgtt tgacggtaaa gggtttccga attttgagaa gcacgtgaaa    2220
tatgatacgc tcgagcacca ccaccaccac cactga                              2256
```

<210> SEQ ID NO 48
<211> LENGTH: 751
<212> TYPE: PRT
<213> ORGANISM: Artificial
<220> FEATURE:
<223> OTHER INFORMATION: 961c-ORF46.1

<400> SEQUENCE: 48

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
```

-continued

```
145                 150                 155                 160
Asn Asp Ile Ala Asp Ser Leu Asp Glu Thr Asn Thr Lys Ala Asp Glu
                165                 170                 175
Ala Val Lys Thr Ala Asn Glu Ala Lys Gln Thr Ala Glu Glu Thr Lys
                180                 185                 190
Gln Asn Val Asp Ala Lys Val Lys Ala Ala Glu Thr Ala Ala Gly Lys
                195                 200                 205
Ala Glu Ala Ala Ala Gly Thr Ala Asn Thr Ala Ala Asp Lys Ala Glu
                210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
                260                 265                 270
Thr Glu Lys Leu Asp Thr Arg Leu Ala Ser Ala Glu Lys Ser Ile Ala
                275                 280                 285
Asp His Asp Thr Arg Leu Asn Gly Leu Asp Lys Thr Val Ser Asp Leu
                290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Gly Ser Gly Gly Gly Gly Ser Asp
                325                 330                 335
Leu Ala Asn Asp Ser Phe Ile Arg Gln Val Leu Asp Arg Gln His Phe
                340                 345                 350
Glu Pro Asp Gly Lys Tyr His Leu Phe Gly Ser Arg Gly Glu Leu Ala
                355                 360                 365
Glu Arg Ser Gly His Ile Gly Leu Gly Lys Ile Gln Ser His Gln Leu
                370                 375                 380
Gly Asn Leu Met Ile Gln Gln Ala Ala Ile Lys Gly Asn Ile Gly Tyr
385                 390                 395                 400
Ile Val Arg Phe Ser Asp His Gly His Glu Val His Ser Pro Phe Asp
                405                 410                 415
Asn His Ala Ser His Ser Asp Ser Asp Glu Ala Gly Ser Pro Val Asp
                420                 425                 430
Gly Phe Ser Leu Tyr Arg Ile His Trp Asp Gly Tyr Glu His His Pro
                435                 440                 445
Ala Asp Gly Tyr Asp Gly Pro Gln Gly Gly Tyr Pro Ala Pro Lys
                450                 455                 460
Gly Ala Arg Asp Ile Tyr Ser Tyr Asp Ile Lys Gly Val Ala Gln Asn
465                 470                 475                 480
Ile Arg Leu Asn Leu Thr Asp Asn Arg Ser Thr Gly Gln Arg Leu Ala
                485                 490                 495
Asp Arg Phe His Asn Ala Gly Ser Met Leu Thr Gln Gly Val Gly Asp
                500                 505                 510
Gly Phe Lys Arg Ala Thr Arg Tyr Ser Pro Glu Leu Asp Arg Ser Gly
                515                 520                 525
Asn Ala Ala Glu Ala Phe Asn Gly Thr Ala Asp Ile Val Lys Asn Ile
                530                 535                 540
Ile Gly Ala Ala Gly Glu Ile Val Gly Ala Gly Asp Ala Val Gln Gly
545                 550                 555                 560
Ile Ser Glu Gly Ser Asn Ile Ala Val Met His Gly Leu Gly Leu Leu
                565                 570                 575
```

Ser Thr Glu Asn Lys Met Ala Arg Ile Asn Asp Leu Ala Asp Met Ala
                580                 585                 590

Gln Leu Lys Asp Tyr Ala Ala Ala Ala Ile Arg Asp Trp Ala Val Gln
            595                 600                 605

Asn Pro Asn Ala Ala Gln Gly Ile Glu Ala Val Ser Asn Ile Phe Met
610                 615                 620

Ala Ala Ile Pro Ile Lys Gly Ile Gly Ala Val Arg Gly Lys Tyr Gly
625                 630                 635                 640

Leu Gly Gly Ile Thr Ala His Pro Ile Lys Arg Ser Gln Met Gly Ala
                645                 650                 655

Ile Ala Leu Pro Lys Gly Lys Ser Ala Val Ser Asp Asn Phe Ala Asp
                660                 665                 670

Ala Ala Tyr Ala Lys Tyr Pro Ser Pro Tyr His Ser Arg Asn Ile Arg
            675                 680                 685

Ser Asn Leu Glu Gln Arg Tyr Gly Lys Glu Asn Ile Thr Ser Ser Thr
690                 695                 700

Val Pro Pro Ser Asn Gly Lys Asn Val Lys Leu Ala Asp Gln Arg His
705                 710                 715                 720

Pro Lys Thr Gly Val Pro Phe Asp Gly Lys Gly Phe Pro Asn Phe Glu
                725                 730                 735

Lys His Val Lys Tyr Asp Thr Leu Glu His His His His His His
            740                 745                 750

<210> SEQ ID NO 49
<211> LENGTH: 1773
<212> TYPE: DNA
<213> ORGANISM: Artificial
<220> FEATURE:
<223> OTHER INFORMATION: 961c-741

<400> SEQUENCE: 49

| | | | | | |
|---|---|---|---|---|---|
| atggccacaa | acgacgacga | tgttaaaaaa | gctgccactg | tggccattgc | tgctgcctac | 60 |
| aacaatggcc | aagaaatcaa | cggtttcaaa | gctggagaga | ccatctacga | cattgatgaa | 120 |
| gacggcacaa | ttaccaaaaa | agacgcaact | gcagccgatg | ttgaagccga | cgactttaaa | 180 |
| ggtctgggtc | tgaaaaaagt | cgtgactaac | ctgaccaaaa | ccgtcaatga | aaacaaacaa | 240 |
| aacgtcgatg | ccaaagtaaa | agctgcagaa | tctgaaatag | aaaagttaac | aaccaagtta | 300 |
| gcagacactg | atgccgcttt | agcagatact | gatgccgctc | tggatgcaac | caccaacgcc | 360 |
| ttgaataaat | ggagagaaaa | tataacgaca | tttgctgaag | agactaagac | aaatatcgta | 420 |
| aaaattgatg | aaaaattaga | agccgtggct | gataccgtcg | acaagcatgc | cgaagcattc | 480 |
| aacgatatcg | ccgattcatt | ggatgaaacc | aacactaagg | cagacgaagc | cgtcaaaacc | 540 |
| gccaatgaag | ccaaacagac | ggccgaagaa | accaaacaaa | acgtcgatgc | aaagtaaaa | 600 |
| gctgcagaaa | ctgcagcagg | caaagccgaa | gctgccgctg | gcacagctaa | tactgcagcc | 660 |
| gacaaggccg | aagctgtcgc | tgcaaaagtt | accgacatca | agctgatat | cgctacgaac | 720 |
| aaagataata | ttgctaaaaa | agcaaacagt | gccgacgtgt | acaccagaga | agagtctgac | 780 |
| agcaaatttg | tcagaattga | tggtctgaac | gctactaccg | aaaaattgga | cacacgcttg | 840 |
| gcttctgctg | aaaaatccat | tgccgatcac | gatactcgcc | tgaacggttt | ggataaaaca | 900 |
| gtgtcagacc | tgcgcaaaga | aaccgccaa | ggccttgcag | aacaagccgc | gctctccggt | 960 |
| ctgttccaac | cttacaacgt | gggtggatcc | ggagggggtg | tgtcgccgc | cgacatcggt | 1020 |
| gcggggcttg | ccgatgcact | aaccgcaccg | ctcgaccata | agacaaagg | tttgcagtct | 1080 |

```
ttgacgctgg atcagtccgt caggaaaaac gagaaactga agctggcggc acaaggtgcg    1140
gaaaaaactt atggaaacgg tgacagcctc aatacgggca aattgaagaa cgacaaggtc    1200
agccgtttcg actttatccg ccaaatcgaa gtggacgggc agctcattac cttggagagt    1260
ggagagttcc aagtatacaa acaaagccat tccgccttaa ccgcctttca gaccgagcaa    1320
atacaagatt cggagcattc cggaagatg gttgcgaaac gccagttcag aatcggcgac    1380
atagcgggcg aacatacatc ttttgacaag cttcccgaag cggcagggc gacatatcgc    1440 gggacggcgt tcggttcaga cgatgccggc ggaaaactga cctacaccat agatttcgcc    1500
gccaagcagg gaaacggcaa aatcgaacat ttgaaatcgc cagaactcaa tgtcgacctg    1560
gccgccgccg atatcaagcc ggatggaaaa cgccatgccg tcatcagcgg ttccgtcctt    1620
tacaaccaag ccgagaaagg cagttactcc ctcggtatct tggcggaaaa agcccaggaa    1680
gttgccggca gcgcggaagt gaaaaccgta acggcatac gccatatcgg ccttgccgcc    1740
aagcaactcg agcaccacca ccaccaccac tga                                 1773
```

<210> SEQ ID NO 50
<211> LENGTH: 590
<212> TYPE: PRT
<213> ORGANISM: Artificial
<220> FEATURE:
<223> OTHER INFORMATION: 961c-741

<400> SEQUENCE: 50

```
Met Ala Thr Asn Asp Asp Val Lys Lys Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240
```

```
Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Val Ala
                325                 330                 335

Ala Asp Ile Gly Ala Gly Leu Ala Asp Ala Leu Thr Ala Pro Leu Asp
            340                 345                 350

His Lys Asp Lys Gly Leu Gln Ser Leu Thr Leu Asp Gln Ser Val Arg
        355                 360                 365

Lys Asn Glu Lys Leu Lys Leu Ala Ala Gln Gly Ala Glu Lys Thr Tyr
    370                 375                 380

Gly Asn Gly Asp Ser Leu Asn Thr Gly Lys Leu Lys Asn Asp Lys Val
385                 390                 395                 400

Ser Arg Phe Asp Phe Ile Arg Gln Ile Glu Val Asp Gly Gln Leu Ile
                405                 410                 415

Thr Leu Glu Ser Gly Glu Phe Gln Val Tyr Lys Gln Ser His Ser Ala
            420                 425                 430

Leu Thr Ala Phe Gln Thr Glu Gln Ile Gln Asp Ser Glu His Ser Gly
        435                 440                 445

Lys Met Val Ala Lys Arg Gln Phe Arg Ile Gly Asp Ile Ala Gly Glu
    450                 455                 460

His Thr Ser Phe Asp Lys Leu Pro Glu Gly Gly Arg Ala Thr Tyr Arg
465                 470                 475                 480

Gly Thr Ala Phe Gly Ser Asp Asp Ala Gly Lys Leu Thr Tyr Thr
                485                 490                 495

Ile Asp Phe Ala Ala Lys Gln Gly Asn Gly Lys Ile Glu His Leu Lys
            500                 505                 510

Ser Pro Glu Leu Asn Val Asp Leu Ala Ala Asp Ile Lys Pro Asp
        515                 520                 525

Gly Lys Arg His Ala Val Ile Ser Gly Ser Val Leu Tyr Asn Gln Ala
    530                 535                 540

Glu Lys Gly Ser Tyr Ser Leu Gly Ile Phe Gly Gly Lys Ala Gln Glu
545                 550                 555                 560

Val Ala Gly Ser Ala Glu Val Lys Thr Val Asn Gly Ile Arg His Ile
                565                 570                 575

Gly Leu Ala Ala Lys Gln Leu Glu His His His His His
            580                 585                 590

<210> SEQ ID NO 51
<211> LENGTH: 4170
<212> TYPE: DNA
<213> ORGANISM: Artificial
<220> FEATURE:
<223> OTHER INFORMATION: 961c-983

<400> SEQUENCE: 51
atggccacaa acgacgacga tgttaaaaaa gctgccactg tggccattgc tgctgcctac      60
```

```
aacaatggcc aagaaatcaa cggtttcaaa gctggagaga ccatctacga cattgatgaa    120
gacggcacaa ttaccaaaaa agacgcaact gcagccgatg ttgaagccga cgactttaaa    180
ggtctgggtc tgaaaaaagt cgtgactaac ctgaccaaaa ccgtcaatga aaacaaacaa    240
aacgtcgatg ccaaagtaaa agctgcagaa tctgaaatag aaaagttaac aaccaagtta    300
gcagacactg atgccgcttt agcagatact gatgccgctc tggatgcaac caccaacgcc    360
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga agagtctgac    780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggcggaggcg gcacttctgc gcccgacttc   1020
aatgcaggcg gtaccggtat cggcagcaac agcagagcaa caacagcgaa atcagcagca   1080
gtatcttacg ccggtatcaa gaacgaaatg tgcaaagaca aagcatgct ctgtgccggt    1140
cgggatgacg ttgcggttac agacagggat gccaaaatca atgccccccc ccgaatctg   1200
cataccggag actttccaaa cccaaatgac gcatacaaga atttgatcaa cctcaaacct   1260
gcaattgaag caggctatac aggacgcggg gtagaggtag gtatcgtcga cacaggcgaa   1320
tccgtcggca gcatatcctt tcccgaactg tatggcagaa aagaacacgg ctataacgaa   1380
aattacaaaa actatacggc gtatatgcgg aaggaagcgc tgaagacgg aggcggtaaa    1440
gacattgaag cttctttcga cgatgaggcc gttatagaga ctgaagcaaa gccgacggat   1500
atccgccacta taaagaaat cggacacatc gatttggtct cccatattat tggcgggcgt   1560
tccgtggacg gcagacctgc aggcggtatt gcgcccgatg cgacgctaca cataatgaat   1620
acgaatgatg aaaccaagaa cgaaatgatg gttcagcca tccgcaatgc atgggtcaag    1680
ctgggcgaac gtggcgtgcg catcgtcaat aacagttttg aacaacatc gagggcaggc    1740
actgccgacc ttttccaaat agccaattcg gaggagcagt accgcaagc gttgctcgac   1800
tattccggcg gtgataaaac agacgagggt atccgcctga tgcaacagag cgattacggc   1860
aacctgtcct accacatccg taataaaaac atgcttttca tcttttcgac aggcaatgac   1920
gcacaagctc agcccaacac atatgcccta ttgccatttt atgaaaaaga cgctcaaaaa   1980
ggcattatca cagtcgcagg cgtagaccgc agtggagaaa agttcaaacg ggaaatgtat   2040
ggagaaccgg gtacagaacc gcttgagtat ggctccaacc attgcggaat tactgccatg   2100
tggtgcctgt cggcacccta tgaagcaagc gtccgtttca cccgtacaaa cccgattcaa   2160
attgccggaa catcctttc cgcacccatc gtaaccggca cggcggctct gctgctgcag   2220
aaatacccgt ggatgagcaa cgacaacctg cgtaccacgt tgctgacgac ggctcaggac   2280
atcggtgcag tcggcgtgga cagcaagttc ggctggggac tgctggatgc gggtaaggcc   2340
atgaacggac ccgcgtcctt tccgttcggc gactttaccg ccgatacgaa aggtacatcc   2400
gatattgcct actccttccg taacgacatt tcaggcacgg gcggcctgat caaaaaaggc   2460
```

```
ggcagccaac tgcaactgca cggcaacaac acctatacgg caaaaccat tatcgaaggc    2520 ggttcgctgg tgttgtacgg caacaacaaa tcggatatgc gcgtcgaaac caaaggtgcg    2580
ctgatttata acggggcggc atccggcggc agcctgaaca gcgacggcat tgtctatctg    2640
gcagataccg accaatccgg cgcaaacgaa accgtacaca tcaaaggcag tctgcagctg    2700
gacggcaaag gtacgctgta cacacgtttg gcaaactgc tgaaagtgga cggtacggcg    2760
attatcggcg gcaagctgta catgtcggca cgcggcaagg gggcaggcta tctcaacagt    2820
accggacgac gtgttcccct cctgagtgcc gccaaaatcg gcaggatta ttctttcttc    2880 acaaacatcg aaaccgacgg cggcctgctg gcttccctcg acagcgtcga aaaacagcg    2940 ggcagtgaag gcgacacgct gtcctattat gtccgtcgcg gcaatgcggc acggactgct    3000
tcggcagcgg cacattccgc gcccgccggt ctgaaacacg ccgtagaaca gggcggcagc    3060
aatctggaaa acctgatggt cgaactggat gcctccgaat catccgcaac acccgagacg    3120
gttgaaactg cggcagccga ccgcacagat atgccgggca tccgccccta cggcgcaact    3180
ttccgcgcag cggcagccgt acagcatgcg aatgccgccg acggtgtacg catcttcaac    3240
agtctcgccg ctaccgtcta tgccgacagt accgccgccc atgccgatat gcagggacgc    3300
cgcctgaaag ccgtatcgga cgggttggac cacaacggca cgggtctgcg cgtcatcgcg    3360
caaacccaac aggacggtgg aacgtgggaa cagggcggtg ttgaaggcaa aatgcgcggc    3420
agtacccaaa ccgtcggcat tgccgcgaaa accgcgaaa atacgacagc agccgccaca    3480
ctgggcatgg gacgcagcac atggagcgaa acagtgcaa atgcaaaaac cgacagcatt    3540
agtctgtttg caggcatacg gcacgatgcg ggcgatatcg gctatctcaa aggcctgttc    3600
tcctacggac gctacaaaaa cagcatcagc cgcagcaccg tgcggacga acatgcggaa    3660 ggcagcgtca acggcacgct gatgcagctg ggcgcactgg gcggtgtcaa cgttccgttt    3720
gccgcaacgg gagatttgac ggtcgaaggc ggtctgcgct acgacctgct caaacaggat    3780
gcattcgccg aaaaaggcag tgctttgggc tggagcggca cagcctcac tgaaggcacg    3840 ctggtcggac tcgcgggtct gaagctgtcg caacccttga gcataaagc cgtcctgttt    3900 gcaacggcgg gcgtggaacg cgacctgaac ggacgcgact acacgtaac gggcggcttt    3960 accggcgcga ctgcagcaac cggcaagacg ggggcacgca atatgccgca cacccgtctg    4020
gttgccggcc tgggcgcgga tgtcgaattc ggcaacggct ggaacggctt ggcacgttac    4080
agctacgccg gttccaaaca gtacggcaac cacagcggac gagtcggcgt aggctaccgg    4140
ttcctcgagc accaccacca ccaccactga                                    4170
```

<210> SEQ ID NO 52
<211> LENGTH: 1389
<212> TYPE: PRT
<213> ORGANISM: Artificial
<220> FEATURE:
<223> OTHER INFORMATION: 961c-983

<400> SEQUENCE: 52

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
```

```
         50                  55                  60
Lys Lys Val Val Thr Asn Leu Thr Lys Thr Val Asn Glu Asn Lys Gln
 65                  70                  75                  80

Asn Val Asp Ala Lys Val Lys Ala Ala Glu Ser Glu Ile Glu Lys Leu
                 85                  90                  95

Thr Thr Lys Leu Ala Asp Thr Asp Ala Leu Ala Asp Thr Asp Ala
                100                 105                 110

Ala Leu Asp Ala Thr Thr Asn Ala Leu Asn Lys Leu Gly Glu Asn Ile
                115                 120                 125

Thr Thr Phe Ala Glu Glu Thr Lys Thr Asn Ile Val Lys Ile Asp Glu
                130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
                180                 185                 190

Gln Asn Val Asp Ala Lys Val Lys Ala Ala Glu Thr Ala Ala Gly Lys
                195                 200                 205

Ala Glu Ala Ala Ala Gly Thr Ala Asn Thr Ala Ala Asp Lys Ala Glu
210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
                260                 265                 270

Thr Glu Lys Leu Asp Thr Arg Leu Ala Ser Ala Glu Lys Ser Ile Ala
                275                 280                 285

Asp His Asp Thr Arg Leu Asn Gly Leu Asp Lys Thr Val Ser Asp Leu
                290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Thr Ser
                325                 330                 335

Ala Pro Asp Phe Asn Ala Gly Gly Thr Gly Ile Gly Ser Asn Ser Arg
                340                 345                 350

Ala Thr Thr Ala Lys Ser Ala Ala Val Ser Tyr Ala Gly Ile Lys Asn
                355                 360                 365

Glu Met Cys Lys Asp Arg Ser Met Leu Cys Ala Gly Arg Asp Asp Val
                370                 375                 380

Ala Val Thr Asp Arg Asp Ala Lys Ile Asn Ala Pro Pro Asn Leu
385                 390                 395                 400

His Thr Gly Asp Phe Pro Asn Pro Asn Asp Ala Tyr Lys Asn Leu Ile
                405                 410                 415

Asn Leu Lys Pro Ala Ile Glu Ala Gly Tyr Thr Gly Arg Gly Val Glu
                420                 425                 430

Val Gly Ile Val Asp Thr Gly Glu Ser Val Gly Ser Ile Ser Phe Pro
                435                 440                 445

Glu Leu Tyr Gly Arg Lys Glu His Gly Tyr Asn Glu Asn Tyr Lys Asn
                450                 455                 460

Tyr Thr Ala Tyr Met Arg Lys Glu Ala Pro Glu Asp Gly Gly Gly Lys
465                 470                 475                 480
```

```
Asp Ile Glu Ala Ser Phe Asp Glu Ala Val Ile Thr Glu Ala
            485             490             495

Lys Pro Thr Asp Ile Arg His Val Lys Glu Ile Gly His Ile Asp Leu
            500             505             510

Val Ser His Ile Ile Gly Gly Arg Ser Val Asp Gly Arg Pro Ala Gly
            515             520             525

Gly Ile Ala Pro Asp Ala Thr Leu His Ile Met Asn Thr Asn Asp Glu
            530             535             540

Thr Lys Asn Glu Met Met Val Ala Ala Ile Arg Asn Ala Trp Val Lys
545             550             555             560

Leu Gly Glu Arg Gly Val Arg Ile Val Asn Asn Ser Phe Gly Thr Thr
            565             570             575

Ser Arg Ala Gly Thr Ala Asp Leu Phe Gln Ile Ala Asn Ser Glu Glu
            580             585             590

Gln Tyr Arg Gln Ala Leu Leu Asp Tyr Ser Gly Gly Asp Lys Thr Asp
            595             600             605

Glu Gly Ile Arg Leu Met Gln Gln Ser Asp Tyr Gly Asn Leu Ser Tyr
            610             615             620

His Ile Arg Asn Lys Asn Met Leu Phe Ile Phe Ser Thr Gly Asn Asp
625             630             635             640

Ala Gln Ala Gln Pro Asn Thr Tyr Ala Leu Leu Pro Phe Tyr Glu Lys
            645             650             655

Asp Ala Gln Lys Gly Ile Ile Thr Val Ala Gly Val Asp Arg Ser Gly
            660             665             670

Glu Lys Phe Lys Arg Glu Met Tyr Gly Glu Pro Gly Thr Glu Pro Leu
            675             680             685

Glu Tyr Gly Ser Asn His Cys Gly Ile Thr Ala Met Trp Cys Leu Ser
            690             695             700

Ala Pro Tyr Glu Ala Ser Val Arg Phe Thr Arg Thr Asn Pro Ile Gln
705             710             715             720

Ile Ala Gly Thr Ser Phe Ser Ala Pro Ile Val Thr Gly Thr Ala Ala
            725             730             735

Leu Leu Leu Gln Lys Tyr Pro Trp Met Ser Asn Asp Asn Leu Arg Thr
            740             745             750

Thr Leu Leu Thr Thr Ala Gln Asp Ile Gly Ala Val Gly Val Asp Ser
            755             760             765

Lys Phe Gly Trp Gly Leu Leu Asp Ala Gly Lys Ala Met Asn Gly Pro
            770             775             780

Ala Ser Phe Pro Phe Gly Asp Phe Thr Ala Asp Thr Lys Gly Thr Ser
785             790             795             800

Asp Ile Ala Tyr Ser Phe Arg Asn Asp Ile Ser Gly Thr Gly Gly Leu
            805             810             815

Ile Lys Lys Gly Gly Ser Gln Leu Gln Leu His Gly Asn Asn Thr Tyr
            820             825             830

Thr Gly Lys Thr Ile Ile Glu Gly Gly Ser Leu Val Leu Tyr Gly Asn
            835             840             845

Asn Lys Ser Asp Met Arg Val Glu Thr Lys Gly Ala Leu Ile Tyr Asn
850             855             860

Gly Ala Ala Ser Gly Gly Ser Leu Asn Ser Asp Gly Ile Val Tyr Leu
865             870             875             880

Ala Asp Thr Asp Gln Ser Gly Ala Asn Glu Thr Val His Ile Lys Gly
            885             890             895
```

```
Ser Leu Gln Leu Asp Gly Lys Gly Thr Leu Tyr Thr Arg Leu Gly Lys
            900                 905                 910

Leu Leu Lys Val Asp Gly Thr Ala Ile Ile Gly Gly Lys Leu Tyr Met
        915                 920                 925

Ser Ala Arg Gly Lys Gly Ala Gly Tyr Leu Asn Ser Thr Gly Arg Arg
    930                 935                 940

Val Pro Phe Leu Ser Ala Ala Lys Ile Gly Gln Asp Tyr Ser Phe Phe
945                 950                 955                 960

Thr Asn Ile Glu Thr Asp Gly Gly Leu Leu Ala Ser Leu Asp Ser Val
                965                 970                 975

Glu Lys Thr Ala Gly Ser Glu Gly Asp Thr Leu Ser Tyr Tyr Val Arg
            980                 985                 990

Arg Gly Asn Ala Ala Arg Thr Ala  Ser Ala Ala Ala His  Ser Ala Pro
        995                 1000                1005

Ala Gly  Leu Lys His Ala Val  Glu Gln Gly Gly Ser  Asn Leu Glu
    1010                1015                1020

Asn Leu  Met Val Glu Leu Asp  Ala Ser Glu Ser Ser  Ala Thr Pro
    1025                1030                1035

Glu Thr  Val Glu Thr Ala Ala  Ala Asp Arg Thr Asp  Met Pro Gly
    1040                1045                1050

Ile Arg  Pro Tyr Gly Ala Thr  Phe Arg Ala Ala Ala  Ala Val Gln
    1055                1060                1065

His Ala  Asn Ala Ala Asp Gly  Val Arg Ile Phe Asn  Ser Leu Ala
    1070                1075                1080

Ala Thr  Val Tyr Ala Asp Ser  Thr Ala His Ala  Asp Met Gln
    1085                1090                1095

Gly Arg  Arg Leu Lys Ala Val  Ser Asp Gly Leu Asp  His Asn Gly
    1100                1105                1110

Thr Gly  Leu Arg Val Ile Ala  Gln Thr Gln Gln Asp  Gly Gly Thr
    1115                1120                1125

Trp Glu  Gln Gly Gly Val Glu  Gly Lys Met Arg Gly  Ser Thr Gln
    1130                1135                1140

Thr Val  Gly Ile Ala Ala Lys  Thr Gly Glu Asn Thr  Thr Ala Ala
    1145                1150                1155

Ala Thr  Leu Gly Met Gly Arg  Ser Thr Trp Ser Glu  Asn Ser Ala
    1160                1165                1170

Asn Ala  Lys Thr Asp Ser Ile  Ser Leu Phe Ala Gly  Ile Arg His
    1175                1180                1185

Asp Ala  Gly Asp Ile Gly Tyr  Leu Lys Gly Leu Phe  Ser Tyr Gly
    1190                1195                1200

Arg Tyr  Lys Asn Ser Ile Ser  Arg Ser Thr Gly Ala  Asp Glu His
    1205                1210                1215

Ala Glu  Gly Ser Val Asn Gly  Thr Leu Met Gln Leu  Gly Ala Leu
    1220                1225                1230

Gly Gly  Val Asn Val Pro Phe  Ala Ala Thr Gly Asp  Leu Thr Val
    1235                1240                1245

Glu Gly  Gly Leu Arg Tyr Asp  Leu Leu Lys Gln Asp  Ala Phe Ala
    1250                1255                1260

Glu Lys  Gly Ser Ala Leu Gly  Trp Ser Gly Asn Ser  Leu Thr Glu
    1265                1270                1275

Gly Thr  Leu Val Gly Leu Ala  Gly Leu Lys Leu Ser  Gln Pro Leu
    1280                1285                1290

Ser Asp  Lys Ala Val Leu Phe  Ala Thr Ala Gly Val  Glu Arg Asp
```

```
                  1295                1300                1305
Leu Asn  Gly Arg Asp Tyr Thr  Val Thr Gly Gly Phe  Thr Gly Ala
        1310                1315                1320

Thr Ala  Ala Thr Gly Lys Thr  Gly Ala Arg Asn Met  Pro His Thr
        1325                1330                1335

Arg Leu  Val Ala Gly Leu Gly  Ala Asp Val Glu Phe  Gly Asn Gly
        1340                1345                1350

Trp Asn  Gly Leu Ala Arg Tyr  Ser Tyr Ala Gly Ser  Lys Gln Tyr
        1355                1360                1365

Gly Asn  His Ser Gly Arg Val  Gly Val Gly Tyr Arg  Phe Leu Glu
        1370                1375                1380

His His  His His His His
        1385

<210> SEQ ID NO 53
<211> LENGTH: 2304
<212> TYPE: DNA
<213> ORGANISM: Artificial
<220> FEATURE:
<223> OTHER INFORMATION: 961cL-ORF46.1

<400> SEQUENCE: 53
atgaaacact ttccatccaa agtactgacc acagccatcc ttgccacttt ctgtagcggc      60
gcactggcag ccacaaacga cgacgatgtt aaaaaagctg ccactgtggc cattgctgct     120
gcctacaaca atggccaaga atcaacggtt tcaaagctg agagaccat ctacgacatt       180
gatgaagacg gcacaattac caaaaaagac gcaactgcag ccgatgttga agccgacgac    240
tttaaaggtc tgggtctgaa aaagtcgtg actaacctga ccaaaaccgt caatgaaaac      300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata cgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc   600
aaaaccgcca atgaagccaa acagacggcc gaagaaacca acaaaacgt cgatgccaaa    660
gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca aacagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggttttggat   960
aaaacagtgt cagacctgcg caaagaaacc cgccaaggcc ttgcagaaca gccgcgctc   1020
tccggtctgt tccaaccta acgtgggg ggatccggag gaggaggatc agatttggca     1080
aacgattctt ttatccggca ggttctcgac cgtcagcatt cgaacccga cgggaaatac    1140
cacctattcg gcagcagggg ggaacttgcc gagcgcagcg ccatatcgg attgggaaaa   1200
atacaaagcc atcagttggg caacctgatg attcaacagg cggccattaa ggaaatatc    1260
ggctacattg tccgctttc cgatcacggg cacgaagtcc attcccctt cgacaaccat    1320
gcctcacatt ccgattctga tgaagccggt agtccgttg acggatttag cctttaccgc    1380
atccattggg acggatacga acaccatccc gccgacggct atgacgggcc acagggcgg    1440
ggctatcccg ctcccaaagg cgcgagggat atatacagct acgacataaa aggcgttgcc   1500
```

```
caaaatatcc gcctcaacct gaccgacaac cgcagcaccg gacaacggct tgccgaccgt    1560
ttccacaatg ccggtagtat gctgacgcaa ggagtaggcg acggattcaa acgcgccacc    1620
cgatacagcc ccgagctgga cagatcgggc aatgccgccg aagccttcaa cggcactgca    1680
gatatcgtta aaaacatcat cggcgcggca ggagaaattg tcggcgcagg cgatgccgtg    1740
cagggcataa gcgaaggctc aaacattgct gtcatgcacg gcttgggtct gctttccacc    1800
gaaaacaaga tggcgcgcat caacgatttg gcagatatgg cgcaactcaa agactatgcc    1860
gcagcagcca tccgcgattg ggcagtccaa accccaatg ccgcacaagg catagaagcc     1920
gtcagcaata tctttatggc agccatcccc atcaaaggga ttggagctgt tcggggaaaa    1980
tacggcttgg gcggcatcac ggcacatcct atcaagcggt cgcagatggg cgcgatcgca    2040
ttgccgaaag ggaaatccgc cgtcagcgac aattttgccg atgcggcata cgccaaatac    2100
ccgtcccctt accattcccg aaatatccgt tcaaacttgg agcagcgtta cggcaaagaa    2160
aacatcacct cctcaaccgt gccgccgtca acggcaaaa atgtcaaact ggcagaccaa     2220
cgccacccga agacaggcgt accgtttgac ggtaaagggt ttccgaattt tgagaagcac    2280
gtgaaatatg atacgtaact cgag                                            2304
```

<210> SEQ ID NO 54
<211> LENGTH: 765
<212> TYPE: PRT
<213> ORGANISM: Artificial
<220> FEATURE:
<223> OTHER INFORMATION: 961cL-ORF46.1

<400> SEQUENCE: 54

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
50                  55                  60

Thr Ile Thr Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
```

-continued

```
               210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
                260                 265                 270

Ala Asp Val Tyr Thr Arg Glu Glu Ser Asp Ser Lys Phe Val Arg Ile
                275                 280                 285

Asp Gly Leu Asn Ala Thr Thr Glu Lys Leu Asp Thr Arg Leu Ala Ser
290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
                340                 345                 350

Gly Gly Gly Gly Ser Asp Leu Ala Asn Asp Ser Phe Ile Arg Gln Val
                355                 360                 365

Leu Asp Arg Gln His Phe Glu Pro Asp Gly Lys Tyr His Leu Phe Gly
370                 375                 380

Ser Arg Gly Glu Leu Ala Glu Arg Ser Gly His Ile Gly Leu Gly Lys
385                 390                 395                 400

Ile Gln Ser His Gln Leu Gly Asn Leu Met Ile Gln Gln Ala Ala Ile
                405                 410                 415

Lys Gly Asn Ile Gly Tyr Ile Val Arg Phe Ser Asp His Gly His Glu
                420                 425                 430

Val His Ser Pro Phe Asp Asn His Ala Ser His Ser Asp Ser Asp Glu
                435                 440                 445

Ala Gly Ser Pro Val Asp Gly Phe Ser Leu Tyr Arg Ile His Trp Asp
450                 455                 460

Gly Tyr Glu His His Pro Ala Asp Gly Tyr Asp Gly Pro Gln Gly Gly
465                 470                 475                 480

Gly Tyr Pro Ala Pro Lys Gly Ala Arg Asp Ile Tyr Ser Tyr Asp Ile
                485                 490                 495

Lys Gly Val Ala Gln Asn Ile Arg Leu Asn Leu Thr Asn Arg Ser
                500                 505                 510

Thr Gly Gln Arg Leu Ala Asp Arg Phe His Asn Ala Gly Ser Met Leu
                515                 520                 525

Thr Gln Gly Val Gly Asp Gly Phe Lys Arg Ala Thr Arg Tyr Ser Pro
530                 535                 540

Glu Leu Asp Arg Ser Gly Asn Ala Ala Glu Ala Phe Asn Gly Thr Ala
545                 550                 555                 560

Asp Ile Val Lys Asn Ile Ile Gly Ala Ala Gly Glu Ile Val Gly Ala
                565                 570                 575

Gly Asp Ala Val Gln Gly Ile Ser Glu Gly Ser Asn Ile Ala Val Met
                580                 585                 590

His Gly Leu Gly Leu Leu Ser Thr Glu Asn Lys Met Ala Arg Ile Asn
                595                 600                 605

Asp Leu Ala Asp Met Ala Gln Leu Lys Asp Tyr Ala Ala Ala Ala Ile
610                 615                 620

Arg Asp Trp Ala Val Gln Asn Pro Asn Ala Ala Gln Gly Ile Glu Ala
625                 630                 635                 640
```

```
Val Ser Asn Ile Phe Met Ala Ala Ile Pro Ile Lys Gly Ile Gly Ala
            645                 650                 655

Val Arg Gly Lys Tyr Gly Leu Gly Gly Ile Thr Ala His Pro Ile Lys
        660                 665                 670

Arg Ser Gln Met Gly Ala Ile Ala Leu Pro Lys Gly Lys Ser Ala Val
    675                 680                 685

Ser Asp Asn Phe Ala Asp Ala Ala Tyr Ala Lys Tyr Pro Ser Pro Tyr
690                 695                 700

His Ser Arg Asn Ile Arg Ser Asn Leu Glu Gln Arg Tyr Gly Lys Glu
705                 710                 715                 720

Asn Ile Thr Ser Ser Thr Val Pro Pro Ser Asn Gly Lys Asn Val Lys
                725                 730                 735

Leu Ala Asp Gln Arg His Pro Lys Thr Gly Val Pro Phe Asp Gly Lys
            740                 745                 750

Gly Phe Pro Asn Phe Glu Lys His Val Lys Tyr Asp Thr
            755                 760                 765

<210> SEQ ID NO 55
<211> LENGTH: 1839
<212> TYPE: DNA
<213> ORGANISM: Artificial
<220> FEATURE:
<223> OTHER INFORMATION: 961cL-741

<400> SEQUENCE: 55
atgaaacact ttccatccaa agtactgacc acagccatcc ttgccacttt ctgtagcggc     60
gcactggcag ccacaaacga cgacgatgtt aaaaaagctg ccactgtggc cattgctgct    120
gcctacaaca atggccaaga atcaacggt ttcaaagctg agagaccat ctacgacatt     180 gatgaagacg gcacaattac caaaaaagac gcaactgcag ccgatgttga agccgacgac    240
tttaaaggtc tgggtctgaa aaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata acgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600 aaaccgcca atgaagccaa acagacggcc gaagaaacca acaaaacgt cgatgccaaa    660 gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca acagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta caacgtgggt ggatccggag ggggtggtgt cgccgccgac   1080
atcggtgcgg ggcttgccga tgcactaacc gcaccgctcg accataaaga caaaggtttg   1140
cagtctttga cgctggatca gtccgtcagg aaaaacgaga actgaagct ggcggcacaa   1200 ggtgcggaaa aaactatgg aaacggtgac agcctcaata cgggcaaatt gaagaacgac   1260
aaggtcagcc gtttcgactt tatccgccaa atcgaagtgg acgggcagct cattaccttg   1320
```

-continued

```
gagagtggag agttccaagt atacaaacaa agccattccg ccttaaccgc ctttcagacc    1380
gagcaaatac aagattcgga gcattccggg aagatggttg cgaaacgcca gttcagaatc    1440
ggcgacatag cgggcgaaca tacatctttt gacaagcttc ccgaaggcgg cagggcgaca    1500
tatcgcggga cggcgttcgg ttcagacgat gccggcggaa aactgaccta caccatagat    1560
ttcgccgcca agcagggaaa cggcaaaatc gaacatttga aatcgccaga actcaatgtc    1620
gacctggccg ccgccgatat caagccggat ggaaaacgcc atgccgtcat cagcggttcc    1680
gtcctttaca accaagccga aaaggcagt tactccctcg gtatctttgg cggaaaagcc     1740
caggaagttg ccggcagcgc ggaagtgaaa accgtaaacg gcatacgcca tatcggcctt    1800
gccgccaagc aactcgagca ccaccaccac caccactga                           1839
```

<210> SEQ ID NO 56
<211> LENGTH: 612
<212> TYPE: PRT
<213> ORGANISM: Artificial
<220> FEATURE:
<223> OTHER INFORMATION: 961cL-741

<400> SEQUENCE: 56

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Lys Val Thr Asp Ile Lys
                245                 250                 255

Ala Asp Ile Ala Thr Asn Lys Asp Asn Ile Ala Lys Lys Ala Asn Ser
            260                 265                 270
```

| | | | | | | | | | | | | |
|---|---|---|---|---|---|---|---|---|---|---|---|---|
|Ala|Asp|Val|Tyr 275|Thr|Arg|Glu|Glu 280|Ser|Asp|Ser|Lys 285|Phe Val Arg Ile|

| | | | | | | | | | | | | |
|---|---|---|---|---|---|---|---|---|---|---|---|---|
|Asp|Gly|Leu|Asn 290|Ala|Thr|Thr|Glu 295|Lys|Leu|Asp|Thr 300|Arg Leu Ala Ser|

| | | | | | | | | | | | | |
|---|---|---|---|---|---|---|---|---|---|---|---|---|
|Ala 305|Glu|Lys|Ser|Ile 310|Ala|Asp|His|Asp 315|Thr|Arg|Leu|Asn Gly Leu Asp 320|

| | | | | | | | | | | | | |
|---|---|---|---|---|---|---|---|---|---|---|---|---|
|Lys|Thr|Val|Ser 325|Asp|Leu|Arg|Lys 330|Glu|Thr|Arg|Gln 335|Gly Leu Ala Glu|

| | | | | | | | | | | | | |
|---|---|---|---|---|---|---|---|---|---|---|---|---|
|Gln|Ala|Ala|Leu 340|Ser|Gly|Leu|Phe 345|Gln|Pro|Tyr|Asn 350|Val Gly Gly Ser|

| | | | | | | | | | | | | |
|---|---|---|---|---|---|---|---|---|---|---|---|---|
|Gly|Gly|Gly|Gly 355|Val|Ala|Ala|Asp 360|Ile|Gly|Ala|Gly 365|Leu Ala Asp Ala|

| | | | | | | | | | | | | |
|---|---|---|---|---|---|---|---|---|---|---|---|---|
|Leu|Thr|Ala|Pro 370|Leu|Asp|His|Lys 375|Asp|Lys|Gly|Leu 380|Gln Ser Leu Thr|

| | | | | | | | | | | | | |
|---|---|---|---|---|---|---|---|---|---|---|---|---|
|Leu 385|Asp|Gln|Ser|Val 390|Arg|Lys|Asn|Glu 395|Lys|Leu|Lys|Leu Ala Ala Gln 400|

| | | | | | | | | | | | | |
|---|---|---|---|---|---|---|---|---|---|---|---|---|
|Gly|Ala|Glu|Lys 405|Thr|Tyr|Gly|Asn 410|Gly|Asp|Ser|Leu 415|Asn Thr Gly Lys|

| | | | | | | | | | | | | |
|---|---|---|---|---|---|---|---|---|---|---|---|---|
|Leu|Lys|Asn|Asp 420|Lys|Val|Ser|Arg 425|Phe|Asp|Phe|Ile 430|Arg Gln Ile Glu|

| | | | | | | | | | | | | |
|---|---|---|---|---|---|---|---|---|---|---|---|---|
|Val|Asp|Gly|Gln 435|Leu|Ile|Thr|Leu 440|Glu|Ser|Gly|Glu 445|Phe Gln Val Tyr|

| | | | | | | | | | | | | |
|---|---|---|---|---|---|---|---|---|---|---|---|---|
|Lys|Gln|Ser|His 450|Ser|Ala|Leu|Thr 455|Ala|Phe|Gln|Thr 460|Glu Gln Ile Gln|

| | | | | | | | | | | | | |
|---|---|---|---|---|---|---|---|---|---|---|---|---|
|Asp 465|Ser|Glu|His|Ser 470|Gly|Lys|Met|Val 475|Ala|Lys|Arg|Gln Phe Arg Ile 480|

| | | | | | | | | | | | | |
|---|---|---|---|---|---|---|---|---|---|---|---|---|
|Gly|Asp|Ile|Ala 485|Gly|Glu|His|Thr 490|Ser|Phe|Asp|Lys 495|Leu Pro Glu Gly|

| | | | | | | | | | | | | |
|---|---|---|---|---|---|---|---|---|---|---|---|---|
|Gly|Arg|Ala|Thr 500|Tyr|Arg|Gly|Thr 505|Ala|Phe|Gly|Ser 510|Asp Asp Ala Gly|

| | | | | | | | | | | | | |
|---|---|---|---|---|---|---|---|---|---|---|---|---|
|Gly|Lys|Leu|Thr 515|Tyr|Thr|Ile|Asp 520|Phe|Ala|Ala|Lys 525|Gln Gly Asn Gly|

| | | | | | | | | | | | | |
|---|---|---|---|---|---|---|---|---|---|---|---|---|
|Lys|Ile|Glu|His 530|Leu|Lys|Ser|Pro 535|Glu|Leu|Asn|Val 540|Asp Leu Ala Ala|

| | | | | | | | | | | | | |
|---|---|---|---|---|---|---|---|---|---|---|---|---|
|Ala 545|Asp|Ile|Lys|Pro 550|Asp|Gly|Lys|Arg 555|His|Ala|Val|Ile Ser Gly Ser 560|

| | | | | | | | | | | | | |
|---|---|---|---|---|---|---|---|---|---|---|---|---|
|Val|Leu|Tyr|Asn 565|Gln|Ala|Glu|Lys 570|Gly|Ser|Tyr|Ser 575|Leu Gly Ile Phe|

| | | | | | | | | | | | | |
|---|---|---|---|---|---|---|---|---|---|---|---|---|
|Gly|Gly|Lys|Ala 580|Gln|Glu|Val|Ala 585|Gly|Ser|Ala|Glu 590|Val Lys Thr Val|

| | | | | | | | | | | | | |
|---|---|---|---|---|---|---|---|---|---|---|---|---|
|Asn|Gly|Ile|Arg 595|His|Ile|Gly|Leu 600|Ala|Ala|Lys|Gln 605|Leu Glu His His|

His His His His
610

<210> SEQ ID NO 57
<211> LENGTH: 4218
<212> TYPE: DNA
<213> ORGANISM: Artificial
<220> FEATURE:
<223> OTHER INFORMATION: 961cL-983

<400> SEQUENCE: 57

```
atgaaacact tccatccaa agtactgacc acagccatcc ttgccacttt ctgtagcggc      60
gcactggcag ccacaaacga cgacgatgtt aaaaaagctg ccactgtggc cattgctgct     120
```

-continued

```
gcctacaaca atggccaaga aatcaacggt ttcaaagctg agagaccat  ctacgacatt    180 gatgaagacg gcacaattac caaaaaagac gcaactgcag ccgatgttga agccgacgac    240
tttaaaggtc tgggtctgaa aaaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata acgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaaccgcca atgaagccaa acagacggcc gaagaaacca acaaaacgt cgatgccaaa    660 gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca aacagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggttttggat   960 aaaacagtgt cagacctgcg caaagaaacc cgccaaggcc ttgcagaaca agccgcgctc   1020
tccggtctgt tccaaccttta caacgtgggt ggatccggcg gaggcggcac ttctgcgccc   1080
gacttcaatg caggcggtac cggtatcggc agcaacagca gagcaacaac agcgaaatca   1140
gcagcagtat cttacgccgg tatcaagaac gaaatgtgca aagacagaag catgctctgt   1200
gccggtcggg atgacgttgc ggttacagac agggatgcca aaatcaatgc cccccccccg   1260
aatctgcata ccggagactt tccaaaccca aatgacgcat acaagaattt gatcaacctc   1320
aaacctgcaa ttgaagcagg ctatacagga cgcggggtag aggtaggtat cgtcgacaca   1380
ggcgaatccg tcggcagcat atccttctcc gaactgtatg gcagaaaaga acacggctat   1440
aacgaaaatt acaaaaacta tacggcgtat atgcggaagg aagcgcctga agacggaggc   1500
ggtaaagaca ttgaagcttc tttcgacgat gaggccgtta tagagactga agcaaagccg   1560
acggatatcc gccacgtaaa agaaatcgga cacatcgatt tggtctccca tattattggc   1620
gggcgttccg tggacggcag acctgcaggc ggtattgcgc ccgatgcgac gctacacata   1680
atgaatacga atgatgaaac caagaacgaa atgatggttg cagccatccg caatgcatgg   1740
gtcaagctgg cgaacgtgg  cgtgcgcatc gtcaataaca gttttggaac aacatcgagg   1800
gcaggcactg ccgacctttt ccaaatagcc aattcggagg agcagtaccg ccaagcgttg   1860
ctcgactatt ccggcggtga taaaacagac gagggtatcc gcctgatgca acagagcgat   1920
tacggcaacc tgtcctacca catccgtaat aaaaacatgc ttttcatctt ttcgacaggc   1980
aatgacgcac aagctcagcc caacacatat gccctattgc cattttatga aaaagacgct   2040
caaaaaggca ttatcacagt cgcaggcgta gaccgcagtg agaaaagtt  caaacgggaa   2100 atgtatggag aaccgggtac agaaccgctt gagtatggct ccaaccattg cggaattact   2160
gccatgtggt gcctgtcggc acccttatgaa gcaagcgtcc gtttcacccg tacaaacccg   2220
attcaaattg ccggaacatc cttttccgca cccatcgtaa ccggcacggc ggctctgctg   2280
ctgcagaaat acccgtggat gagcaacgac aacctgcgta ccacgttgct gacgacggct   2340
caggacatcg tgtcagtcgg cgtggacagc aagttcggct ggggactgct ggatgcgggt   2400
aaggccatga acggacccgc gtcctttccg ttcggcgact ttaccgccga tacgaaaggt   2460
```

```
acatccgata ttgcctactc cttccgtaac gacatttcag gcacgggcgg cctgatcaaa    2520
aaaggcggca gccaactgca actgcacggc aacaacacct atacgggcaa aaccattatc    2580
gaaggcggtt cgctggtgtt gtacggcaac aacaaatcgg atatgcgcgt cgaaaccaaa    2640
ggtgcgctga tttataacgg ggcggcatcc ggcggcagcc tgaacagcga cggcattgtc    2700
tatctggcag ataccgacca atccggcgca aacgaaaccg tacacatcaa aggcagtctg    2760
cagctggacg gcaaaggtac gctgtacaca cgtttgggca aactgctgaa agtggacggt    2820
acggcgatta tcggcggcaa gctgtacatg tcggcacgcg gcaaggggc aggctatctc    2880 aacagtaccg gacgacgtgt tcccttcctg agtgccgcca aaatcgggca ggattattct    2940
ttcttcacaa acatcgaaac cgacggcggc ctgctggctt ccctcgacag cgtcgaaaaa    3000
acagcgggca gtgaaggcga cacgctgtcc tattatgtcc gtcgcggcaa tgcggcacgg    3060
actgcttcgg cagcggcaca ttccgcgccc gccggtctga acacgccgt agaacagggc    3120 ggcagcaatc tggaaaacct gatggtcgaa ctggatgcct ccgaatcatc cgcaacaccc    3180
gagacggttg aaactgcggc agccgaccgc acagatatgc cggcatccg cccctacggc    3240 gcaactttcc gcgcagcggc agccgtacga catgcgaatg ccgccgacgg tgtacgcatc    3300
ttcaacagtc tcgccgctac cgtctatgcc gacagtaccg ccgcccatgc cgatatgcag    3360
ggacgccgcc tgaaagccgt atcggacggg ttggaccaca acggcacggg tctgcgcgtc    3420
atcgcgcaaa cccaacagga cggtggaacg tgggaacagg cggtgttga aggcaaaatg    3480 cgcggcagta cccaaaccgt cggcattgcc gcgaaaaccg gcgaaaatac gacagcagcc    3540
gccacactgg gcatgggacg cagcacatgg agcgaaaaca gtgcaaatgc aaaaaccgac    3600
agcattagtc tgtttgcagg catacggcac gatgcgggcg atatcggcta tctcaaaggc    3660
ctgttctcct acgacgcta caaaaacagc atcagccgca gcaccggtgc ggacgaacat    3720
gcggaaggca gcgtcaacgg cacgctgatg cagctgggcg cactgggcgg tgtcaacgtt    3780
ccgtttgccg caacgggaga tttgacggtc gaaggcggtc tgcgctacga cctgctcaaa    3840
caggatgcat cgccgaaaaa aggcagtgct ttgggctgga gcggcaacag cctcactgaa    3900
ggcacgctgg tcggactcgc gggtctgaag ctgtcgcaac ccttgagcga taaagccgtc    3960
ctgtttgcaa cggcgggcgt ggaacgcgac ctgaacggac gcgactacac ggtaacgggc    4020
ggctttaccg gcgcgactgc agcaaccggc aagacggggg cacgcaatat gccgcacacc    4080
cgtctggttg ccggcctggg cgcggatgtc gaattcggca acgctggaa cggcttggca    4140 cgttacagct acgccggttc caaacagtac ggcaaccaca gcggacgagt cggcgtaggc    4200
taccggttct gactcgag                                                 4218
```

<210> SEQ ID NO 58
<211> LENGTH: 1403
<212> TYPE: PRT
<213> ORGANISM: Artificial
<220> FEATURE:
<223> OTHER INFORMATION: 961cL-983

<400> SEQUENCE: 58

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Ala Tyr Asn Asn Gly Gln Glu Ile
            35                  40                  45

-continued

Asn Gly Phe Lys Ala Gly Glu Thr Ile Tyr Asp Ile Asp Glu Asp Gly
 50                  55                  60

Thr Ile Thr Lys Lys Asp Ala Thr Ala Ala Asp Val Glu Ala Asp Asp
 65                  70                  75                  80

Phe Lys Gly Leu Gly Leu Lys Lys Val Val Thr Asn Leu Thr Lys Thr
                 85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Thr Asn Ala Leu Asn
130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
        275                 280                 285

Asp Gly Leu Asn Ala Thr Thr Glu Lys Leu Asp Thr Arg Leu Ala Ser
290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Gly Ser
            340                 345                 350

Gly Gly Gly Gly Thr Ser Ala Pro Asp Phe Asn Ala Gly Gly Thr Gly
        355                 360                 365

Ile Gly Ser Asn Ser Arg Ala Thr Thr Ala Lys Ser Ala Ala Val Ser
370                 375                 380

Tyr Ala Gly Ile Lys Asn Glu Met Cys Lys Asp Arg Ser Met Leu Cys
385                 390                 395                 400

Ala Gly Arg Asp Asp Val Ala Val Thr Asp Arg Asp Ala Lys Ile Asn
                405                 410                 415

Ala Pro Pro Pro Asn Leu His Thr Gly Asp Phe Pro Asn Pro Asn Asp
            420                 425                 430

Ala Tyr Lys Asn Leu Ile Asn Leu Lys Pro Ala Ile Glu Ala Gly Tyr
        435                 440                 445

Thr Gly Arg Gly Val Glu Val Gly Ile Val Asp Thr Gly Glu Ser Val
450                 455                 460

Gly Ser Ile Ser Phe Pro Glu Leu Tyr Gly Arg Lys Glu His Gly Tyr

```
            465                 470                 475                 480
        Asn Glu Asn Tyr Lys Asn Tyr Thr Ala Tyr Met Arg Lys Glu Ala Pro
                        485                 490                 495
        Glu Asp Gly Gly Gly Lys Asp Ile Glu Ala Ser Phe Asp Asp Glu Ala
                        500                 505                 510
        Val Ile Glu Thr Glu Ala Lys Pro Thr Asp Ile Arg His Val Lys Glu
                        515                 520                 525
        Ile Gly His Ile Asp Leu Val Ser His Ile Ile Gly Gly Arg Ser Val
                        530                 535                 540
        Asp Gly Arg Pro Ala Gly Gly Ile Ala Pro Asp Ala Thr Leu His Ile
        545                 550                 555                 560
        Met Asn Thr Asn Asp Glu Thr Lys Asn Glu Met Met Val Ala Ala Ile
                            565                 570                 575
        Arg Asn Ala Trp Val Lys Leu Gly Glu Arg Gly Val Arg Ile Val Asn
                        580                 585                 590
        Asn Ser Phe Gly Thr Thr Ser Arg Ala Gly Thr Ala Asp Leu Phe Gln
                    595                 600                 605
        Ile Ala Asn Ser Glu Glu Gln Tyr Arg Gln Ala Leu Leu Asp Tyr Ser
                    610                 615                 620
        Gly Gly Asp Lys Thr Asp Glu Gly Ile Arg Leu Met Gln Gln Ser Asp
        625                 630                 635                 640
        Tyr Gly Asn Leu Ser Tyr His Ile Arg Asn Lys Asn Met Leu Phe Ile
                        645                 650                 655
        Phe Ser Thr Gly Asn Asp Ala Gln Ala Gln Pro Asn Thr Tyr Ala Leu
                        660                 665                 670
        Leu Pro Phe Tyr Glu Lys Asp Ala Gln Lys Gly Ile Ile Thr Val Ala
                        675                 680                 685
        Gly Val Asp Arg Ser Gly Glu Lys Phe Lys Arg Glu Met Tyr Gly Glu
                        690                 695                 700
        Pro Gly Thr Glu Pro Leu Glu Tyr Gly Ser Asn His Cys Gly Ile Thr
        705                 710                 715                 720
        Ala Met Trp Cys Leu Ser Ala Pro Tyr Glu Ala Ser Val Arg Phe Thr
                        725                 730                 735
        Arg Thr Asn Pro Ile Gln Ile Ala Gly Thr Ser Phe Ser Ala Pro Ile
                        740                 745                 750
        Val Thr Gly Thr Ala Ala Leu Leu Leu Gln Lys Tyr Pro Trp Met Ser
                        755                 760                 765
        Asn Asp Asn Leu Arg Thr Thr Leu Leu Thr Thr Ala Gln Asp Ile Gly
                        770                 775                 780
        Ala Val Gly Val Asp Ser Lys Phe Gly Trp Gly Leu Leu Asp Ala Gly
        785                 790                 795                 800
        Lys Ala Met Asn Gly Pro Ala Ser Phe Pro Phe Gly Asp Phe Thr Ala
                        805                 810                 815
        Asp Thr Lys Gly Thr Ser Asp Ile Ala Tyr Ser Phe Arg Asn Asp Ile
                        820                 825                 830
        Ser Gly Thr Gly Gly Leu Ile Lys Lys Gly Gly Ser Gln Leu Gln Leu
                        835                 840                 845
        His Gly Asn Asn Thr Tyr Thr Gly Lys Thr Ile Ile Glu Gly Gly Ser
                        850                 855                 860
        Leu Val Leu Tyr Gly Asn Asn Lys Ser Asp Met Arg Val Glu Thr Lys
        865                 870                 875                 880
        Gly Ala Leu Ile Tyr Asn Gly Ala Ala Ser Gly Gly Ser Leu Asn Ser
                        885                 890                 895
```

-continued

```
Asp Gly Ile Val Tyr Leu Ala Asp Thr Asp Gln Ser Gly Ala Asn Glu
            900                 905                 910

Thr Val His Ile Lys Gly Ser Leu Gln Leu Asp Gly Lys Gly Thr Leu
            915                 920                 925

Tyr Thr Arg Leu Gly Lys Leu Leu Lys Val Asp Gly Thr Ala Ile Ile
            930                 935                 940

Gly Gly Lys Leu Tyr Met Ser Ala Arg Gly Lys Gly Ala Gly Tyr Leu
945                 950                 955                 960

Asn Ser Thr Gly Arg Arg Val Pro Phe Leu Ser Ala Ala Lys Ile Gly
            965                 970                 975

Gln Asp Tyr Ser Phe Phe Thr Asn Ile Glu Thr Asp Gly Gly Leu Leu
            980                 985                 990

Ala Ser Leu Asp Ser Val Glu Lys  Thr Ala Gly Ser Glu  Gly Asp Thr
            995                 1000                1005

Leu Ser  Tyr Tyr Val Arg Arg  Gly Asn Ala Ala Arg  Thr Ala Ser
            1010                1015                1020

Ala Ala  Ala His Ser Ala Pro  Ala Gly Leu Lys His  Ala Val Glu
            1025                1030                1035

Gln Gly  Gly Ser Asn Leu Glu  Asn Leu Met Val Glu  Leu Asp Ala
            1040                1045                1050

Ser Glu  Ser Ser Ala Thr Pro  Glu Thr Val Glu Thr  Ala Ala Ala
            1055                1060                1065

Asp Arg  Thr Asp Met Pro Gly  Ile Arg Pro Tyr Gly  Ala Thr Phe
            1070                1075                1080

Arg Ala  Ala Ala Val Gln His  Ala Asn Ala Ala  Asp Gly Val
            1085                1090                1095

Arg Ile  Phe Asn Ser Leu Ala  Ala Thr Val Tyr Ala  Asp Ser Thr
            1100                1105                1110

Ala Ala  His Ala Asp Met Gln  Gly Arg Arg Leu Lys  Ala Val Ser
            1115                1120                1125

Asp Gly  Leu Asp His Asn Gly  Thr Gly Leu Arg Val  Ile Ala Gln
            1130                1135                1140

Thr Gln  Gln Asp Gly Gly Thr  Trp Glu Gln Gly Gly  Val Glu Gly
            1145                1150                1155

Lys Met  Arg Gly Ser Thr Gln  Thr Val Gly Ile Ala  Ala Lys Thr
            1160                1165                1170

Gly Glu  Asn Thr Thr Ala Ala  Ala Thr Leu Gly Met  Gly Arg Ser
            1175                1180                1185

Thr Trp  Ser Glu Asn Ser Ala  Asn Ala Lys Thr Asp  Ser Ile Ser
            1190                1195                1200

Leu Phe  Ala Gly Ile Arg His  Asp Ala Gly Asp Ile  Gly Tyr Leu
            1205                1210                1215

Lys Gly  Leu Phe Ser Tyr Gly  Arg Tyr Lys Asn Ser  Ile Ser Arg
            1220                1225                1230

Ser Thr  Gly Ala Asp Glu His  Ala Glu Gly Ser Val  Asn Gly Thr
            1235                1240                1245

Leu Met  Gln Leu Gly Ala Leu  Gly Gly Val Asn Val  Pro Phe Ala
            1250                1255                1260

Ala Thr  Gly Asp Leu Thr Val  Glu Gly Gly Leu Arg  Tyr Asp Leu
            1265                1270                1275

Leu Lys  Gln Asp Ala Phe Ala  Glu Lys Gly Ser Ala  Leu Gly Trp
            1280                1285                1290
```

-continued

| | | | | | | | | | | |
|---|---|---|---|---|---|---|---|---|---|---|
|Ser|Gly|Asn|Ser|Leu|Thr|Glu|Gly|Thr|Leu|Val|Gly|Leu|Ala|Gly|
| |1295| | | |1300| | | |1305| |

Leu Lys Leu Ser Gln Pro Leu Ser Asp Lys Ala Val Leu Phe Ala
    1310                1315                1320

Thr Ala Gly Val Glu Arg Asp Leu Asn Gly Arg Asp Tyr Thr Val
    1325                1330                1335

Thr Gly Gly Phe Thr Gly Ala Thr Ala Ala Thr Gly Lys Thr Gly
    1340                1345                1350

Ala Arg Asn Met Pro His Thr Arg Leu Val Ala Gly Leu Gly Ala
    1355                1360                1365

Asp Val Glu Phe Gly Asn Gly Trp Asn Gly Leu Ala Arg Tyr Ser
    1370                1375                1380

Tyr Ala Gly Ser Lys Gln Tyr Gly Asn His Ser Gly Arg Val Gly
    1385                1390                1395

Val Gly Tyr Arg Phe
    1400

<210> SEQ ID NO 59
<211> LENGTH: 25
<212> TYPE: DNA
<213> ORGANISM: Artificial
<220> FEATURE:
<223> OTHER INFORMATION: fu (961 )-741(MC58)-His Fwd

<400> SEQUENCE: 59
cgcggatccg gagggggtgg tgtcg                                          25

<210> SEQ ID NO 60
<211> LENGTH: 27
<212> TYPE: DNA
<213> ORGANISM: Artificial
<220> FEATURE:
<223> OTHER INFORMATION: fu (961 )-741(MC58)-His Rev

<400> SEQUENCE: 60
cccgctcgag ttgcttggcg gcaaggc                                        27

<210> SEQ ID NO 61
<211> LENGTH: 25
<212> TYPE: DNA
<213> ORGANISM: Artificial
<220> FEATURE:
<223> OTHER INFORMATION: fu (961 )-983-His Fwd

<400> SEQUENCE: 61
cgcggatccg gcggaggcgg cactt                                          25

<210> SEQ ID NO 62
<211> LENGTH: 26
<212> TYPE: DNA
<213> ORGANISM: Artificial
<220> FEATURE:
<223> OTHER INFORMATION: fu (961 )-983-His Rev

<400> SEQUENCE: 62
cccgctcgag gaaccggtag cctacg                                         26

<210> SEQ ID NO 63
<211> LENGTH: 41
<212> TYPE: DNA
<213> ORGANISM: Artificial
<220> FEATURE:
<223> OTHER INFORMATION: fu (961)- Orf46.1-His Fwd

<400> SEQUENCE: 63
cgcggatccg gtggtggtgg ttcagatttg gcaaacgatt c        41

<210> SEQ ID NO 64
<211> LENGTH: 29
<212> TYPE: DNA
<213> ORGANISM: Artificial
<220> FEATURE:
<223> OTHER INFORMATION: fu (961)- Orf46.1-His Rev

<400> SEQUENCE: 64
cccgctcgag cgtatcatat ttcacgtgc        29

<210> SEQ ID NO 65
<211> LENGTH: 25
<212> TYPE: DNA
<213> ORGANISM: Artificial
<220> FEATURE:
<223> OTHER INFORMATION: fu (961 c-L)-741(MC58) Fwd

<400> SEQUENCE: 65
cgcggatccg gaggggtgg tgtcg        25

<210> SEQ ID NO 66
<211> LENGTH: 28
<212> TYPE: DNA
<213> ORGANISM: Artificial
<220> FEATURE:
<223> OTHER INFORMATION: fu (961 c-L)-741(MC58) Rev

<400> SEQUENCE: 66
cccgctcgag ttattgcttg gcggcaag        28

<210> SEQ ID NO 67
<211> LENGTH: 25
<212> TYPE: DNA
<213> ORGANISM: Artificial
<220> FEATURE:
<223> OTHER INFORMATION: fu (961c-L )-983 Fwd

<400> SEQUENCE: 67
cgcggatccg gcggaggcgg cactt        25

<210> SEQ ID NO 68
<211> LENGTH: 28
<212> TYPE: DNA
<213> ORGANISM: Artificial
<220> FEATURE:
<223> OTHER INFORMATION: fu (961c-L )-983 Rev

<400> SEQUENCE: 68
cccgctcgag tcagaaccgg tagcctac        28

<210> SEQ ID NO 69
<211> LENGTH: 41
<212> TYPE: DNA
<213> ORGANISM: Artificial
<220> FEATURE:
<223> OTHER INFORMATION: fu (961c-L)- Orf46.1 Fwd

<400> SEQUENCE: 69
cgcggatccg gtggtggtgg ttcagatttg gcaaacgatt c        41

<210> SEQ ID NO 70

```
<211> LENGTH: 32
<212> TYPE: DNA
<213> ORGANISM: Artificial
<220> FEATURE:
<223> OTHER INFORMATION: fu (961c-L)- Orf46.1 Rev

<400> SEQUENCE: 70
cccgctcgag ttacgtatca tatttcacgt gc                                    32

<210> SEQ ID NO 71
<211> LENGTH: 42
<212> TYPE: DNA
<213> ORGANISM: Artificial
<220> FEATURE:
<223> OTHER INFORMATION: fu-(DG287)-919-His Fwd

<400> SEQUENCE: 71
cgcggatccg gtggtggtgg tcaaagcaag agcatccaaa cc                         42

<210> SEQ ID NO 72
<211> LENGTH: 30
<212> TYPE: DNA
<213> ORGANISM: Artificial
<220> FEATURE:
<223> OTHER INFORMATION: fu-(DG287)-919-His Rev

<400> SEQUENCE: 72
cccaagcttt tcgggcggta ttcgggcttc                                       30

<210> SEQ ID NO 73
<211> LENGTH: 39
<212> TYPE: DNA
<213> ORGANISM: Artificial
<220> FEATURE:
<223> OTHER INFORMATION: fu-(DG287)-953-His Fwd

<400> SEQUENCE: 73
cgcggatccg gtggtggtgg tgccacctac aaagtggac                             39

<210> SEQ ID NO 74
<211> LENGTH: 28
<212> TYPE: DNA
<213> ORGANISM: Artificial
<220> FEATURE:
<223> OTHER INFORMATION: fu-(DG287)-953-His Rev

<400> SEQUENCE: 74
gcccaagctt ttgtttggct gcctcgat                                         28

<210> SEQ ID NO 75
<211> LENGTH: 34
<212> TYPE: DNA
<213> ORGANISM: Artificial
<220> FEATURE:
<223> OTHER INFORMATION: fu-(DG287)-961-His Fwd

<400> SEQUENCE: 75
cgcggatccg gtggtggtgg tacaagcgac gacg                                  34

<210> SEQ ID NO 76
<211> LENGTH: 28
<212> TYPE: DNA
<213> ORGANISM: Artificial
<220> FEATURE:
<223> OTHER INFORMATION: fu-(DG287)-961-His Rev

<400> SEQUENCE: 76
```

```
gcccaagctt ccactcgtaa ttgacgcc                                              28
```

<210> SEQ ID NO 77
<211> LENGTH: 41
<212> TYPE: DNA
<213> ORGANISM: Artificial
<220> FEATURE:
<223> OTHER INFORMATION: fu-(DG287)-Orf46.1-His Fwd

<400> SEQUENCE: 77

```
cgcggatccg gtggtggtgg ttcagatttg gcaaacgatt c                               41
```

<210> SEQ ID NO 78
<211> LENGTH: 28
<212> TYPE: DNA
<213> ORGANISM: Artificial
<220> FEATURE:
<223> OTHER INFORMATION: fu-(DG287)-Orf46.1-His Rev

<400> SEQUENCE: 78

```
cccaagcttc gtatcatatt tcacgtgc                                              28
```

<210> SEQ ID NO 79
<211> LENGTH: 44
<212> TYPE: DNA
<213> ORGANISM: Artificial
<220> FEATURE:
<223> OTHER INFORMATION: fu-(DG287-919)-Orf46.1-His Fwd

<400> SEQUENCE: 79

```
cccaagcttg gtggtggtgg tggttcagat ttggcaaacg attc                            44
```

<210> SEQ ID NO 80
<211> LENGTH: 29
<212> TYPE: DNA
<213> ORGANISM: Artificial
<220> FEATURE:
<223> OTHER INFORMATION: fu-(DG287-919)-Orf46.1-His Rev

<400> SEQUENCE: 80

```
cccgctcgag cgtatcatat ttcacgtgc                                             29
```

<210> SEQ ID NO 81
<211> LENGTH: 45
<212> TYPE: DNA
<213> ORGANISM: Artificial
<220> FEATURE:
<223> OTHER INFORMATION: fu-(DG287-Orf46.1)-919-His Fwd

<400> SEQUENCE: 81

```
cccaagcttg gtggtggtgg tggtcaaagc aagagcatcc aaacc                           45
```

<210> SEQ ID NO 82
<211> LENGTH: 28
<212> TYPE: DNA
<213> ORGANISM: Artificial
<220> FEATURE:
<223> OTHER INFORMATION: fu-(DG287-Orf46.1)-919-His Rev

<400> SEQUENCE: 82

```
cccgctcgag cgggcggtat tcgggctt                                              28
```

<210> SEQ ID NO 83
<211> LENGTH: 32
<212> TYPE: DNA

<213> ORGANISM: Artificial
<220> FEATURE:
<223> OTHER INFORMATION: fu DG287(394.98)-... Fwd

<400> SEQUENCE: 83
cgcggatccg ctagccccga tgttaaatcg gc          32

<210> SEQ ID NO 84
<211> LENGTH: 29
<212> TYPE: DNA
<213> ORGANISM: Artificial
<220> FEATURE:
<223> OTHER INFORMATION: fu DG287(394.98)-...Rev

<400> SEQUENCE: 84
cggggatcca tcctgctctt ttttgccgg             29

<210> SEQ ID NO 85
<211> LENGTH: 36
<212> TYPE: DNA
<213> ORGANISM: Artificial
<220> FEATURE:
<223> OTHER INFORMATION: fu Orf1-(Orf46.1)-His Fwd

<400> SEQUENCE: 85
cgcggatccg ctagcggaca cacttatttc ggcatc     36

<210> SEQ ID NO 86
<211> LENGTH: 30
<212> TYPE: DNA
<213> ORGANISM: Artificial
<220> FEATURE:
<223> OTHER INFORMATION: fu Orf1-(Orf46.1)-His Rev

<400> SEQUENCE: 86
cgcggatccc cagcggtagc ctaatttgat            30

<210> SEQ ID NO 87
<211> LENGTH: 41
<212> TYPE: DNA
<213> ORGANISM: Artificial
<220> FEATURE:
<223> OTHER INFORMATION: fu (Orf1)-Orf46.1-His Fwd

<400> SEQUENCE: 87
cgcggatccg gtggtggtgg ttcagatttg gcaaacgatt c    41

<210> SEQ ID NO 88
<211> LENGTH: 28
<212> TYPE: DNA
<213> ORGANISM: Artificial
<220> FEATURE:
<223> OTHER INFORMATION: fu (Orf1)-Orf46.1-His Rev

<400> SEQUENCE: 88
cccaagcttc gtatcatatt tcacgtgc              28

<210> SEQ ID NO 89
<211> LENGTH: 36
<212> TYPE: DNA
<213> ORGANISM: Artificial
<220> FEATURE:
<223> OTHER INFORMATION: fu (919)-Orf46.1-His Fwd1

<400> SEQUENCE: 89
gcggcgtcga cggtggcgga ggcactggat cctcag     36

<210> SEQ ID NO 90
<211> LENGTH: 35
<212> TYPE: DNA
<213> ORGANISM: Artificial
<220> FEATURE:
<223> OTHER INFORMATION: fu (919)-Orf46.1-His Fwd2

<400> SEQUENCE: 90
ggaggcactg gatcctcaga tttggcaaac gattc                                35

<210> SEQ ID NO 91
<211> LENGTH: 29
<212> TYPE: DNA
<213> ORGANISM: Artificial
<220> FEATURE:
<223> OTHER INFORMATION: fu (919)-Orf46.1-His Rev

<400> SEQUENCE: 91
cccgctcgag cgtatcatat ttcacgtgc                                      29

<210> SEQ ID NO 92
<211> LENGTH: 25
<212> TYPE: DNA
<213> ORGANISM: Artificial
<220> FEATURE:
<223> OTHER INFORMATION: Fu (orf46)-287-His Fwd

<400> SEQUENCE: 92
cggggatccg ggggcggcgg tggcg                                          25

<210> SEQ ID NO 93
<211> LENGTH: 30
<212> TYPE: DNA
<213> ORGANISM: Artificial
<220> FEATURE:
<223> OTHER INFORMATION: Fu (orf46)-287-His Rev

<400> SEQUENCE: 93
cccaagctta tcctgctctt ttttgccggc                                     30

<210> SEQ ID NO 94
<211> LENGTH: 42
<212> TYPE: DNA
<213> ORGANISM: Artificial
<220> FEATURE:
<223> OTHER INFORMATION: Fu (orf46)-919-His Fwd

<400> SEQUENCE: 94
cgcggatccg gtggtggtgg tcaaagcaag agcatccaaa cc                       42

<210> SEQ ID NO 95
<211> LENGTH: 28
<212> TYPE: DNA
<213> ORGANISM: Artificial
<220> FEATURE:
<223> OTHER INFORMATION: Fu (orf46)-919-His Rev

<400> SEQUENCE: 95
cccaagcttc gggcggtatt cgggcttc                                       28

<210> SEQ ID NO 96
<211> LENGTH: 26
<212> TYPE: DNA
<213> ORGANISM: Artificial
<220> FEATURE:

```
<223> OTHER INFORMATION: Fu (orf46-919)-287-His Fwd

<400> SEQUENCE: 96
ccccaagctt gggggcggcg gtggcg                                          26

<210> SEQ ID NO 97
<211> LENGTH: 31
<212> TYPE: DNA
<213> ORGANISM: Artificial
<220> FEATURE:
<223> OTHER INFORMATION: Fu (orf46-919)-287-His Rev

<400> SEQUENCE: 97
cccgctcgag atcctgctct tttttgccgg c                                    31

<210> SEQ ID NO 98
<211> LENGTH: 45
<212> TYPE: DNA
<213> ORGANISM: Artificial
<220> FEATURE:
<223> OTHER INFORMATION: Fu (orf46-287)-919-His Fwd

<400> SEQUENCE: 98
cccaagcttg gtggtggtgg tggtcaaagc aagagcatcc aaacc                     45

<210> SEQ ID NO 99
<211> LENGTH: 28
<212> TYPE: DNA
<213> ORGANISM: Artificial
<220> FEATURE:
<223> OTHER INFORMATION: Fu (orf46-287)-919-His Rev

<400> SEQUENCE: 99
cccgctcgag cgggcggtat tcgggctt                                        28

<210> SEQ ID NO 100
<211> LENGTH: 35
<212> TYPE: DNA
<213> ORGANISM: Artificial
<220> FEATURE:
<223> OTHER INFORMATION: (DG741)-961c-His Fwd1

<400> SEQUENCE: 100
ggaggcactg gatccgcagc cacaaacgac gacga                                35

<210> SEQ ID NO 101
<211> LENGTH: 36
<212> TYPE: DNA
<213> ORGANISM: Artificial
<220> FEATURE:
<223> OTHER INFORMATION: (DG741)-961c-His Fwd2

<400> SEQUENCE: 101
gcggcctcga gggtggcgga ggcactggat ccgcag                               36

<210> SEQ ID NO 102
<211> LENGTH: 28
<212> TYPE: DNA
<213> ORGANISM: Artificial
<220> FEATURE:
<223> OTHER INFORMATION: (DG741)-961c-His Rev

<400> SEQUENCE: 102
cccgctcgag acccagcttg taaggttg                                        28
```

```
<210> SEQ ID NO 103
<211> LENGTH: 35
<212> TYPE: DNA
<213> ORGANISM: Artificial
<220> FEATURE:
<223> OTHER INFORMATION: (DG741 )-961-His Fwd1

<400> SEQUENCE: 103
ggaggcactg gatccgcagc cacaaacgac gacga                              35

<210> SEQ ID NO 104
<211> LENGTH: 36
<212> TYPE: DNA
<213> ORGANISM: Artificial
<220> FEATURE:
<223> OTHER INFORMATION: (DG741 )-961-His Fwd2

<400> SEQUENCE: 104
gcggcctcga gggtggcgga ggcactggat ccgcag                             36

<210> SEQ ID NO 105
<211> LENGTH: 28
<212> TYPE: DNA
<213> ORGANISM: Artificial
<220> FEATURE:
<223> OTHER INFORMATION: (DG741 )-961-His Rev

<400> SEQUENCE: 105
cccgctcgag ccactcgtaa ttgacgcc                                      28

<210> SEQ ID NO 106
<211> LENGTH: 38
<212> TYPE: DNA
<213> ORGANISM: Artificial
<220> FEATURE:
<223> OTHER INFORMATION: (DG741 )-983-His Fwd

<400> SEQUENCE: 106
gcggcctcga gggatccggc ggaggcggca cttctgcg                           38

<210> SEQ ID NO 107
<211> LENGTH: 26
<212> TYPE: DNA
<213> ORGANISM: Artificial
<220> FEATURE:
<223> OTHER INFORMATION: (DG741 )-983-His Rev

<400> SEQUENCE: 107
cccgctcgag gaaccggtag cctacg                                        26

<210> SEQ ID NO 108
<211> LENGTH: 35
<212> TYPE: DNA
<213> ORGANISM: Artificial
<220> FEATURE:
<223> OTHER INFORMATION: (DG741 )-orf46.1-His Fwd1

<400> SEQUENCE: 108
ggaggcactg gatcctcaga tttggcaaac gattc                              35

<210> SEQ ID NO 109
<211> LENGTH: 37
<212> TYPE: DNA
<213> ORGANISM: Artificial
<220> FEATURE:
<223> OTHER INFORMATION: (DG741 )-orf46.1-His Fwd2
```

```
<400> SEQUENCE: 109
gcggcgtcga cggtggcgga ggcactggat cctcaga                              37

<210> SEQ ID NO 110
<211> LENGTH: 29
<212> TYPE: DNA
<213> ORGANISM: Artificial
<220> FEATURE:
<223> OTHER INFORMATION: (DG741 )-orf46.1-His Rev

<400> SEQUENCE: 110
cccgctcgag cgtatcatat ttcacgtgc                                       29

<210> SEQ ID NO 111
<211> LENGTH: 35
<212> TYPE: DNA
<213> ORGANISM: Artificial
<220> FEATURE:
<223> OTHER INFORMATION: (DG983)-741(MC58) -His Fwd

<400> SEQUENCE: 111
gcggcctcga gggatccgga gggggtggtg tcgcc                                35

<210> SEQ ID NO 112
<211> LENGTH: 25
<212> TYPE: DNA
<213> ORGANISM: Artificial
<220> FEATURE:
<223> OTHER INFORMATION: (DG983)-741(MC58) -His Rev

<400> SEQUENCE: 112
cccgctcgag ttgcttggcg gcaag                                           25

<210> SEQ ID NO 113
<211> LENGTH: 35
<212> TYPE: DNA
<213> ORGANISM: Artificial
<220> FEATURE:
<223> OTHER INFORMATION: (DG983)-961c-His Fwd1

<400> SEQUENCE: 113
ggaggcactg gatccgcagc cacaaacgac gacga                                35

<210> SEQ ID NO 114
<211> LENGTH: 36
<212> TYPE: DNA
<213> ORGANISM: Artificial
<220> FEATURE:
<223> OTHER INFORMATION: (DG983)-961c-His Fwd2

<400> SEQUENCE: 114
gcggcctcga gggtggcgga ggcactggat ccgcag                               36

<210> SEQ ID NO 115
<211> LENGTH: 28
<212> TYPE: DNA
<213> ORGANISM: Artificial
<220> FEATURE:
<223> OTHER INFORMATION: (DG983)-961c-His Rev

<400> SEQUENCE: 115
cccgctcgag acccagcttg taaggttg                                        28

<210> SEQ ID NO 116
<211> LENGTH: 35
```

```
<212> TYPE: DNA
<213> ORGANISM: Artificial
<220> FEATURE:
<223> OTHER INFORMATION: (DG983)-961-His Fwd1

<400> SEQUENCE: 116
ggaggcactg gatccgcagc cacaaacgac gacga                              35

<210> SEQ ID NO 117
<211> LENGTH: 36
<212> TYPE: DNA
<213> ORGANISM: Artificial
<220> FEATURE:
<223> OTHER INFORMATION: (DG983)-961-His Fwd2

<400> SEQUENCE: 117
gcggcctcga gggtggcgga ggcactggat ccgcag                             36

<210> SEQ ID NO 118
<211> LENGTH: 28
<212> TYPE: DNA
<213> ORGANISM: Artificial
<220> FEATURE:
<223> OTHER INFORMATION: (DG983)-961-His Rev

<400> SEQUENCE: 118
cccgctcgag ccactcgtaa ttgacgcc                                      28

<210> SEQ ID NO 119
<211> LENGTH: 35
<212> TYPE: DNA
<213> ORGANISM: Artificial
<220> FEATURE:
<223> OTHER INFORMATION: (DG983)- Orf46.1-His Fwd1

<400> SEQUENCE: 119
ggaggcactg gatcctcaga tttggcaaac gattc                              35

<210> SEQ ID NO 120
<211> LENGTH: 37
<212> TYPE: DNA
<213> ORGANISM: Artificial
<220> FEATURE:
<223> OTHER INFORMATION: (DG983)- Orf46.1-His Fwd2

<400> SEQUENCE: 120
gcggcgtcga cggtggcgga ggcactggat cctcaga                            37

<210> SEQ ID NO 121
<211> LENGTH: 29
<212> TYPE: DNA
<213> ORGANISM: Artificial
<220> FEATURE:
<223> OTHER INFORMATION: (DG983)- Orf46.1-His Rev

<400> SEQUENCE: 121
cccgctcgag cgtatcatat ttcacgtgc                                     29
```